US012807702B2

(12) United States Patent
Ioannou et al.

(10) Patent No.: US 12,807,702 B2
(45) **Date of Patent: *Nov. 24, 2026**

(54) HUMANIZED ANTIBODIES WHICH BIND SORTILIN, ENCODING NUCLEIC ACIDS THEREOF AND METHODS OF USE THEREOF

(71) Applicant: Prothena Biosciences Limited, Dublin (IE)

(72) Inventors: Andriani Ioannou, San Francisco, CA (US); Tarlochan S Nijjar, Orinda, CA (US); Philip James Dolan, III, Oakland, CA (US); Wagner Zago, San Carlos, CA (US)

(73) Assignee: Prothena Biosciences Limited, Dublin (IE)

( * ) Notice: Subject to any disclaimer, the term of this patent is extended or adjusted under 35 U.S.C. 154(b) by 850 days.

This patent is subject to a terminal disclaimer.

(21) Appl. No.: 18/011,764

(22) PCT Filed: Jun. 23, 2021

(86) PCT No.: PCT/US2021/070764

§ 371 (c)(1),
(2) Date: Dec. 20, 2022

(87) PCT Pub. No.: WO2021/263279

PCT Pub. Date: Dec. 30, 2021

(65) Prior Publication Data

US 2023/0235048 A1 Jul. 27, 2023

Related U.S. Application Data

(60) Provisional application No. 63/043,481, filed on Jun. 24, 2020.

(51) Int. Cl.
*C07K 16/28* (2006.01)

(52) U.S. Cl.
CPC .......... *C07K 16/28* (2013.01); *C07K 2317/24* (2013.01); *C07K 2317/565* (2013.01); *C07K 2317/76* (2013.01)

(58) Field of Classification Search
CPC .................. C07K 16/28; C07K 16/286; C07K 2317/24; C07K 2317/565; C07K 2317/76; C07K 2317/34; C07K 2317/56; C07K 2317/71; C07K 2317/92; C07K 2317/94; A61K 2039/505; A61P 25/28
See application file for complete search history.

(56) References Cited

U.S. PATENT DOCUMENTS

| | | | |
|---|---|---|---|
| 4,634,664 | A | 1/1987 | Oestberg |
| 4,634,666 | A | 1/1987 | Engleman et al. |
| 5,057,540 | A | 10/1991 | Kensil et al. |
| 5,194,594 | A | 3/1993 | Khawli et al. |
| 5,208,036 | A | 5/1993 | Eppstein et al. |
| 5,225,539 | A | 7/1993 | Winter |
| 5,264,618 | A | 11/1993 | Felgner et al. |
| 5,279,833 | A | 1/1994 | Rose |
| 5,283,185 | A | 2/1994 | Epand et al. |
| 5,304,489 | A | 4/1994 | Rosen |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,569,825 | A | 10/1996 | Lonberg et al. |
| 5,585,089 | A | 12/1996 | Queen et al. |
| 5,624,821 | A | 4/1997 | Winter et al. |
| 5,625,126 | A | 4/1997 | Lonberg et al. |
| 5,633,425 | A | 5/1997 | Lonberg et al. |
| 5,643,576 | A | 7/1997 | Johnston et al. |
| 5,661,016 | A | 8/1997 | Lonberg et al. |
| 5,733,743 | A | 3/1998 | Johnson et al. |
| 5,736,142 | A | 4/1998 | Sette et al. |
| 5,741,957 | A | 4/1998 | Deboer et al. |
| 5,770,429 | A | 6/1998 | Lonberg et al. |
| 5,786,464 | A | 7/1998 | Seed |
| 5,789,650 | A | 8/1998 | Lonberg et al. |
| 5,814,318 | A | 9/1998 | Lonberg et al. |
| 5,834,597 | A | 11/1998 | Tso et al. |
| 5,837,242 | A | 11/1998 | Holliger et al. |
| 5,849,992 | A | 12/1998 | Meade et al. |
| 5,858,657 | A | 1/1999 | Winter et al. |
| 5,859,205 | A | 1/1999 | Adair et al. |
| 5,871,907 | A | 2/1999 | Winter et al. |
| 5,874,299 | A | 2/1999 | Lonberg et al. |
| 5,877,218 | A | 3/1999 | Herzig et al. |
| 5,877,397 | A | 3/1999 | Lonberg |

(Continued)

FOREIGN PATENT DOCUMENTS

| | | |
|---|---|---|
| GB | 2220211 | 1/1990 |
| JP | 2018-517401 A | 7/2018 |

(Continued)

OTHER PUBLICATIONS

Kurnellas M, et al. (2023) Journal of Translational Medicine. 21:387. 18 pages. (https://doi.org/10.1186/s12967-023-04251-y).*
Lee WC, et al. (2014) Human Molecular Genetics. 23(6):1467-1478. (doi: 10.1093/hmg/ddt534).*
Arduin E, et al. (2015). Molecular Immunology. 63:456-463. (https://doi.org/10.1016/j.molimm.2014.09.017).*
Kuo TT and Aveson VG (Sep./Oct. 2011) mAbs 3:5, 422-430. (DOI: 10.4161/mabs.3.5.16983).*
Kipriyanov et al., "Generation and production of engineered antibodies," Molecular biotechnology, 2004, 26.1:39-60.
Janeway et al., "The interaction of the antibody molecule with specific antigen," Immunobiology: The Immune System in Health and Disease, 2001, 5 pages.
Arrant et al., "Progranulin Gene Therapy Improves Lysosomal Dysfunction and Microglial Pathology Associated with Frontotemporal Dementia and Neuronal Ceroid Lipofuscinosis," Journal of Neuroscience, Feb. 28, 2018, 38(9): 2341-2358.

(Continued)

*Primary Examiner* — Robert S Landsman
(74) *Attorney, Agent, or Firm* — Fish & Richardson P.C.

(57) ABSTRACT

The invention provides antibodies that specifically bind sortilin. The antibodies inhibit or delay pathologies associated with changes in progranulin levels and associated symptomatic deterioration.

27 Claims, 32 Drawing Sheets

Specification includes a Sequence Listing.

(56) References Cited

U.S. PATENT DOCUMENTS

| | | | |
|---|---|---|---|
| 5,888,809 | A | 3/1999 | Allison |
| 6,063,598 | A | 5/2000 | Enenkel et al. |
| 6,114,148 | A | 9/2000 | Seed et al. |
| 6,180,370 | B1 | 1/2001 | Queen et al. |
| 6,407,213 | B1 | 6/2002 | Carter et al. |
| 6,881,557 | B2 | 4/2005 | Foote |
| 7,569,339 | B2 | 8/2009 | Kaufmann et al. |
| 8,455,622 | B2 | 6/2013 | McDonagh et al. |
| 10,058,610 | B2 | 8/2018 | Lantto et al. |
| 10,087,255 | B2 | 10/2018 | Rosenthal et al. |
| 2005/0009150 | A1 | 1/2005 | Basi et al. |
| 2005/0100965 | A1 | 5/2005 | Ghayur et al. |
| 2017/0267761 | A1 | 9/2017 | Ronn et al. |
| 2018/0244770 | A1 | 8/2018 | Monroe et al. |
| 2018/0265586 | A1 | 9/2018 | Rosenthal et al. |
| 2019/0127475 | A1 | 5/2019 | Rosenthal et al. |
| 2021/0032347 | A1 | 2/2021 | Bao et al. |
| 2023/0348588 | A1 | 11/2023 | Dolan, III et al. |
| 2024/0117039 | A1 | 4/2024 | Ioannou et al. |
| 2024/0117040 | A1 | 4/2024 | Ioannou et al. |

FOREIGN PATENT DOCUMENTS

| | | | |
|---|---|---|---|
| JP | 2018-529635 | A | 10/2018 |
| WO | WO 1991/010741 | | 7/1991 |
| WO | WO 1991/017271 | | 11/1991 |
| WO | WO 1992/001047 | | 1/1992 |
| WO | WO 1992/020791 | | 11/1992 |
| WO | WO 1993/012227 | | 6/1993 |
| WO | WO 1994/012629 | | 6/1994 |
| WO | WO 1995/007707 | | 3/1995 |
| WO | WO 1996/034625 | | 11/1996 |
| WO | WO 1998/023635 | | 6/1998 |
| WO | WO 1998/040100 | | 9/1998 |
| WO | WO 2003/057838 | | 7/2003 |
| WO | WO 2004/050884 | | 3/2004 |
| WO | WO 2005/019442 | | 6/2004 |
| WO | WO 2008/012142 | | 7/2004 |
| WO | WO 2008/081008 | | 3/2005 |
| WO | WO 2008/107388 | | 10/2005 |
| WO | WO 2007/098184 | | 8/2007 |
| WO | WO 2009/027471 | | 1/2008 |
| WO | WO 2011/072204 | | 6/2011 |
| WO | WO 2011/109400 | | 9/2011 |
| WO | WO 2016/120811 | | 8/2016 |
| WO | WO 2016/164637 | A1 | 10/2016 |
| WO | WO 2017/009327 | | 1/2017 |
| WO | WO 2017/091512 | | 6/2017 |
| WO | WO 2019/016247 | | 1/2019 |
| WO | WO 2021/263279 | | 12/2021 |
| WO | WO 2023/122766 | | 6/2023 |

OTHER PUBLICATIONS

Extended European Search Report in European Appln No. 21829181.3, mailed on Jun. 21, 2024, 14 pages.

International Preliminary Report on Patentability in International Appln. No. PCT/US2022/082299, mailed on Jul. 4, 2024, 10 pages.

Li et al., "Frontotemporal Lobar Degeneration: Mechanisms and Therapeutic Strategies," Mol Neurobiol, Nov. 4, 2015, 53(9): 6091-6105.

Paushter et al., "The lysosomal function of progranulin, a guardian against neurodegeneration," Acta Neuropathologica, May 9, 2018, 136(1): 1-17.

Oganesyan et al. "Structural insights into neonatal Fc receptor-based recycling mechanisms," The Journal of biological chemistry, 2014, 289(11):7812-24.

Stapleton et al., "Human IgG lacking effector functions demonstrate lower FcRn-binding and reduced transplacental transport," Molecular Immunology, 2018, 95(1-9).

Vidarsson et al., "IgG subclasses and allotypes: from structure to effector functions," Frontiers in immunology, Oct. 20, 2014, 5:1-17.

Alexander et al., "Development of high potency universal DR-restricted helper epitopes by modification of high affinity DR-blocking peptides," *Immunity* 1(9):751-761, Dec. 1994.

Atwal et al., "A Therapeutic Antibody Targeting BACE1 Inhibits Amyloid-β Production in Vivo," *Sci. Trans. Med.* 3(84):84ra43, May 2011.

Baker et al., "Mutations in progranulin cause tau-negative frontotemporal dementia linked to chromosome 17," *Nature* 442(7105):916-919, Aug. 2006.

Banner et al., "Mapping the conformational space accessible to BACE2 using surface mutants and cocrystals with Fab fragments, Fynomers and Xaperones," *Acta. Crystallogr. D. Biol. Crystallogr.* 69(Pt6):1124-1137, Jun. 2013.

Bertschinger et al., "Selection of single domain binding proteins by covalent DNA display," *Protein Eng. Des. Sel.* 20(2):57-68, Feb. 2007.

Bett et al, "Packaging capacity and stability of human adenovirus type 5 vectors," *J. Virol.* 67(10):5911-5921, Oct. 1993.

Bowers et al., "Decreased Mutation Frequencies among Immunoglobulin G Variable Region Genes during Viremic HIV-1 Infection," *Plos One* 9(1), E81913:1-13, Jan. 2014.

Brack et al., "A Bispecific HER2-Targeting FynomAb with Superior Antitumor Activity and Novel Mode of Action," *Mol. Cancer Ther.* 13(8):2030-2039, Aug. 2014.

Carrasquillo et al., "Genome-wide screen identifies rs646776 near sortilin as a regulator of progranulin levels in human plasma," *Am. J. Hum. Genet.* 87(6):890-897, Dec. 2010.

Chang et al., "Progranulin deficiency causes impairment of autophagy and TDP-43 accumulation," *J. Exp. Med.* 214(9):2611-2628, 2017.

Chicz et al., "Specificity and Promiscuity among Naturally Processed Peptides Bound to HLA-DR Alleles ," *J. Exp. Med.* 178:27-47, Jul. 1993.

Chothia et al., "Canonical structures for the hypervariable regions of immunoglobulins," *J. Mol. Biol.* 196(4):901-917, Aug. 1987.

Chothia et al., "Conformations of immunoglobulin hypervariable regions," *Nature* 342:878-883, Dec. 1989.

Cruts et al., "Null mutations in progranulin cause ubiquitin-positive frontotemporal dementia linked to chromosome 17921," *Nature* 442(7105):920-924, Aug. 2006.

Dall'Acqua et al., "Properties of human IgG1s engineered for enhanced binding to the neonatal Fc receptor (FcRn)," *J. Biol. Chem.* 281(33):23514-23523, Aug. 2006.

Deshpande et al., "The RCSB Protein Data Bank: a redesigned query system and relational database based on the mmCIF schema," *Nucleic Acids Res.* 33:D233-D237, 2005.

Dimattia et al., "Antigenic Switching of Hepatitis B Virus by Alternative Dimerization of the Capsid Protein," *Structure Article* 21:133-142, Jan. 2013.

Dubensky et al., "Sindbis Virus DNA-Based Expression Vectors: Utility for In Vitro and In Vivo Gene Transfer," *J. Virol.* 70(1), 508-519, Jan. 1996.

Edelman et al., "The Covalent Structure of an Entire γg Immunoglobulin Molecule," *Proc. Natl. Acad. USA* 63(1):78-85, Mar. 1969.

Friden et al., "Anti-transferrin receptor antibody and antibody-drug conjugates cross the blood-brain barrier," *Proc. Natl. Acad. Sci. USA* 88(11):4771-4775, Jun. 1991.

Friden et al., "Blood-Brain Barrier Penetration and in Vivo Activity of an NGF Conjugate," *Science* 259(5093):373-377, Jan. 1993.

GENBank accession No. FR820882, "*Homo sapiens* partial mRNA for immunoglobulin kappa variable 1-39 (IGKV1-39/D1-39 gene), patient CLL #GE401," 2 pages, Feb. 2011.

Grabulovski et al., "A Novel, Non-immunogenic Fyn SH3-derived Binding Protein with Tumor Vascular Targeting Properties," *J Biol. Chem.* 282(5):3196-3204, Feb. 2007.

Hinton et al., "Engineered Human IgG Antibodies with Longer Serum Half-lives in Primates," *Biol. Chem.* 279(8):6213-6216, Feb. 2004.

Hou et al., "Ageing as a risk factor for neurodegenerative disease," Nature Reviews, *Neurology* 15:565-581, Oct. 2019.

Hu et al., "Sortilin-mediated endocytosis determines levels of the frontotemporal dementia protein, progranulin," *Neuron* 68(4):654-667, Nov. 2010.

(56) References Cited

OTHER PUBLICATIONS

International Preliminary Report on Patentability in International Appln. No. PCT/US2021/070764, mailed on Jan. 5, 2023, 17 pages.
International Search Report and Written Opinion in International Appln. No. PCT/US2021/070764, mailed on Nov. 23, 2021, 21 pages.
International Search Report and Written Opinion in International Appln. No. PCT/US2022/082299, mailed on Jun. 15, 2023, 15 pages.
Jimenz-Gomez et al., "Modulated selection of IGHV gene somatic hypermutation during systemic maturation of human plasma cells," *J. Leukoc. Biol.* 87(3), 523-530, Mar. 2010.
Junghans et al., "Anti-Tac-H, a Humanized Antibody to the Interleukin 2 Receptor with New Features for Immunotherapy in Malignant and Immune Disorders," *Cancer Res.* 50:1495-1502, Mar. 1990.
Lazar et al., "Engineered antibody Fc variants with enhancedeffector function," *Proc. Natl. Acad. Sci.* 103(11):4005-4010, Mar. 2006.
Lefranc et al., IMGT unique numbering for immunoglobulin and T cell receptor constant domains and lg superfamily C-like domains, *Dev. Comp. Immunol.* 29, 185-203, 2005.
Liu, et al., "N-terminal glutamate to pyroglutamate conversion in vivo for human IgG2 antibodies," J. Biol. Chem. 286(13):11211-11217, Apr. 2011.
Mendsaikhan et al., "Microglial Progranulin: Involvement in Alzheimer's Disease and Neurodegenerative Diseases," *Cells* 8(3):230, Mar. 2019.
Neuberger, "Generating high-avidity human Mabs in mice," *Nat. Biotechnol.* 14:826, 1996.
Pascalis et al., "Grafting of "Abbreviated" Complementarity-Determining Regions Containing Specificity-Determining Residues Essential for Ligand Contact to Engineer a Less Immunogenic Humanized Monoclonal Antibody," *J Immunol.* 169(9):3076-3084, Sep. 2002.
Powilleit et al., "Exploiting the Yeast L-A Viral Capsid for the In Vivo Assembly of Chimeric VLPs as Platform in Vaccine Development and Foreign Protein Expression," *PLoS One* 2(5):e415, 12 pages, 2007.
Sheng et al., "Progranulin polymorphism rs5848 is associated with increased risk of Alzheimer's disease," *Gene* 542(2):141-145, Jun. 2014.
Songsivilai et al., "Bispecific antibody: a tool for diagnosis and treatment of disease," *Clin. Exp. Immunol.* 79(3):315-321, Mar. 1990.
Southwood et al., "Several Common HLA-DR Types Share Largely Overlapping Peptide Binding Repertoires," *J. Immunology* 160(7):3363-3373, 1998.
Stoute et al., "A Preliminary Evaluation of a Recombinant Circumsporozoite Protein Vaccine against Plasmodium falciparum Malaria," N Engl. J Med. 336:86-91, Jan. 1997.
Tamura et al., "Structural correlates of an anticarcinoma antibody: identification of specificity-determining residues (SDRs) and development of a minimally immunogenic antibody variant by retention of SDRs only," *J. Immunol.* 164(3):1432-1441, Feb. 2000.
Vajdos et al., "Comprehensive Functional Maps of the Antigen-binding Site of an Anti-ErbB2 Antibody Obtained with Shotgun Scanning Mutagenesis," *J. of Mol. Biol.* 320(2):415-428, Jul. 2002.
Wang et al., "Two-stage PCR protocol allowing introduction of multiple mutations, deletions and insertions using QuikChange Site-Directed Mutagenesis," *BioTechniques* 26(4):680-682, Apr. 1999.
Witzig, "Radioimmunotherapy for patients with relapsed B-cell non-Hodgkin lymphoma," *Cancer Chemother. Pharmacol.* 48 Suppl 1:S91-S95, Jul. 2001.
Wu et al., "Generation and Characterization of a Dual Variable Domain Immunoglobulin (DVD-IgTM) Molecule," *Antibody Engineering* 2:239-250, Jan. 2010.
Xiao et al., "High Efficiency, Long-Term Clinical Expression of Cottontail Rabbit Papillomavirus (CRPV) DNA in Rabbit Skin Following Particle-Mediated DNA Transfer," Nucleic Acids. Res. 24(13): 2620-2622, Jul. 1996.
Yu et al., "Boosting brain uptake of a therapeutic antibody by reducing its affinity for a transcytosis target," *Sci. Trans. Med.* 3(84):84ra44, May 2011.
Zhou et al., "Adeno-associated Virus 2-mediated High Efficiency Gene Transfer into Immature and Mature Subsets of Hematopoietic Progenitor Cells in Human Umbilical Cord Blood," *J. Exp. Med.* 179: 1867-1875, Jun. 1994.

* cited by examiner

```
                                   10                  20                  30                  40
             E V Q L V E S G G D L V K P G G S L K L S C A A P G F T F S T Y G M S W V R Q T  40
5E20VH       E V Q L V E S G G D L V K P G G S L K L S C A A P G F T F S T Y G M S W V R Q T  40
IGHV3-21*01  . . . . . . . . . G . . . . . . . . R . . . . . S . . . . . S . S . N . . . . A  40
AEX29086 VH  . . . . L . . . . G . . Q . . . . . R . . . . . S . . . . . S . A . . . . . . A  40
5E20VHv1     . . . . L . . . . G . . Q . . . . . R . . . . . S . . . . . . . . . . . . . . A  40
5E20VHv2     . . . . . . . . . G . . Q . . . . . R . . . . . S . . . . . . . . . . . . . . A  40
5E20VHv3     . . . . . . . . . G . . Q . . . . . R . . . . . S . . . . . . . . . . . . . . A  40
5E20VHv4     . . . . . . . . . G . . Q . . . . . R . . . . . S . . . . . . . . . . . . . . A  40
5E20VHv5     . . . . . . . . . G . . Q . . . . . R . . . . . S . . . . . . . . . . . . . . A  40
5E20VHv6     . . . . . . . . . G . . Q . . . . . R . . . . . S . . . . . . . . . . . . . . .  40
5E20VHv7     . . . . . . . . . G . . Q . . . . . R . . . . . S . . . . . . . . . . . . . . .  40

                                   50                  60                  70                  80
5E20VH       P D K R L E W V A I I S S G G S Y T Y Y S D T V K G R F T I S R D N A K N T L Y  80
IGHV3-21*01  . G . G . . . . S S . . S S . . I . . A . S . . . . . . . . . . . . . . . S . .  80
AEX29086 VH  . G . G . . . . S A . . G S . G S . . . A . S . R . . . . . . . . . S . . . . .  80
5E20VHv1     . G . G . . . . . . . . . . . . . . . . . . . . . . . . . . . . . . S . . . . .  80
5E20VHv2     . G . G . . . . . . . . . . . . . . . . . . . . . . . . . . . . . . S . . S . .  80
5E20VHv3     . G . . . . . . . . . . . . . . . . . . . . . . . . . . . . . . . . S . . S . .  80
5E20VHv4     . . . . . . . . . . . . . . . . . . . . . . . . . . . . . . . . . . S . . S . .  80
5E20VHv5     . . . . . . . . . . . . . . . . . . . . . . . . . . . . . . . . . . S . . S . .  80
5E20VHv6     . G . . . . . . . . . . . . . . . . . . . . . . . . . . . . . . . . S . . S . .  80
5E20VHv7     . . . . . . . . . . . . . . . . . . . . . . . . . . . . . . . . . . S . . S . .  80
```

FIG. 1A

```
                                      90                  100                 110
              ------------------------+-------------------+-------------------+-------------
5E20VH        L Q M S S L K S E D T A M Y Y C S R S S S H W Y F D V W G T G T T V T V S S    118
IGHV3-21*01   . . . N . . R A . . . . V . . . A . D - - - - A . . . . . Q . . M . . . . .    114
AEX29086 VH   . . . N . . R A . . . . V . . . A K . G T P . . . . Y . . . Q . . L . . . . .    118
5E20VHv1      . . . N . . R A . . . . V . . . . . . . . . . . . . . . . Q . . L . . . . .    118
5E20VHv2      . . . N . . R A . . . . V . . . . . . . . . . . . . . . . Q . . L . . . . .    118
5E20VHv3      . . . N . . R A . . . . V . . . . . . . . . . . . . . . . Q . . L . . . . .    118
5E20VHv4      . . . N . . R A . . . . V . . . . . . . . . . . . . . . . Q . . L . . . . .    118
5E20VHv5      . . . N . . . A . . . . V . . . . . . . . . . . . . . . . Q . . L . . . . .    118
5E20VHv6      . . . N . . R A . . . . V . . . . . . . . . . . . . . . . Q . . L . . . . .    118
5E20VHv7      . . . N . . R A . . . . V . . . . . . . . . . . . . . . . Q . . L . . . . .    118
```

FIG. 1B

```
                                  10                  20                  30                  40
5E20VL        D I L M T Q S P S S M S V S L G D T V S I T C H A S Q G I S S N I G W L Q Q K P   40
IGKV1-12*01   . . Q . . . . . . . V . A . V . . R . T . . . R . . . . . . . W L A . Y . . . .   40
BAH04687 VL   . . Q . . . . . . . L . A . V . . R . T . . . R . . . S . . . Y L N . Y . . . .   40
5E20VLv1      . . Q . . . . . . . L . A . V . . R . T . . . . . . . . . . . . . . . . . . . .   40
5E20VLv2      . . Q . . . . . . . V . A . V . . R . T . . . . . . . . . . . . . . . . . . . .   40
5E20VLv3      . . Q . . . . . . . V . A . V . . R . T . . . . . . . . . . . . . . . . . . . .   40
5E20VLv4      . . Q . . . . . . . V . A . V . . R . T . . . . . . . . . . . . . . . . . . . .   40

                                  50                  60                  70                  80
5E20VH        G K S F K G L I Y H G T N L K D G V P S R F S G S G S G A D F S L T I S S L E S   80
IGKV1-12*01   . . A P . L . . . A A S S . Q S . . . . . . . . . . . . T . . T . . . . . . Q P   80
BAH04687 VL   . . A P . L . . . A A S S . Q S . . . . . . . . . . . . T . . T . . . . . . Q P   80
5E20VLv1      . . A . . . . . . . . . . . . . . . . . . . . . . . . . . . . T . . . . . . Q P   80
5E20VLv2      . . A . . . . . . . . . . . . . . . . . . . . . . . . . . . . T . . . . . . Q P   80
5E20VLv3      . . A . . . . . . . . . . . . . . . . . . . . . . . . . . . . T . . . . . . Q P   80
5E20VLv4      . . A . . . . . . . . . . . . . . . . . . . . . . . . . . . . T . . . . . . Q P   80

                                  90                  100
5E20VL        E D F A D Y F C V Q Y A Q F P Y T F G G G T K L E K R                             107
IGKV1-12*01   . . . . T . Y . Q . A N S . . . . . . Q . . . . . . .                             107
BAH04687 VL   . . . . T . Y . Q . S Y S T . L . . . . . . . V . I .                             107
5E20VLv1      . . . . T . . . . . . . . . . . . . . . . . . V . I .                             107
5E20VLv2      . . . . T . . . . . . . . . . . . . . Q . . . V . I .                             107
5E20VLv3      . . . . T . . . . . . . . . . . . . . Q . . . V . . .                             107
5E20VLv4      . . . . . . . . . . . . . . . . . . . Q . . . V . . .                             107
```

FIG. 2

```
                                     10                  20                  30                  40
8H24_VH               Q A Y L Q Q S G T E L V R P G A S V K M S C K A S G Y T F T S Y S M H W V K Q T   40
IGHV1-60*08_IGHJ1*01  . V Q . V . . . A . V K K . . S . . . V . . . . . . G . . S . . T I S . . R . A   40
AAC51714VH Frwk       . V Q . V . . . A . V K K . . S . . . V . . . . . . G . . S . . A I S . . R . A   40
h8H24VHv1             . . Q . V . . . A . V K K . . S . . . V . . . . . . . . . . . . . . . . . R . A   40
h8H24VHv2             . . Q . V . . . A . V . K . . S . . . V . . . . . . . . . . . . . . . . . R . A   40

                                     50                  60                  70                  80
8H24_VH               P R Q G L E W I G A I Y P G N D A T S Y N Q K F K G K A T L T V D K S S S T A Y   80
IGHV1-60*08_IGHJ1*01  . G . . . . . M . R . I . I L G T A N . A . . . Q . R V . I . A . . . T . . . .   80
AAC51714VH Frwk       . G . . . . . M . G . I . I F G T A N . A . . . Q . R V . I . A . . . T . . . .   80
h8H24VHv1             . G . . . . . . . . . . . . . . . . . . . . . . . . R . . . . . . . . T . . . .   80
h8H24VHv2             . G . . . . . . . . . . . . . . . . . . . . . . . . R . . . . . . . . T . . . .   80

                                     90                  100                110
8H24_VH               M Q L S S L T S E D S A V Y F C A R E G Y Y G - S S F E A W F A S W G Q G T L V   119
IGHV1-60*08_IGHJ1*01  . E . . . . R . . . T . . . Y . . . A - - - - - E Y . Q H - - - - . . . . . . .   111
AAC51714VH Frwk       . E . . . . R . . . T . . . Y . . . A Y C S S T . C Y K T G . V - . . . . . . .   119
h8H24VHv1             . E . . . . R . . . T . . . . . . . . . . . . - . . . . . . . . . . . . . . T .   119
h8H24VHv2             . E . . . . R . . . T . . . . . . . . . . . . - . . . . . . . . . . . . . . T .   119

                      120
8H24 VH               T V S A                                                                            123
IGHV1-60*08 IGHJ1*01  . . . S                                                                            115
AAC51714VH Frwk       . . . S                                                                            123
h8H24VHv1             . . . S                                                                            123
h8H24VHv2             . . . S                                                                            123
```

FIG. 3

```
                                  10                  20                  30
8H24 VL               D V L M T Q T P L S L P V S L G D Q A S I S C R S S Q S I V H S N - G N T Y L E  39
IGKV2-40*01_IGKJ4*01  . I V . . . . . . . . . . T P . E P . . . . . . . . . . . L L D . D D . . . . . D  40
ABC66914VL Frwk       . I V . . . . . . . . . . T P . E P . . . . . . . . . . . L L . . . - . Y N . . D  39
h8H24VLv1             . . V . . . . . . . . . . T P . E P . . . . . . . . . . . . . . . . - . . . . . .  39
h8H24VLv2             . . V . . . . . S . . . . T P . E P . . . . . . . . . . . . . . . . - . . . . . .  39

                      40                  50                  60                  70
8H24 VL               W Y L Q K P G Q S P K L L I Y K V S N R F S G V P D R F S G S G S G T D F T L K  79
IGKV2-40*01_IGKJ4*01  . . . . . . . . . . Q . . . . T L . Y . A . . . . . . . . . . . . . . . . . . .  80
ABC66914VL Frwk       . . . . . . . . . . Q . . . . L G . . . A . . . . . . . . . . . . . . . . . . .  79
h8H24VLv1             . . . . . . . . . . Q . . . . . . . . . . . . . . . . . . . . . . . . . . . . .  79
h8H24VLv2             . . . . . . . . . . Q . . . . . . . . . . . . . . . . . . . . . . . . . . . . T  79

                      80                  90                  100                 110
8H24 VL               I S R V E A E D L G V Y Y C F Q G S H V L P T F G G G T K L E I K  112
IGKV2-40*01_IGKJ4*01  . . . . . . . . V . . . . . M . R I E F P L . . . . . . . V . . .  113
ABC66914VL Frwk       . . . . . . . . V . . . . . M . A L Q T P L . . . . . . . V . . .  112
h8H24VLv1             . . . . . . . . V . . . . . . . . . . . . . . . . . . . . V . . .  112
h8H24VLv2             . . . . . . . . V . . . . . . . . . . . . . . . . . . . . V . . .  112
```

FIG. 4

```
                   10        20        30        40
11M14_VH           EVQLVESGGDLVKPGGSLKLSCAASGFTFNIYGMSWVRQT  40
IGHV3-48*03        .........G..Q.....R..........SS.E.N....A  40
ACS96198 VH hFrwk  .........G..Q.....R..........SS.E.N....A  40
11M14VHv2b         .........G..Q.....R....................A  40
11M14VHv1b         .........G..Q.....R....................A  40
11M14VHv3b         .........G..Q.....R....................A

                           50        60        70        80
11M14_VH           PDKRLEWVATISSGGIYTYYPDILKGRFTISRDNAKNTLY  80
IGHV3-48*03        .G.G....SY...S.STI..A.SV.............S..  80
ACS96198 VH hFrwk  .G.G....SY...S.STI..A.SV.............S..  80
11M14VHv2b         .G.G.................................S..  80
11M14VHv1b         .G.G.................................S..  80
11M14VHv3b         .G.G.................................S..

                   90        100       110
11M14 VH           LQMSSLKSEDTAMYYCARHPGGAMDYWGQGTSVTVSS     117
IGHV3-48*03        ...N..RA....V.....Y----F.......L.....     113
ACS96198 VH hFrwk  ...N..RA....V.....ENIA.F.......L.....     117
11M14VHv1b         ...N..RA....V..................L.....     117
11M14VHv2b         ...N.GRA....V..................L.....     117
11M14VHv3b         G..N..RA....V..................L.....     117
```

FIG. 5

```
                                      10                  20                  30                  40
11M14 VL            D I Q M T Q S P A S L S V S V G E T V T I T C R V S E N I Y S N L A W Y Q Q K Q   40
IGKV1-39*01         . . . . . . . . S . . . A . . . D R . . . . . . A . Q S . S . Y . N . . . . . P   40
CBZ39892VL hFrwk    . . . . . . . . S . . . A . . . D R . . . . . . A . Q S . S . Y . N . . . . . P   40
11M14VLv1b          . . . . . . . . S . . . A . . . D R . . . . . . . . . . . . . . . . . . . . . P   40
11M14VLv2b          . . . . . . . . S . . . A . . . D R . . . . . . . . . . . . . . . . . . . . . P   40
11M14VLv3b          . . . . . . . . S . . . A . . . D R . . . . . . . . . . . . . . . . . . . . . P   40
11M14VLv4b          . . . . . . . . S . . . A . . . D R . . . . . . . . . . . . . . . . . . . . . P

                                        50                  60                  70               80
11M14 VL            G K S P H L L V Y A A T N L A D G V P S R F S G S G S G T Q Y S L K I N S L Q S   80
IGKV1-39*01         . . A . K . . I . . . S S . Q S . . . . . . . . . . . . . D F T . T . S . . . P   80
CBZ39892VL hFrwk    . . A . K . . I . . . S S . Q S . . . . . . . . . . . . . D F T . T . . . . . P   80
11M14VLv1b          . . A . K . . . . . . . . . . . . . . . . . . . . . . . . D . T . T . . . . . P   80
11M14VLv2b          . . . . K . . . . . . . . . . . . . . . . . . . . . . . . D . T . T . S . . . P   80
11M14VLv3b          . . . . K . . . . . . . . G . . . . . . . . . . . . . . . D . T . T . S . . . P   80
11M14VLv4b          . . . . K . . . . . . . . I . . . . . . . . . . . . . . . D . T . T . S . . . P   80

                                      90                  100
11M14 VL            E D F G S Y Y C Q H F W G T P P W T F G G G T K L E I K                          108
IGKV1-39*01         . . . A T . . . . Q S Y S . . - Y . . . Q . . . . . . .                          107
CBZ39892VL hFrwk    . . . A T . . . . Q S Y S . . . Y . . . Q . . . . . . .                          108
11M14VLv1b          . . . A T . . . . . . . . . . . . . . . Q . . . . . . .                          108
11M14VLv2b          . . . A T . . . . . . . . . . . . . . . Q . . . . . . .                          108
11M14VLv3b          . . . A T . . . . . . . . . . . . . . . Q . . . . . . .                          108
11M14VLv4b          . . . A T . . . . . . . . . . . . . . . Q . . . . . . .
```

FIG. 6

Purified anti-huSortilin mAb Binding & PGRN Blocking Assay: *ELISA*

| Clone Name | EC50 (nM) Ab Binding to hSortilin-ECD | % Blocking at 7.4nM mAb |
|---|---|---|
| 8H24 | 0.4 | 89 |
| 2C14 | 1 | 79 |
| 2F18 | 0.7 | 76 |
| 5E20 | 1.1 | 76 |
| 11M14 | 0.8 | 75 |
| 2P22 | 0.8 | 67 |
| 9N18 | 0.8 | 65 |
| 2G1 | 3.1 | 59 |
| 11H24 | 1.6 | 54 |
| 6B15 | 3.8 | 51 |
| 10B6 | 0.6 | 50 |
| 5L16 | 3.6 | 40 |
| 6M23 | 4 | 34 |
| 3M18 | 2.2 | 30 |
| 9E6 | 0.6 | 30 |
| 7A22 | 8.3 | 29 |
| 5M13 | 2.7 | 27 |
| 4J22 | 0.6 | 24 |
| 6F4 | 0.5 | 23 |
| 4A1 | 0.4 | 22 |
| goat α-hSortilin | 2.4 | 15 |
| 10E12 | 2.7 | 14 |
| 6K16 | 2.3 | 12 |
| 7B18 | 2.5 | 4 |
| 7L14 | 1 | 1 |
| 4N2 | 5.8 | -3 |
| 9C7 | 1 | -4 |
| 1M16 | 3.1 | -7 |
| 10O16 | 1.1 | -8 |

FIG. 8D

Most anti-Sort mAbs do not compete with Neurotensin for binding to Sortilin

| Clone Name | Competes with Neurotensin | Potentially low Affinity mAb |
|---|---|---|
| 2C14 | No | |
| 2F18 | No | |
| 2P22 | No | |
| 5E20 | No | |
| 6B15 | No | |
| 8H24 | No | |
| 9N18 | No | |
| 4A1 | No | |
| 6F4 | No | |
| 10B6 | No | |
| 11H24 | No | |
| 11M14 | No | |
| 2G1 | No | Yes |
| 5L16 | No | Yes |
| 4N2 | No | Yes |
| 9C7 | No | Yes |
| 3M18 | No | Yes |
| 5M13 | No | Yes |
| 9E6 | Weakly | |
| 7B18 | Weakly | |
| 7A22 | Weakly | Yes |
| 1M16 | Weakly | Yes |
| 6K16 | Weakly | Yes |
| 7L14 | Weakly | Yes |
| 4J22 | Yes | |
| 6M23 | Yes | Yes |
| 10E12 | Yes | Yes |

FIG. 9A

Purified anti-huSortilin mAb Binding Assay: *Cell-based*

| Ab Name | Binding to hSortiln clone A (67nM) | Binding to U251MG (67nM) | Comments |
|---|---|---|---|
| 2C14 | Yes | Yes | |
| 2F18 | Yes | Yes | |
| 5E20 | Yes | Yes | |
| 6B15 | Yes | Yes | |
| 8H24 | Yes | Yes | |
| 9N18 | Yes | Yes | |
| 11M14 | Yes | Yes | |
| 1M16 | Yes | Yes | |
| 7L14 | Yes | Yes | |
| 9E6 | Yes | Yes | |
| 4N2 | Yes | Yes | |
| 11H24 | Yes | Yes | Background binding to HEK WTcells |
| 10B6 | Yes | Yes | Background binding to HEK WTcells |
| 7A22 | Yes | Yes | Background binding to HEK WTcells |
| 3M18 | Yes | Slight | |
| 4A1 | Yes | Slight | |
| 6F4 | Yes | Slight | |
| 2P22 | Yes | Slight | |
| 5L16 | Yes | Slight | |
| 6M23 | Yes | Minimal | |
| 2G1 | Yes | Minimal | |
| 5M13 | Yes | Minimal | |
| 7B18 | Yes | No | |
| 9C7 | Yes | No | |
| 4J22 | Yes | No | |
| 6K16 | Yes | No | |
| 10E12 | Yes | No | |
| 10O16 | minimal | No | Almost no binding in cell-based assay |

FIG. 10C

Purified anti-huSortilin mAb PGRN Blocking Assay: *Cell-based* Titration

| Clone Name | % Max blocking at 11nM mAb |
|---|---|
| 8H24 | 66 |
| 2C14 | 64 |
| 5E20 | 54 |
| 11M14 | 48 |
| 9N18 | 45 |
| 2F18 | 41 |
| 2P22 | 40 |
| 6B15 | 33 |
| 6M23 | 32 |
| 11H24 | 28 |
| 5L16 | 11 |
| 7A22 | 7 |
| goat α - hSortilin | 11 |
| 4A1 | -3 |
| 3M18 | 6 |
| 6K16 | -6 |
| 4N2 | -2 |
| 9C7 | 1 |
| 5M13 | 0 |
| 2G1 | -1 |
| 6F4 | -10 |
| 10B6 | -1 |
| 9E6 | -12 |
| 1M16 | -4 |
| 10E12 | -10 |

FIG. 12B

Extracellular PGRN & Surface Sortilin Levels after 72 hr mAb treatment at 50nM

| Ab Name | PGRN Fold over control | % Surface Sortilin Levels |
|---|---|---|
| 8H24 | 2.6 | 48 |
| 6M23 | 2.4 | 60 |
| 1M16 | 2.4 | 42 |
| 11M14 | 2.5 | 55 |
| 5E20 | 2.4 | 46 |
| 2F18 | 2.4 | 54 |
| 2P22 | 2.0 | 54 |
| 11H24 | 2.2 | 46 |
| 6B15 | 2.3 | 52 |
| 6K16 | 1.8 | 31 |
| 2C14 | 2.0 | 61 |
| 5M13 | 2.2 | 51 |
| 7L14 | 1.8 | 24 |
| 6F4 | 1.6 | 23 |
| 10B6 | 2.0 | 39 |
| 9E6 | 1.8 | 21 |
| 5L16 | 1.4 | 48 |
| 9N18 | 1.6 | 77 |
| 3M18 | 1.4 | 30 |
| 10E12 | 1.4 | 44 |
| 2G1 | 1.5 | 29 |
| 7A22 | 1.3 | 94 |
| 4A1 | 1.2 | 24 |
| 4N2 | 1.8 | 69 |
| 9C7 | 1.0 | 92 |
| Isotype control | 0.8 | 104 |
| No Mab | 1.0 | 101 |
| gt anti-hSortilin pAb | 2.1 | 27 |

FIG. 13B

HUMANIZED ANTIBODIES WHICH BIND SORTILIN, ENCODING NUCLEIC ACIDS THEREOF AND METHODS OF USE THEREOF

CROSS REFERENCE TO RELATED APPLICATION

This application is the National Stage of International Application No. PCT/US2021/070764 filed Jun. 23, 2021, which claims the benefit of U.S. Provisional Patent Application No. 63/043,481 filed Jun. 24, 2020, which are incorporated by reference in their entirety for all purposes.

REFERENCE TO A SEQUENCE LISTING

The Sequence Listing written in file 561308SEQLIST.txt is 353,813 bytes, was created on Jun. 22, 2021, and is hereby incorporated by reference.

BACKGROUND OF THE INVENTION

Frontotemporal dementia (FTD) is an early-onset dementia affecting 50,000-60,000 individuals in the United States. Reductions in brain levels of progranulin (PGRN) are associated with genetic forms of frontotemporal dementia (FTD). Heterozygous loss-of-function mutations in the human progranulin gene cause FTD by a mechanism of haploinsufficiency (Baker, M. et al. Nature 2006, 442:916-9; Cruts, M. et al. Nature 2006, 442,: 920-924). Genetic forms of FTD with a missing functional copy of the Progranulin gene (FTD-GRN) and ~50% reduction on progranulin levels represent approximately 10% of all FTD population. Mutations that moderately reduce progranulin levels increase the risk for Alzheimer's disease and Parkinson's disease (Sheng, J. et al., Gene; 2014, 542(2):141-5; Mendsaikhan, A., et al., Cells: 2019, 8(3), 230). Progranulin is a neurotrophic/anti-inflammatory factor, and deficiencies may disrupt homeostasis between microglia and neurons and promote neurodegeneration. Progranulin may also play a role in regulating the formation and function of the lysosome.

Sortilin (SORT1) has been identified as a modifier of progranulin levels by mediating its endocytosis (Carrasquillo, M. M. et al. Am J Hum Genet 2010; 87(6):890-7; Hu, F. et al. Neuron 2010; 68(4):654-67). Targeted disruption of the sortilin-progranulin interaction may increase levels of extracellular progranulin, potentially reversing disease phenotype in FTD-GRN patients Modulation of progranulin levels has been reported with an antibody targeting the progranulin receptor sortilin (SORT1) in healthy humans. For instance, Alector's AL001completed phase 1 and is currently in phase 2 (See, https://investors.alector.com/static-files/7418b689-c5b7-43ac-a16a-3c64e1a14e80). Increased progranulin in plasma and CSF relative to baseline has been reported in healthy volunteers administered an anti-sortilin antibody. Sortilin is also a receptor/transporter for other factors (e.g. neurotensin).

BRIEF SUMMARY OF THE CLAIMED INVENTION

In one aspect, the invention provides an isolated monoclonal antibody that competes for binding to human sortilin with antibody 5E20, 8H24, 11M14, 5M13, 2F18, 2P22, 6B15, 2C14, 9N18, or 4N2. Some antibodies bind to the same epitope on human sortilin as antibody 5E20, 8H24, 11M14, 5M13, 2F18, 2P22, 6B15, 2C14, 9N18, or 4N2.

In another aspect, the invention provides an antibody specifically binding to human sortilin comprising three light chain CDRs and three heavy chain CDRs of monoclonal antibody 5E20, wherein 5E20 is a mouse antibody characterized by a heavy chain variable region having an amino acid sequence comprising SEQ ID NO:4 and a light chain variable region having an amino acid sequence comprising SEQ ID NO:10. For example, the antibody can be a humanized antibody.

In some antibodies, the CDRs are of a definition selected from the group of Kabat, Chothia, Kabat/Chothia Composite, AbM and Contact. In some antibodies, the humanized mature heavy chain variable region comprises the three Kabat/Chothia Composite heavy chain CDRs of 5E20 (SEQ ID NOS:5-7) and the humanized mature light chain variable region comprises the three Kabat/Chothia Composite light chain CDRs of 5E20 (SEQ ID NOS:11-13). In some antibodies, the humanized mature heavy chain variable region comprises the three Kabat heavy chain CDRs of 5E20 (SEQ ID NO:14, SEQ ID NO:6, and SEQ ID NO:7) and the humanized mature light chain variable region comprises the three Kabat light chain CDRs of 5E20 (SEQ ID NOS:11-13). In some antibodies, the humanized mature heavy chain variable region comprises the three Chothia heavy chain CDRs of 5E20 (SEQ ID NO:15, SEQ ID NO:16, and SEQ ID NO:7) and the humanized mature light chain variable region comprises the three Chothia light chain CDRs of 5E20 (SEQ ID NOS:11-13). In some antibodies, the humanized mature heavy chain variable region comprises the three AbM heavy chain CDRs of 5E20 (SEQ ID NO:5, SEQ ID NO:17, and SEQ ID NO:7) and the humanized mature light chain variable region comprises the three AbM light chain CDRs of 5E20 (SEQ ID NOS:11-13). In some antibodies, the humanized mature heavy chain variable region comprises the three Contact heavy chain CDRs of 5E20 (SEQ ID NOS:18-20) and the humanized mature light chain variable region comprises the three Contact light chain CDRs of 5E20 (SEQ ID NOS:21-23).

Some antibodies comprise a humanized mature heavy chain variable region having an amino acid sequence at least 90% identical to any one of SEQ ID NOS:163-169, and a humanized mature light chain variable region having an amino acid sequence at least 90% identical to any one of SEQ ID NOS:173-176.

In some antibodies, at least one of the following positions in the VH region is occupied by the amino acid as specified: H5 is occupied by L or V, H40 is occupied by A or T, H42 is occupied by G or D, H44 is occupied by G or R, H49 is occupied by A, H77 is occupied by T or S, H83 is occupied by R or K, H93 is occupied by S, H94 is occupied by R.

In some antibodies, positions H49, H93, and H94 in the VH region are occupied by A, S. and R, respectively. In some antibodies, positions H5, H49, H77, H93, and H94 in the VH region are occupied by V, A, S, S, and R, respectively. In some antibodies, positions H5, H44, H49, H77, H93, and H94 in the VH region are occupied by V, R, A, S, S, and R, respectively. In some antibodies, positions H5, H42, H44, H49, H77, H93, and H94 in the VH region are occupied by V, D, R, A, S, S, and R, respectively. In some antibodies, positions H5, H42, H44, H49, H77, H83, H93, and H94 in the VH region are occupied by V, D, R, A, S, K, S, and R, respectively. In some antibodies, positions H5, H40, H44, H49, H77, H93, and H94 in the VH region are occupied by V, T, R, A, S, S, and R, respectively. In some antibodies, positions H5, H40, H42, H44, H49, H77, H93, and H94 in the VH region are occupied by V, T, D, R, A, S, S, and R, respectively.

In some antibodies, at least one of the following positions in the VL region is occupied by the amino acid as specified: L11 is L or V, L36 is L, L44 is F, L46 is G, L69 is A, L85 is T or D, L87 is F, L100 is G or Q, L106 is I or K. In some antibodies, positions L36, L44, L46, L69, and L87 in the VL region are occupied by L, F, G, A, and F, respectively. In some antibodies, positions L11, L36, L44, L46, L69, and L87 in the VL region are occupied by V, L, F, G, A, and F, respectively. In some antibodies, positions L11, L36, L44, L46, L69, L87, L100, and L106 in the VL region are occupied by V, L, F, G, A, F, Q, and K, respectively. In some antibodies, positions L11, L36, L44, L46, L69, L85, L87, L100, and L106 in the VL region are occupied by V, L, F, G, A, D, F, Q, and K, respectively.

Some antibodies comprise a mature heavy chain variable region having an amino acid sequence at least 95% identical to at least one of SEQ ID NO: 163-169 and a mature light chain variable region having an amino acid sequence at least 95% identical to at least one of SEQ ID NOS:173-176. Some antibodies comprise a mature heavy chain variable region having an amino acid sequence at least 98% identical to SEQ ID NOS:163-169 and a mature light chain variable region having an amino acid sequence at least 98% identical to SEQ ID NOS:173-176. In some antibodies, the mature heavy chain variable region has an amino acid sequence of any one of SEQ ID NOS:163-169, and the mature light chain variable region has an amino acid sequence of any one of SEQ ID NOS:173-176.

In some antibodies, the mature heavy chain variable region has an amino acid sequence of SEQ ID NO:163 and the mature light chain variable region has an amino acid sequence of SEQ ID NO:173. In some antibodies, the mature heavy chain variable region has an amino acid sequence of SEQ ID NO:164 and the mature light chain variable region has an amino acid sequence of SEQ ID NO:173. In some antibodies, the mature heavy chain variable region has an amino acid sequence of SEQ ID NO: 165 and the mature light chain variable region has an amino acid sequence of SEQ ID NO:173. In some antibodies, the mature heavy chain variable region has an amino acid sequence of SEQ ID NO:166 and the mature light chain variable region has an amino acid sequence of SEQ ID NO: 173. In some antibodies, the mature heavy chain variable region has an amino acid sequence of SEQ ID NO:167 and the mature light chain variable region has an amino acid sequence of SEQ ID NO:173. In some antibodies, the mature heavy chain variable region has an amino acid sequence of SEQ ID NO:168 and the mature light chain variable region has an amino acid sequence of SEQ ID NO:173.

In some antibodies, the mature heavy chain variable region has an amino acid sequence of SEQ ID NO:169 and the mature light chain variable region has an amino acid sequence of SEQ ID NO:173. In some antibodies, the mature heavy chain variable region has an amino acid sequence of SEQ ID NO:163 and the mature light chain variable region has an amino acid sequence of SEQ ID NO:174. In some antibodies, the mature heavy chain variable region has an amino acid sequence of SEQ ID NO: 164 and the mature light chain variable region has an amino acid sequence of SEQ ID NO:174. In some antibodies, the mature heavy chain variable region has an amino acid sequence of SEQ ID NO:165 and the mature light chain variable region has an amino acid sequence of SEQ ID NO: 174. In some antibodies, the mature heavy chain variable region has an amino acid sequence of SEQ ID NO:166 and the mature light chain variable region has an amino acid sequence of SEQ ID NO:174. In some antibodies, the mature heavy chain variable region has an amino acid sequence of SEQ ID NO:167 and the mature light chain variable region has an amino acid sequence of SEQ ID NO:174. In some antibodies, the mature heavy chain variable region has an amino acid sequence of SEQ ID NO:168 and the mature light chain variable region has an amino acid sequence of SEQ ID NO: 174.

In some antibodies, the mature heavy chain variable region has an amino acid sequence of SEQ ID NO:169 and the mature light chain variable region has an amino acid sequence of SEQ ID NO:174. In some antibodies, the mature heavy chain variable region has an amino acid sequence of SEQ ID NO: 163 and the mature light chain variable region has an amino acid sequence of SEQ ID NO:175. In some antibodies, the mature heavy chain variable region has an amino acid sequence of SEQ ID NO: 164 and the mature light chain variable region has an amino acid sequence of SEQ ID NO: 175. In some antibodies, the mature heavy chain variable region has an amino acid sequence of SEQ ID NO:165 and the mature light chain variable region has an amino acid sequence of SEQ ID NO:175. In some antibodies, the mature heavy chain variable region has an amino acid sequence of SEQ ID NO:166 and the mature light chain variable region has an amino acid sequence of SEQ ID NO:175. In some antibodies, the mature heavy chain variable region has an amino acid sequence of SEQ ID NO:167 and the mature light chain variable region has an amino acid sequence of SEQ ID NO:175. In some antibodies, the mature heavy chain variable region has an amino acid sequence of SEQ ID NO:168 and the mature light chain variable region has an amino acid sequence of SEQ ID NO: 175.

In some antibodies, the mature heavy chain variable region has an amino acid sequence of SEQ ID NO:169 and the mature light chain variable region has an amino acid sequence of SEQ ID NO:175. In some antibodies, the mature heavy chain variable region has an amino acid sequence of SEQ ID NO: 163 and the mature light chain variable region has an amino acid sequence of SEQ ID NO:176. In some antibodies, the mature heavy chain variable region has an amino acid sequence of SEQ ID NO: 164 and the mature light chain variable region has an amino acid sequence of SEQ ID NO: 176. In some antibodies, the mature heavy chain variable region has an amino acid sequence of SEQ ID NO:165 and the mature light chain variable region has an amino acid sequence of SEQ ID NO:176. In some antibodies, the mature heavy chain variable region has an amino acid sequence of SEQ ID NO:166 and the mature light chain variable region has an amino acid sequence of SEQ ID NO:176. In some antibodies, the mature heavy chain variable region has an amino acid sequence of SEQ ID NO:167 and the mature light chain variable region has an amino acid sequence of SEQ ID NO:176. In some antibodies, the mature heavy chain variable region has an amino acid sequence of SEQ ID NO:168 and the mature light chain variable region has an amino acid sequence of SEQ ID NO: 176. In some antibodies, the mature heavy chain variable region has an amino acid sequence of SEQ ID NO:169 and the mature light chain variable region has an amino acid sequence of SEQ ID NO:176.

In another aspect, the invention provides an antibody specifically binding to human sortilin comprising three light chain CDRs and three heavy chain CDRs of monoclonal antibody 81124, wherein 81124 is a mouse antibody characterized by a heavy chain variable region having an amino acid sequence comprising SEQ ID NO:28 and a light chain variable region having an amino acid sequence comprising SEQ ID NO:34. For example, the antibody can be a humanized antibody.

In some antibodies, the CDRs are of a definition selected from the group of Kabat, Chothia, Kabat/Chothia Composite, AbM and Contact. In some antibodies, the humanized mature heavy chain variable region comprises the three Kabat/Chothia Composite heavy chain CDRs of 81124 (SEQ ID NOS:29-31) and the humanized mature light chain variable region comprises the three Kabat/Chothia Composite light chain CDRs of 81124 (SEQ ID NOS:35-37). In some antibodies, the humanized mature heavy chain variable region comprises the three Kabat heavy chain CDRs of 81124 (SEQ ID NO:38, SEQ ID NO:30, and SEQ ID NO:31) and the humanized mature light chain variable region comprises the three Kabat light chain CDRs of 8H24 (SEQ ID NOS:35-37). In some antibodies, the humanized mature heavy chain variable region comprises the three Chothia heavy chain CDRs of 8H24 (SEQ ID NO:39, SEQ ID NO:40, and SEQ ID NO:31) and the humanized mature light chain variable region comprises the three Chothia light chain CDRs of 8H24 (SEQ ID NOS:35-37). In some antibodies, the humanized mature heavy chain variable region comprises the three AbM heavy chain CDRs of 8H24 (SEQ ID NO:29, SEQ ID NO:41, and SEQ ID NO:31) and the humanized mature light chain variable region comprises the three AbM light chain CDRs of 8H24 (SEQ ID NOS:35-37). In some antibodies, the humanized mature heavy chain variable region comprises the three Contact heavy chain CDRs of 8H24 (SEQ ID NOS:42-44) and the humanized mature light chain variable region comprises the three Contact light chain CDRs of 8H24 (SEQ ID NOS:45-47).

Some antibodies comprise a humanized mature heavy chain variable region having an amino acid sequence at least 90% identical to any one of SEQ ID NOS:180-181, and a humanized mature light chain variable region having an amino acid sequence at least 90% identical to any one of SEQ ID NOS:185-186.

In some antibodies, at least one of the following positions in the VH region is occupied by the amino acid as specified: H2 is occupied by A, H12 is occupied by K or V, H48 is occupied by I, H67 is occupied by A, H71 is occupied by V, H91 is occupied by F, H108 is occupied by T.

In some antibodies, positions H2, H48, H67, H71, H91, and H108 in the VH region are occupied by A, I, A, V, F, and T, respectively. In some antibodies, H2, H12, H48, H67, H71, H91, and H108 in the VH region are occupied by A, V, I, A, V, F, and T, respectively. In some antibodies, at least one of the following positions in the VL region is occupied by the amino acid as specified: L2 is V, L9 is L or S, L74 is K or T.

In some antibodies, position L2 in the VL region is occupied by V. In some antibodies, positions L2, L9, and L74 in the VL region are occupied by V, S, and T, respectively.

Some antibodies comprise a mature heavy chain variable region having an amino acid sequence at least 95% identical to at least one of SEQ ID NO: 180-181 and a mature light chain variable region having an amino acid sequence at least 95% identical to at least one of SEQ ID NOS:185-186. Some antibodies comprise a mature heavy chain variable region having an amino acid sequence at least 98% identical to SEQ ID NOS:180-181 and a mature light chain variable region having an amino acid sequence at least 98% identical to SEQ ID NOS:185-186. In some antibodies, the mature heavy chain variable region has an amino acid sequence of any one of SEQ ID NOS:180-181, and the mature light chain variable region has an amino acid sequence of any one of SEQ ID NOS:185-186.

In some antibodies, the mature heavy chain variable region has an amino acid sequence of SEQ ID NO:180 and the mature light chain variable region has an amino acid sequence of SEQ ID NO:185. In some antibodies, the mature heavy chain variable region has an amino acid sequence of SEQ ID NO:180 and the mature light chain variable region has an amino acid sequence of SEQ ID NO:186. In some antibodies, the mature heavy chain variable region has an amino acid sequence of SEQ ID NO: 181 and the mature light chain variable region has an amino acid sequence of SEQ ID NO:185. In some antibodies, the mature heavy chain variable region has an amino acid sequence of SEQ ID NO:181 and the mature light chain variable region has an amino acid sequence of SEQ ID NO: 186.

In another aspect, the invention provides an antibody specifically binding to human sortilin comprising three light chain CDRs and three heavy chain CDRs of monoclonal antibody 11M14, wherein 11M14 is a mouse antibody characterized by a heavy chain variable region having an amino acid sequence comprising SEQ ID NO:52 and a light chain variable region having an amino acid sequence comprising SEQ ID NO:58), except that position L54 can be L, G, or I. For example, the antibody can be a humanized antibody.

In some antibodies, the CDRs are of a definition selected from the group of Kabat, Chothia, Kabat/Chothia Composite, AbM and Contact. In some antibodies, the humanized mature heavy chain variable region comprises the three Kabat/Chothia Composite heavy chain CDRs of 11M14 (SEQ ID NOS:53-55) and the humanized mature light chain variable region comprises the three Kabat/Chothia Composite light chain CDRs of 11M14 (SEQ ID NOS:59-61), except that position L54 can be L, G, or I. In some antibodies, the humanized mature heavy chain variable region comprises the three Kabat heavy chain CDRs of 11M14 (SEQ ID NO:62, SEQ ID NO:54, and SEQ ID NO:55) and the humanized mature light chain variable region comprises the three Kabat light chain CDRs of 11M14 (SEQ ID NOS:59-61), except that position L54 can be L, G, or I. In some antibodies, the humanized mature heavy chain variable region comprises the three Chothia heavy chain CDRs of 11M14 (SEQ ID NO:63, SEQ ID NO:64, and SEQ ID NO:55) and the humanized mature light chain variable region comprises the three Chothia light chain CDRs of 11M14 (SEQ ID NOS:59-61), except that position L54 can be L, G, or I. In some antibodies, the humanized mature heavy chain variable region comprises the three AbM heavy chain CDRs of 11M14 (SEQ ID NO:53, SEQ ID NO:65, and SEQ ID NO:55) and the humanized mature light chain variable region comprises the three AbM light chain CDRs of 11M14 (SEQ ID NOS:59-61), except that position L54 can be L, G, or I. In some antibodies, the humanized mature heavy chain variable region comprises the three Contact heavy chain CDRs of 11M14 (SEQ ID NOS:66-68) and the humanized mature light chain variable region comprises the three Contact light chain CDRs of 11M14 (SEQ ID NOS:69-71), except that position L54 can be L, G, or I.

Some antibodies comprise a humanized mature heavy chain variable region having an amino acid sequence at least 90% identical to any one of SEQ ID NOS:190-192, and a humanized mature light chain variable region having an amino acid sequence at least 90% identical to any one of SEQ ID NOS:196-199.

In some antibodies, at least one of the following positions in the VH region is occupied by the amino acid as specified: H49 is occupied by A, H80 is occupied by L or G, H82c is occupied by L or G. In some antibodies, position H49 in the VH region is occupied by A. In some antibodies, positions H49 and H82c in the VH region are occupied by A and G, respectively. In some antibodies, positions H49 and H80 in the VH region are occupied by A and G, respectively.

In some antibodies, at least one of the following positions in the VL region is occupied by the amino acid as specified: L43 is A or S, L48 is V, L54 is L, G, or I, L71 is Y, L76 is N or S. In some antibodies, positions L48 and L71 in the VL region are occupied by V and Y respectively. In some antibodies, positions L43, L48, L71, and L76 in the VL region are occupied by S, V, Y, and S, respectively. In some antibodies, positions L43, L48, L54, L71, and L76 in the VL region are occupied by S, V, G, Y, and S, respectively. In some antibodies, positions L43, L48, L54, L71, and L76 in the VL region are occupied by S, V, I, Y, and S, respectively.

Some antibodies comprise a mature heavy chain variable region having an amino acid sequence at least 95% identical to at least one of SEQ ID NO: 190-192 and a mature light chain variable region having an amino acid sequence at least 95% identical to at least one of SEQ ID NOS:196-199. Some antibodies comprise a mature heavy chain variable region having an amino acid sequence at least 98% identical to SEQ ID NOS:190-192 and a mature light chain variable region having an amino acid sequence at least 98% identical to SEQ ID NOS:196-199. In some antibodies, the mature heavy chain variable region has an amino acid sequence of any one of SEQ ID NOS:190-192, and the mature light chain variable region has an amino acid sequence of any one of SEQ ID NOS:196-199.

In some antibodies, the mature heavy chain variable region has an amino acid sequence of SEQ ID NO:190 and the mature light chain variable region has an amino acid sequence of SEQ ID NO:196. In some antibodies, the mature heavy chain variable region has an amino acid sequence of SEQ ID NO:190 and the mature light chain variable region has an amino acid sequence of SEQ ID NO:197. In some antibodies, the mature heavy chain variable region has an amino acid sequence of SEQ ID NO: 190 and the mature light chain variable region has an amino acid sequence of SEQ ID NO:198. In some antibodies, the mature heavy chain variable region has an amino acid sequence of SEQ ID NO:190 and the mature light chain variable region has an amino acid sequence of SEQ ID NO: 199. In some antibodies, the mature heavy chain variable region has an amino acid sequence of SEQ ID NO:191 and the mature light chain variable region has an amino acid sequence of SEQ ID NO:196. In some antibodies, the mature heavy chain variable region has an amino acid sequence of SEQ ID NO:191 and the mature light chain variable region has an amino acid sequence of SEQ ID NO:197.

In some antibodies, the mature heavy chain variable region has an amino acid sequence of SEQ ID NO:191 and the mature light chain variable region has an amino acid sequence of SEQ ID NO:198. In some antibodies, the mature heavy chain variable region has an amino acid sequence of SEQ ID NO:191 and the mature light chain variable region has an amino acid sequence of SEQ ID NO:199. In some antibodies, the mature heavy chain variable region has an amino acid sequence of SEQ ID NO: 192 and the mature light chain variable region has an amino acid sequence of SEQ ID NO:196. In some antibodies, the mature heavy chain variable region has an amino acid sequence of SEQ ID NO:192 and the mature light chain variable region has an amino acid sequence of SEQ ID NO: 197. In some antibodies, the mature heavy chain variable region has an amino acid sequence of SEQ ID NO:192 and the mature light chain variable region has an amino acid sequence of SEQ ID NO:198. In some antibodies, the mature heavy chain variable region has an amino acid sequence of SEQ ID NO:192 and the mature light chain variable region has an amino acid sequence of SEQ ID NO:199.

In another aspect, the invention provides an antibody specifically binding to human sortilin comprising three light chain CDRs and three heavy chain CDRs of monoclonal antibody 5M13, wherein 5M13 is a mouse antibody characterized by a heavy chain variable region having an amino acid sequence comprising SEQ ID NO:78 and a light chain variable region having an amino acid sequence comprising SEQ ID NO:84. In some antibodies, the three heavy chain CDRs are as defined by Kabat-Chothia Composite (SEQ ID NOS:79-81) and the three light chain CDRs are as defined by Kabat-Chothia Composite (SEQ ID NOS:85-87).

In another aspect, the invention provides an antibody specifically binding to human sortilin comprising three light chain CDRs and three heavy chain CDRs of monoclonal antibody 2F18, wherein 2F18 is a mouse antibody characterized by a heavy chain variable region having an amino acid sequence comprising SEQ ID NO:90 and a light chain variable region having an amino acid sequence comprising SEQ ID NO:96. In some antibodies, the three heavy chain CDRs are as defined by Kabat-Chothia Composite (SEQ ID NOS:91-93) and the three light chain CDRs are as defined by Kabat-Chothia Composite (SEQ ID NOS:97-99).

In another aspect, the invention provides an antibody specifically binding to human sortilin comprising three light chain CDRs and three heavy chain CDRs of monoclonal antibody 2P22, wherein 2P22 is a mouse antibody characterized by a heavy chain variable region having an amino acid sequence comprising SEQ ID NO:102 and a light chain variable region having an amino acid sequence comprising SEQ ID NO:108. In some antibodies, the three heavy chain CDRs are as defined by Kabat-Chothia Composite (SEQ ID NOS:103-105) and the three light chain CDRs are as defined by Kabat-Chothia Composite (SEQ ID NOS:109-111).

In another aspect, the invention provides an antibody specifically binding to human sortilin comprising three light chain CDRs and three heavy chain CDRs of monoclonal antibody 6B15, wherein 6B15 is a mouse antibody characterized by a heavy chain variable region having an amino acid sequence comprising SEQ ID NO:114 and a light chain variable region having an amino acid sequence comprising SEQ ID NO:120. In some antibodies, the three heavy chain CDRs are as defined by Kabat-Chothia Composite (SEQ ID NOS:115-117) and the three light chain CDRs are as defined by Kabat-Chothia Composite (SEQ ID NOS:121-123).

In another aspect, the invention provides an antibody specifically binding to human sortilin comprising three light chain CDRs and three heavy chain CDRs of monoclonal antibody 2C14, wherein 2C14 is a mouse antibody characterized by a heavy chain variable region having an amino acid sequence comprising SEQ ID NO:126 and a light chain variable region having an amino acid sequence comprising SEQ ID NO:132. In some antibodies, the three heavy chain CDRs are as defined by Kabat-Chothia Composite (SEQ ID NOS:127-129) and the three light chain CDRs are as defined by Kabat-Chothia Composite (SEQ ID NOS:133-135).

In another aspect, the invention provides an antibody specifically binding to human sortilin comprising three light chain CDRs and three heavy chain CDRs of monoclonal antibody 9N18, wherein 9N18 is a mouse antibody characterized by a heavy chain variable region having an amino acid sequence comprising SEQ ID NO:138 and a light chain variable region having an amino acid sequence comprising SEQ ID NO:144. In some antibodies, the three heavy chain CDRs are as defined by Kabat-Chothia Composite (SEQ ID NOS:139-141) and the three light chain CDRs are as defined by Kabat-Chothia Composite (SEQ ID NOS:145-147).

In another aspect, the invention provides an antibody specifically binding to human sortilin comprising three light chain CDRs and three heavy chain CDRs of monoclonal antibody 4N2, wherein 4N2 is a mouse antibody characterized by a heavy chain variable region having an amino acid sequence comprising SEQ ID NO:150 and a light chain variable region having an amino acid sequence comprising SEQ ID NO:156. In some antibodies, the three heavy chain CDRs are as defined by Kabat-Chothia Composite (SEQ ID NOS:151-153) and the three light chain CDRs are as defined by Kabat-Chothia Composite (SEQ ID NOS:157-159).

For example, the antibody can be a humanized antibody.

The antibody can be an intact antibody or a binding fragment. Some of the antibodies have a human IgG1 isotype, while others may have a human IgG2 or IgG4 isotype. Some antibodies have the mature light chain variable region fused to a light chain constant region and the mature heavy chain variable region fused to a heavy chain constant region. The heavy chain constant region of some antibodies is a mutant form of a natural human heavy chain constant region which has reduced binding to a Fcγ receptor relative to the natural human heavy chain constant region.

The heavy chain constant region of some antibodies is a mutant form of a natural human heavy chain constant region which has enhanced binding to a neonatal Fcγ receptor relative to the natural human heavy chain constant region.

Some antibodies comprise a heavy chain of SEQ ID NO:244 and a light chain of SEQ ID NO:245. Some antibodies comprise a heavy chain of SEQ ID NO:246 and a light chain of SEQ ID NO:247. Some antibodies comprise a heavy chain of SEQ ID NO:248 and a light chain of SEQ ID NO:249. Some antibodies comprise a heavy chain of SEQ ID NO:250 and a light chain of SEQ ID NO:245. Some antibodies comprise a heavy chain of SEQ ID NO:251 and a light chain of SEQ ID NO:247. Some antibodies comprise a heavy chain of SEQ ID NO:252 and a light chain of SEQ ID NO:249.

In another aspect, the invention provides a pharmaceutical composition comprising any of the antibodies disclosed herein and a pharmaceutically-acceptable carrier. In another aspect, the invention provides a nucleic acid encoding the heavy chain and/or light chain of any of the antibodies disclosed herein.

In yet another aspect, the invention provides methods of humanizing any non-human antibody described herein, for example mouse antibody 5E20, wherein 5E20 is characterized by a mature heavy chain variable region of SEQ ID NO:4 and a mature light chain variable region of SEQ ID NO:10; mouse antibody 8H24, wherein 8H24 is characterized by a mature heavy chain variable region of SEQ ID NO:28 and a mature light chain variable region of SEQ ID NO:34; mouse antibody 11M14, wherein 11M14 is characterized by a mature heavy chain variable region of SEQ ID NO:52 and a mature light chain variable region of SEQ ID NO:58; mouse antibody 5M13, wherein 5M13 is characterized by a mature heavy chain variable region of SEQ ID NO:78 and a mature light chain variable region of SEQ ID NO:84; mouse antibody 2F18, wherein 2F18 is characterized by a mature heavy chain variable region of SEQ ID NO:90 and a mature light chain variable region of SEQ ID NO:96; mouse antibody 2P22, wherein 2P22 is characterized by a mature heavy chain variable region of SEQ ID NO:102 and a mature light chain variable region of SEQ ID NO:108; mouse antibody 6B15, wherein 6B15 is characterized by a mature heavy chain variable region of SEQ ID NO:114 and a mature light chain variable region of SEQ ID NO:120; mouse antibody 2C14, wherein 2C14 is characterized by a mature heavy chain variable region of SEQ ID NO:126 and a mature light chain variable region of SEQ ID NO:132; mouse antibody 9N18, wherein 9N18 is characterized by a mature heavy chain variable region of SEQ ID NO:138 and a mature light chain variable region of SEQ ID NO:144; or mouse antibody 4N2, wherein 4N2 is characterized by a mature heavy chain variable region of SEQ ID NO:150 and a mature light chain variable region of SEQ ID NO:156. Such methods can involve selecting one or more acceptor antibody sequences; identifying amino acid residues of the mouse antibody to be retained; synthesizing a nucleic acid encoding a humanized heavy chain comprising CDRs of the mouse antibody heavy chain and a nucleic acid encoding a humanized light chain comprising CDRs of the mouse antibody light chain; and expressing the nucleic acids in a host cell to produce a humanized antibody.

Methods of producing antibodies, for example humanized, chimeric or veneered form of 5E20, 8H24, 11M14, 5M13, 2F18, 2P22, 6B15, 2C14, 9N18, or 4N2, are also provided. In such methods, cells transformed with nucleic acids encoding the heavy and light chains of the antibody are cultured so that the cells secrete the antibody. The antibody can then be purified from the cell culture media.

Cell lines producing any of the antibodies disclosed herein, for example a a humanized, chimeric, or veneered form of 5E20, 8H24, 11M14, 5M13, 2F18, 2P22, 6B15, 2C14, 9N18, or 4N2, can be produced by introducing a vector encoding heavy and light chains of the antibody and a selectable marker into cells, propagating the cells under conditions to select for cells having increased copy number of the vector, isolating single cells from the selected cells; and banking cells cloned from a single cell selected based on yield of antibody.

Some cells can be propagated under selective conditions and screened for cell lines naturally expressing and secreting at least 100 mg/L/$10^6$ cells/24 hours.

The invention also provides methods of increasing progranulin levels in a subject having or at risk of developing a a disease or disorder associated with changes in progranulin levels, comprising administering to the subject an effective dose of an antibody disclosed herein, thereby increasing progranulin levels in the subject.

The invention also provides methods of treating or effecting prophylaxis of a disease or disorder associated with changes in progranulin levels in a subject, comprising administering an effective dose of an antibody disclosed herein, and thereby treating or effecting prophylaxis of the disease or disorder. Some methods further comprise detecting progranulin levels in a subject. Some methods further comprise comprising monitoring progranulin levels in a subject.

In some methods, the disease or disorder associated with changes in progranulin levels is frontotemporal dementia, Alzheimer's disease, Parkinson's disease, anyotrophic lateral sclerosis, Batten disease, a neurodegenerative disorder, or a neurodegenerative disorder associated with aging. In some methods, the disease or disorder associated with changes in progranulin levels is frontotemporal dementia.

The invention also provides methods of detecting sortilin in a subject having or at risk of a disease associated with a disease or disorder associated with changes in progranulin levels, comprising administering to a subject an antibody disclosed herein, and detecting the antibody bound to sortilin in the subject.

In another aspect, the invention provides an isolated monoclonal antibody that specifically binds to a peptide consisting of residues FTESFLT (SEQ ID NO:202). In another aspect, the invention provides an isolated monoclonal antibody that specifically binds to a peptide consisting of residues ESFL (SEQ ID NO:203). In another aspect, the invention provides an isolated monoclonal antibody that specifically binds to human sortilin at an epitope within a motif of the formula E(S/Q/D)FL (SEQ ID NO:206). In another aspect, the invention provides an isolated monoclonal antibody that specifically binds to a peptide consisting of residues DGCILGYKEQFL (SEQ ID NO:204). In another aspect, the invention provides an isolated monoclonal antibody that specifically binds to a peptide consisting of residues PSICLCSLEDFL (SEQ ID NO:205).

In another aspect, the invention provides an isolated monoclonal antibody that specifically binds to a peptide consisting of residues RTEFGMAIGP (SEQ ID NO:213), In another aspect, the invention provides an isolated monoclonal antibody that specifically binds to a peptide consisting of residues WGFTESFLTS (SEQ ID NO:214).

In another aspect, the invention provides an isolated monoclonal antibody that specifically binds an epitope defined by amino acid residues D74, R76, F97, K110, Y535, L560, and E557 of SEQ ID NO:215. In another aspect, the invention provides an An isolated monoclonal antibody that specifically binds an epitope defined by amino acid residues K110, Y535, E557, T561, Q563, D74, P510, S558, F559, and L560 of SEQ ID NO:215. In another aspect, the invention provides an An isolated monoclonal antibody that specifically binds an epitope defined by amino acid residues E557, S558, F559, L560, P510, and Y535 of SEQ ID NO:215.

The invention also provides methods of treating or effecting prophylaxis of a disease or disorder associated with changes in progranulin levels in a subject comprising administering an immunogen comprising a sortilin peptide of up to 20 contiguous amino acids of SEQ ID NO:1 to which antibody 5E20, 8H24, 11M14, 5M13, 2F18, 2P22, 6B15, 2C14, 9N18, or 4N2 specifically binds, wherein the peptide induces formation of antibodies specifically binding to sortilin in the subject.

BRIEF DESCRIPTION OF THE DRAWINGS

FIGS. 1A-1B depict an alignment of heavy chain variable regions of the mouse 5E20 antibody (5E20VH; SEQ ID NO:4) and humanized versions of the 5E20 antibody (hu5E20VHv1, hu5E20VHv2, hu5E20VHv3, hu5E20VHv4, hu5E20VHv5, hu5E20VHv6, and hu5E20VHv7) with human germline heavy chain variable region sequence IGHV3-21*01 (SEQ ID NO:162), with human acceptor heavy chain variable region sequence AEX29086-VH_huFrwk (AEX29086 VH; SEQ ID NO:161). hu5E20VHv1 (5E20VHv1) is SEQ ID NO:163, hu5E20VHv2 (5E20VHv2) is SEQ ID NO:164, hu5E20VHv3 (5E20VHv3) is SEQ ID NO:165, hu5E20VHv4 (5D20VHv4) is SEQ ID NO:166, hu5E20VHv5 (5E20VHv5) is SEQ ID NO:167, hu5E20VHv6 (5E20VHv6) is SEQ ID NO:168, and hu5E20VHv7 (5E20VHv7) is SEQ ID NO:169. The CDRs of mouse 5E20 VH, as defined by Kabat/Chothia Composite, are in boldface.

FIG. 2 depicts an alignment of light chain variable regions of the mouse 5E20 antibody (5E20VL, SEQ ID NO:10) and humanized versions of the 5E20 antibody (hu5E20VLv1, hu5E20VLv2, hu5E20VLv3, and hu5E20VLv4) with human germline light chain variable region sequence #IGKV1-12*01 (SEQ ID NO:172) and with human acceptor BAH04687-VL_huFrwk (BAH04687 VL; SEQ ID NO:171). hu5E20VLv1 (5D20VLv1) is SEQ ID NO:173, hu5E20VLv2 (5D20VLv2) is SEQ ID NO:174, hu5E20VLv3 (5E20VLv3) is SEQ ID NO:175, and hu5E20VLv4 (5E20VLv4) is SEQ ID NO:176. The CDRs of mouse 5E20 VL, as defined by Kabat/Chothia Composite, are in boldface.

FIG. 3 depicts an alignment of heavy chain variable regions of the mouse 8H24 antibody (8H24_VH, SEQ ID NO:28) and humanized versions of the 8H24 antibody (hu8H24VHv1 and hu8H24VHv2) with human germline heavy chain variable region sequence IGHV1-69*08_IGHJ1*01 (SEQ ID NO:179) and with human acceptor heavy chain variable region sequence AAC51714-VH_huFrwk (AAC51714VH Frwk, SEQ ID NO:178). hu8H24VHv1 (h8H24VLv1) is SEQ ID NO:180 and hu8H24VHv2 (h8H24VHv2) is SEQ ID NO:181. The CDRs of mouse 8H24 VH, as defined by Kabat/Chothia Composite, are in boldface.

FIG. 4 depicts an alignment of light chain variable regions of the mouse 8H24 (8H24 VL) SEQ ID NO:34) and humanized versions of the 8H24 antibody (hu8H24VLv1 and hu8H24VLv2) with human germline light chain variable region sequence IGKV2-40*01 (IGKV2-40*01_IGKJ4*01, SEQ ID NO:184) and with human acceptor ABC66914-VL_huFrwk (ABC66914VL Frwk SEQ ID NO: 183). hu8H24VLv1 (hH824VLv1) is SEQ ID NO:185 and hu8H24VLv2 (hH824VLv2) is SEQ ID NO:186. The CDRs of mouse 8H24 VL, as defined by Kabat/Chothia Composite, are in boldface.

FIG. 5 depicts an alignment of heavy chain variable regions of the mouse 11M14 antibody (11M14_VH; SEQ ID NO:52) and humanized versions of the 11M14 antibody (hu11M14VHv1b, hu11M14VHv2b, and hu11M14VHv3b) with human germline heavy chain variable region sequence IGHV3-48*03 (SEQ ID NO:189) and with human acceptor heavy chain variable region sequence ACS96198-VH_huFrwk (ASC96198 VH hFrwk, SEQ ID NO:188) hu11M14VHv1b (11M14VHv1b) is SEQ ID NO:190, hu11M14VHv2b (11M14VHv2b) is SEQ ID NO:191, and hu11M14VHv3b (11M14VHv3b) is SEQ ID NO:192. The CDRs of mouse 11M14 VH, as defined by Kabat/Chothia Composite, are in boldface.

FIG. 6 depicts an alignment of light chain variable regions of the mouse 11M14 antibody (11M14 VL, SEQ ID NO:58) and humanized versions of the 11M14 antibody (hu11M14VLv1b, hu11M14VLv2b, hu11M14VLv3b, and hu11M14VLv4b,) with human germline light chain variable region sequence IGKV1-39*01 (SEQ ID NO:195) and with human acceptor CBZ39892-VL_huFrwk (CBZ39892VL hFrwk, SEQ ID NO:194). hu11M14VLv1b (11M14VLv1b) is SEQ ID NO:196, hu 11M14VLv2b (11M14VLv2b) is SEQ ID NO:197, hu11M14VLv3b (11M14VLv3b) is SEQ ID NO:198, and hu11M14VLv4b (11M14VLv4b) is SEQ ID NO:199. The CDRs of mouse 11M14 VL, as defined by Kabat/Chothia Composite, are in boldface.

FIGS. 8A-8D provide data on the binding of selected purified monoclonal antibodies to sortilin and inhibition of progranulin binding to sortilin. FIGS. 8A-8C depict binding of selected purified monoclonal antibodies to sortilin (left graphs) and inhibition of progranulin binding to sortilin (in percentage PGRN blocking, right graphs) by ELISA. FIG. 8D is a table showing EC50 (nM) of Ab binding to human sortilin-ECD and percentage blocking at 7.4 nM mAb for selected purified antibodies.

FIGS. 9A-9D depict results of a competition assay by Biacore to determine whether selected monoclonal antibodies block the binding of neurotensin to sortilin. FIG. 9A is a table that summarizes the results of the assays for selected monoclonal antibodies. Examples of data are shown in the 3 graphs of FIGS. 9B-9D: no competition for 8H24 (FIG. 9B), weak competition with 1M16 (FIG. 9C), and competition with 4J22 (FIG. 9D).

FIGS. 10A-10C show the results of binding of selected purified monoclonal antibodies to human sortilin overexpressed by HEK 293 cells vs parental HEK cell line, and to U251MG cells (human glioblastoma cells line) which endogenously express sortilin. The left-hand plots in FIGS. 10A and 10B depict binding of monoclonal antibodies 6B15, 7B18, 10B6, and 10016 in the HEK 293 cells assay (left column of plots) and in the U251MG cells assay (right column of plots). FIG. 10C is a table summarizing the results of the assays for selected monoclonal antibodies.

FIGS. 12A-12B depict the dose response of inhibition of hu PGRN binding to cell surface human Sortilin-expressing HEK293 cells. FIG. 12A depicts binding curves for antibodies with different efficacy FIG. 12B is a table summarizing the results of the assay for selected monoclonal antibodies. (% maximum binding at 11 nM mAb)

FIGS. 13A-13B depict extracellular PGRN and cell surface sortilin levels after treatment of U251MG cells with selected purified monoclonal antibodies. FIG. 13A is a plot that depicts the assay results as a correlation graph for selected monoclonal antibodies. FIG. 13B is a table that summarizes the results of the assay for selected monoclonal antibodies.

BRIEF DESCRIPTION OF THE SEQUENCES

Figure 7:
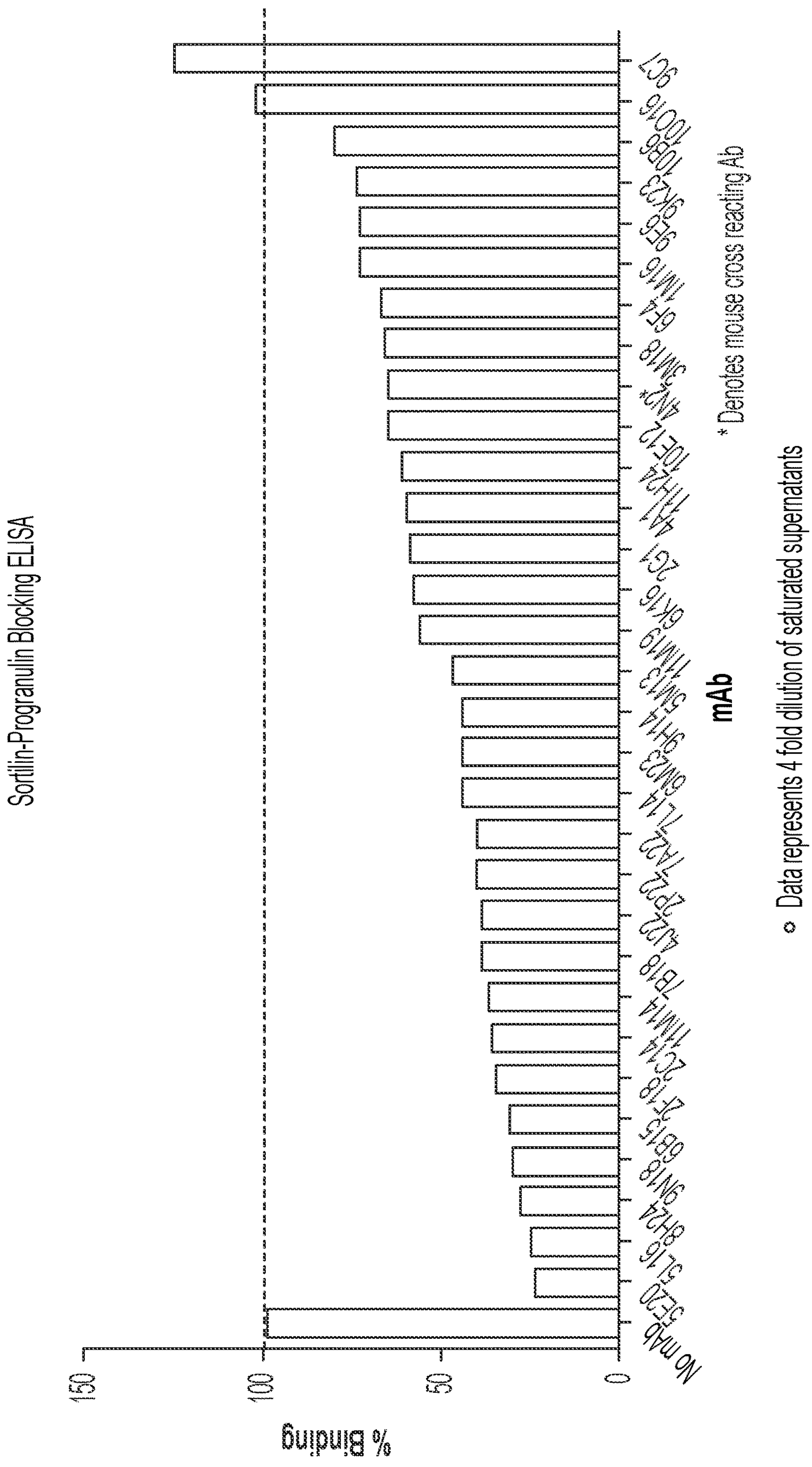
FIG. 7 depicts inhibition of binding of human progranulin (in percentage PGRN binding) to human sortilin by ELISA by non-clonal mouse antibody supernatants.

SEQ ID NO:1 sets forth the amino acid sequence of human sortilin extracellular domain.

SEQ ID NO:2 sets forth the nucleotide sequence of a murine 5E20VH (mIgG1):

SEQ ID NO:3 sets forth the amino acid sequence of signal peptide for murine 5E20VH.

SEQ ID NO: 4 sets forth the amino acid sequence of murine 5E20VH.

SEQ ID NO:5 sets forth the amino acid sequence of murine 5E20_Kabat Chothia Composite CDR-H1.

SEQ ID NO:6 sets forth the amino acid sequence of murine 5E20_Kabat Chothia Composite CDR-H2.

SEQ ID NO:7 sets forth the amino acid sequence of murine 5E20_Kabat Chothia Composite CDR-H3.

SEQ ID NO:8 sets forth the nucleotide sequence of a murine 5E20VL (kappa):

SEQ ID NO:9 sets forth the amino acid sequence of signal peptide for murine 5E20VL.

SEQ ID NO:10 sets forth the amino acid sequence of murine 5E20VL Vk.

SEQ ID NO:11 sets forth the amino acid sequence of murine 5E20_Kabat Chothia Composite CDR-L1.

SEQ ID NO:12 sets forth the amino acid sequence of murine 5E20_Kabat Chothia Composite CDR-L2.

SEQ ID NO:13 sets forth the amino acid sequence of murine 5E20_Kabat Chothia Composite CDR-L3.

SEQ ID NO:14 sets forth the amino acid sequence of Kabat CDR-H1 of mouse 5E20 antibody.

SEQ ID NO:15 sets forth the amino acid sequence of Chothia CDR-H1 of mouse 5E20 antibody.

SEQ ID NO:16 sets forth the amino acid sequence of Chothia CDR-H2 of mouse 5E20 antibody.

SEQ ID NO:17 sets forth the amino acid sequence of AbM CDR-H2 of mouse 5E20 antibody.

SEQ ID NO:18 sets forth the amino acid sequence of Contact CDR-H1 of mouse 5E20 antibody.

SEQ ID NO:19 sets forth the amino acid sequence of Contact CDR-H2 of mouse 5E20 antibody.

SEQ ID NO:20 sets forth the amino acid sequence of Contact CDR-H3 of mouse 5E20 antibody.

SEQ ID NO:21 sets forth the amino acid sequence of Contact CDR-L1 of mouse 5E20 antibody.

SEQ ID NO:22 sets forth the amino acid sequence of Contact CDR-L2 of mouse 5E20 antibody.

SEQ ID NO:23> Contact CDR-L3 of mouse 5E20 antibody.

SEQ ID NO:24 sets forth the amino acid sequence of a chimeric 5E20 heavy chain.

SEQ ID NO:25 sets forth the amino acid sequence of a chimeric 5E20 light chain.

SEQ ID NO: 26 sets forth the nucleotide sequence of a murine 8H24VH (IgG2c).

SEQ ID NO:27 sets forth the amino acid sequence of murine 8H24VH signal peptide.

SEQ ID NO:28 sets forth the amino acid sequence of murine 8H24Vh.

SEQ ID NO:29 sets forth the amino acid sequence of murine 8H24_Kabat Chothia Composite CDR-H1.

SEQ ID NO:30 sets forth the amino acid sequence of murine 8H24_Kabat Chothia Composite CDR-H2.

SEQ ID NO:31 sets forth the amino acid sequence of murine 8H24_Kabat Chothia Composite CDR-H3.

SEQ ID NO:32 sets forth the nucleotide sequence of a murine 8H24VL (kappa).

SEQ ID NO:33 sets forth the amino acid sequence of murine 8H24VL signal peptide.

SEQ ID NO:34 sets forth the amino acid sequence of murine 8H24Vk.

SEQ ID NO:35 sets forth the amino acid sequence of murine 8H24_Kabat Chothia Composite CDR-L1.

SEQ ID NO:36 sets forth the amino acid sequence of murine 8H24_Kabat Chothia Composite CDR-L2.

SEQ ID NO:37 sets forth the amino acid sequence of murine 8H24_Kabat Chothia Composite CDR-L3.

SEQ ID NO:38 sets forth the amino acid sequence of Kabat CDR-H1 of mouse 8H24 antibody.

SEQ ID NO:39 sets forth the amino acid sequence of Chothia CDR-H1 of mouse 8H24 antibody.

SEQ ID NO:40 sets forth the amino acid sequence of Chothia CDR-H2 of mouse 8H24 antibody.

SEQ ID NO:41 sets forth the amino acid sequence of AbM CDR-H2 of mouse 8H24 antibody.

SEQ ID NO:42 sets forth the amino acid sequence of Contact CDR-H1 of mouse 8H24 antibody.

SEQ ID NO:43 sets forth the amino acid sequence of Contact CDR-H2 of mouse 8H24 antibody.

SEQ ID NO:44 sets forth the amino acid sequence of Contact CDR-H3 of mouse 8H24 antibody.

SEQ ID NO:45 sets forth the amino acid sequence of Contact CDR-L1 of mouse 8H24 antibody.

SEQ ID NO:46 sets forth the amino acid sequence of Contact CDR-L2 of mouse 8H24 antibody.

SEQ ID NO:47 sets forth the amino acid sequence of Contact CDR-L3 of mouse 8H24 antibody.

SEQ ID NO:48 sets forth the amino acid sequence of a chimeric 8H24 heavy chain.

SEQ ID NO:49 sets forth the amino acid sequence of a chimeric 8H24 light chain.

SEQ ID NO:50 sets forth the nucleotide sequence of a murine 11M14VH (IgG1).

SEQ ID NO:51 sets forth the amino acid sequence of murine 11M14VH signal peptide.

SEQ ID NO:52 sets forth the amino acid sequence of murine 11M14Vh.

SEQ ID NO:53 sets forth the amino acid sequence of murine 11M14_Kabat Chothia Composite CDR-H1.

SEQ ID NO:54 sets forth the amino acid sequence of murine 11M14_Kabat Chothia Composite CDR-H2.

SEQ ID NO:55 sets forth the amino acid sequence of murine 11M14_Kabat Chothia Composite CDR-H3.

SEQ ID NO:56 sets forth the nucleotide sequence of a murine 11M14Vk (kappa).

SEQ ID NO:57 sets forth the amino acid sequence of murine 11M14Vk signal peptide.

SEQ ID NO:58 sets forth the amino acid sequence of murine 11M14Vk.

SEQ ID NO:59 sets forth the amino acid sequence of murine 11M14_Kabat Chothia Composite CDR-L1.

SEQ ID NO:60 sets forth the amino acid sequence of murine 11M14_Kabat Chothia Composite CDR-L2.

SEQ ID NO:61 sets forth the amino acid sequence of murine 11M14_Kabat Chothia Composite CDR-L3.

SEQ ID NO:62 sets forth the amino acid sequence of Kabat CDR-H1 of mouse 11M14 antibody.

SEQ ID NO:63 sets forth the amino acid sequence of Chothia CDR-H1 of mouse 11M14 antibody.

SEQ ID NO:64 sets forth the amino acid sequence of Chothia CDR-H2 of mouse 11M14 antibody.

SEQ ID NO:65 sets forth the amino acid sequence of AbM CDR-H2 of mouse 11M14 antibody.

SEQ ID NO:66 sets forth the amino acid sequence of Contact CDR-H1 of mouse 11M14 antibody.

SEQ ID NO:67 sets forth the amino acid sequence of Contact CDR-H2 of mouse 11M14 antibody.

SEQ ID NO:68 sets forth the amino acid sequence of Contact CDR-H3 of mouse 11M14 antibody.

SEQ ID NO:69 sets forth the amino acid sequence of Contact CDR-L1 of mouse 11M14 antibody.

SEQ ID NO:70 sets forth the amino acid sequence of Contact CDR-L2 of mouse 11M14 antibody.

SEQ ID NO:71 sets forth the amino acid sequence of Contact CDR-L3 of mouse 11M14 antibody.

SEQ ID NO:72 sets forth the amino acid sequence of Alternate Kabat-Chothia CDR-L2 (present in Hu11M14VLv3b, SEQ ID NO:198).

SEQ ID NO:73 sets forth the amino acid sequence of Alternate Kabat-Chothia CDR-L2 (present in Hu11M14VLv4b, SEQ ID NO:199).

SEQ ID NO:74 sets forth the amino acid sequence of Alternate Contact CDR-L2 (present in Hu11M14VLv3b, SEQ ID NO:198).

SEQ ID NO:75 sets forth the amino acid sequence of Alternate Contact CDR-L2 (present in Hu11M14VLv4b, SEQ ID NO:199).

SEQ ID NO:76 sets forth the nucleotide sequence of a murine 5M13VH (IgG1).

SEQ ID NO:77 sets forth the amino acid sequence of murine 5M13VH signal peptide.

SEQ ID NO:78> murine 5M13VH amino acid sequence.

SEQ ID NO:79 sets forth the amino acid sequence of murine 5M13_Kabat Chothia Composite CDR-H1.

SEQ ID NO:80 sets forth the amino acid sequence of murine 5M13_Kabat Chothia Composite CDR-H2.

SEQ ID NO:81 sets forth the amino acid sequence of murine 5M13_Kabat Chothia Composite CDR-H3.

SEQ ID NO: 82 sets forth the nucleotide sequence of a murine 5M13VL (kappa).

SEQ ID NO:83 sets forth the amino acid sequence of murine 5M13VL signal peptide.

SEQ ID NO:84 sets forth the amino acid sequence of murine 5M13VL Vk.

SEQ ID NO:85 sets forth the amino acid sequence of murine 5M13_Kabat Chothia Composite CDR-L1.

SEQ ID NO:86 sets forth the amino acid sequence of murine 5M13_Kabat Chothia Composite CDR-L2.

SEQ ID NO:87 sets forth the amino acid sequence of murine 5M13_Kabat Chothia Composite CDR-L3.

SEQ ID NO:88 sets forth the nucleotide sequence of a murine 2F18VH (mIgG1).

SEQ ID NO:89 sets forth the amino acid sequence of murine 2F18VH signal peptide.

SEQ ID NO:90 sets forth the amino acid sequence of murine 2F18VH.

SEQ ID NO:91 sets forth the amino acid sequence of murine 2F18_Kabat Chothia Composite CDR-H1.

SEQ ID NO:92 sets forth the amino acid sequence of murine 2F18_Kabat Chothia Composite CDR-H2.

SEQ ID NO:93 sets forth the amino acid sequence of murine 2F18_Kabat Chothia Composite CDR-H3.

SEQ ID NO:94 sets forth the nucleotide sequence of a murine 2F18VL (kappa).

SEQ ID NO: 95 sets forth the amino acid sequence of murine 2F18VL signal peptide.

SEQ ID NO:96 sets forth the amino acid sequence of murine Vk_2F18VL.

SEQ ID NO:97 sets forth the amino acid sequence of murine 2F18_Kabat Chothia Composite CDR-L1.

SEQ ID NO:98 sets forth the amino acid sequence of murine 2F18_Kabat Chothia Composite CDR-L2.

SEQ ID NO:99 sets forth the amino acid sequence of murine 2F18_Kabat Chothia Composite CDR-L3.

SEQ ID NO:100 sets forth the nucleotide sequence of a murine 2P22VH (IgG2b).

SEQ ID NO:101 sets forth the amino acid sequence of murine 2P22VH signal peptide.

SEQ ID NO:102 sets forth the amino acid sequence of murine 2P22VH.

SEQ ID NO:103 sets forth the amino acid sequence of murine 2P22_Kabat Chothia Composite CDR-H1.

SEQ ID NO:104 sets forth the amino acid sequence of murine 2P22_Kabat Chothia Composite CDR-H2.

SEQ ID NO:105 sets forth the amino acid sequence of murine 2P22_Kabat Chothia Composite CDR-H3.

SEQ ID NO:106 sets forth the nucleotide sequence of a murine 2P22VL (kappa).

SEQ ID NO:107 sets forth the amino acid sequence of mouse 2P22VL signal peptide.

SEQ ID NO:108 sets forth the amino acid sequence of murine Vk_2P22VL.

SEQ ID NO:109 sets forth the amino acid sequence of murine 2P22_Kabat Chothia Composite CDR-L1.

SEQ ID NO:110 sets forth the amino acid sequence of murine 2P22_Kabat Chothia Composite CDR-L2.

SEQ ID NO:111 sets forth the amino acid sequence of murine 2P22_Kabat Chothia Composite CDR-L3.

SEQ ID NO:112 sets forth the nucleotide sequence of a murine 6B15VH (IgG1).

SEQ ID NO:113 sets forth the amino acid sequence of 6B15VH signal peptide.

SEQ ID NO:114 sets forth the amino acid sequence of murine 6B15VH.

SEQ ID NO:115 sets forth the amino acid sequence of murine 6B15_Kabat Chothia Composite CDR-H1.

SEQ ID NO:116 sets forth the amino acid sequence of murine 6B15_Kabat Chothia Composite CDR-H2.

SEQ ID NO:117 sets forth the amino acid sequence of murine 6B15_Kabat Chothia Composite CDR-H3.

SEQ ID NO:118 sets forth the nucleotide sequence of a murine 6B15VL (kappa).

SEQ ID NO:119 sets forth the amino acid sequence of 6B15VL signal peptide.

SEQ ID NO:120 sets forth the amino acid sequence of murine 6B15VL Vk_6B15.

SEQ ID NO:121 sets forth the amino acid sequence of murine 6B15_Kabat Chothia Composite CDR-L1.

SEQ ID NO:122 sets forth the amino acid sequence of murine 6B15_Kabat Chothia Composite CDR-L2.

SEQ ID NO:123 sets forth the amino acid sequence of murine 6B15_Kabat Chothia Composite CDR-L3.

SEQ ID NO:124 sets forth the nucleotide sequence of a murine 2C14VH (IgG1).

SEQ ID NO:125 sets forth the amino acid sequence of mouse 2C14VH signal peptide.

SEQ ID NO:126 sets forth the amino acid sequence of murine 2C14VH.

SEQ ID NO:127 sets forth the amino acid sequence of murine 2C14 Kabat Chothia Composite CDR-H1.

SEQ ID NO:128 sets forth the amino acid sequence of murine 2C14 Kabat Chothia Composite CDR-H2.

SEQ ID NO:129 sets forth the amino acid sequence of murine 2C14 Kabat Chothia Composite CDR-H3.

SEQ ID NO:130 sets forth the nucleotide sequence of a murine 2C14VL (kappa).

SEQ ID NO:131 sets forth the amino acid sequence of mouse 2C14VL signal peptide.

SEQ ID NO:132 sets forth the amino acid sequence of murine 2C14VL Vk_2C14.

SEQ ID NO:133 sets forth the amino acid sequence of murine 2C14_Kabat Chothia Composite CDR-L1.

SEQ ID NO:134 sets forth the amino acid sequence of murine 2C14_Kabat Chothia Composite CDR-L2.

SEQ ID NO:135 sets forth the amino acid sequence of murine 2C14_Kabat Chothia Composite CDR-L3.

SEQ ID NO:136 sets forth the nucleotide sequence of a murine 9N18VH (IgG2b).

SEQ ID NO:137 sets forth the amino acid sequence of mouse 9N18VH signal peptide.

SEQ ID NO:138 sets forth the amino acid sequence of murine 9N18VH.

SEQ ID NO:139 sets forth the amino acid sequence of murine 9N18_Kabat Chothia Composite CDR-H1.

SEQ ID NO:140 sets forth the amino acid sequence of murine 9N18_Kabat Chothia Composite CDR-H2.

SEQ ID NO:141 sets forth the amino acid sequence of murine 9N18_Kabat Chothia Composite CDR-H3.

SEQ ID NO:142 sets forth the nucleotide sequence of a murine 9N18VL (kappa).

SEQ ID NO:143 sets forth the amino acid sequence of mouse 9N18VL signal peptide.

SEQ ID NO:144 sets forth the amino acid sequence of murine 9N18VL Vk_9N18.

SEQ ID NO:145 sets forth the amino acid sequence of murine 9N18_Kabat Chothia Composite CDR-L1.

SEQ ID NO:146 sets forth the amino acid sequence of murine 9N18_Kabat Chothia Composite CDR-L2.

SEQ ID NO:147 sets forth the amino acid sequence of murine 9N18_Kabat Chothia Composite CDR-L3.

SEQ ID NO:148 sets forth the nucleotide sequence of a murine 4N2VH (IgG3).

SEQ ID NO:149 sets forth the amino acid sequence of murine 4N2VH signal peptide.

SEQ ID NO:150 sets forth the amino acid sequence of murine 4N2VH Vh_4N2.

SEQ ID NO:151 sets forth the amino acid sequence of murine 4N2_Kabat Chothia Composite CDR-H1.

SEQ ID NO:152 sets forth the amino acid sequence of murine 4N2_Kabat Chothia Composite CDR-H2.

SEQ ID NO:153 sets forth the amino acid sequence of murine 4N2_Kabat Chothia Composite CDR-H3.

SEQ ID NO:154 sets forth the nucleotide sequence of a murine 4N2VL (kappa).

SEQ ID NO:155 sets forth the amino acid sequence of murine 4N2VL signal peptide.

SEQ ID NO:156 sets forth the amino acid sequence of murine 4N2VL Vk_4N2.

SEQ ID NO:157 sets forth the amino acid sequence of murine 4N2_Kabat Chothia Composite CDR-L1.

SEQ ID NO:158 sets forth the amino acid sequence of murine 4N2_Kabat Chothia Composite CDR-L2.

SEQ ID NO:159 sets forth the amino acid sequence of murine 4N2_Kabat Chothia Composite CDR-L3.

SEQ ID NO:160 sets forth the amino acid sequence of 3V6F-VH_mSt.

SEQ ID NO:161 sets forth the amino acid sequence of AEX29086-VH_huFrwk.

SEQ ID NO:162 sets forth the amino acid sequence of IGHV3-21*01.

SEQ ID NO:163 sets forth the amino acid sequence of h5E20VHv1.

SEQ ID NO:164 sets forth the amino acid sequence of h5E20VHv2.

SEQ ID NO:165 sets forth the amino acid sequence of h5E20VHv3.

SEQ ID NO:166 sets forth the amino acid sequence of h5E20VHv4.

SEQ ID NO:167 sets forth the amino acid sequence of h5E20VHv5.

SEQ ID NO:168 sets forth the amino acid sequence of h5E20VHv6.

SEQ ID NO:169 sets forth the amino acid sequence of h5E20VHv7.

SEQ ID NO:170 sets forth the amino acid sequence of 3V6F-VL_mSt.

SEQ ID NO:171 sets forth the amino acid sequence of BAH04687-VL_huFrwk.

SEQ ID NO:172 sets forth the amino acid sequence of IGKV1-12*01.

SEQ ID NO:173 sets forth the amino acid sequence of h5E20VLv1.

SEQ ID NO:174 sets forth the amino acid sequence of h5E20VL v2.

SEQ ID NO:175 sets forth the amino acid sequence of h5E20VLv3.

SEQ ID NO:176 sets forth the amino acid sequence of h5E20VLv4.

SEQ ID NO:177 sets forth the amino acid sequence of 1MRC-VH_mSt.

SEQ ID NO:178 sets forth the amino acid sequence of AAC51714-VH_huFrwk.

SEQ ID NO:179 sets forth the amino acid sequence of IGHV1-69*08_IGHJ1*01.

SEQ ID NO:180 sets forth the amino acid sequence of h8H24VHv1.

SEQ ID NO:181 sets forth the amino acid sequence of h8H24VHv2.

SEQ ID NO:182 sets forth the amino acid sequence of 1M RC-VL_mSt.

SEQ ID NO:183 sets forth the amino acid sequence of ABC66914-VL_huFrwk.

SEQ ID NO:184 sets forth the amino acid sequence of IGKV2-40*01.

SEQ ID NO:185 sets forth the amino acid sequence of h8H24VLv1.

SEQ ID NO:186 sets forth the amino acid sequence of h8H24VLv2.

SEQ ID NO:187 sets forth the amino acid sequence of 1MQK-VH_mSt.

SEQ ID NO:188 sets forth the amino acid sequence of ACS96198-VH_huFrwk.

SEQ ID NO:189 sets forth the amino acid sequence of IGHV3-48*03.

SEQ ID NO:190 sets forth the amino acid sequence of h11M14VHv1b.

SEQ ID NO:191 sets forth the amino acid sequence of h11M14VHv2b.

SEQ ID NO:192 sets forth the amino acid sequence of h11M14VHv3b.

SEQ ID NO:193 sets forth the amino acid sequence of 1MQK-VL_mSt.

SEQ ID NO:194 sets forth the amino acid sequence of CBZ39892-VL_huFrwk.

SEQ ID NO:195 sets forth the amino acid sequence of IGKV1-39*01.

SEQ ID NO:196 sets forth the amino acid sequence of h11M14VLv1b.

SEQ ID NO:197 sets forth the amino acid sequence of h11M14VLv2b.

SEQ ID NO:198 sets forth the amino acid sequence of h11M14VLv3b.

SEQ ID NO:199 sets forth the amino acid sequence of h11M14VLv4b.

SEQ ID NO:200 sets forth the amino acid sequence of HA peptide.

SEQ ID NO:201 sets forth the amino acid sequence of c-Myc peptide.

SEQ ID NO:202 sets forth the amino acid sequence of consensus motif of a peptide bound by antibody 5E20.

SEQ ID NO:203: sets forth the amino acid sequence of consensus motif of a peptide bound by antibody 5E20.

SEQ ID NO:204 sets forth the amino acid sequence of peptide bound by antibody 5E20.

SEQ ID NO:205 sets forth the amino acid sequence of peptide bound by antibody 5E20.

SEQ ID NO:206 sets forth the amino acid sequence of sequence motif bound by antibody 5E20.

SEQ ID NO:207 sets forth the amino acid sequence of a linker.

SEQ ID NO:208 sets forth the amino acid sequence of chimeric 11M14 heavy chain.

SEQ ID NO:209 sets forth the amino acid sequence of chimeric 11M14 light chain.

SEQ ID NO:210 sets forth the amino acid sequence of residues 523-610 of sortilin.

SEQ ID NO:211 sets forth the amino acid sequence of a sortilin peptide.

SEQ ID NO:212 sets forth the amino acid sequence of a sortilin peptide.

SEQ ID NO:213 sets forth the amino acid sequence of a peptide bound by antibody 8H24.

SEQ ID NO:214 sets forth the amino acid sequence of a peptide bound by antibody 11M14.

SEQ ID NO:215; sets forth the amino acid sequence of human sortilin extracellular domain minus signal peptide.

SEQ ID NO:216 sets forth the amino acid sequence of hSORT1_ECD_Emut1.

SEQ ID NO:217 sets forth the amino acid sequence of hSORT1_ECD_Emut2a.

SEQ ID NO:218 sets forth the amino acid sequence of hSORT1_ECD_Emut2b.

SEQ ID NO:219 sets forth the amino acid sequence of hSORT1_ECD_Emut3.

SEQ ID NO:220 sets forth the amino acid sequence of hSORT1_ECD_Emut4.

SEQ ID NO:221 sets forth the amino acid sequence of hSORT1_ECD_Emut5.

SEQ ID NO:222 sets forth the amino acid sequence of hSORT1_ECD_Emut6N.

SEQ ID NO:223 sets forth the amino acid sequence of hSORT1_ECD_Emut8N.

SEQ ID NO:224 sets forth the amino acid sequence of hSORT1_ECD_Emut11N.

SEQ ID NO:225 sets forth the amino acid sequence of hSORT1_ECD_Emut14N.

SEQ ID NO:226 sets forth the amino acid sequence of hSORT1_ECD_Emut16.

SEQ ID NO:227 sets forth the amino acid sequence of hSORT1_ECD_Emut17.

SEQ ID NO:228 sets forth the amino acid sequence of hSORT1_ECD_Emut18.

SEQ ID NO:229 sets forth the amino acid sequence of hSORT1_ECD_Emut19.

SEQ ID NO:230 sets forth the amino acid sequence of hSORT1_ECD_Emut20.

SEQ ID NO:231 sets forth the amino acid sequence of hSORT1_ECD_Emut21.

SEQ ID NO:232 sets forth the amino acid sequence of hSORT1_ECD_Emut22.

SEQ ID NO:233 sets forth the amino acid sequence of hSORT1_ECD_Emut23.

SEQ ID NO:234 sets forth the amino acid sequence of hSORT1_ECD_Emut24.

SEQ ID NO: 235 sets forth the amino acid sequence of hSORT1_ECD_Emut25.

SEQ ID NO: 236 sets forth the amino acid sequence of hSORT1_ECD_Emut26.

SEQ ID NO:237 sets forth the amino acid sequence of hSORT1_ECD_Emut27.

SEQ ID NO:238 sets forth the amino acid sequence of hSORT1_ECD_Emut28.

SEQ ID NO:239 sets forth the amino acid sequence of hSORT1_ECD_Emut29.

SEQ ID NO:240 sets forth the amino acid sequence of hSORT1_ECD_Emut30.

SEQ ID NO:241 sets forth the amino acid sequence of hSORT1_ECD_Emut31.

SEQ ID NO:242 sets forth the amino acid sequence of hSORT1_ECD_Emut32.

SEQ ID NO: 243 sets forth the amino acid sequence of hSORT1_ECD_Emut33.

SEQ ID NO:244 sets forth the amino acid sequence of hu11M14_H1b_IgG1 LALA_YTE—heavy chain.

SEQ ID NO:245 sets forth the amino acid sequence of hu11M14_L3b-light chain.

SEQ ID NO:246 sets forth the amino acid sequence of hu8H24_H1_IgG1 LALA_YTE—heavy chain.

SEQ ID NO:247 sets forth the amino acid sequence of hu8H24_L2_light chain.

SEQ ID NO:248 sets forth the amino acid sequence of hu5E20_H7_IgG1 LALA_YTE—heavy chain.

SEQ ID NO:249 sets forth the amino acid sequence of hu5E20_L4_light chain.

SEQ ID NO:250 sets forth the amino acid sequence of hu11M14_H1b_IgG1 LALA_—heavy chain.

SEQ ID NO:251 sets forth the amino acid sequence of hu8H24_H1_IgG1 LALA—heavy chain.

SEQ ID NO:252 sets forth the amino acid sequence of hu5E20_H7_IgG1 LALA_heavy chain.

Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity and/or avidity of at least $10^6$, $10^7$, $10^8$, $10^9$, $10^{10}$, $10^{11}$, or $10^{12}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Paul, W., ed., 2nd ed. Raven Press, N.Y., 1989, Ch. 7 (incorporated by reference in its entirety for all purposes).

When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
| L2 | L50--L56 | L50--L56 | L50--L56 | L50--L56 | L46--L55 |
| L3 | L89--L97 | L89--L97 | L89--L97 | L89--L97 | L89--L96 |
| H1 | H31--H35B | H26--H32 . . . H34* | H26--H35B* | H26--H35B | H30--H35B |
| H2 | H50--H65 | H52--H56 | H50--H65 | H50--H58 | H47--H58 |
| H3 | H95--H102 | H95--H102 | H95--H102 | H95--H102 | H93--H101 |

*CDR-H1 by Chothia can end at H32, H33, or H34 (depending on the length of the loop).
This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3. When the application discloses a VL sequence with R as the C-terminal residue, the R can alternatively be considered as being the N-terminal residue of the light chain constant region. Thus, the application should also be understood as disclosing the VL sequence without the C-terminal R.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, MD, 1987 and 1991), the Chothia definition (Chothia & Lesk, *J. Mol. Biol.* 196:901-917, 1987; Chothia et al., Nature 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number.

The term "antibody" includes intact antibodies and binding fragments thereof. Typically, fragments compete with the intact antibody from which they were derived for specific binding to the target including separate heavy chains, light chains Fab, Fab', $F(ab')_2$, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.,* 79:315-321 (1990); Kostelny et al., *J. Immunol.,* 148:1547-53 (1992)). In some bispecific antibodies, the two different heavy/light chain pairs include a humanized 5E20, 8H24, 11M14, 5M13, 2F18, 2P22, 6B15, 2C14, 9N18, or 4N2 heavy chain/light chain pair and a heavy chain/light chain pair specific for a different epitope on sortilin than that bound by 5E20, 8H24, 11M14, 5M13, 2F18, 2P22, 6B15, 2C14, 9N18, or 4N2.

In some bispecific antibodies, one heavy chain/light chain pair is a humanized 5E20 antibody, humanized 8H24 antibody, humanized 11M14 antibody, humanized 5M13 antibody, humanized 2F18 antibody, humanized 2P22 antibody, humanized 6B15 antibody, humanized 2C14 antibody, humanized 9N18 antibody, or humanized 4N2 antibody as further disclosed below and the other heavy chain/light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., *Proc. Natl. Acad. Sci. USA* 88:4771-4775, 1991; Friden et al., *Science* 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal et al., *Sci. Trans. Med.* 3, 84ra43, 2011; Yu et al., *Sci. Trans. Med.* 3, 84ra44, 2011).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include progranulin-related disease-affected tissue, or at least not known or suspect to include diseased tissues of a given type. Control samples can be obtained from individuals not afflicted with the progranulin-related disease. Alternatively, control samples can be obtained from patients afflicted with the progranulin-related disease. Such samples can be obtained at the same time as a biological sample thought to comprise the progranulin-related disease or on a different occasion. A biological sample and a control sample can both be obtained from the same tissue. Preferably, control samples consist essentially or entirely of normal, healthy tissues and can be used in comparison to a biological sample thought to comprise progranulin-related disease-affected regions. Preferably, the tissue in the control sample is the same type as the tissue in the biological sample. Preferably, the progranulin-related disease-affected cells thought to be in the biological sample arise from the same cell type (e.g., neurons or glia) as the type of cells in the control sample.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

The term "positive response to treatment" refers to a more favorable response in an individual patient or average response in a population of patients relative to an average response in a control population not receiving treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses insubstantial variations, such as values within a standard margin of error of measurement (e.g., SEM) of a stated value.

Statistical significance means $p \leq 0.05$.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that bind to sortilin.

Exemplary antibodies of the invention are 5E20, 8H24, 11M14, 5M13, 2F18, 2P22, 6B15, 2C14, 9N18, and 4N2. Some antibodies of the invention serve to treat, inhibit progression, or delay diseases or disorders associated with changes in progranulin levels. Although an understanding of mechanism is not required for practice of the invention, an increase in extracellular progranulin levels may occur as a result of the antibody binding sortilin, among other mechanisms. The antibodies of the invention or agents that induce such antibodies can be used in methods of treating or effecting prophylaxis of frontotemporal dementia and other diseases and disorders associated with changes in progranulin levels, including Alzheimer's disease, Parkinson's disease, arnyotrophic lateral sclerosis, Batten Disease (a type of neuronal ceroid lipofuscinosis (NCL), neurodegenerative disorders, and neurodegenerative disorders associated with aging. Neurodegenerative disorders associated with aging tend to progress in an irreversible manner and are are typically associated with one or more biological hallmarks of aging: genomic instability, telomere attrition, epigenetic alterations, loss of proteostasis, mitochondrial dysfunction, cellular senescence, deregulated nutrient sensing, stem cell exhaustion and altered intercellular communication (See for example Hou, Y. et al., 2019, Nature Reviews Neurology 15, pages 565-581).

II. Target Molecules

Unless otherwise apparent from the context, reference to sortilin means a natural human form of sortilin including all isoforms, including soluble forms, irrespective of whether posttranslational modification (e.g., phosphorylation, glycation, or acetylation) is present. The amino acid sequence of the extracellular domain of sortilin is indicated below. The 33 amino acid signal peptide is indicated by boldface.

```
MERPWGAADGLSRWPHGLGLLLLLQLLPPSTLSQDRLDAPPPPAAPLPR
WSGPIGVSWGLRAAAAGGAFPRGGRWRRSAPGEDEECGRVRDFVAKLAN
NTHQHVFDDLRGSVSLSWVGDSTGVILVLTTFHVPLVIMTFGQSKLYRS
EDYGKNFKDITDLINNTFIRTEFGMAIGPENSGKVVLTAEVSGGSRGGR
IFRSSDFAKNFVQTDLPFHPLTQMMYSPQNSDYLLALSTENGLWVSKNF
GGKWEEIHKAVCLAKWGSDNTIFFTTYANGSCKADLGALELWRTSDLGK
SFKTIGVKIYSFGLGGRFLFASVMADKDTTRRIHVSTDQGDTWSMAQLP
SVGQEQFYSILAANDDMVFMHVDEPGDTGFGTIFTSDDRGIVYSKSLDR
HLYTTTGGETDFTNVTSLRGVYITSVLSEDNSIQTMITFDQGGRWTHLR
KPENSECDATAKNKNECSLHIHASYSISQKLNVPMAPLSEPNAVGIVIA
HGSVGDAISVMVPDVYISDDGGYSWTKMLEGPHYYTILDSGGIIVAIEH
SSRPINVIKFSTDEGQCWQTYTFTRDPIYFTGLASEPGARSMNISIWGF
TESFLTSQWVSYTIDFKDILERNCEEKDYTIWLAHSTDPEDYEDGCILG
YKEQFLRLRKSSVCQNGRDYVVTKQPSICLCSLEDFLCDFGYYRPENDS
KCVEQPELKGHDLEFCLYGREEHLTTNGYRKIPGDKCQGGVNPVREVKD
LKKKCTSNFLSPEKQNSKSNS (SEQ ID NO: 1; UniProtKB/
Swiss-Prot: Q99523)
```

The amino acid sequence of the extracellular domain of sortilin without the 33-amino acid signal peptide is indicated below.

```
                                   (SEQ ID NO: 215)
QDRLDAPPPPAAPLPRWSGPIGVSWGLRAAAAGGAFPRGGRWRRSAPGE
DEECGRVRDFVAKLANNTHQHVFDDLRGSVSLSWVGDSTGVILVLTTFH
VPLVIMTFGQSKLYRSEDYGKNFKDITDLINNTFIRTEFGMAIGPENSG
KVVLTAEVSGGSRGGRIFRSSDFAKNFVQTDLPFHPLTQMMYSPQNSDY
LLALSTENGLWVSKNFGGKWEEIHKAVCLAKWGSDNTIFFTTYANGSCK
ADLGALELWRTSDLGKSFKTIGVKIYSFGLGGRFLFASVMADKDTTRRI
HVSTDQGDTWSMAQLPSVGQEQFYSILAANDDMVFMHVDEPGDTGFGTI
FTSDDRGIVYSKSLDRHLYTTTGGETDFTNVTSLRGVYITSVLSEDNSI
QTMITFDQGGRWTHLRKPENSECDATAKNKNECSLHIHASYSISQKLNV
PMAPLSEPNAVGIVIAHGSVGDAISVMVPDVYISDDGGYSWTKMLEGPH
YYTILDSGGIIVAIEHSSRPINVIKFSTDEGQCWQTYTFTRDPIYFTGL
```

-continued

```
ASEPGARSMNISIWGFTESFLTSQWVSYTIDFKDILERNCEEKDYTIWL

AHSTDPEDYEDGCILGYKEQFLRLRKSSVCQNGRDYVVTKQPSICLCSL

EDFLCDFGYYRPENDSKCVEQPELKGHDLEFCLYGREEHLTTNGYRKIP

GDKCQGGVNPVREVKDLKKKCTSNFLSPEKQNSKSNS
```

Reference to sortilin includes known natural variations which are listed in the Swiss-Prot database and permutations thereof, as well as mutations associated with pathologies.

Additionally, reference to sortilin includes sortilin with known post-translational modifications. Examples of known post-translational modifications are listed in the UniProtKB/Swiss-Prot database.

Unless otherwise apparent from context, reference to sortilin, or its fragments includes the natural human amino acid sequences including isoforms, mutants, and allelic variants thereof.

III. Antibodies

A. Binding Specificity and Functional Properties

The invention provides antibodies that specifically bind to sortilin. The examples describe isolation of eight mouse monoclonal antibodies against human sortilin. The epitope specificities of three of these antibodies have been mapped.

From a primary screening the epitope specificity of antibody 5E20 was mapped to being within approximately residues 555-561 of human sortilin ECD of SEQ ID NO:215 (FTESFLT, SEQ ID NO:202). On further screening the epitope was mapped to residues E557, S558, F559, L560 P510, and Y535 of the sortilin ECD of SEQ ID NO:215.

From a primary screening the epitope specificity of antibody 8H24 was mapped to being within approximately residues 134-143 of human sortilin ECD of SEQ ID NO:215 (RTEFGMAIGP, SEQ ID NO:213). On further screening the epitope was mapped to residues D74, R76, F97, K110, Y535, L560, and E557 of the sortilin ECD of SEQ ID NO:215.

From a primary screening the epitope specificity of antibody 11M14 was mapped to being within approximately residues 553-562 of human sortilin ECD of SEQ ID NO:215. On further screening the epitope was mapped to residues K110, Y535, E557, T561, Q563, D74, P510, S558, F559, and L560 of the sortilin ECD of SEQ ID NO:215.

Some antibodies specifically bind to an epitope within E(S/Q/D)FL (SEQ ID NO:206). Some antibodies of the invention specifically bind to a peptide comprising or consisting of residues 588-594 of sortilin ECD of SEQ ID NO:1 (corresponding to residues 555-561 of sortilin ECD of SEQ ID NO:215), namely residues FTESFLT (SEQ ID NO:202). Some antibodies of the invention specifically bind to a peptide comprising or consisting of residues 590-593 of sortilin ECD of SEQ ID NO:1 (corresponding to residues 557-560 of sortilin ECD of SEQ ID NO:215), namely ESFL (SEQ ID NO:203). Some antibodies of the invention specifically bind to a peptide comprising or consisting of residues 632-643 of sortilin ECD of SEQ ID NO:1 (corresponding to residues 599-610 of SEQ ID NO:215), namely DGCILGYKEQFL) (SEQ ID NO:204). Some antibodies of the invention specifically bind to a peptide comprising or consisting of residues 663-674 of sortilin ECD of SEQ ID NO:1 (corresponding to residues 630-641 of sortilin ECD of SEQ ID NO:15), namely PSICLCSLEDFL (SEQ ID NO:205). Some antibodies of the invention specifically bind to a peptide comprising or consisting of the consensus motif E(S/Q/D)FL (SEQ ID NO:206).).

Some antibodies bind within the amino acid sequence HYYTILDSGGIIVAIEHSSRPINVIKFSTDE-GQCWQTYTFTRDPIYFTGLASEPGARSMNISI WGFT-ESFLTSQWVSYTIDFKDILER (SEQ ID NO:210) (corresponding to residues 523-610 of sortilin ECD of SEQ ID NO:1). Some antibodies specifically bind to a peptide within the preceeding sequence. Peptides within this sequence include amino acid sequences that comprise or consist of TGL, FTESFLTSQW (SEQ ID NO:211), or LTSQW (SEQ ID NO:212).

Some antibodies specifically bind to a peptide comprising or consisting of amino acid sequence RTEFGMAIGP) (SEQ ID NO:213, corresponding to residues 167-176 of the sortilin ECD of SEQ ID NO:1, corresponding to residues 134-143 of sortilin ECD of SEQ ID NO:215). Some antibodies specifically bind to a peptide comprising or consisting of amino acid sequence WGFTESFLTS (SEQ ID NO:214, corresponding to residues 586-595 of the sortilin ECD of SEQ ID NO:1, corresponding to residues 553-562 of sortilin ECD of SEQ ID NO:215). Some antibodies specifically bind residues D74, R76, F97, K110, Y535, L560, and E557 of the sortilin ECD of SEQ ID NO:215. Some antibodies specifically bind residues K110, Y535, E557, T561, Q563, D74, P510, S558, F559, and L560 of the sortilin ECD of SEQ ID NO:215. Some antibodies specifically bind residues E557, S558, F559, L560, P510, and Y535 of the sortilin ECD of SEQ ID NO:215. That is, binding of the antibody to the sortilin ECD can be reduced by mutations of any of the residues specified as forming an epitope.

These antibodies can be obtained by immunizing with a sortilin polypeptide purified from a natural source or recombinantly expressed. The invention also provides antibodies binding to the same epitope as any of the foregoing antibodies, such as, for example, the epitope of 5E20, 8H24, 11M14, 5M13, 2F18, 2P22, 6B15, 2C14, 9N18, or 4N2. Also included are antibodies competing for binding to sortilin with any of the foregoing antibodies, such as, for example, competing with 5E20, 8H24, 11M14, 5M13, 2F18, 2P22, 6B15, 2C14, 9N18, or 4N2. In an embodiment, antibodies binding to the same epitope as a reference antibody such as 5E20, 8H24, 11M14, 5M13, 2F18, 2P22, 6B15, 2C14, 9N18, or 4N2 or competing with the reference antibody share one or more of its functional properties, such as capacity to inhibit progranulin internalization into cells. Optionally, such property is possessed to the same extent within experimental error, or greater than that of the reference antibody. Some antibodies specifically binding to sortilin increase progranulin levels without inhibiting binding of other SORT1 ligands, such as neurotensin, to sortilin. Some antibodies specifically binding to sortilin do so without inducing internalization of sortilin.

The above-mentioned antibodies can be generated de novo by immunizing with a sortilin peptide comprising or consisting of amino acid sequence FTESFLT (SEQ ID NO:202), comprising or consisting of amino acid sequence ESFL (SEQ ID NO:203), comprising or consisting of amino acid sequence DGCILGYKEQFL) (SEQ ID NO:204), comprising or consisting of amino acid sequence PSICLCSLEDFL (SEQ ID NO:205), comprising or consisting of amino acid sequence E(S/Q/D)FL (SEQ ID NO:206), comprising or consisting of amino acid sequence RTEFGMAIGP) (SEQ ID NO:213), comprising or consisting of amino acid sequence WGFTESFLTS (SEQ ID NO:214), or by immunizing with a full length sortilin ECD polypeptide or fragment thereof comprising such residues and screening for specific binding to a peptide including such residues. Antibodies against conformational epitopes such as an epitope comprising or consisting of residues D74, R76, F97, K110, Y535, L560, and E557 of the sortilin ECD of SEQ ID NO:215, comprising or consisting of residues K110, Y535, E557, T561, Q563, D74, P510, S558, F559, and L560 of the sortilin ECD of SEQ ID NO:215, or comprising or consisting of residues E557, S558, F559, L560, P510, and Y535 of the sortilin ECD of SEQ ID NO:215 can be generated by immunizing with a full length ECD or fragment thereof including the residues of the epitope, Such sortilin peptides are preferably attached to a heterologous conjugate molecule that helps elicit an antibody response to the peptide. Attachment can be direct or via a spacer peptide or amino acid. Cysteine is used as a spacer amino acid because its free SH group facilitates attachment of a carrier molecule. A polyglycine linker (e.g., 2-6 glycines), with or without a cysteine residue between the glycines and the peptide can also be used. The carrier molecule serves to provide a T-cell epitope that helps elicit an antibody response against the peptide. Several carriers are commonly used particularly keyhole limpet hemocyanin (KLH), ovalbumin and bovine serum albumin (BSA). Peptide spacers can be added to peptide immunogen as part of solid phase peptide synthesis. Carriers are typically added by chemical cross-linking. Some examples of chemical crosslinkers that can be used include cross-N-maleimido-6-aminocaproyl ester or m-maleimidobenzoyl-N-hydroxysuccinimide ester (MBS) (see for example, Harlow, E. et al., Antibodies: A Laboratory Manual, Cold Spring Harbor Laboratory Press, Cold Spring Harbor, N.Y. 1988; Sinigaglia et al., Nature, 336:778-780 (1988); Chicz et al., J. Exp. Med., 178:27-47 (1993); Hammer et al., Cell 74:197-203 (1993); Falk K. et al., Immunogenetics, 39:230-242 (1994); WO 98/23635; and, Southwood et al. J. Immunology, 160:3363-3373 (1998)). The carrier and spacer if present can be attached to either end of the immunogen.

A peptide with optional spacer and carrier can be used to immunize laboratory animals or B-cells as described in more detail below. Hybridoma supernatants can be tested for ability to bind a sortilin peptide comprising or consisting of amino acid sequence FTESFLT (SEQ ID NO:202), comprising or consisting of amino acid sequence ESFL (SEQ ID NO:203), comprising or consisting of amino acid sequence DGCILGYKEQFL) (SEQ ID NO:204), comprising or consisting of amino acid sequence PSICLCSLEDFL (SEQ ID NO:205), comprising or consisting of amino acid sequence E(S/Q/D)FL (SEQ ID NO:206), comprising or consisting of amino acid sequence RTEFGMAIGP (SEQ ID NO:213), comprising or consisting of amino acid sequence WGFTESFLTS (SEQ ID NO:214). For conformational epitopes, antibodies binding to the extracellular domain of sortilin can be screened for competition with a reference antibody and/or to determine that binding is reduced by mutation of some or all residues within the epitope. When several residues of a conformational epitope are clustered within the length of a typical linear epitope (e.g., up to about 15 residues), a peptide comprising or consisting of these residues can be used to elicit an antibody. Thus, for example for an epitope defined by residues D74, R76, F97, K110, Y535, L560, and E557 of the sortilin ECD of SEQ ID NO:215, a peptide comprising or consisting of residues 557-560 of the sortilin ECD of SEQ ID NO:215 can be used to elicit an antibody. For an epitope defined by residues K110, Y535, E557, T561, Q563, D74, P510, S558, F559, and L560 of the sortilin ECD of SEQ ID NO:215, a peptide comprising or consist of residues 557-561 of the sortilin ECD of SEQ ID NO:215 can be used to elicit an antibody. For an epitope defined by residues E557, S558, F559, L560, P510, and Y535 of the sortilin ECD of SEQ ID NO:215], a peptide comprising or consisting of residues 557-560 of the sortilin ECD of SEQ ID NO:215 can be used to elicit an antibody. The peptide can be attached to a carrier or other tag to facilitate the screening assay. In this case, the carrier or tag is preferentially different than the combination of spacer and carrier molecule used for immunization to eliminate antibodies specific for the spacer or carrier rather than the sortilin peptide.

An antibody designated 5E20 is an exemplary antibody specifically binding to sortilin. 5E20 has mature variable heavy and light regions (after cleavage of signal peptide) characterized by SEQ ID NO:4 and SEQ ID NO:10 respectively. Unless otherwise apparent from context, reference to 5E20 should be understood as referring to any of the mouse, chimeric, veneered, and humanized forms of this antibody. The antibody has been deposited as [DEPOSIT NUMBER]. This antibody specifically binds a peptide comprising or consisting of amino acid sequence FTESFLT (SEQ ID NO:202), comprising or consisting of amino acid sequence ESFL (SEQ ID NO:203), comprising or consisting of amino acid sequence DGCILGYKEQFL (SEQ ID NO:204), comprising or consisting of amino acid sequence PSICLCSLEDFL (SEQ ID NO:205), or comprising or consisting of amino acid sequence E(S/Q/D)FL (SEQ ID NO:206), or specifically binds residues E557, S558, F559, L560 and P510, and Y535 of the sortilin ECD of SEQ ID NO:215. Kabat/Chothia Composite CDRs of the heavy chain of 5E20 are designated SEQ ID NOS:5-7, respectively, and Kabat-Chothia Composite CDRs of the light chain of 5E20 are designated SEQ ID NOS:11-13, respectively. An exemplary signal peptide sequence for mouse 5E20 variable heavy chain is SEQ ID NO:3. An exemplary signal peptide sequence for mouse 5E20 variable light chain is SEQ ID NO:9.

An antibody designated 8H24 is another exemplary antibody specifically binding to sortilin. 8H24 has mature variable heavy and light regions (after cleavage of signal peptide) characterized by SEQ ID NO:28 and SEQ ID NO:34 respectively. Unless otherwise apparent from the context, reference to 8H24 should be understood as referring to any of the mouse, chimeric, veneered, and humanized forms of this antibody. 8H24 has been deposited as [DEPOSIT NUMBER]. This antibody specifically binds a peptide comprising or consisting of amino acid sequence RTEFGMAIGP (SEQ ID NO:213) or specifically binds residues D74, R76, F97, K110, Y535, L560, and E557 of the sortilin ECD of SEQ ID NO:215. Kabat/Chothia Composite CDRs of the heavy chain of 8H24 are designated SEQ ID NOS:29-31, respectively, and Kabat/Chothia Composite CDRs of the light chain of 8H24 are designated SEQ ID NOS:35-37, respectively. An exemplary signal peptide sequence for mouse 8H24 variable heavy chain is SEQ ID NO:27. An exemplary signal peptide sequence for mouse 8H24 variable light chain is SEQ ID NO:33.

An antibody designated 11M14 is another exemplary antibody specifically binding to sortilin. 11M14 has mature variable heavy and light regions (after cleavage of signal peptide) characterized by SEQ ID NO:52 and SEQ ID NO:58 respectively. Unless otherwise apparent from the context, reference to 11M14 should be understood as referring to any of the mouse, chimeric, veneered, and humanized forms of this antibody. 11M14 has been deposited as [DEPOSIT NUMBER]. This antibody specifically binds a peptide comprising or consisting of amino acid sequence WGFTESFLTS (SEQ ID NO:214) or specifically binds residues K110, Y535, E557, T561, Q563, D74, P510, S558, F559, and L560 of the sortilin ECD of SEQ ID NO:215. Kabat/Chothia Composite CDRs of the heavy chain of 11M14 are designated SEQ ID NOS:53-55, respectively, and Kabat/Chothia Composite CDRs of the light chain of 11M14 are designated SEQ ID NOS:59-61, respectively. An exemplary signal peptide sequence for mouse 11M14 variable heavy chain is SEQ ID NO:51. An exemplary signal peptide sequence for mouse 11M14 variable light chain is SEQ ID NO:57.

An antibody designated 5M13 is another exemplary antibody specifically binding to sortilin. 5M13 has mature variable heavy and light regions (after cleavage of signal peptide) characterized by SEQ ID NO:78 and SEQ ID NO:84 respectively. Unless otherwise apparent from the context, reference to 5M13 should be understood as referring to any of the mouse, chimeric, veneered, and humanized forms of this antibody. 5M13 has been deposited as [DEPOSIT NUMBER]. Kabat/Chothia Composite CDRs of the heavy chain of 5M13 are designated SEQ ID NOS:79-81, respectively, and Kabat/Chothia Composite CDRs of the light chain of 5M13 are designated SEQ ID NOS:85-87, respectively. An exemplary signal peptide sequence for mouse 5M13 variable heavy chain is SEQ ID NO:77. An exemplary signal peptide sequence for mouse 5M13 variable light chain is SEQ ID NO:83.

An antibody designated 2F18 is another exemplary antibody specifically binding to sortilin. 2F18 has mature variable heavy and light regions (after cleavage of signal peptide) characterized by SEQ ID NO:90 and SEQ ID NO:96 respectively. Unless otherwise apparent from the context, reference to 2F18 should be understood as referring to any of the mouse, chimeric, veneered, and humanized forms of this antibody. 2F18 has been deposited as [DEPOSIT NUMBER]. Kabat/Chothia Composite CDRs of the heavy chain of 2F18 are designated SEQ ID NOS:91-93, respectively, and Kabat/Chothia Composite CDRs of the light chain of 2F18 are designated SEQ ID NOS:97-99, respectively. An exemplary signal peptide sequence for mouse 2F18 variable heavy chain is SEQ ID NO:89. An exemplary signal peptide sequence for mouse 2F18 variable light chain is SEQ ID NO:95.

An antibody designated 2P22 is another exemplary antibody specifically binding to sortilin. 2P22 has mature variable heavy and light regions (after cleavage of signal peptide) characterized by SEQ ID NO:102 and SEQ ID NO:108 respectively. Unless otherwise apparent from the context, reference to 2P22 should be understood as referring to any of the mouse, chimeric, veneered, and humanized forms of this antibody. 2P22 has been deposited as [DEPOSIT NUMBER]. Kabat/Chothia Composite CDRs of the heavy chain of 2P22 are designated SEQ ID NOS:103-105, respectively, and Kabat/Chothia Composite CDRs of the light chain of 2P22 are designated SEQ ID NOS:109-111, respectively. An exemplary signal peptide sequence for mouse 2P22 variable heavy chain is SEQ ID NO:101. An exemplary signal peptide sequence for mouse 2P22 variable light chain is SEQ ID NO:107.

An antibody designated 6B15 is another exemplary antibody specifically binding to sortilin. 6B15 has mature variable heavy and light regions (after cleavage of signal peptide) characterized by SEQ ID NO:114 and SEQ ID NO:120 respectively. Unless otherwise apparent from the context, reference to 6B15 should be understood as referring to any of the mouse, chimeric, veneered, and humanized forms of this antibody. 6B15 has been deposited as [DEPOSIT NUMBER]. Kabat/Chothia Composite CDRs of the heavy chain of 6B15 are designated SEQ ID NOS:115-117, respectively, and Kabat/Chothia Composite CDRs of the light chain of 6B15 are designated SEQ ID NOS:121-123, respectively. An exemplary signal peptide sequence for mouse 6B15 variable heavy chain is SEQ ID NO:113. An exemplary signal peptide sequence for mouse 6B15 variable light chain is SEQ ID NO:119.

An antibody designated 2C14 is another exemplary antibody specifically binding to sortilin. 2C14 has mature variable heavy and light regions (after cleavage of signal peptide) characterized by SEQ ID NO:126 and SEQ ID NO:132 respectively. Unless otherwise apparent from the context, reference to 2C14 should be understood as referring to any of the mouse, chimeric, veneered, and humanized forms of this antibody. 2C14 has been deposited as [DEPOSIT NUMBER]. Kabat/Chothia Composite CDRs of the heavy chain of 2C4 are designated SEQ ID NOS:127-129, respectively, and Kabat/Chothia Composite CDRs of the light chain of 2C4 are designated SEQ ID NOS:133-135, respectively. An exemplary signal peptide sequence for mouse 2C14 variable heavy chain is SEQ ID NO:125. An exemplary signal peptide sequence for mouse 2C14 variable light chain is SEQ ID NO:131.

An antibody designated 9N18 is another exemplary antibody specifically binding to sortilin. 9N18 has mature variable heavy and light regions (after cleavage of signal peptide) characterized by SEQ ID NO:138 and SEQ ID NO:144 respectively. Unless otherwise apparent from the context, reference to 9N18 should be understood as referring to any of the mouse, chimeric, veneered, and humanized forms of this antibody. 9N18 has been deposited as [DEPOSIT NUMBER]. Kabat/Chothia Composite CDRs of the heavy chain of 9N18 are designated SEQ ID NOS:139-141, respectively, and Kabat/Chothia Composite CDRs of the light chain of 9N18 are designated SEQ ID NOS:145-147, respectively. An exemplary signal peptide sequence for mouse 9N18 variable heavy chain is SEQ ID NO:137. An exemplary signal peptide sequence for mouse 9N18 variable light chain is SEQ ID NO: 143.

An antibody designated 4N2 is another exemplary antibody specifically binding to sortilin. 4N2 has mature variable heavy and light regions (after cleavage of signal peptide) characterized by SEQ ID NO:150 and SEQ ID NO:156 respectively. Unless otherwise apparent from the context, reference to 4N2 should be understood as referring to any of the mouse, chimeric, veneered, and humanized forms of this antibody. 4N2 has been deposited as [DEPOSIT NUMBER]. Kabat/Chothia Composite CDRs of the heavy chain of 4N2 are designated SEQ ID NOS:151-153, respectively, and Kabat/Chothia Composite CDRs of the light chain of 4N2 are designated SEQ ID NOS:157-159, respectively. An exemplary signal peptide sequence for mouse 4N2 variable heavy chain is SEQ ID NO:149 An exemplary signal peptide sequence for mouse 4N2 variable light chain is SEQ ID NO:155.

Some antibodies of the invention bind to the same or overlapping epitope as an antibody designated 5E20, 8H24, 11M14, 5M13, 2F18, 2P22, 6B15, 2C14, 9N18, or 4N2. Other antibodies having such a binding specificity can be produced by immunizing mice with sortilin or a portion thereof including the desired epitope (e.g. a sortilin peptide comprising or consisting of the amino acid sequence FTESFLT (SEQ ID NO:202), comprising or consisting of amino acid sequence ESFL (SEQ ID NO:203), comprising or consisting of amino acid sequence DGCILGYKEQFL) (SEQ ID NO:204), comprising or consisting of amino acid sequence PSICLCSLEDFL (SEQ ID NO:205), or comprising or consisting of amino acid sequence E(S/Q/D)FL (SEQ ID NO:206), comprising or consisting of amino acid sequence RTEFGMAIGP) (SEQ ID NO:213), comprising or consisting of amino acid sequence WGFTESFLTS (SEQ ID NO:214). To elicit antibodies binding to a conformational epitope comprising or consisting of residues D74, R76, F97, K110, Y535, L560, and E557 of the sortilin ECD of SEQ ID NO:215, comprising or consisting of residues K110, Y535, E557, T561, Q563, D74, P510, S558, F559, and L560 of the sortilin ECD of SEQ ID NO:215, or an epitope comprising or consisting of residues E557, S558, F559, L560, P510, and Y535 of the sortilin ECD of SEQ ID NO:215, a full length ECD or fragment thereof including the residues of the peptides can be used. Resulting antibodies can be screened for binding to sortilin optionally in competition with an antibody having the variable regions of mouse 5E20, 8H24, 11M14, 5M13, 2F18, 2P22, 6B15, 2C14, 9N18, or 4N2. Fragments of sortilin including the desired epitope can be linked to a carrier that helps elicit an antibody response to the fragment and/or be combined with an adjuvant the helps elicit such a response. Such antibodies can be screened for differential binding to sortilin or a fragment thereof compared with mutants of specified residues. Screening against such mutants more precisely defines the binding specificity to allow identification of antibodies whose binding is inhibited by mutagenesis of particular residues and which are likely to share the functional properties of other exemplified antibodies. The mutations can be systematic replacement substitution with alanine (or serine if an alanine is present already) one residue at a time, or more broadly spaced intervals, throughout the target or throughout a section thereof in which an epitope is known to reside. If the same set of mutations significantly reduces the binding of two antibodies, the two antibodies bind the same epitope.

Antibodies having the binding specificity of a selected murine antibody (e.g., 5E20, 8H24, 11M14, 5M13, 2F18, 2P22, 6B15, 2C14, 9N18, or 4N2) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for sortilin or a fragment thereof (e.g., at least $10^8$ and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for sortilin or a fragment thereof are selected. The resulting antibodies usually have the same or similar epitope specificity as the murine starting material.

Kabat/Chothia Composite CDRs of the heavy chain of 5E20 are designated SEQ ID NOS:5-7, respectively, and Kabat/Chothia Composite CDRs of the light chain of 5E20 are designated SEQ ID NOS:11-13, respectively.

Table 2 indicates the 5E20 CDRs as defined by Kabat, Chothia, Composite of Chothia and Kabat (also referred to herein as "Kabat/Chothia Composite"), AbM, and Contact.

TABLE 2

5E20 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L1 | L24--L34<br>SEQ ID NO: 11 | L24--L34<br>SEQ ID NO: 11 | L24--L34<br>SEQ ID NO: 11 | L24--L34<br>SEQ ID NO: 11 | L30--L36<br>SEQ ID NO: 21 |
| L2 | L50--L56<br>SEQ ID NO: 12 | L50--L56<br>SEQ ID NO: 12 | L50--L56<br>SEQ ID NO: 12 | L50--L56<br>SEQ ID NO: 12 | L46--L55<br>SEQ ID NO: 22 |
| L3 | L89--L97<br>SEQ ID NO: 13 | L89--L97<br>SEQ ID NO: 13 | L89--L97<br>SEQ ID NO: 13 | L89--L97<br>SEQ ID NO: 13 | L89--L96<br>SEQ ID NO: 23 |
| H1 | H31--H35B<br>SEQ ID NO: 14 | H26--H32<br>SEQ ID NO: 15 | H26--H35B<br>SEQ ID NO: 5 | H26--H35B<br>SEQ ID NO: 5 | H30--H35B<br>SEQ ID NO: 18 |
| H2 | H50--H65<br>SEQ ID NO: 6 | H52--H56<br>SEQ ID NO: 16 | H50--H65<br>SEQ ID NO: 6 | H50--H58<br>SEQ ID NO: 17 | H47--H58<br>SEQ ID NO: 19 |
| H3 | H95--H102<br>SEQ ID NO: 7 | H95--H102<br>SEQ ID NO: 7 | H95--H102<br>SEQ ID NO: 7 | H95--H102<br>SEQ ID NO: 7 | H93--H101<br>SEQ ID NO: 20 |

Kabat/Chothia Composite CDRs of the heavy chain of 8H24 are designated SEQ ID NOS:29-31, respectively, and Kabat/Chothia Composite CDRs of the light chain of 8H24 are designated SEQ ID NOS:35-37, respectively.

Table 3 indicates the 8H24 CDRs as defined by Kabat, Chothia, Composite of Chothia and Kabat (also referred to herein as "Kabat/Chothia Composite"), AbM, and Contact.

TABLE 3

| 8H24 CDRs as defined by Kabat, Chothia, Composite of Chothia and Kabat, AbM, and Contact | | | | | |
|---|---|---|---|---|---|
| Loop | Kabat | Chothia | Composite of Chothia & Kabat | AbM | Contact |
| L1 | L24--L34<br>SEQ ID NO: 35 | L24--L34<br>SEQ ID NO: 35 | L24--L34<br>SEQ ID NO: 35 | L24--L34<br>SEQ ID NO: 35 | L30--L36<br>SEQ ID NO: 45 |
| L2 | L50--L56<br>SEQ ID NO: 36 | L50--L56<br>SEQ ID NO: 36 | L50--L56<br>SEQ ID NO: 36 | L50--L56<br>SEQ ID NO: 36 | L46--L55<br>SEQ ID NO: 46 |
| L3 | L89--L97<br>SEQ ID NO: 37 | L89--L97<br>SEQ ID NO: 37 | L89--L97<br>SEQ ID NO: 37 | L89--L97<br>SEQ ID NO: 37 | L89--L96<br>SEQ ID NO: 47 |
| H1 | H31--H35B<br>SEQ ID NO: 38 | H26--H32<br>SEQ ID NO: 39 | H26--H35B<br>SEQ ID NO: 29 | H26--H35B<br>SEQ ID NO: 29 | H30--H35B<br>SEQ ID NO: 42 |
| H2 | H50--H65<br>SEQ ID NO: 30 | H52--H56<br>SEQ ID NO: 40 | H50--H65<br>SEQ ID NO: 30 | H50--H58<br>SEQ ID NO: 41 | H47--H58<br>SEQ ID NO: 43 |
| H3 | H95--H102<br>SEQ ID NO: 31 | H95--H102<br>SEQ ID NO: 31 | H95--H102<br>SEQ ID NO: 31 | H95--H102<br>SEQ ID NO: 31 | H93--H101<br>SEQ ID NO: 44 |

Kabat/Chothia Composite CDRs of the heavy chain of 11M14 are designated SEQ ID NOS:53-55, respectively, and Kabat/Chothia Composite CDRs of the light chain of 11M14 are designated SEQ ID NOS:59-61 respectively.

Table 4 indicates the 11M14 CDRs as defined by Kabat, Chothia, Composite of Chothia and Kabat (also referred to herein as "Kabat/Chothia Composite"), AbM, and Contact.

TABLE 4

| 11M14 CDRs as defined by Kabat, Chothia, Composite of Chothia and Kabat, AbM, and Contact | | | | | |
|---|---|---|---|---|---|
| Loop | Kabat | Chothia | Composite of Chothia & Kabat | AbM | Contact |
| L1 | L24-L34<br>SEQ ID NO: 59 | L24-L34<br>SEQ ID NO: 59 | L24-L34<br>SEQ ID NO: 59 | L24-L34<br>SEQ ID NO: 59 | L30-L36<br>SEQ ID NO: 69 |
| L2 | L50-L56<br>SEQ ID NO: 60 | L50-L56<br>SEQ ID NO: 60 | L50-L56<br>SEQ ID NO: 60 | L50-L56<br>SEQ ID NO: 60 | L46-L55<br>SEQ ID NO: 70 |
| L3 | L89-L97<br>SEQ ID NO: 61 | L89-L97<br>SEQ ID NO: 61 | L89-L97<br>SEQ ID NO: 61 | L89-L97<br>SEQ ID NO: 61 | L89-L96<br>SEQ ID NO: 71 |
| H1 | H31-H35B<br>SEQ ID NO: 62 | H26-H32<br>SEQ ID NO: 63 | H26-H35B<br>SEQ ID NO: 53 | H26-H35B<br>SEQ ID NO: 53 | H30-H35B<br>SEQ ID NO: 66 |
| H2 | H50-H65<br>SEQ ID NO: 54 | H52-H56<br>SEQ ID NO: 64 | H50-H65<br>SEQ ID NO: 54 | H50-H58<br>SEQ ID NO: 65 | H47-H58<br>SEQ ID NO: 67 |
| H3 | H95-H102<br>SEQ ID NO: 55 | H95-H102<br>SEQ ID NO: 55 | H95-H102<br>SEQ ID NO: 55 | H95-H102<br>SEQ ID NO: 55 | H93-H101<br>SEQ ID NO: 68 |

Kabat/Chothia Composite CDRs of the heavy chain of 5M13 are designated SEQ ID NOS:79-81, respectively, and Kabat/Chothia Composite CDRs of the light chain of 5M13 are designated SEQ ID NOS:85-87, respectively.

Kabat/Chothia Composite CDRs of the heavy chain of 2F18 are designated SEQ ID NOS:91-93, respectively, and Kabat/Chothia Composite CDRs of the light chain of 2F18 are designated SEQ ID NOS:97-99, respectively.

Kabat/Chothia Composite CDRs of the heavy chain of 2P22 are designated SEQ ID NOS:103-105, respectively, and Kabat/Chothia Composite CDRs of the light chain of 2P22 are designated SEQ ID NOS:109-111, respectively.

Kabat/Chothia Composite CDRs of the heavy chain of 6B15 are designated SEQ ID NOS:115-117, respectively, and Kabat/Chothia Composite CDRs of the light chain of 6B15 are designated SEQ ID NOS:121-123, respectively.

Kabat/Chothia Composite CDRs of the heavy chain of 2C14 are designated SEQ ID NOS:127-129, respectively, and Kabat/Chothia Composite CDRs of the light chain of 2C14 are designated SEQ ID NOS:133-135, respectively.

Kabat/Chothia Composite CDRs of the heavy chain of 9N18 are designated SEQ ID NOS:139-141, respectively, and Kabat/Chothia Composite CDRs of the light chain of 9N18 are designated SEQ ID NOS:145-147, respectively.

Kabat/Chothia Composite CDRs of the heavy chain of 4N2 are designated SEQ ID NOS:151-153, respectively, and Kabat/Chothia Composite CDRs of the light chain of 4N2 are designated SEQ ID NOS:157-159, respectively.

Other antibodies can be obtained by mutagenesis of cDNA encoding the heavy and light chains of an exemplary antibody, such as 5E20, 8H24, 11M14, 5M13, 2F18, 2P22, 6B15, 2C14, 9N18, or 4N2. Monoclonal antibodies that are at least 70%, 80%, 90%, 95%, 96%, 97%, 98%, or 99% identical to 5E20, 8H24, 11M14, 5M13, 2F18, 2P22, 6B15, 2C14, 9N18, or 4N2 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one or all six CDR(s) as defined by any conventional definition, but preferably Kabat, that are 90%, 95%, 99% or 100% identical to corresponding CDRs of 5E20, 8H24, 11M14, 5M13, 2F18, 2P22, 6B15, 2C14, 9N18, or 4N2 are also included.

The invention also provides antibodies having some or all (e.g., 3, 4, 5, and 6) CDRs entirely or substantially from 5E20, 8H24, 11M14, 5M13, 2F18, 2P22, 6B15, 2C14, 9N18, or 4N2. Such antibodies can include a heavy chain variable region that has at least two, and usually all three, CDRs entirely or substantially from the heavy chain variable region of 5E20, 8H24, 11M14, 5M13, 2F18, 2P22, 6B15, 2C14, 9N18, or 4N2 and/or a light chain variable region having at least two, and usually all three, CDRs entirely or substantially from the light chain variable region of 5E20, 8H24, 11M14, 5M13, 2F18, 2P22, 6B15, 2C14, 9N18, or 4N2. The antibodies can include both heavy and light chains. A CDR is substantially from a corresponding 5E20, 8H24, 11M14, 5M13, 2F18, 2P22, 6B15, 2C14, 9N18, or 4N2 CDR when it contains no more than 4, 3, 2, or 1 substitutions, insertions, or deletions, except that CDR-H2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 5E20, 8H24, 11M14, 5M13, 2F18, 2P22, 6B15, 2C14, 9N18, or 4N2 in the amino acid sequence of the mature heavy and/or light chain variable regions and maintain their functional properties, and/or differ from 5E20, 8H24, 11M14, 5M13, 2F18, 2P22, 6B15, 2C14, 9N18, or 4N2 by a small number of functionally inconsequential amino acid substitutions (e.g., conservative substitutions), deletions, or insertions.

Some antibodies identified by such assays can bind to sortilin.

The invention further provides a means for specifically binding to a peptide consisting of residues E(S/Q/D)FL (SEQ ID NO:206), residues FTESFLT (SEQ ID NO:202), residues ESFL (SEQ ID NO:203), residues DGCILGYKEQFL (SEQ ID NO:204), or residues PSICLCSLEDFL (SEQ ID NO:205), or specifically binds residues E557, S558, F559, L560, P510, and Y535 of the sortilin ECD of SEQ ID NO:215. An exemplary means is an antibody comprising the heavy chain CDRs of SEQ ID NOS:5-7 and light chain CDRs of SEQ ID NOS.:11-13.

The invention further provides a means for specifically binding to a peptide consisting of residues RTEFGMAIGP (SEQ ID NO:213) or specifically binding residues D74, R76, F97, K110, Y535, L560, and E557 of the sortilin ECD of SEQ ID NO:215. An exemplary means is an antibody comprising the heavy chain CDRs of SEQ ID NOS: 29-31 and light chain CDRs of SEQ ID NOS. 35-37.

The invention further provides a means for specifically binding to a peptide consisting of residues WGFTESFLTS (SEQ ID NO:214) or specifically binding residues K110, Y535, E557, T561, Q563, D74, P510, S558, F559, and L560 of the sortilin ECD of SEQ ID NO:215. An exemplary means is an antibody comprising the heavy chain CDRs of SEQ ID NOS: 53-55and light chain CDRs of SEQ ID NOS. 59-61.

B. Non-Human Antibodies

The production of other non-human antibodies, e.g., murine, guinea pig, primate, rabbit or rat, against sortilin or a fragment thereof (e.g., a peptide comprising an amino acid sequence of FTESFLT (SEQ ID NO:202), ESFL (SEQ ID NO:203), DGCILGYKEQFL) (SEQ ID NO:204), or PSICLCSLEDFL (SEQ ID NO:205), E(S/Q/D)FL (SEQ ID NO:206), RTEFGMAIGP) (SEQ ID NO:213), or WGFTESFLTS (SEQ ID NO:214) can be accomplished by, for example, immunizing the animal with sortilin or a fragment thereof. See Harlow & Lane, *Antibodies, A Laboratory Manual* (CSHP NY, 1988) (incorporated by reference for all purposes). Antibodies against conformational epitopes such as an epitope comprising, residues D74, R76, F97, K110, Y535, L560, and E557 of the sortilin ECD of SEQ ID NO:215, residues K110, Y535, E557, T561, and Q563, D74, P510, S558, F559, and L560 of the sortilin ECD of SEQ ID NO:215, or residues E557, S558, F559, L560 and P510, and Y535 of the sortilin ECD of SEQ ID NO:215 can be elicited using a full-length ECD or sufficient of the ECD to span the epitope residues. Optionally, the immunogen can be an extracellular domain (ECD) of recombinant human Sortilin with a C-terminal HIS tag (ECD-huSortilin-HIS). Optionally, the animal is immunized with a sortilin fragment comprising a peptide represented by E(S/Q/D)FL (SEQ ID NO:206), linked to a carrier. Optionally, the peptide is FTESFLT (SEQ ID NO:202), ESFL (SEQ ID NO:203), DGCILGYKEQFL) (SEQ ID NO:204), PSICLCSLEDFL (SEQ ID NO:205), RTEFGMAIGP (SEQ ID NO:213), or WGFTESFLTS (SEQ ID NO:214). Such an immunogen can be obtained from a natural source, by peptide synthesis, or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant can be used for immunization of laboratory animals. Rabbits or guinea pigs are typically used for making polyclonal antibodies. Mice are typically used for making monoclonal antibodies. Antibodies are screened for specific binding to sortilin or an epitope within sortilin (e.g., FTESFLT (SEQ ID NO:202), ESFL (SEQ ID NO:203), DGCILGYKEQFL) (SEQ ID NO:204), PSICLCSLEDFL (SEQ ID NO:205), E(S/Q/D)FL (SEQ ID NO:206), RTEFGMAIGP (SEQ ID NO:213), WGFTESFLTS (SEQ ID NO:214), or to an epitope defined by residues D74, R76, F97, K110, Y535, L560, and E557 of the sortilin ECD of SEQ ID NO:215, or to an epitope defined by residues K110, Y535, E557, T561, Q563, D74, P510, S558, F559, and L560 of the sortilin ECD of SEQ ID NO:215, or to an epitope defined by residues E557, S558, F559, L560 and P510, and Y535 of the sortilin ECD of SEQ ID NO:215). Optionally, the screening can be performed against 15 amino acid peptides comprising FTESFLT (SEQ ID NO:202), ESFL (SEQ ID NO:203), DGCILGYKEQFL) (SEQ ID NO:204), PSICLCSLEDFL (SEQ ID NO:205), RTEFGMAIGP (SEQ ID NO:213), or WGFTESFLTS (SEQ ID NO:214), or a consensus motif represented by E(S/Q/D)FL (SEQ ID NO:206). Optionally, the peptides comprise or consist of FTESFLT (SEQ ID NO:202), ESFL (SEQ ID NO:203), DGCILGYKEQFL) (SEQ ID NO:204), PSICLCSLEDFL (SEQ ID NO:205), RTEFGMAIGP (SEQ ID NO:213), or WGFTESFLTS (SEQ ID NO:214). Such screening can be accomplished by determining binding of an antibody to a collection of sortilin variants, such as sortilin variants of SEQ ID NOs: 216-243, or such as sortilin variants comprising or consisting of amino acid residues 588-594 or 590-593 or 632-643 or 663-674 or 167-176 or 586-595 of SEQ ID NO:1), or mutations within these residues, and determining which sortilin variants bind to the antibody. Binding can be assessed, for example, by Western blot, FACS or ELISA.

C. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition but preferably defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical. To be classified as humanized under the 2014 World Health Organization (WHO) International non-proprietary names (INN) definition of humanized antibodies, an antibody must have at least 85% identity to human germline antibody sequences (i.e., prior to somatic hypermutation). Mixed antibodies are antibodies for which one antibody chain (e.g., heavy chain) meets the threshold but the other chain (e.g., light chain) does not meet the threshold. An antibody is classified as chimeric if neither chain meets the threshold, even though the variable framework regions for both chains were substantially human with some murine backmutations. See, Jones et al. (2016) The INNs and outs of antibody nonproprietary names, mAbs 8:1, 1-9, DOI: 10.1080/19420862.2015.1114320. See also "WHO-INN: International nonproprietary names (INN) for biological and biotechnological substances (a review)" (Internet) 2014. Available from: http://www. who.int/medicines/services/inn/BioRev2014.pdf), incorporated herein by reference. For the avoidance of doubt, the term "humanized" as used herein is not intended to be limited to the 2014 WHO INN definition of humanized antibodies. Some of the humanized antibodies provided herein have at least 85% sequence identity to human germline sequences and some of the humanized antibodies provided herein have less than 85% sequence identity to human germline sequences. Some of the heavy chains of the humanized antibodies provided herein have from about 60% to 100% sequence identity to human germ line sequences, such as, for example, in the range of about 60% to 69%, 70% to 79%, 80% to 84%, or 85% to 89%. Some heavy chains fall below the 2014 WHO INN definition and have, for example, about 64%, 65%, 66%, 67%, 68%, 69%, 70%, 71%, 72%, 73%, 74%, 75%, 76%, 77%, 78%, 79%, 80%, 81%, or 82%, 83%, or 84% sequence identity to human germ line sequences, while other heavy chains meet the 2014 WHO INN definition and have about 85%, 86%, 87%, 88%, 89% or greater sequence identity to human germ line sequences. Some of the light chains of the humanized antibodies provided herein have from about 60% to 100% sequence identity to human germ line sequences, such as, for example, in the range of about 80% to 84% or 85% to 89%. Some light chains fall below the 2014 WHO INN definition and have, for example, about 81%, 82%, 83% or 84% sequence identity to human germ line sequences, while other light chains meet the 2014 WHO INN definition and have about 85%, 86%, 87%, 88%, 89% or greater sequence identity to human germ line sequences. Some humanized antibodies provided herein that are "chimeric" under the 2014 WHO INN definition have heavy chains with less than 85% identity to human germ line sequences paired with light chains having less than 85% identity to human germ line sequences. Some humanized antibodies provided herein are "mixed" under the 2014 WHO INN definition, for example, having a heavy chain with at least 85% sequence identity to human germ line sequences paired with a light chain having less than 85% sequence identity to human germ line sequences, or vice versa. Some humanized antibodies provided herein meet the 2014 WHO INN definition of "humanized" and have a heavy chain with at least 85% sequence identity to human germ line sequences paired with a light chain having at least 85% sequence identity to human germ line sequences. Some humanized antibodies provided herein meet the 2014 WHO INN definition of "mixed." Exemplary 5E20 antibodies that meet the 2014 WHO INN definition of "mixed" include antibodies having a mature heavy chain with the amino acid sequence of any of SEQ ID NOS:163-166 and SEQ ID NO:168 paired with a mature light chain sequence having an amino acid sequence of any of SEQ ID NO:173-176. Exemplary 8H24 antibodies that meet the 2014 WHO INN definition of "mixed" include antibodies having a mature heavy chain with the amino acid sequence of SEQ ID NO: 180 or SEQ ID NO:181 paired with a mature light chain sequence having an amino acid sequence of SEQ ID NO:185 or SEQ ID NO:186. Exemplary 11M14 antibodies that meet the 2014 WHO INN definition of "mixed" include antibodies having a mature heavy chain with the amino acid sequence of any of SEQ ID NOS:190-192 paired with a mature light chain sequence having an amino acid sequence of any of SEQ ID NOS:196-199. Additional humanized 5E20 antibodies of the invention include antibodies having a mature heavy chain having an amino acid sequence of SEQ ID NOS:167 or SEQ ID NO:169 paired with a mature light chain having an amino acid sequence of any of SEQ ID NOS:173-176.

Although humanized antibodies often incorporate all six CDRs (defined by any conventional definition but preferably as defined by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mol. Biol.,* 320: 415-428, 2002; Iwahashi et al., *Mol. Immunol.* 36:1079-1091, 1999; Tamura et al, *J. Immunol.,* 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity and/or for meeting the WHO INN definition of "humanized". However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Some humanized antibodies have the same (within experimental error) or improved functional properties, e.g., binding affinity for human sortilin, increasing extracellular progranulin in plasma while minimizing decrease in surface sortilin as described in the examples as a murine antibody from which they were derived. For example, some humanized antibodies have a binding affinity within a factor of 3, 2 or 1 of the murine antibody from which they were derived or an affinity indistinguishable within experimental error. Some humanized antibodies increase extracellular progranulin in plasma while minimizing decrease in surface sortilin as described in the examples within a factor of 3, 2 or 1 of the murine antibody from which they were derived or inhibit the same within experimental error as the mouse antibody from which they were derived.

An example of an acceptor sequence for the 5E20 heavy chain is the human mature heavy chain variable region of human antibody AEX29086 VH (AEX29086-VH_huFrwk; SEQ ID NO:161). The heavy chain variable domains of 5E20 and AEX29086 VH share identical lengths for the CDR-H1, H2 loops. An example of an acceptor sequence for the 5E20 heavy chain is the human mature heavy chain variable region IMGT #IGHV3-21*01 (SEQ ID NO:162). An example of an acceptor sequence for the 5E20 light chain is the human mature light chain variable region human antibody BAH04687 VL (BAH04687-VL_huFrwk; SEQ ID NO:171). The variable light domain of 5E20 and BAH04687 antibody share identical lengths for the CDR-L1, L2 and L3 loops. An example of an acceptor sequence for the 5E20 light chain is the human mature light chain variable region IGKV1-12*01 (SEQ ID NO:172).

An example of an acceptor sequence for the 8H24 heavy chain is the human antibody AAC51714 VH (GenBank Acc. #AAC51714-VH_huFrwk; SEQ ID NO:178). The variable heavy domains of 8H24 and AAC51714 also share identical lengths for the CDR-H1, H2 loops. An example of an acceptor sequence for the 8H24 heavy chain is the human mature heavy chain variable region IMGT #IGHV1-69*08_IGHJ1*01 (SEQ ID NO:179). An example of an acceptor sequence for the 8H24 light chain is the human mature light chain variable region human antibody ABC66914 VL (GenBank Acc. #ABC66914-VL_huFrwk; SEQ ID NO:183)). The variable light domain of 8H24 and ABC66914 antibody also share identical lengths for the CDR-L1, L2 and L3 loops. An example of an acceptor sequence for the 8H24 light chain is the human mature light chain variable region IMGT #IGKV2-40*01 (SEQ ID NO:184).

An example of an acceptor sequence for the 11M14 heavy chain is the human mature heavy chain variable region of human Ig heavy chain ACS96198 (GenBank Acc. #ACS96198-VH_huFrwk (SEQ ID NO:188). human Ig heavy chain ACS96198 has the same canonical classes as 11M14 heavy chain variable region CDRs. An example of an acceptor sequence for the 11M14 heavy chain is the human mature heavy chain variable region IMGT #IGHV3-48*03 (SEQ ID NO:189). An example of an acceptor sequence for the 11M14 light chain is the a human kappa light chain with NCBI accession code CBZ39892 (GenBank Acc. #CBZ39892-VL_huFrwk (SEQ ID NO:194). This has the same canonical classes for CDR-L1 & L2. An example of an acceptor sequence for the 11M14 light chain is the human mature light chain variable region with IMGT #IGKV1-39*01 (SEQ ID NO:195).

If more than one human acceptor antibody sequence is selected, a composite or hybrid of those acceptors can be used, and the amino acids used at different positions in the humanized light chain and heavy chain variable regions can be taken from any of the human acceptor antibody sequences used.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;
(2) is adjacent to a CDR region or within a CDR as defined by Chothia but not Kabat;
(3) otherwise interacts with a CDR region (e.g., is within about 6 Å of a CDR region), (e.g., identified by modeling the light or heavy chain on the solved structure of a homologous known immunoglobulin chain); or
(4) is a residue participating in the VL-VH interface.

In an embodiment, humanized sequences are generated using a two-stage PCR protocol that allows introduction of multiple mutations, deletions, and insertions using QuikChange site-directed mutagenesis [Wang, W. and Malcolm, B. A. (1999) BioTechniques 26:680-682)].

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, *J. Mol. Biol.* 196:901-917 (1987); Thornton & Martin, *J. Mol. Biol.* 263:800-815 (1996)). Framework residues that support antigen-binding loop conformations and play a role in fine-tuning the fit of an antibody to antigen are sometimes referred to as vernier residues (Foote & Winter, *J. Mol. Biol* 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Other framework residues that are candidates for substitution are N-terminal glutamine residues (Q) that may be replaced with glutamic acid (E) to minimize potential for pyroglutamate conversion [Y. Diana Liu, et al., 2011, J. Biol. Chem., 286: 11211-11217]. Glutamic acid (E) conversion to pyroglutamate (pE) occurs more slowly than from glutamine (Q). Because of the loss of a primary amine in the glutamine to pE conversion, antibodies become more acidic. Incomplete conversion produces heterogeneity in the antibody that can be observed as multiple peaks using charge-based analytical methods. Heterogeneity differences may indicate a lack of process control.

Exemplary humanized antibodies include humanized forms of mouse 5E20, designated Hu5E20.

The mouse antibody 5E20 comprises mature heavy and light chain variable regions having amino acid sequences comprising SEQ ID NO:4 and SEQ ID NO:10, respectively. The invention provides 7 exemplified humanized mature heavy chain variable regions: hu5E20VHv1, hu5E20VHv2, hu5E20VHv3, hu5E20VHv4, hu5E20VHv5, hu5E20VHv6, and hu5E20VHv7. The invention further provides 4 exemplified mature light chain variable regions hu5E20VLv1, hu5E20VLv2, hu5E20VLv3, and hu5E20VLv4. FIGS. 1 and 2 show alignments of the heavy chain variable region and light chain variable region, respectively, of murine 5E20 and various humanized antibodies.

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, reducing aggregation potential, and other reasons, the following 18 variable region framework positions were considered as candidates for substitutions in the 4 exemplified human mature light chain variable regions and the 7 exemplified human mature heavy chain variable regions, as further specified in the examples: L11 (L11V), L36 (Y36L), L44 (P44F), L46 (L46G), L69 (T69A), L85 (T85D), L87 (Y87F), L100 (G100Q), L106 (I106K), H5 (L5V), H40 (A40T), H42 (G42D), H44 (G44R), H49 (S49A), H77 (T77S), H83 (R83K), H93 (A93S), H94 (K94R).

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions hu5E20VHv1/hu5E20VLv1, hu5E20VHv1/hu5E20VLv2, hu5E20VHv1/hu5E20VLv3, hu5E20VHv1/hu5E20VLv4, hu5E20VHv2/hu5E20VLv1, hu5E20VHv2/hu5E20VLv2, hu5E20VHv2/hu5E20VLv3, hu5E20VHv2/hu5E20VLv4, hu5E20VHv3/hu5E20VLv1, hu5E20VHv3/hu5E20VLv2, hu5E20VHv3/hu5E20VLv3, hu5E20VHv3/hu5E20VLv4, hu5E20VHv4/hu5E20VLv1, hu5E20VHv4/hu5E20VLv2, hu5E20VHv4/hu5E20VLv3, hu5E20VHv4/hu5E20VLv4, hu5E20VHv5/hu5E20VLv1, hu5E20VHv5/hu5E20VLv2, hu5E20VHv5/hu5E20VLv3, hu5E20VHv5/hu5E20VLv4, hu5E20VHv6/hu5E20VLv1, hu5E20VHv6/hu5E20VLv2, hu5E20VHv6/hu5E20VLv3, hu5E20VHv6/hu5E20VLv4, hu5E20VHv7/hu5E20VLv1, hu5E20VHv7/hu5E20VLv2, hu5E20VHv7/hu5E20VLv3, hu5E20VHv7/hu5E20VLv4.

Exemplified antibodies include any permutations or combinations of the exemplified mature heavy chain variable regions hu5E20VHv1 (SEQ ID NO:163), hu5E20VHv2 (SEQ ID NO:164), hu5E20VHv3(SEQ ID NO: 165), hu5E20VHv4 (SEQ ID NO:166), hu5E20VHv5 (SEQ ID NO:167), hu5E20VHv6 (SEQ ID NO:168), and hu5E20VHv7 (SEQ ID NO:169), with any of the exemplified mature light chain variable regions hu5E20VLv1 (SEQ ID NO:173), hu5E20VLv2 (SEQ ID NO:174). hu5E20VLv3 (SEQ ID NO:175), and hu5E20VLv4(SEQ ID NO:176).

The invention provides variants of the 5E20 humanized antibody in which the humanized mature heavy chain variable region shows at least 90%, 95%, 96%, 97%, 98%, or 99% identity to hu5E20VHv1 (SEQ ID NO:163), hu5E20VHv2 (SEQ ID NO:164), hu5E20VHv3(SEQ ID NO:165), hu5E20VHv4 (SEQ ID NO:166), hu5E20VHv5 (SEQ ID NO:167), hu5E20VHv6 (SEQ ID NO:168), or hu5E20VHv7 (SEQ ID NO:169), and the humanized mature light chain variable region shows at least 90%, 95%, 96%, 97%, 98%, or 99% identity to hu5E20VLv1 (SEQ ID NO:173), hu5E20VLv2 (SEQ ID NO:174). hu5E20VLv3 (SEQ ID NO:175), or hu5E20VLv4(SEQ ID NO:176). In some such antibodies at least 1, 2, 3, 4, 5, 6, 7, 8, 9, 10, 11, 12, 13, 14, 15, 16, 17, or all 18 of the backmutations or other mutations in SEQ ID NOS:163-169, and SEQ ID NOS:173-176 are retained.

In some humanized 5E20 antibodies, at least one of the following positions in the VH region is occupied by the amino acid as specified: H5 is occupied by L or V, H40 is occupied by A or T, H42 is occupied by G or D, H44 is occupied by G or R, H49 is occupied by A, H77 is occupied by T or S, H83 is occupied by R or K, H93 is occupied by S, H94 is occupied by R.

In some humanized 5E20 antibodies, positions H49, H93, and H94 in the VH region are occupied by A, S. and R, respectively, as in hu5E20VHv1. In some humanized 5E20 antibodies, positions H5, H49, H77, H93, and H94 in the VH region are occupied by V, A, S, S, and R, respectively, as in hu5E20VHv2. In some humanized 5E20 antibodies, positions H5, H44, H49, H77, H93, and H94 in the VH region are occupied by V, R, A, S, S, and R, respectively, as in hu5E20VHv3. In some humanized 5E20 antibodies, positions H5, H42, H44, H49, H77, H93, and H94 in the VH region are occupied by V, D, R, A, S, S, and R, respectively, as in hu5E20VHv4. In some humanized 5E20 antibodies, positions H5, H42, H44, H49, H77, H83, H93, and H94 in the VH region are occupied by V, D, R, A, S, K, S, and R, respectively, as in hu5E20VHv5. In some humanized 5E20 antibodies, positions H5, H40, H44, H49, H77, H93, and H94 in the VH region are occupied by V, T, R, A, S, S, and R, respectively, as in hu5E20VHv6. In some humanized 5E20 antibodies, positions H5, H40, H42, H44, H49, H77, H93, and H94 in the VH region are occupied by V, T, D, R, A, S, S, and R, respectively, as in hu5E20VHv7.

In some humanized 5E20 antibodies, at least one of the following positions in the VL region is occupied by the amino acid as specified: L11 is L or V, L36 is L, L44 is F, L46 is G, L69 is A, L85 is T or D, L87 is F, L100 is G or Q, L106 is I or K. In some humanized 5E20 antibodies, positions L36, L44, L46, L69, and L87 in the VL region are occupied by L, F, G, A, and F, respectively, as in hu5E20VLv1. In some humanized 5E20 antibodies, positions L11, L36, L44, L46, L69, and L87 in the VL region are occupied by V, L, F, G, A, and F, respectively, as in 5E20VLv2. In some humanized 5E20 antibodies, positions L11, L36, L44, L46, L69, L87, L100, and L106 in the VL region are occupied by V, L, F, G, A, F, Q, and K, respectively, as in hu5E20VLv3. In some humanized 5E20 antibodies, positions L11, L36, L44, L46, L69, L85, L87, L100, and L106 in the VL region are occupied by V, L, F, G, A, D, F, Q, and K, respectively, as in hu5E20VLv4.

In some humanized 5E20 antibodies, the variable heavy chain has >85% identity to human sequence. In some humanized 5E20 antibodies, the variable light chain has >85% identity to human sequence. In some humanized 5E20 antibodies, each of the variable heavy chain and variable light chain has >85% identity to human germline sequence. In some humanized 5E20 antibodies, the three heavy chain CDRs are as defined by Kabat/Chothia Composite (SEQ ID NOS:5-7) and the three light chain CDRs are as defined by Kabat/Chothia Composite (SEQ ID NOS: 11-13).

Exemplary humanized antibodies include humanized forms of mouse 8H24, designated Hu8H24.

The mouse antibody 8H24 comprises mature heavy and light chain variable regions having amino acid sequences comprising SEQ ID NO:28 and SEQ ID NO:34, respectively. The invention provides 2 exemplified humanized mature heavy chain variable regions: hu8H24VHv1 and hu8H24VHv2. The invention further provides 2 exemplified mature light chain variable regions hu8H24VLv1 and hu8H24VLv2. FIGS. 3 and 4 show alignments of the heavy chain variable region and light chain variable region, respectively, of murine 8H24 and various humanized antibodies.

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, reducing aggregation potential, and other reasons, the following 10 variable region framework positions were considered as candidates for substitutions in the 2 exemplified human mature light chain variable regions and the 2 exemplified human mature heavy chain variable regions, as further specified in the examples: L2 (I2V), L9 (L9S), L74 (K74T), H2 (V2A), H12 (K12V), H48 (M48I), H67 (V67A), H71 (A71V), H91 (Y91F), H108 (L108T).

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions hu8H24VHv1/hu8H24VLv1, hu8H24VHv1/hu8H24VLv2, hu8H24VHv2/hu8H24VLv1, hu8H24VHv2/hu8H24VLv2.

Exemplified antibodies include any permutations or combinations of the exemplified mature heavy chain variable regions hu8H24VHv1 (SEQ ID NO:180) and hu8H24VHv2 (SEQ ID NO:181), with any of the exemplified mature light chain variable regions hu8H24VLv1 (SEQ ID NO:185) and hu8H24VLv2 (SEQ ID NO:186).

The invention provides variants of the 8H24 humanized antibody in which the humanized mature heavy chain variable region shows at least 90%, 95%, 96%, 97%, 98%, or 99% identity to hu8H24VHv1 (SEQ ID NO:180) or hu8H24VHv2 (SEQ ID NO:181) and the humanized mature light chain variable region shows at least 90%, 95%, 96%, 97%, 98%, or 99% identity to hu8H24VLv1 (SEQ ID NO:185) or hu8H24VLv2 (SEQ ID NO:186). In some such antibodies at least 1, 2, 3, 4, 5, 6, 7, 8, 9, or 10 of the backmutations or other mutations in SEQ ID NOS:180-181, and SEQ ID NOS:185-186 are retained.

In some humanized 8H24 antibodies, at least one of the following positions in the VH region is occupied by the amino acid as specified: H2 is occupied by A, H12 is occupied by K or V, H48 is occupied by I, H67 is occupied by A, H71 is occupied by V, H91 is occupied by F, H108 is occupied by T. In some humanized 8H24 antibodies, positions H2, H48, H67, H71, H91, and H108 in the VH region are occupied by A, I, A, V, F, and T, respectively, as in hu8H24VHv1. In some humanized 8H24 antibodies, positions H2, H12, H48, H67, H71, H91, and H108 in the VH region are occupied by A, V, I, A, V, F, and T, respectively, as in hu8H24VHv2.

In some humanized 8H24 antibodies, at least one of the following positions in the VL region is occupied by the amino acid as specified: L2 is V, L9 is L or S, L74 is K or T. In some humanized 8H24 antibodies, position L2 in the VL region are occupied by V, as in hu8H24VLv1. In some humanized 8H24 antibodies, positions L2, L9, and L74 in the VL region are occupied by V, S, and T, respectively, as in hu8H24VLv2.

In some humanized 8H24 antibodies, the variable heavy chain has ≥85% identity to human sequence. In some humanized 8H24 antibodies, the variable light chain has ≥85% identity to human sequence. In some humanized 8H24 antibodies, each of the variable heavy chain and variable light chain has ≥85% identity to human germline sequence. In some humanized 8H24 antibodies, the three heavy chain CDRs are as defined by Kabat/Chothia Composite (SEQ ID NOS:29-31) and the three light chain CDRs are as defined by Kabat/Chothia Composite (SEQ ID NOS:35-37).

Exemplary humanized antibodies include humanized forms of mouse 11M14, designated Hu11M14.

The mouse antibody 11M14 comprises mature heavy and light chain variable regions having amino acid sequences comprising SEQ ID NO:52 and SEQ ID NO:58, respectively. The invention provides 3 exemplified humanized mature heavy chain variable regions: hu11M14VHv1b, hu11M14VHv2b, and hu11M14VHv3b. The invention further provides 4 exemplified mature light chain variable regions hu11M14VLv1b, hu11M14VLv2b, hu11M14VLv3b, and hu11M14VLv4b. FIGS. 5 and 6 show alignments of the heavy chain variable region and light chain variable region, respectively, of murine 11M14 and various humanized antibodies.

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 7 variable region framework positions were considered as candidates for substitutions in the 4 exemplified human mature light chain variable regions and the 3 exemplified human mature heavy chain variable regions, as further specified in the examples: L43 (A43S), L48 (I48V), L71 (F71Y), L76 (N76S), H49 (S49A), H80 (L80G), H82c (L82cG).

The following variable region CDR position was considered as a candidate for substitution in the 4 exemplified human mature light chain variable regions, as further specified in the examples: L54 (L54G, L54I). In some humanized 11M14 antibodies, Kabat-Chothia Composite CDR-L2 has an amino acid sequence comprising SEQ ID NO:72. In some humanized 11M14 antibodies, Kabat-Chothia Composite CDR-L2 has an amino acid sequence comprising SEQ ID NO:73.

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions hu11M14VHv1b/hu11M14VLv1b, hu11M14VHv1b/hu11M14VLv2b, hu11M14VHv1b/hu11M14VLv3b, hu11M14VHv1b/hu11M14VLv4b, hu11M14VHv2b/hu11M14VLv1b, hu11M14VHv2b/hu11M14VLv2b, hu11M14VHv2b/hu11M14VLv3b, hu11M14VHv2b/hu11M14VLv4b, hu11M14VHv3b/hu11M14VLv1b, hu11M14VHv3b/hu11M14VLv2b, hu11M14VHv3b/hu11M14VLv3b, hu11M14VHv3b/hu11M14VLv4b.

Exemplified antibodies include any permutations or combinations of the exemplified mature heavy chain variable regions hu11M14VHv1b (SEQ ID NO:190), hu11M14VHv2b (SEQ ID NO:191), and hu11M14VHv3b (SEQ ID NO:192) with any of the exemplified mature light chain variable regions hu11M14VLv1b (SEQ ID NO:196), hu11M14VLv2b (SEQ ID NO:197), hu11M14VLv3b (SEQ ID NO:198), and hu11M14VLv4b (SEQ ID NO:199).

The invention provides variants of the 11M14 humanized antibody in which the humanized mature heavy chain variable region shows at least 90%, 95%, 96%, 97%, 98%, or 99% identity to hu11M14VHv1b (SEQ ID NO:190), hu11M14VHv2b (SEQ ID NO:191), or hu11M14VHv3b (SEQ ID NO:192) and the humanized mature light chain variable region shows at least 90%, 95%, 96%, 97%, 98%, or 99% identity to hu11M14VLv1b (SEQ ID NO:196), hu11M14VLv2b (SEQ ID NO:197), hu11M14VLv3b (SEQ ID NO:198), or hu11M14VLv4b (SEQ ID NO:199). In some such antibodies at least 1, 2, 3, 4, 5, 6, 7, or all 8 of the positions subject to backmutations or other mutations in SEQ ID NOS:190-192, and SEQ ID NOS:196-199 are likewise backmutated or otherwise mutated.

In some humanized 11M14 antibodies, at least one of the following positions in the VH region is occupied by the amino acid as specified: H49 is occupied by A, H80 is occupied by L or G, H82c is occupied by L or G. In some humanized 11M14 antibodies, position H49 in the VH region is occupied by A, as in hu11M14VHv1b. In some humanized 11M14 antibodies, positions H49 and H82c in the VH region are occupied by A and G, respectively, as in hu11M14VHv2b. In some humanized 11M14 antibodies, positions H49 and H80 in the VH region are occupied by A and G, respectively, as in hu11M14VHv3b.

In some humanized 11M14 antibodies, at least one of the following positions in the VL region is occupied by the amino acid as specified: L43 is A or S, L48 is V, L54 is L, G, or I, L71 is Y, L76 is N or S. In some humanized 11M14 antibodies, positions L48 and L71 in the VL region are occupied by V and Y respectively, as in hu11M14VLv1b. In some humanized 11M14 antibodies, positions L43, L48, L71, and L76 in the VL region are occupied by S, V, Y, and S, respectively, as in hu11M14VLv2b. In some humanized 11M14 antibodies, positions L43, L48, L54, L71, and L76 in the VL region are occupied by S, V, G, Y, and S, respectively, as in hu11M14VLv3b. In some humanized 11M14 antibodies, positions L43, L48, L54, L71, and L76in the VL region are occupied by S, V, I, Y, and S, respectively, as in hu11M14VLv4b.

The heavy chain variable region of any of the above referenced antibodies can be modified to further reduce immunogenicity. For example, in some of the humanized antibodies position H80 in the VH region is occupied by G. For example, in some of the humanized antibodies, position H82c in the VH region is occupied by G. The light chain variable region of any of the above referenced antibodies can be modified to further reduce immunogenicity. For example, in some of the humanized antibodies position L54 in the VL region is occupied by G or I.

In some of the humanized antibodies, position H82c in the VH region is occupied by G, as in hu11M14VHv3b. In some of the humanized antibodies, position L54 in the VL region is occupied by G, as in hu11M14VLv3b. In some of the humanized antibodies, position L54 in the VL region is occupied by I, as in hu11M14VLv4b.

In some humanized 11M14 antibodies, Kabat-Chothia Composite CDR-L2 has an amino acid sequence comprising SEQ ID NO:72. In some humanized 11M14 antibodies, Kabat-Chothia Composite CDR-L2 has an amino acid sequence comprising SEQ ID NO:73.

In some humanized 11M14 antibodies, the variable heavy chain has ≥85% identity to human sequence. In some humanized 11M14 antibodies, the variable light chain has ≥85% identity to human sequence. In some humanized 11M14 antibodies, each of the variable heavy chain and variable light chain has ≥85% identity to human germline sequence. In some humanized 11M14 antibodies, the three heavy chain CDRs are as defined by Kabat/Chothia Composite (SEQ ID NOS:53-55) and the three light chain CDRs are as defined by Kabat/Chothia Composite (SEQ ID NOS: 59-61), except that position L54 can be L, G, or I.

The CDR regions of such humanized 5E20, 8H24, 11M14, 5M13, 2F18, 2P22, 6B15, 2C14, 9N18, and 4N2 antibodies can be identical or substantially identical to the CDR regions of 5E20, 8H24, 11M14, 5M13, 2F18, 2P22, 6B15, 2C14, 9N18, or 4N2. The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu5E20, Hu8H24, or Hu11M14 heavy and light chains by a small number (e.g., typically no more than 1, 2, 3, 5, 10, or 15) of replacements, deletions or insertions. Such differences are usually in the framework but can also occur in the CDRs.

A possibility for additional variation in humanized 5E20, 8H24, 11M14, 5M13, 2F18, 2P22, 6B15, 2C14, 9N18, and 4N2 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in humanized 5E20, 8H24, 11M14, 5M13, 2F18, 2P22, 6B15, 2C14, 9N18, and 4N2 variants (whether or not conservative) have no substantial effect on the binding affinity or potency of the humanized mAb, that is, its ability to bind to sortilin.

Figure 21:
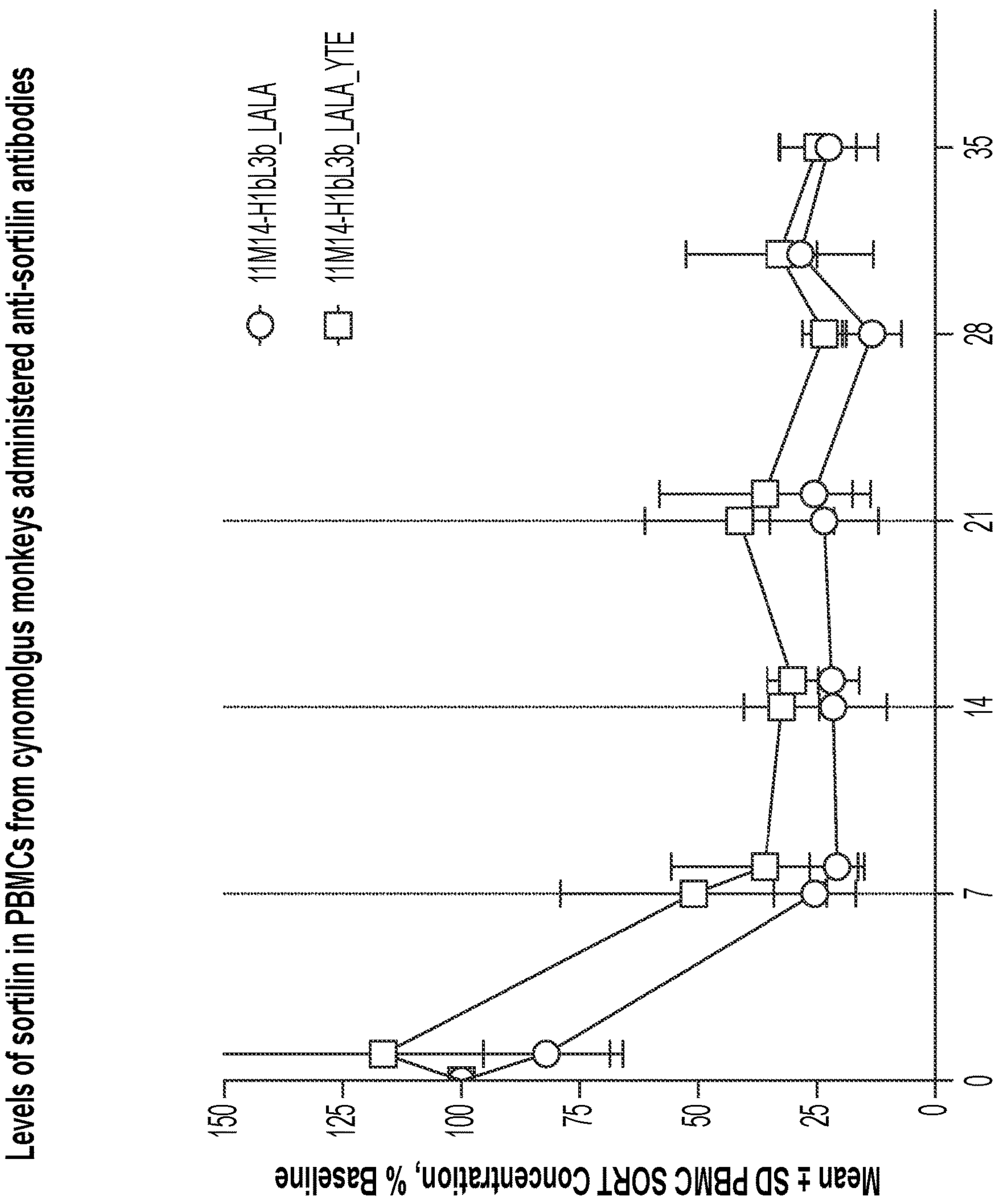
FIG. 21 depicts sortilin levels in cynomolgus monkey PBMCs after 4 weekly repeat 60 mg/kg doses of hu11M14 H1bL3b_IgG1_LALA or hu11M14 H1bL3b_IgG1_LALA_YTE. Mean±SD Sortilin levels in cynomolgus monkey PBMCs as a percent of Baseline with 4 weekly doses of 60 mg/kg anti-sortilin antibodies. N=4 animals per group. Sortilin levels normalized to total protein levels.

Humanized variants hu11M14 H1bL3b_IgG1 LALA, hu11M14 H1bL3b_IgG1 LALA_YTE, hu8H24 H1L2_IgG1_LALA, and hu5E20 H7L4_IgG1_LALA increase plasma and CSF progranulin levels in non-human primates (Examples 21-22, FIGS. 15-16 and 19-20). Humanized variants hu11M14 H1bL3b_IgG1 LALA_and hu11M14 H1bL3b_IgG1 LALA_YTE reduce sortilin levels in PBMCs from non-human primates (Example 23, FIG. 21). hu11M14 H1bL3b_IgG1 LALA_-YTE shows improved pharmacokinetics and plasma pharmacodynamics profile over hu11M14 H1bL3b_IgG1 LALA (Example 23, FIGS. 17-18).

Hu11M14VHv1bVLv3b is also referred to as hu11M14H1bL3b. Hu5E20VHv7VLv4 is also referred to as hu5E20H7L4. Hu8H24VHv1VLv2 is also referred to as hu8H24H1L2.

D. Chimeric and Veneered Antibodies

The invention further provides chimeric and veneered forms of non-human antibodies, particularly the 5E20, 8H24, 11M14, 5M13, 2F18, 2P22, 6B15, 2C14, 9N18, and 4N2 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 5E20, 8H24, 11M14, 5M13, 2F18, 2P22, 6B15, 2C14, 9N18, and 4N2 antibodies are included in the invention.

E. Human Antibodies

Human antibodies specifically binding to sortilin or a fragment thereof (e.g., a peptide comprising or consisting of amino acid sequence FTESFLT (SEQ ID NO:202), ESFL (SEQ ID NO:203), DGCILGYKEQFL) (SEQ ID NO:204), PSICLCSLEDFL (SEQ ID NO:205), E(S/Q/D)FL (SEQ ID NO:206), RTEFGMAIGP) (SEQ ID NO:213), WGFTESFLTS (SEQ ID NO:214), or an epitope defined by residues D74, R76, F97, K110, Y535, L560, and E557 of the sortilin ECD of SEQ ID NO:215, or to an epitope defined by residues K110, Y535, E557, T561, Q563, D74, P510, S558, F559, and L560 of the sortilin ECD of SEQ ID NO:215, or to an epitope defined by residues E557, S558, F559, L560, P510, and Y535 of the sortilin ECD of SEQ ID NO:215, are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for a particular epitope specificity by using only a fragment of sortilin, such as a sortilin fragment comprising or consisting of an amino acid sequence of FTESFLT (SEQ ID NO:202), ESFL (SEQ ID NO:203), DGCILGYKEQFL) (SEQ ID NO:204), PSICLCSLEDFL (SEQ ID NO:205), E(S/Q/D)FL (SEQ ID NO:206), RTEFGMAIGP) (SEQ ID NO:213), or WGFTESFLTS (SEQ ID NO:214), as the target antigen, and/or by screening antibodies against a collection of sortilin variants, such as sortilin variants of SEQ ID NOs: 216-243, or such as sortilin variants containing various mutations within amino acid residues 588-594 or 590-593 or 632-643 or 663-674 or 167-176 or 586-595 of SEQ ID NO:1.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397; 5,874,299; 5,814,318; 5,789,650; 5,770,429; 5,661,016; 5,633,425; 5,625,126; 5,569,825; 5,545,806; Neuberger, Nat. Biotechnol. 14:826 (1996); and Kucherlapati, WO 91/10741 (1991)) phage display methods (see, e.g., Dower et al., WO 91/17271; McCafferty et al., WO 92/01047; U.S. Pat. Nos. 5,877,218; 5,871,907; 5,858,657; 5,837,242; 5,733,743; and 5,565,332); and methods described in WO 2008/081008 (e.g., immortalizing memory B cells isolated from humans, e.g., with EBV, screening for desired properties, and cloning and expressing recombinant forms).

F. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. Numbering conventions for constant regions include EU numbering (Edelman, G. M. et al., Proc. Natl. Acad. USA, 63, 78-85 (1969)), Kabat numbering (Kabat, *Sequences of Proteins of Immunological Interest* (National Institutes of Health, Bethesda, MD, 1991, IMGT unique numbering (Lefranc M.-P. et al., IMGT unique numbering for immunoglobulin and T cell receptor constant domains and Ig superfamily C-like domains, Dev. Comp. Immunol., 29, 185-203 (2005), and IMGT exon numbering (Lefranc, supra).

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγTRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine. In some antibodies, the isotype is human IgG2 or IgG4.

In some antibodies the 'L ALA' double mutation (Leu234Ala together with. Leu235Ala) is used for diminished effector functions (Lund, J., et al. (1992) *Mol. Immunol.,* 29, 53-59; Tamm and Schmidt, 1997, Int Rev Immunol 16(1-2):57-85). Fc variant L234A/L235A (LALA) (numbering according to IU nomenclature) mutant has been shown to have either eliminated or reduced interaction with FcγRs (FcγRIa, FcγRIIa, FcγRIIa and FcγRIIIa) and exhibit significantly reduced effector function. Additionally, Fc LALA mutants have also been shown to have diminished interaction with complement proteins resulting in reduced complement-dependent cytotoxicity (CDC). Exemplary antibody heavy chain sequences incorporating the LALA mutations are SEQ ID ID NO:244, SEQ ID NO:246, SEQ ID NO:248, SEQ ID NO:250, SEQ ID NO:251, and SEQ ID NO:252.

In some antibodies, the "YTE" (M252T/S254T/T256E) (numbering according to Eu nomenclature) mutations in the Fe region are used (W. F. Dall'Acqua et al. 2006 J. Biol. Chem. 281:23514-23). YTE mutant has been shown to have enhanced binding/interaction to the neonatal Fc receptor (FcRn); thereby leading to antibody half-life extension in circulation. In some antibodies, 'LALA' double mutation and YTE mutations are used. Exemplary antibody heavy chain sequences incorporating the LALA and YTE mutations are SEQ ID ID NO:244, SEQ ID NO:246, and SEQ ID NO:248.

Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3with or without the C-terminal lysine. Reference to a human constant region includes a constant region with any natural allotype or any permutation of residues occupying positions in natural allotypes.

G. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions.

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mcl for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells or induced pluripotent stem cells (iPSCs), and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 ug or 100 ug per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809).

IV. Active Immunogens

An agent used for active immunization serves to induce in a patient the same types of antibody described in connection with passive immunization above. Agents used for active immunization can be the same types of immunogens used for generating monoclonal antibodies in laboratory animals, e.g., a peptide of 3-15 or 3-12 or 5-12, or 5-8 contiguous amino acids from a region of sortilin corresponding to residues 588-594 or 590-593 or 632-643 or 663-674 or 167-176 of 586-595 of SEQ ID NO:1, such as, for example, a sortilin peptide including or consisting of residues 588-594 or 590-593 or 632-643 or 663-674 or 167-176 or 586-595 of SEQ ID NO:1) or a sortilin peptide comprising or consisting of amino acid sequence FTESFLT (SEQ ID NO:202), a sortilin peptide comprising or consisting of amino acid sequence ESFL (SEQ ID NO:203), a sortilin peptide comprising or consisting of amino acid sequence DGCILGYKEQFL (SEQ ID NO:204), or a sortilin peptide comprising or consisting of amino acid sequence PSICLCSLEDFL (SEQ ID NO:205), or a sortilin peptide comprising or consisting of amino acid sequence E(S/Q/D)FL (SEQ ID NO:206), a sortilin peptide comprising or consisting of amino acid sequence RTEFGMAIGP) (SEQ ID NO:213), a sortilin peptide comprising or consisting of amino acid sequence WGFTESFLTS (SEQ ID NO:214), a sortilin peptide comprising or consisting of some or all of the amino acid residues D74, R76, F97, K110, Y535, L560, and E557 of the sortilin ECD of SEQ ID NO:215, a sortilin peptide comprising or consisting of some or all of amino acid residues K110, Y535, E557, T561, Q563, D74, P510, S558, F559, and L560 of the sortilin ECD of SEQ ID NO:215, or a sortilin peptide comprising or consisting of some or all of the amino acid residues E557, S558, F559, L560, P510, and Y535 of the sortilin ECD of SEQ ID NO:215. For conformational epitopes with widely separated residues, peptides can be selected against some of the residues sufficiently proximate within one another to form a linear epitope. For inducing antibodies binding to the same or overlapping epitope as 5E20, 8H24, 11M14, 5M13, 2F18, 2P22, 6B15, 2C14, 9N18, and 4N2, the epitope specificity of these antibodies can be mapped (e.g., by testing binding to a series of overlapping peptides spanning sortilin). A fragment of sortilin consisting of or including or overlapping the epitope can then be used as an immunogen.

The heterologous carrier and adjuvant, if used may be the same as used for generating monoclonal antibody, but may also be selected for better pharmaceutical suitability for use in humans. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-S-glycerine cysteine ($Pam_3Cys$), mannan (a mannose polymer), or glucan (a $\beta 1\rightarrow 2$ polymer)), cytokines (e.g., IL-1, IL-1 alpha and $\beta$ peptides, IL-2, 7-INF, IL-10, GM-CSF), and chemokines (e.g., MIP1-α and β, and RANTES). Immunogens may be linked to the carriers with or without spacers amino acids (e.g., gly-gly). Additional carriers include virus-like particles. Virus-like particles (VLPs), also called pseudovirions or virus-derived particles, represent subunit structures composed of multiple copies of a viral capsid and/or envelope protein capable of self-assembly into VLPs of defined spherical symmetry in vivo. (Powilleit, et al., (2007) PLoS ONE 2(5):e415.) Alternatively, peptide immunogens can be linked to at least one artificial T-cell epitope capable of binding a large proportion of MHC Class II molecules., such as the pan DR epitope ("PADRE"). PADRE is described in U.S. Pat. No. 5,736,142, WO 95/07707, and Alexander J et al, Immunity, 1:751-761 (1994). Active immunogens can be presented in multimeric form in which multiple copies of an immunogen and/or its carrier are presented as a single covalent molecule.

Fragments are often administered with pharmaceutically acceptable adjuvants. The adjuvant increases the titer of induced antibodies and/or the binding affinity of induced antibodies relative to the situation if the peptide were used alone. A variety of adjuvants can be used in combination with an immunogenic fragment of sortilin to elicit an immune response. Some adjuvants augment the intrinsic response to an immunogen without causing conformational changes in the immunogen that affect the qualitative form of the response. Some adjuvants include aluminum salts, such as aluminum hydroxide and aluminum phosphate, 3 De-O-acylated monophosphoryl lipid A (MPL™) (see GB 2220211 (RIBI ImmunoChem Research Inc., Hamilton, Montana, now part of Corixa). Stimulon™ QS-21 is a triterpene glycoside or saponin isolated from the bark of the *Quillaja Saponaria* Molina tree found in South America (see Kensil et al., in *Vaccine Design: The Subunit and Adjuvant Approach* (eds. Powell & Newman, Plenum Press, NY, 1995); U.S. Pat. No. 5,057,540), (Aquila BioPharmaceuticals, Framingham, MA; now Antigenics, Inc., New York, NY). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Ribi adjuvants are oil-in-water emulsions. Ribi contains a metabolizable oil (squalene) emulsified with saline containing Tween 80. Ribi also contains refined mycobacterial products which act as immunostimulants and bacterial monophosphoryl lipid A. Another adjuvant is CpG (WO 98/40100). Adjuvants can be administered as a component of a therapeutic composition with an active agent or can be administered separately, before, concurrently with, or after administration of the therapeutic agent.

Analogs of natural fragments of sortilin that induce antibodies against sortilin can also be used. For example, one or more or all L-amino acids can be substituted with D amino acids in such peptides. Also the order of amino acids can be reversed (retro peptide). Optionally a peptide includes all D-amino acids in reverse order (retro-inverso peptide). Peptides and other compounds that do not necessarily have a significant amino acid sequence similarity with sortilin peptides but nevertheless serve as mimetics of sortilin peptides and induce a similar immune response. Anti-idiotypic antibodies against monoclonal antibodies to sortilin as described above can also be used. Such anti-Id antibodies mimic the antigen and generate an immune response to it (see Essential Immunology, Roit ed., Blackwell Scientific Publications, Palo Alto, CA 6th ed., p. 181).

Peptides (and optionally a carrier fused to the peptide) can also be administered in the form of a nucleic acid encoding the peptide and expressed in situ in a patient. A nucleic acid segment encoding an immunogen is typically linked to regulatory elements, such as a promoter and enhancer that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. Antibodies can also be administered in the form of nucleic acids encoding the antibody heavy and/or light chains. If both heavy and light chains are present, the chains are preferably linked as a single chain antibody. Antibodies for passive administration can also be prepared e.g., by affinity chromatography from sera of patients treated with peptide immunogens.

The DNA can be delivered in naked form (i.e., without colloidal or encapsulating materials). Alternatively a number of viral vector systems can be used including retroviral systems (see, e.g., Lawrie and Tumin, Cur. Opin. Genet. Develop. 3, 102-109 (1993)) including retrovirus derived vectors such MMLV, HIV-1, and ALV; adenoviral vectors {see, e.g., Bett et al, J. Virol. 67, 591 1 (1993)); adeno-associated virus vectors {see, e.g., Zhou et al., J. Exp. Med. 179, 1867 (1994)), lentiviral vectors such as those based on HIV or FIV gag sequences, viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., Human Gene Therapy 6, 325-333 (1995); Woo et al, WO 94/12629 and Xiao & Brandsma, Nucleic Acids. Res. 24, 2630-2622 (1996)).

DNA encoding an immunogen, or encoding the antibody heavy and/or light chains, or a vector containing the same, can be packaged into liposomes. Suitable lipids and related analogs are described by U.S. Pat. Nos. 5,208,036, 5,264,618, 5,279,833, and 5,283,185. Vectors and DNA encoding an immunogen or encoding the antibody heavy and/or light chains can also be adsorbed to or associated with particulate carriers, examples of which include polymethyl methacrylate polymers and polylactides and poly(lactide-co-glycolides), (see, e.g., McGee et al., J. Micro Encap. 1996).

Vectors or segments therefrom encoding the antibody heavy and/or light chains can be incorporated in cells ex vivo, for example to cells explanted from an individual patient (e.g., lymphocytes, bone marrow aspirates, tissue biopsy) or universal donor hematopoietic stem cells, followed by reimplantation of the cells into a patient, usually after selection for cells which have incorporated the transgenes. (see, e.g., WO 2017/091512). Exemplary patient-derived cells include patient derived induced pluripotent stem cells (iPSCs) or other types of stem cells (embryonic, hematopoietic, neural, or mesenchymal).

A vector or segment therefrom encoding the antibody heavy and/or light chains can be introduced into any region of interest in cells ex vivo, such as an albumin gene or other safe harbor gene. Cells incorporating the vector can be implanted with or without prior differentiation. Cells can be implanted into a specific tissue, such as a secretory tissue or a location of pathology, or systemically, such as by infusion into the blood. For example, cells can be implanted into a secretory tissue of a patient, such as the liver, optionally with prior differentiation to cells present in that tissue, such as hepatocytes in the case of a liver. Expression of the antibody in the liver results in secretion of the antibody to the blood.

H. Antibody Screening Assays

Antibodies can be initially screened for the intended binding specificity as described above. Active immunogens can likewise be screened for capacity to induce antibodies with such binding specificity. In this case, an active immunogen is used to immunize a laboratory animal and the resulting sera tested for the appropriate binding specificity.

Antibodies having the desired binding specificity can then be tested in cellular and animal models. An exemplary cellular model are HEK 293 cells expressing recombinant huSortilin on their surface. Another exemplary cellular model are U251MG cells (human glioblastoma cells line) which endogenously express sortilin on their cell surface. Human cellular models include IPSC-derived cortical neurons from or microglia expressing FTD-GRN mutations. Exemplary mouse cellular models are primary neurons from GRN+/− and/or GRN−/− transgenic mice+AAV-TDP43CT-GFP (Chang, M. C. et al., J. Exp. Med. 2017; 214 (9): 2611-2628). TDP43CT forms cytoplasmic clusters and GRN−/− neurons accumulated about 40% higher levels of TDP43CT than WT neuron. This phenotype was rescued with addition of recombinant PRGN (10 μM).

The activity of antibodies or active agents can be assessed by various criteria including increase in extracellular progranulin and inhibition or delay or behavioral deficits. Active immunogens can also be tested for induction of antibodies in the sera. Both passive and active immunogens can be tested for passage of antibodies across the blood brain barrier into the brain of a wild type or transgenic animal. Antibodies or fragments inducing an antibody can also be tested in non-human primates without disease or that naturally or through induction develop symptoms of diseases characterized by changes in progranulin levels; for example as in Examples 21-22 and FIGS. 14-21. Tests on an antibody or active agent are usually performed in conjunction with a control in which a parallel experiment is conduct except that the antibody or active agent is absent (e.g., replaced by vehicle). Reduction, delay or inhibition of signs or symptoms disease attributable to an antibody or active agent under test can then be assessed relative to the control.

V. Patients Amenable to Treatment

Changes in progranulin levels have been found in several diseases including frontotemporal dementia, Alzheimer's disease, Parkinson's disease, anyotrophic lateral sclerosis, Batten disease, neurodegenerative disorders, and neurodegenerative disorders associated with aging. The present regimen can also be used in treatment or prophylaxis of any of these diseases. Because of the widespread association between neurological diseases and conditions and changes in progranulin levels, the present regimen can be used in treatment or prophylaxis of any subject showing reduced levels of progranulin (e.g., in the plasma or CSF) compared with a mean value in individuals without neurological disease. The present regimen can also be used in treatment or prophylaxis of neurological disease in individuals having a mutation in progranulin associated with neurological disease. The present methods are particularly suitable for treatment or prophylaxis of frontotemporal dementia. In some embodiments, the methods further comprise detecting, measuring, and/or monitoring progranulin levels, for example as in Example 8.

Patients amenable to treatment include individuals at risk of disease but not showing symptoms, as well as patients presently showing symptoms. Patients at risk of disease include those having a known genetic risk of disease. Such individuals include those having relatives who have experienced this disease, and those whose risk is determined by analysis of genetic or biochemical markers. Genetic markers of risk include mutations in progranulin, such as FTD-GRN as discussed above. Individuals presently suffering from frontotemporal dementia can be recognized by PET imaging, from characteristic dementia, as well as the presence of risk factors described above. In addition, a number of diagnostic tests are available for identifying individuals who have frontotemporal dementia. These include measurement of CSF and plasma progranulin levels.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody levels over time. If the response falls, a booster dosage is indicated.

I. Nucleic Acids

The invention further provides nucleic acids encoding any of the heavy and light chains described above (e.g., SEQ ID NOS:4, 10, 24-25, 28, 34, 48-49, 52, 58, 78, 84, 90, 96, 102, 108, 114, 120, 126, 132, 138, 144, 150, 156, 163-169, 173-176, 180-181, 185-186, 190-192, 196-199). Exemplary nucleotide sequences include SEQ ID NOS:2, 8, 26, 32, 50, 56, 76, 82, 88, 94, 100, 106, 112, 118, 124, 130, 136, 142, 148, and 154. Optionally, such nucleic acids further encode a signal peptide and can be expressed with the signal peptide linked to the variable region. Coding sequences of nucleic acids can be operably linked with regulatory sequences to ensure expression of the coding sequences, such as a promoter, enhancer, ribosome binding site, transcription termination signal, and the like. The regulatory sequences can include a promoter, for example, a prokaryotic promoter or a eukaryotic promoter. The nucleic acids encoding heavy or light chains can be codon-optimized for expression in a host cell. The nucleic acids encoding heavy and light chains can encode a selectable gene. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

J. Conjugated Antibodies

Conjugated antibodies that specifically bind to antigens, such as sortilin, are useful in detecting the presence of sortilin; monitoring and evaluating the efficacy of therapeutic agents being used to treat patients diagnosed with a disease or disorder associated with changes in progranulin levels, frontotemporal dementia, Alzheimer's disease, Parkinson's disease, amyotrophic lateral sclerosis, Batten disease, a neurodegenerative disorder, or a neurodegenerative disorders associated with aging; increasing extracellular progranulin levels, or treating or effecting prophylaxis of disease or disorder associated with changes in progranulin levels, frontotemporal dementia, Alzheimer's disease, Parkinson's disease, amyotrophic lateral sclerosis, Batten disease, a neurodegenerative disorder, or a neurodegenerative disorder associated with aging in a patient. For example, such antibodies can be conjugated with other therapeutic moieties, other proteins, other antibodies, and/or detectable labels. See WO 03/057838; U.S. Pat. No. 8,455,622. Such therapeutic moieties can be any agent that can be used to treat, combat, ameliorate, prevent, or improve an unwanted condition or disease in a patient, such as disease or disorder associated with changes in progranulin levels, frontotemporal dementia, Alzheimer's disease, Parkinson's disease, amyotrophic lateral sclerosis, Batten disease, a neurodegenerative disorder, or a neurodegenerative disorder associated with aging. In some embodiments, the methods further comprise detecting, measuring, and/or monitoring progranulin levels, for example as in Example 8.

Conjugated therapeutic moieties can include, neurotrophic agents, neuroprotective agents, radiotherapeutic agents, radioactive (radiopharmaceuticals), fluorescent, paramagnetic tracers, ultrasound contrast agents, immunomodulators, or any biologically active agents that facilitate or enhance the activity of the antibody, or modify bioavailability, and distribution in the body or within organs. A neurotrophic agent can be any agent, including chemical or proteinaceous agents, that promotes neuron maintenance, growth, or differentiation. A neuroprotective agent can be agent, including chemical or proteinaceous agents, that protects neurons from acute insult or degenerative processes. An immunomodulator can be any agent that stimulates or inhibits the development or maintenance of an immunologic response. A radiotherapeutic agent can be any molecule or compound that emits radiation. If such therapeutic moieties are coupled to a sortilin-specific antibody, such as the antibodies described herein, the coupled therapeutic moieties will have a specific affinity for sortilin- and progranulin-related disease-affected cells over normal cells. In addition, smaller quantities of the therapeutic moieties can be used.

Some such antibodies can be modified to act as immunotoxins. See, e.g., U.S. Pat. No. 5,194,594. For example, ricin, a cellular toxin derived from plants, can be coupled to antibodies by using the bifunctional reagents S-acetylmercaptosuccinic anhydride for the antibody and succinimidyl 3-(2-pyridyldithio)propionate for ricin. See Pietersz et al., Cancer Res. 48(16):4469-4476 (1998). The coupling results in loss of B-chain binding activity of ricin, while impairing neither the toxic potential of the A-chain of ricin nor the activity of the antibody. Similarly, saporin, an inhibitor of ribosomal assembly, can be coupled to antibodies via a disulfide bond between chemically inserted sulfhydryl groups. See Polito et al., *Leukemia* 18:1215-1222 (2004).

Some such antibodies can be linked to radioisotopes. Examples of radioisotopes include, for example, yttrium$^{90}$ (90Y), indium$^{111}$ (111In), $^{131}$I, $^{99}$mTc, radiosilver-111, radiosilver-199, and Bismuth$^{213}$. Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.,* 48 Suppl 1:S91-S95 (2001).

Some such antibodies can be linked to other therapeutic moieties. Such therapeutic moieties can be, for example, cytotoxic, cytostatic, neurotrophic, or neuroprotective. For example, antibodies can be conjugated with toxic chemotherapeutic drugs such as maytansine, geldanamycin, tubulin inhibitors such as tubulin binding agents (e.g., auristatins), or minor groove binding agents such as calicheamicin. Other representative therapeutic moieties include agents known to be useful for treatment, management, or amelioration of a disease or disorder associated with changes in progranulin levels, frontotemporal dementia, Alzheimer's disease, Parkinson's disease, amyotrophic lateral sclerosis, Batten disease, a neurodegenerative disorder, or a neurodegenerative disorder associated with aging.

Antibodies can also be coupled with other proteins. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., *J. Biol. Chem.* 282:3196-3204 (2007); Bertschinger et al., *Protein Eng. Des. Sel.* 20:57-68 (2007); Schlatter et al., *MAbs.* 4:497-508 (2011); Banner et al., *Acta. Crystallogr. D. Biol. Crystallogr.* 69(Pt6):1124-1137 (2013); and Brack et al., *Mol. Cancer Ther.* 13:2030-2039 (2014).

The antibodies disclosed herein can also be coupled or conjugated to one or more other antibodies (e.g., to form antibody heteroconjugates). Such other antibodies can bind to different epitopes within sortilin or can bind to a different target antigen.

Antibodies can also be coupled with a detectable label. Such antibodies can be used, for example, for detect sortilin in in a subject having or being treated for a disease or disorder associated with changes in progranulin levels, frontotemporal dementia, Alzheimer's disease, Parkinson's disease, amyotrophic lateral sclerosis, Batten disease, a neurodegenerative disorder, or a neurodegenerative disorder associated with aging, and/or for assessing efficacy of treatment. Such antibodies are particularly useful for performing such determinations in subjects having or being susceptible to of a disease or disorder associated with changes in progranulin levels, frontotemporal dementia, Alzheimer's disease, Parkinson's disease, anyotrophic lateral sclerosis, Batten disease, a neurodegenerative disorder, or a neurodegenerative disorder associated with aging, or in appropriate biological samples obtained from such subjects. In some embodiments, the methods further comprise detecting, measuring, and/or monitoring progranulin levels, for example as in Example 8. Representative detectable labels that may be coupled or linked to an antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as radiosilver-111, radiosilver-199, Bismuth$^{213}$, iodine ($^{131}$I, $^{125}$I, $^{123}$I, $^{121}$I,), carbon ($^{14}$C), sulfur ($^{5}$S), tritium ($^{3}$H), indium ($^{115}$In, $^{113}$In, $^{112}$In, $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies; non-radioactive paramagnetic metal ions; and molecules that are radiolabelled or conjugated to specific radioisotopes.

Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.,* 48 Suppl 1:S91-S95 (2001).

Therapeutic moieties, other proteins, other antibodies, and/or detectable labels may be coupled or conjugated, directly or indirectly through an intermediate (e.g., a linker), to an antibody of the invention. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., *Immunol. Rev.,* 62:119-58 (1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

VI. Pharmaceutical Compositions and Methods of Use

In prophylactic applications, an antibody or agent for inducing an antibody or a pharmaceutical composition the same is administered to a patient susceptible to, or otherwise at risk of a disease (e.g., frontotemporal dementia) in regimen (dose, frequency and route of administration) effective to reduce the risk, lessen the severity, or delay the onset of at least one sign or symptom of the disease. In particular, the regimen is preferably effective to increase extracellular progranulin levels in the brain, or plasma and/or inhibit/or delay development of behavioral deficits. In therapeutic applications, an antibody or agent to induce an antibody is administered to a patient suspected of, or already suffering from a disease (e.g., frontotemporal dementia) in a regimen (dose, frequency and route of administration) effective to ameliorate or at least inhibit further deterioration of at least one sign or symptom of the disease. In particular, the regimen is preferably effective to increase or at least normalize levels of progranulin and/or behavioral deficits.

A regimen is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the $p<0.05$ or 0.01 or even 0.001 level.

Effective doses of vary depending on many different factors, such as means of administration, target site, physiological state of the patient, whether the patient is a FTD-GRN carrier, whether the patient is human or an animal, other medications administered, and whether treatment is prophylactic or therapeutic.

Exemplary dosage ranges for antibodies are from about 0.01 to 60 mg/kg, or from about 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimen entail administration once per every two weeks or once a month or once every 3 to 6 months.

The amount of an agent for active administration varies from 0.1-500 μg per patient and more usually from 1-100 or 1-10 μg per injection for human administration. The timing of injections can vary significantly from once a day, to once a year, to once a decade. A typical regimen consists of an immunization followed by booster injections at time intervals, such as 6 week intervals or two months. Another regimen consists of an immunization followed by booster injections 1, 2 and 12 months later. Another regimen entails an injection every two months for life. Alternatively, booster injections can be on an irregular basis as indicated by monitoring of immune response. Exemplary doses and dosing regimens for non-human primates are in Examples 21-22, and FIGS. 14-21.

Antibodies or agents for inducing antibodies are preferably administered via a peripheral route (i.e., one in which an administered or induced antibody crosses the blood brain barrier to reach an intended site in the brain.) Routes of administration include topical, intravenous, oral, subcutaneous, intraarterial, intracranial, intrathecal, intraperitoneal, intranasal, intraocular, intradermal, or intramuscular. Some routes for administration of antibodies are intravenous and subcutaneous. Some routes for active immunization are subcutaneous and intramuscular. This type of injection is most typically performed in the arm or leg muscles. In some methods, agents are injected directly into a particular tissue where deposits have accumulated, for example intracranial injection.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The present regimen can be administered in combination with another agent effective in treatment or prophylaxis of the disease being treated. For example, in the case of frontotemporal dementia, the present regimen can be combined with an antidepressant, such as trazodone and selective serotonin reuptake inhibitors (e.g., citalopram (Celexa), paroxetine (Paxil) or sertraline (Zoloft)); and/or an antipsychotic medication (e.g., such as olanzapine (Zyprexa) or quetiapine (Seroquel), Alector's AL001, or antibodies as described in published US patent application US20170267761 A1). In some embodiments, the methods further comprise detecting, measuring, and/or monitoring progranulin levels, for example as in Example 8.

Antibodies are administered in an effective regimen meaning a dosage, route of administration and frequency of administration that delays the onset, reduces the severity, inhibits further deterioration, and/or ameliorates at least one sign or symptom of a disorder being treated. If a patient is already suffering from a disorder, the regimen can be referred to as a therapeutically effective regimen. If the patient is at elevated risk of the disorder relative to the general population but is not yet experiencing symptoms, the regimen can be referred to as a prophylactically effective regimen. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody are 0.1-60 mg/kg (e.g., 0.5, 3, 10, 30, or 60 mg/kg), or 0.5-5 mg/kg body weight (e.g., 0.5, 1, 2, 3, 4 or 5 mg/kg) or 10-4000 mg or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Some antibodies can be administered into the systemic circulation by intravenous or subcutaneous administration. Intravenous administration can be, for example, by infusion over a period such as 30-90 min.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

A. Diagnostics and Monitoring Methods

Also provided are methods of detecting sortilin in a subject, for example, by measuring sortilin in a sample from a subject or by in vivo imaging of sortilin in a subject. Such methods are useful to diagnose or confirm diagnosis of diseases associated with sortilin or progranulin or susceptibility thereto. The methods can also be used on asymptomatic subjects. The methods are also useful for monitoring disease progression and/or response to treatment in subjects who have been previously diagnosed with a disease associated with sortilin and progranulin, such as, for example, frontotemporal dementia, Alzheimer's disease, Parkinson's disease, amyotrophic lateral sclerosis, Batten disease, a neurodegenerative disorder, or a neurodegenerative disorder associated with aging. In some embodiments, the methods further comprise detecting, measuring, and/or monitoring progranulin levels, for example as in Example 8.

The methods work by administering a reagent, such as any of the antibodies that binds sortilin described in this application (e.g., a mouse, humanized, chimeric or veneered 5E20, 8H24, 11M14, 5M13, 2F18, 2P22, 6B15, 2C14, 9N18, and 4N2 antibody), to the subject and then detecting the agent after it has bound. Antibodies specifically binding to sortilin at an epitope within amino acid residues FTESFLT (SEQ ID NO:202), ESFL (SEQ ID NO:203), DGCILGYKEQFL) (SEQ ID NO:204), PSICLCSLEDFL (SEQ ID NO:205), or E(S/Q/D)FL (SEQ ID NO:207), RTEFGMAIGP (SEQ ID NO:213), or WGFTESFLTS (SEQ ID NO:214), or to an epitope defined by residues D74, R76, F97, K110, Y535, L560, and E557 of the sortilin ECD of SEQ ID NO:215, or to an epitope defined by residues K110, Y535, E557, T561, Q563, D74, P510, S558, F559, and L560 of the sortilin ECD of SEQ ID NO:215, or to an epitope defined by residues E557, S558, F559, L560, P510, and Y535 of the sortilin ECD of SEQ ID NO:215. can be used. In some methods, the antibody binds to a peptide consisting of an epitope within amino acid residues FTESFLT (SEQ ID NO:202), ESFL (SEQ ID NO:203), DGCILGYKEQFL) (SEQ ID NO:204), PSICLCSLEDFL (SEQ ID NO:205), E(S/Q/D)FL (SEQ ID NO:207), RTEFGMAIGP (SEQ ID NO:213), or WGFTESFLTS (SEQ ID NO:214). Antibodies typically bind to an epitope of sortilin. If desired, the clearing response can be avoided by using antibody fragments lacking a full length constant region, such as Fabs. In some methods, the same antibody can serve as both a treatment and diagnostic reagent.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for sortilin is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using positron emission tomography (PET) or single-photon emission computed tomography (SPECT).

Diagnosis is performed by comparing the number, size, and/or intensity of labeled loci to corresponding base line values. The base line values can represent the mean levels in a population of undiseased individuals. Base line values can also represent previous levels determined in the same subject. For example, base line values can be determined in a subject before beginning treatment, and measured values thereafter compared with the base line values. If the patient has reductions in cell surface sortilin, then the therapy may be adjusted to increase cell surface sortilin to normal levels.

The methods of in vivo imaging of sortilin are useful to monitor cell surface sortilin in patients being treated with agents to increase extracellular progranulin, for example in patients being treated for a disease or disorder associated with changes in progranulin levels, frontotemporal dementia, Alzheimer's disease, Parkinson's disease, amyotrophic lateral sclerosis, Batten disease, a neurodegenerative disorder, or a neurodegenerative disorder associated with aging, or susceptibility to such a disease. For example, the methods can be used on a patient being treated for frontotemporal dementia. If the patient has reductions in cell surface sortilin, then the therapy may be adjusted to increase cell surface sortilin to normal levels. In some embodiments, the methods further comprise detecting, measuring, and/or monitoring progranulin levels, for example as in Example 8.

In some patients, diagnosis of a disease or disorder associated with changes in progranulin levels may be aided by performing a PET scan. A PET scan can be performed using, for example, a conventional PET imager and auxiliary equipment. The scan typically includes one or more regions of the brain known in general to be associated with a disease or disorder associated with changes in progranulin levels and one or more regions in which to serve as controls.

The signal detected in a PET scan can be represented as a multidimensional image. The multidimensional image can be in two dimensions representing a cross-section through the brain, in three dimensions, representing the three dimensional brain, or in four dimensions representing changes in the three dimensional brain over time. A color scale can be used with different colors indicating different amounts of label and, inferentially, sortilin protein detected. The results of the scan can also be presented numerically, with numbers relating to the amount of label detected and consequently amount of sortilin. The label present in a region of the brain known to be associated with a particular disease or disorder associated with changes in progranulin levels (e.g., frontotemporal dementia) can be compared with the label present in a region known not to be associated with the disease or disorder to provide a ratio indicative of the extent of deposits within the former region. For the same radiolabeled ligand, such ratios provide a comparable measure of sortilin and changes thereof between different patients.

In some methods, a PET scan is performed concurrent with or in the same patient visit as an MRI or CAT scan. An MRI or CAT scan provides more anatomical detail of the brain than a PET scan. However, the image from a PET scan can be superimposed on an MRI or CAT scan image more precisely indicating the location of PET ligand and inferentially sortilin relative to anatomical structures in the brain. Some machines can perform both PET scanning and MRI or CAT scanning without the patient changing positions between the scans facilitating superimposition of images.

Suitable PET ligands include radiolabeled antibodies of the invention (e.g., a mouse, humanized, chimeric or veneered 5E20, 8H24, 11M14, 5M13, 2F18, 2P22, 6B15, 2C14, 9N18, or 4N2 antibody. The radioisotope used can be, for example, $C^{11}$, $N^{13}$, $O^{15}$, $F^{18}$, or $I^{123}$. The interval between administering the PET ligand and performing the scan can depend on the PET ligand and particularly its rate of uptake and clearing into the brain, and the half-life of its radiolabel.

PET scans can also be performed as a prophylactic measure in asymptomatic patients or in patients who have symptoms of mild cognitive impairment but have not yet been diagnosed with a disease or disorder associated with changes in progranulin levels but are at elevated risk of developing a disease or disorder associated with changes in progranulin levels. For asymptomatic patients, scans are particularly useful for individuals considered at elevated risk of a disease or disorder associated with changes in progranulin levels because of a family history, genetic or biochemical risk factors, or mature age. Prophylactic scans can commence for example, at a patient age between 45 and 75 years. In some patients, a first scan is performed at age 50 years.

Prophylactic scans can be performed at intervals of for example, between six months and ten years, preferably between 1-5 years. In some patients, prophylactic scans are performed annually.

The foregoing description of diagnosing, monitoring, and adjusting treatment for diseases and disorders associated with sortilin and progranulin has been largely focused on using PET scans. However, any other technique for visualizing and/or measuring sortilin that is amenable to the use of sortilin antibodies of the invention (e.g., a mouse, humanized, chimeric or veneered 5E20, 8H24, 11M14, 5M13, 2F18, 2P22, 6B15, 2C14, 9N18, or 4N2 antibody) can be used in place of PET scans to perform such methods.

Also provided are methods of detecting an immune response against sortilin in a patient suffering from or susceptible to diseases and disorders associated with sortilin and progranulin. The methods can be used to monitor a course of therapeutic and prophylactic treatment with the agents provided herein. The antibody profile following passive immunization typically shows an immediate peak in antibody concentration followed by an exponential decay. Without a further dose, the decay approaches pretreatment levels within a period of days to months depending on the half-life of the antibody administered. For example, the half-life of some human antibodies is of the order of 20 days.

In some methods, a baseline measurement of antibody to sortilin in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regimen in other subjects. If the measured antibody level is significantly less than a reference level (e.g., less than the mean minus one or, preferably, two standard deviations of the reference value in a population of subjects benefiting from treatment) administration of an additional dose of antibody is indicated.

Biological samples obtained from a subject having, suspected of having, or at risk of having a disease or disorder associated with changes in progranulin levels, frontotemporal dementia, Alzheimer's disease, Parkinson's disease, amyotrophic lateral sclerosis, Batten disease, a neurodegenerative disorder, or a neurodegenerative disorder associated with aging can be contacted with the antibodies disclosed herein to assess the presence of sortilin. For example, levels of sortilin in such subjects may be compared to those present in healthy subjects. Alternatively, levels of sortilin in such subjects receiving treatment for the disease may be compared to those of subjects who have not been treated for a disease or disorder associated with changes in progranulin levels, frontotemporal dementia, Alzheimer's disease, Parkinson's disease, amyotrophic lateral sclerosis, Batten disease, a neurodegenerative disorder, or a neurodegenerative disorder associated with aging. Some such tests involve a biopsy of tissue obtained from such subjects. ELISA assays may also be useful methods, for example, for assessing sortilin in fluid samples.

VII. Kits

The invention further provides kits (e.g., containers) comprising an antibody disclosed herein and related materials, such as instructions for use (e.g., package insert). The instructions for use may contain, for example, instructions for administration of the antibody and optionally one or more additional agents. The containers of antibody may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

VIII. Other Applications

The antibodies can be used for detecting sortilin, or fragments thereof, in the context of clinical diagnosis or treatment or in research. For example, the antibodies can be used to detect the presence of sortilin in a biological sample. Binding of the antibodies to the biological sample can be compared to binding of the antibodies to a control sample. The control sample and the biological sample can comprise cells of the same tissue origin. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of sortilin) to the biological sample(s) is increased, decreased, or the same relative to antibody binding to the control sample(s). Increased binding of the antibody to the biological sample(s) relative to the control sample(s) indicates the presence of sortilin in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of the sortilin in a biological sample to monitor and evaluate the efficacy of a therapeutic agent being used to treat a patient diagnosed with a disease or disorder associated with changes in progranulin levels, frontotemporal dementia, Alzheimer's disease, Parkinson's disease, anyotrophic lateral sclerosis, Batten disease, a neurodegenerative disorder, or a neurodegenerative disorder associated with aging. In some embodiments, the methods further comprise detecting, measuring, and/or monitoring progranulin levels, for example as in Example 8. A biological sample from a patient diagnosed with a disease or disorder associated with changes in progranulin levels, frontotemporal dementia, Alzheimer's disease, Parkinson's disease, amyotrophic lateral sclerosis, Batten disease, a neurodegenerative disorder, or a neurodegenerative disorder associated with aging is evaluated to establish a baseline for the binding of the antibodies to the sample (i.e., a baseline for the presence of the sortilin in the sample) before commencing therapy with the therapeutic agent. In some instances, multiple biological samples from the patient are evaluated on multiple occasions to establish both a baseline and measure of random variation independent of treatment. A therapeutic agent is then administered in a regimen. The regimen may include multiple administrations of the agent over a period of time. Optionally, binding of the antibodies (i.e., presence of sortilin) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of sortilin) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., reduced cell surface sortilin), then the therapy may be adjusted to increase cell surface sortilin to normal levels. Assessment of antibody binding can be made in conjunction with assessing other signs and symptoms of with a disease or disorder associated with changes in progranulin levels, frontotemporal dementia, Alzheimer's disease, Parkinson's disease, anyotrophic lateral sclerosis, Batten disease, a neurodegenerative disorder, or a neurodegenerative disorder associated with aging. In some embodiments, the methods further comprise detecting, measuring, and/or monitoring progranulin levels, for example as in Example 8.

The antibodies can also be used as research reagents for laboratory research in detecting sortilin, or fragments thereof. In such uses, antibodies can be labeled with fluorescent molecules, spin-labeled molecules, enzymes, or radioisotopes, and can be provided in the form of kit with all the necessary reagents to perform the detection assay. The antibodies can also be used to purify sortilin, or binding partners of sortilin, e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Generation of Mouse Anti-Human Sortilin Antibodies

A. Immunizations

Eight approximately 6-week-old female mice of various stains (2×Swiss webster, 2×NZB/w, 2×AJ, 1×SJL and 1×Balb/C) were immunized subcutaneously in the Hock (lateral tarsal region just above the ankle) as in Table 5 below, with the extracellular domain (ECD) of recombinant human Sortilin with a C-terminal HIS tag (ECD-huSortilin-HIS). Immunogens in PBS were mixed 1:1 with the appropriate adjuvants (see table below) for the first 8 injections, then received a final injection without any adjuvant. Mice were then titered against ECD-huSortilin-HIS (R&D Systems) and an irrelevant HIS tagged protein to ensure specificity to Sortilin on days 17 and 24 of the 28 day immunization schedule.

TABLE 5

Immunization Schedule

| Day | Adjuvant | Amount | Route of administration |
|---|---|---|---|
| Day 0 | CFA (Sigma) | 10 ug/60 uL per injection | Hock |
| Day 3 | Titermax (Sigma) | 10 ug/60 uL per injection | Hock |
| Day 7 | Titermax (Sigma) | 10 ug/60 uL per injection | Hock |
| Day 9 | RIBI (Sigma) | 10 ug/60 uL per injection | Hock |
| Day 11 | RIBI(Sigma) | 10 ug/60 uL per injection | Hock |
| Day 15 | GERBU (V-Biognostics) | 10 ug/60 uL per injection | Hock |
| Day 18 | Titermax (Sigma) | 10 ug/60 uL per injection | Hock |
| Day 22 | RIBI (Sigma) | 10 ug/60 uL per injection | Hock |
| Day 25 | None | 20 ug/60 uL per injection | Hock |
| Day 17 | | Bleed -1$^{st}$ Titers | |
| Day 24 | | Bleed -2$^{nd}$ Titers | |

B. Fusions & Screening

All mice showed antigen-specific titers and were sacrificed. The popliteal, inguinal and mesenteric lymph nodes and spleens were collected (spleens from all mice were pooled and lymph nodes from all mice were pooled) and processed. Splenocytes were cryopreserved and B cell enrichment (Stem Cell Technologies) was carried out on pooled lymphocytes according to the manufacturers protocol. Approximately 80 million B cells were fused at a 1:1 ratio with SP2/0 mouse myeloma cells (ATCC) by electrofusion. ⅓ of the fused cells were plated in 11×384 well plates in fusion media (80 ul/well) and incubated in 37° C.-5% $CO_2$ and the remaining cells were cryopreserved.

After 8-10 days supernatants were screened by ELISA. For the primary screen, 384-well ELISA plates (chemiluminescence compatible) were coated with 1 ug/mL recombinant ECD-huSortilin-HIS (20 uL/well) and incubated overnight at 4° C. all plates were blocked with 3% BSA in PBS for 1 hour at room temperature. Plates were then washed with Tris buffered saline containing 0.1% Tween20 (TBST) three times. 20 μL of supernatants were added to the analogous wells in the ELISA plates, incubated and then washed as above. Goat anti-mouse IgG specific-HRP (Jackson Immunoresearch) diluted 1:7000 in 1% BSA in TBST was then added at 20 uL per well to react with the bound antibodies and was incubated for 1 hour before being washed as above. Super signal Pico chemiluminescent ELISA substrate (ThermoFisher) was used for detection. 20 μL of substrate was added to each well and Relative Light Units (RLU) were measured immediately using the SpectraMax Paradigm (Molecular Devices). The top 576 wells (based on RLU signal) were transferred to 96 well plates and cultured for 2 days. A confirmation screen was then conducted using ECD-huSortilin-HIS and an irrelevant His protein to determine whether the antibodies were Sortilin specific. 105 non-clonal hybridomas were selected from the confirmation screen and cultured further for both cryopreservation and to produce saturated supernatants for further testing. 105 saturated supernatants were tested for blocking Progranulin (ligand of sortilin) binding to sortilin by ELISA (methods as in Example 4). Results are depicted in FIG. 7. 29 antibodies blocked the binding of progranulin to sortilin. The 29 blocking hybridomas and 2 non-blocking (negative controls) hybridomas were thawed and cloned to produce monoclonal antibodies.

Example 2: Cloning and Monoclonal Antibody Purification

Cloning of hybridomas was done by serial dilutions or using the clonepix 2 (molecular Devices). Hybridomas that were cloned using the Clonepix2 were done so by following the manufacturers protocol. For serial dilution cloning, cells were counted and plated at a density of 0.5 cells per well into 12 of a 384-well plate in cloning media and incubated at 37° C.-5% $CO_2$. The next day, each well was examined visually under the microscope and wells with a single colony of cells were marked as monoclonal. After 7-8 days of culture supernatants were screened by ELISA for binding to ECD-huSortilin-HIS. 28 monoclonal antibodies were successfully cloned. The 28 hybridomas were expanded for cryopreservation and antibody purification. Antibodies were purified using Protein A chromatography utilizing standard methods. Following purification, the antibodies were exchanged into 1×PBS and protein concentrations were determined by absorbance at 280 nm. Purified monoclonal antibodies (mAbs) then moved on for further screening.

Example 3: Sortilin Binding ELISA

Figure 8A:
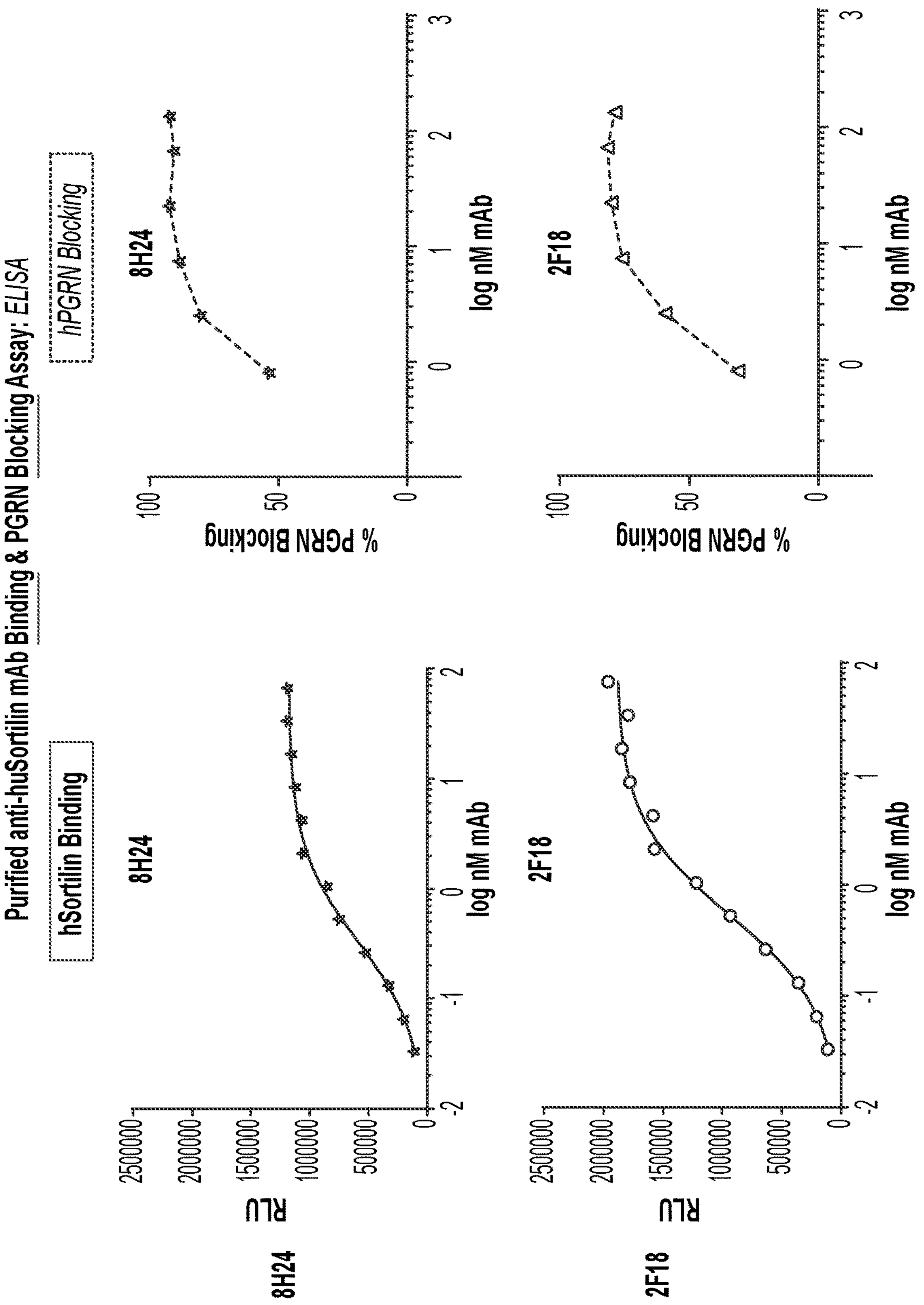
Figure 8B:
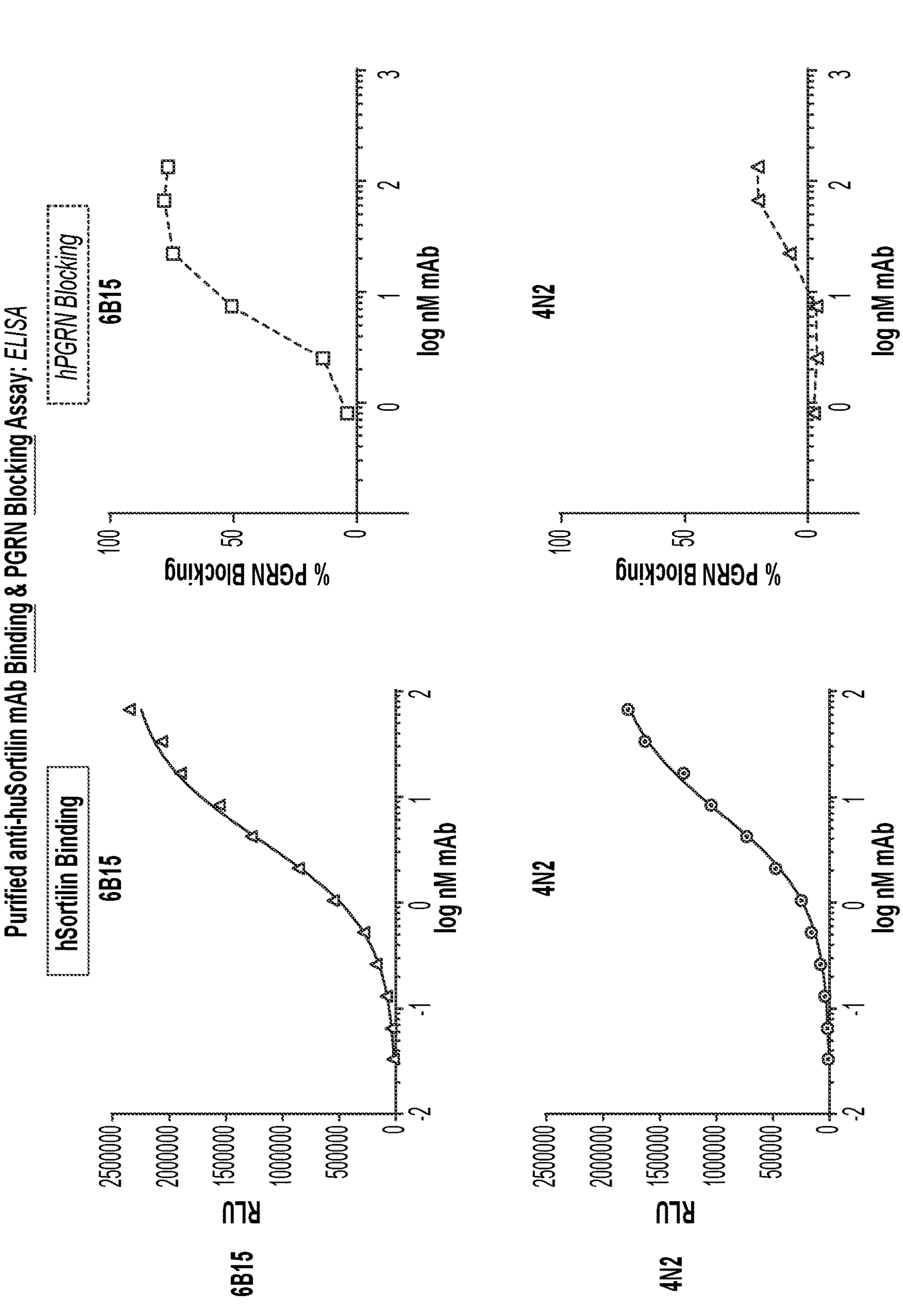
Figure 8C:
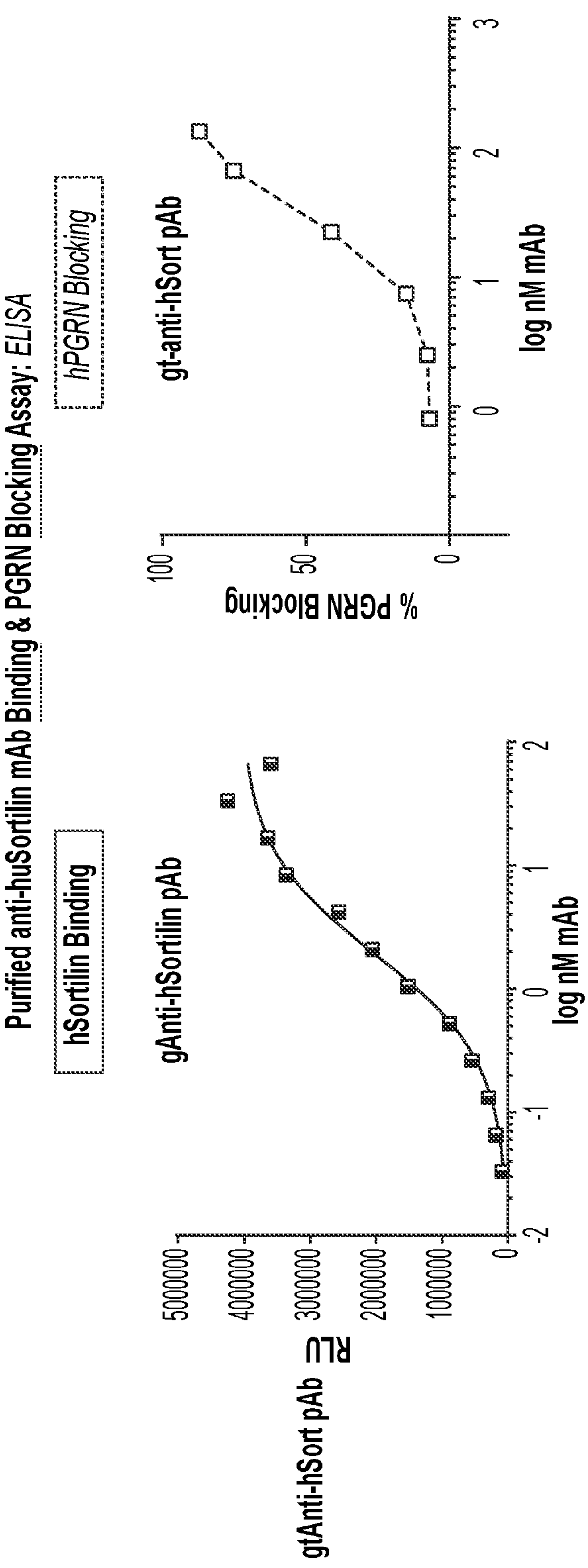

Purified anti-huSortilin mAb binding to huSortilin was characterized by ELISA (ELISA protocol as in Example 1) using a 12 point titration of mAb concentration. mAbs were diluted 2-fold from a starting concentration of 67 nM and then added to ECD-huSortilin-HIS coated plates. Data was analyzed and $EC_{50}$ (nM) was calculated using graphed Prism. Commercially available goat anti-huSortilin (R&D Biosystems) was used as a positive control. Results are depicted in FIG. 8.

Example 4 Progranulin Blocking ELISA

Blocking ELISA Using Non-Clonal Saturated Supernatants

To select which hybridomas to clone, saturated supernatants were examined for blocking the binding of Progranulin to Sortilin. Untagged human progranulin (huPGRN, Adipogen) was first biotinylated at a ratio of 5:1 using EZ-Link NHS-PEG4-Biotin (Thermo Fisher) and ZebaSpin Columns following manufacturers protocols. Results are depicted in FIG. 7.

384-well ELISA plates were coated with 2ug/mL recombinant ECD-huSortilin-HIS (20 uL/well) and incubated overnight at 4° C. all plates were blocked with 3% BSA in PBS for 1 hour at room temperature. Plates were then washed with TBST three times. Saturated supernatants were diluted 4-fold in 1% BSA in TBST. 20 μL of diluted supernatant was added to the wells and incubated for 1 hour at room temperature. Plates were then washed with TBST and 20 μL of 2ug/mL huPGRN-Biotin was added to each well and incubated for 1 hour at room temperature and then washed as above. Streptavidin-HRP (GE Life Sciences) diluted 1:10,000 in 1% BSA in TBST was then added at 20 uL per well to react with the bound huPGRN-Biotin and was incubated for 1 hour before being washed and detected using Super signal Pico chemiluminescent ELISA substrate (ThermoFisher) as above. Hybridomas (of corresponding Supernatants) which Blocked the binding of huPGRN to huSortilin by at least 30% compared to no Ab control were selected for cloning.

Blocking ELISA Using Purified mAbs 28 purified anti-huSortilin mAbs were further characterized for ability to block PGRN binding to Sortilin. Blocking ELISA was conducted as above using 6 point 3-fold dilutions of mAbs in 1% BSA in TBST starting at 134 nM. Data was analyzed and % blocking was calculated using Microsoft Excel and GraphPad Prism. Results are depicted in FIG. 8.

Example 5: Neurotensin Competition Biacore Assays

Figure 9B:
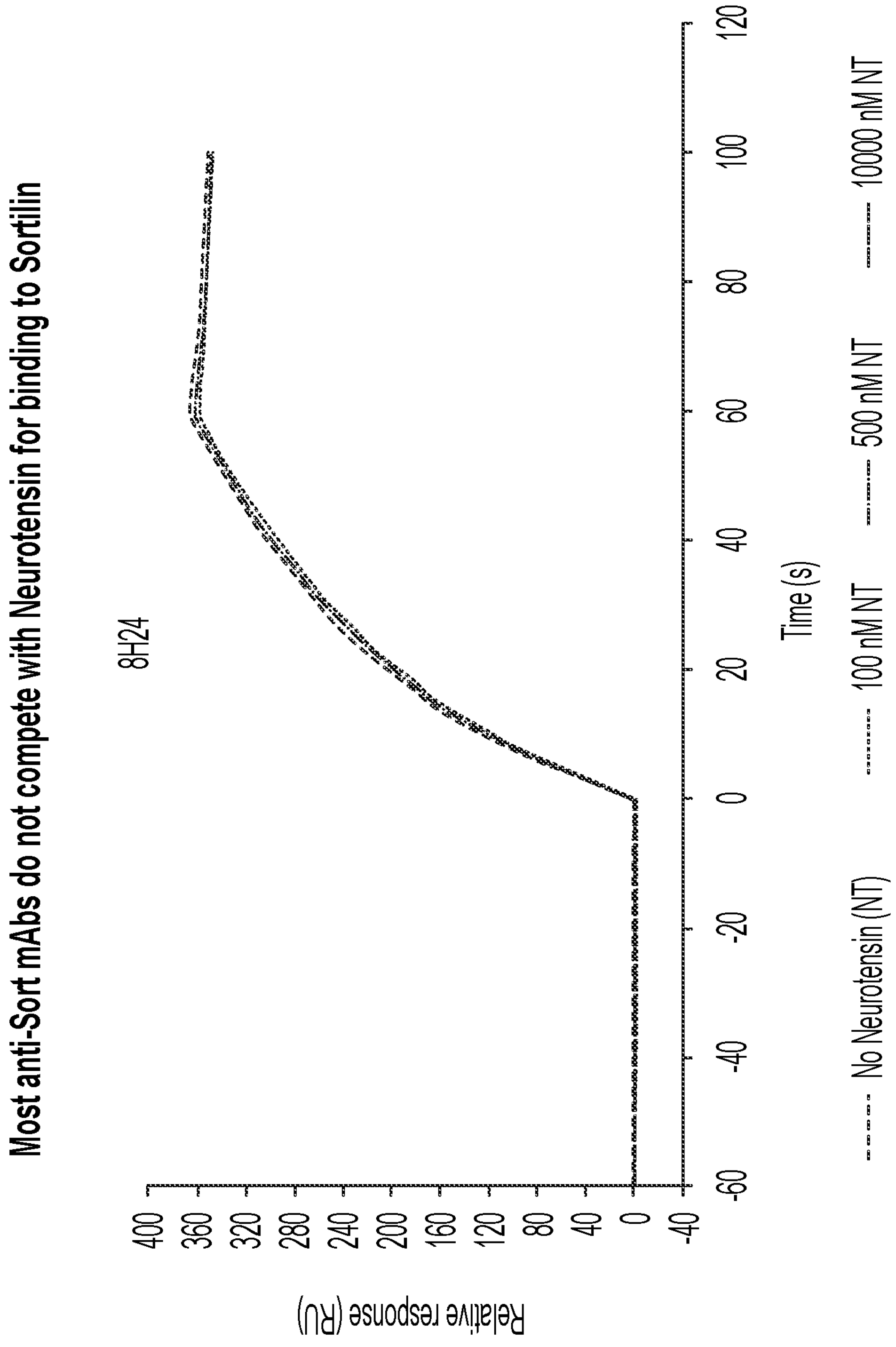
Figure 9C:
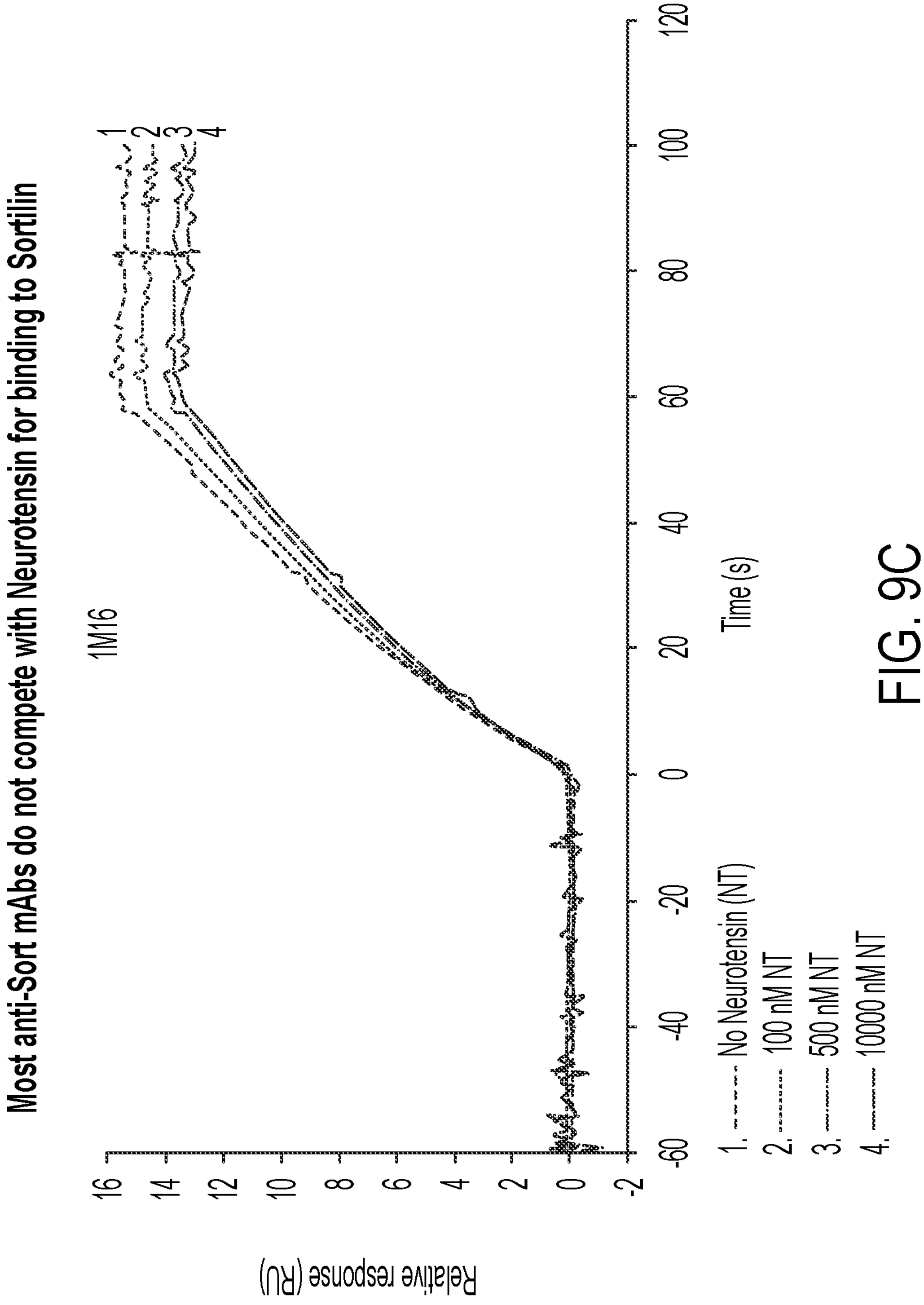
Figure 9D:
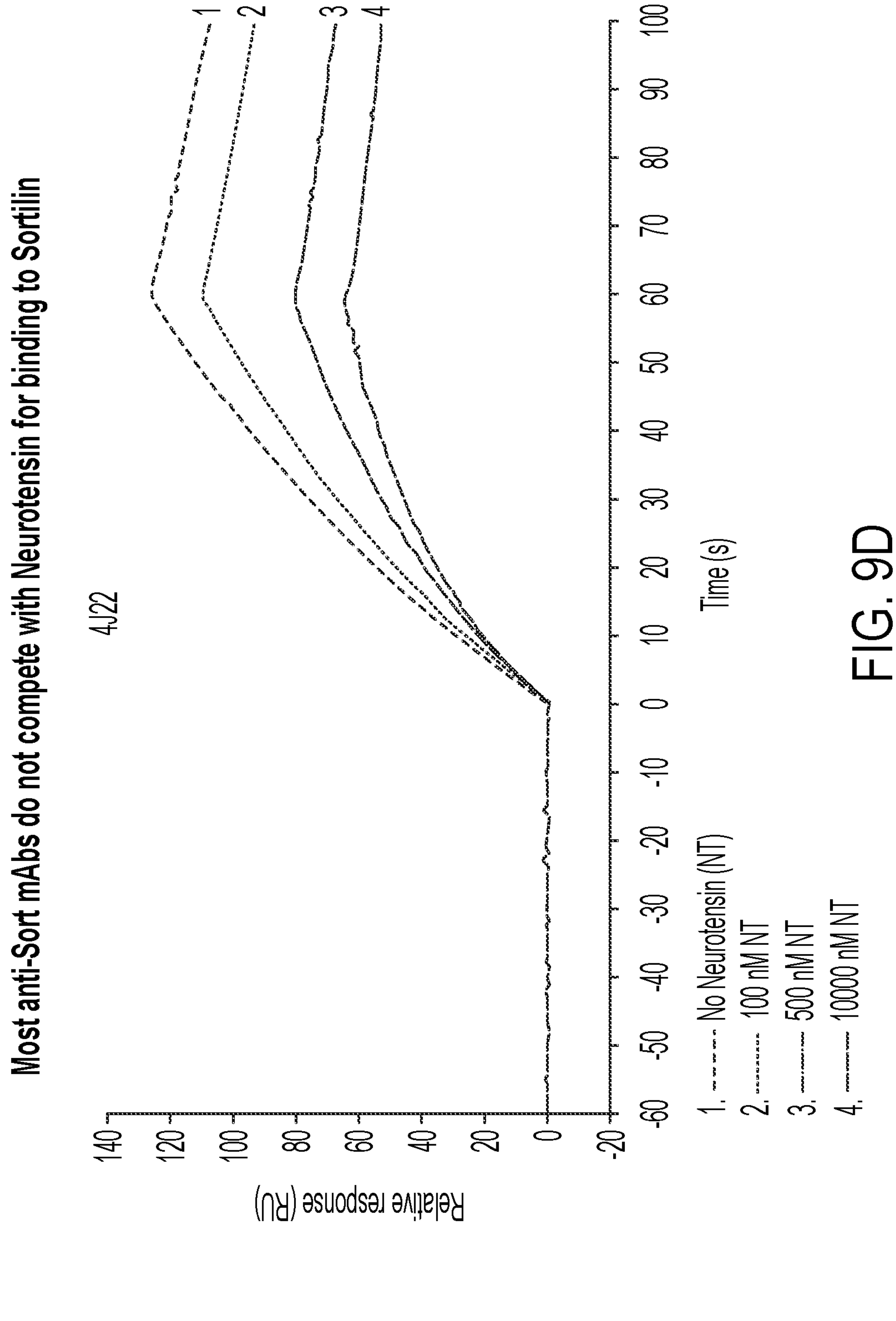

PGRN and Neurotensin (NT) are known to bind similar regions on sortilin. Surface Plasmon Resonance (SPR) (Biacore T200 instrument) was used to examine whether anti-huSortilin mAbs block the binding of NT to Sortilin. Briefly, 25 nM anti-huSortilin mAb was captured on CM5 anti-mouse Fc chip (60 seconds association). Then 100 nM recombinant ECD-huSortilin-HIS pre-incubated with 0 nm, 100 nM, 500 nM or 1000 nM NT (Tocris) (60 second association, 30 second dissociation) was flowed across the captured mAb surface. The chip surface was regenerated using 10 nM glycine pH 1.5 between cycles. The data was analyzed and graphed using the Biacore T200 evaluation software 2.0.15.12933. 18 anti-Sortilin mAbs did not compete with NT for binding to Sortilin, 6 showed some competition and 3 clearly competed with NT for binding to Sortilin. Results are depicted in FIG. 9.

Example 6: Sortilin Binding Cell-Based Assays

Figure 10A:
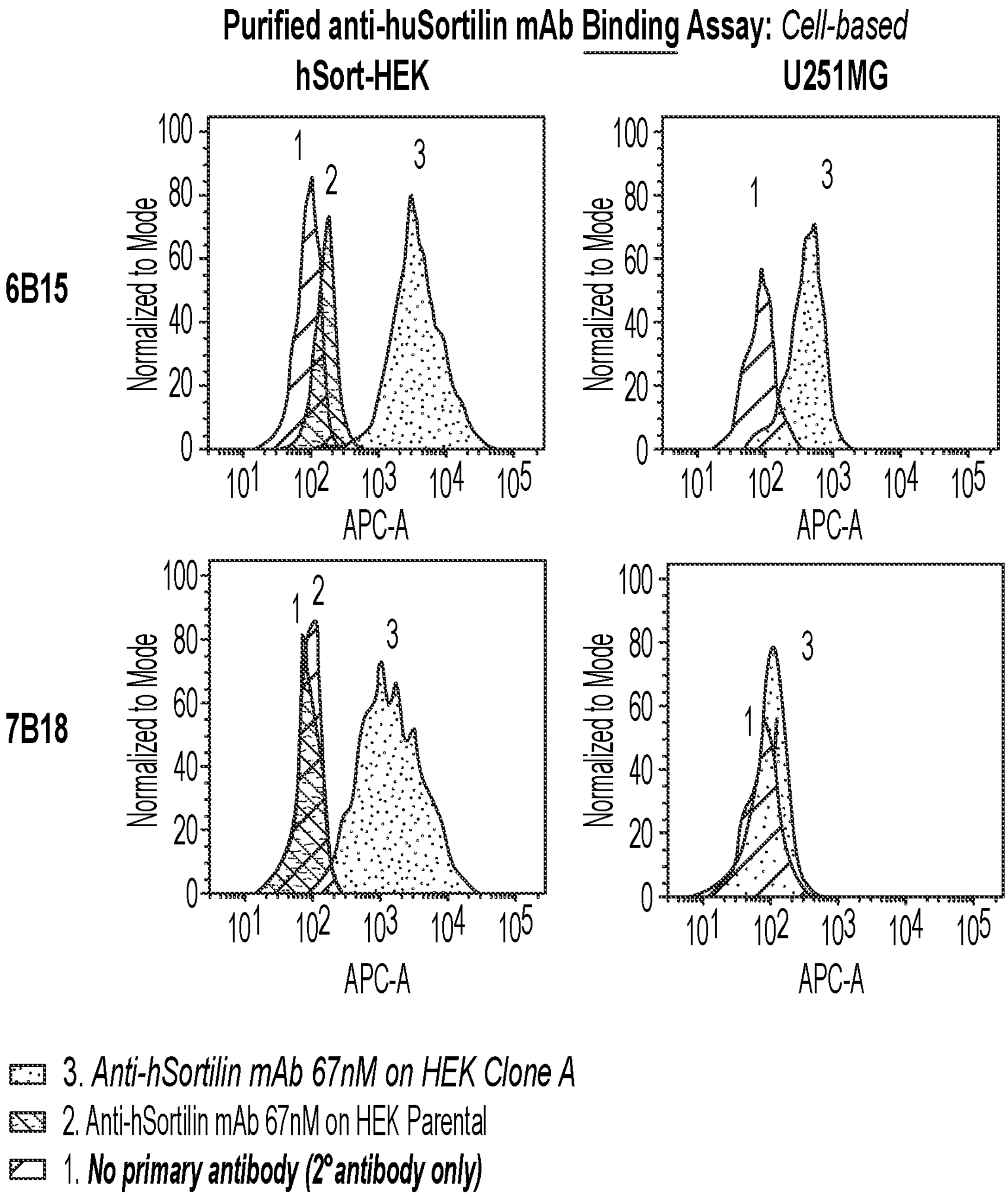
Figure 10B:
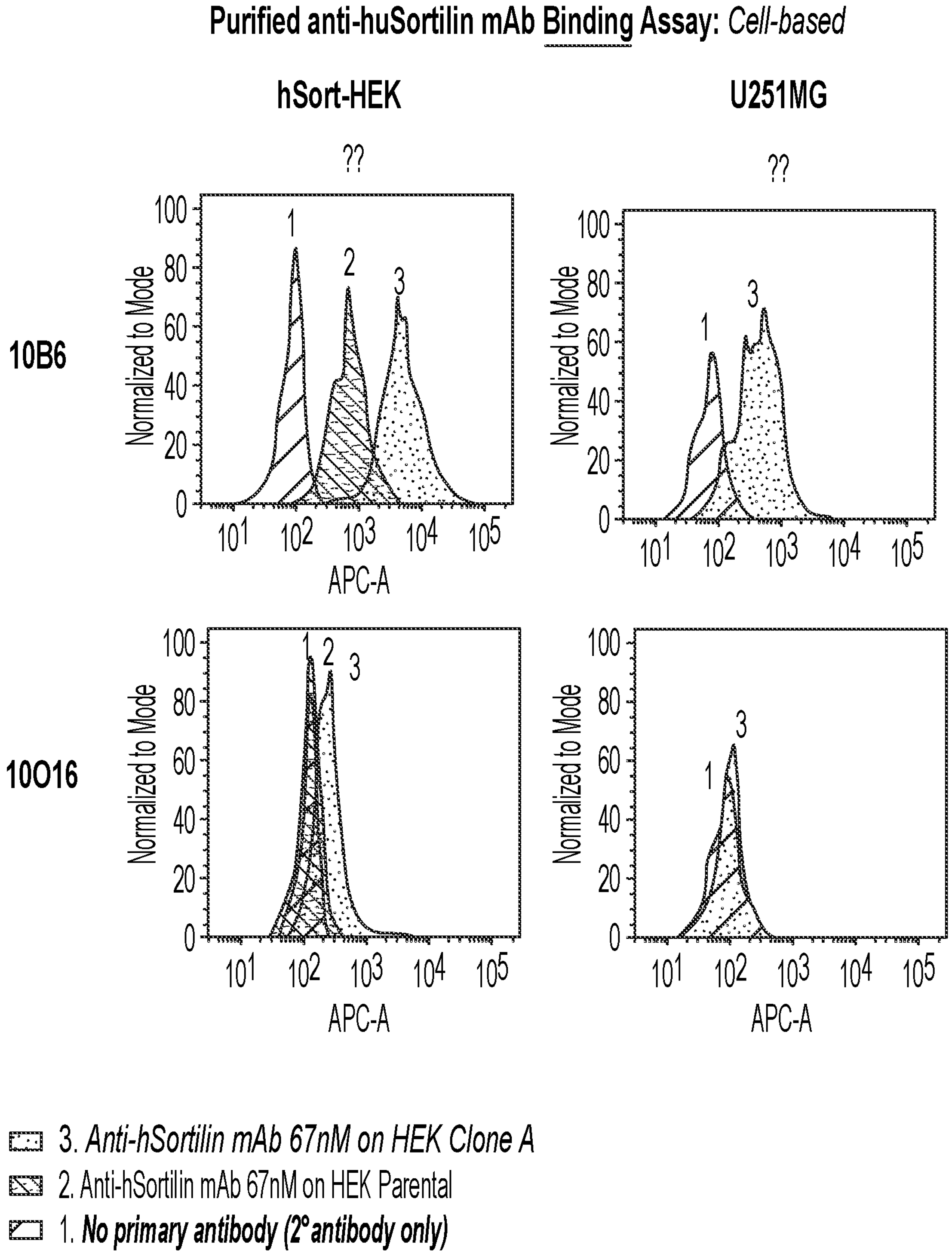

The ability of the purified anti-sortilin mAbs to bind recombinant huSortilin expressed on the surface of HEK 293 cells and to U251MG cells (human glioblastoma cells line) which endogenously express sortilin on their cell surface was then examined. Parental HEK 293 cells were used as a negative control. All 28 purified anti-sortilin mAbs were tested at a single concentration (67 nM). Cells were harvested and plated at 20K cells per well in a 96-well plate. mAbs, diluted in PBS+2% FBS were added to the wells (50 uL/well) and cells were incubated on ice for 1 hour. Cells were then washed twice in PBS+2% FBS and incubated for 30 minutes on ice with 50 uL per well Sug/mL Alexa-Fluor647goat-anti-mouse IgG (Jackson Immunoresearch) in PBS+2% FBS. Cells were then washed twice as above and resuspended in 100 uL PBS+2% FBS. Data was acquired using the BD LSR II and analyzed using FlowJo software version 10.6. Calculation of Median Fluorescent Intensity (MFI) values showed that all 28 anti-sortilin mAbs bound huSortilin expressing HEK293 cells. 3 of which also showed background binding to parental HEK cells. 22 mAbs showed varying degrees of binding to sortilin on the surface of U251MG cells. 6 mAbs showed no binding to U251 cells. Results are depicted in FIG. 10.

Example 7: Progranulin Blocking Titration Cell-Based Assays

Figure 11:
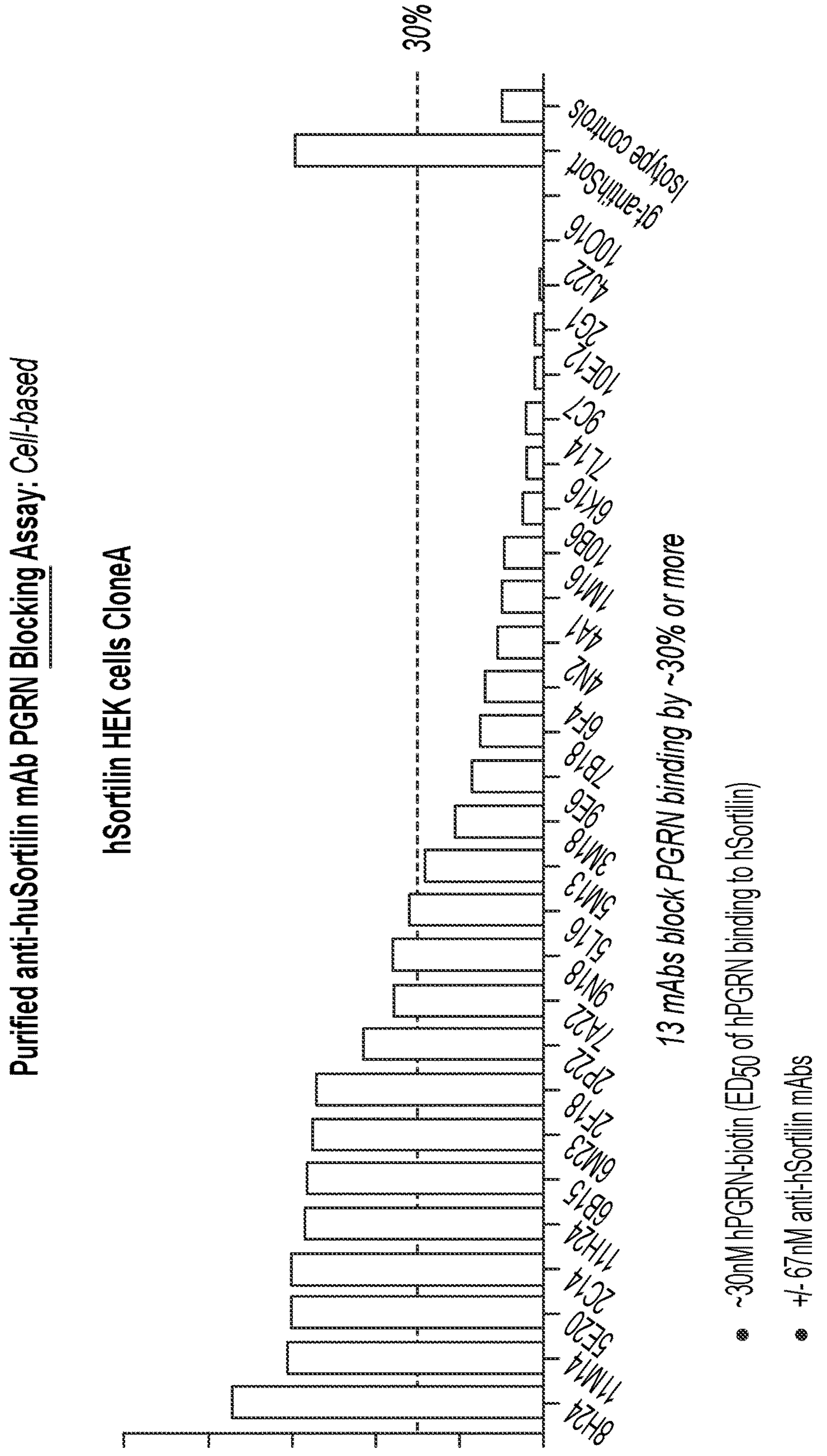
FIG. 11 depicts inhibition of hu PGRN binding to human Sortilin-expressing HEK293 cells (in percentage PGRN blocking) by selected purified monoclonal antibodies.

All 28 purified anti-sortilin mAbs were tested at a single concentration (67 nM) to determine their ability to block huPGRN-Biotin binding to cell surface huSortilin expressing HEK293 cells. Cells were cultured using standard methods. Cells were harvested and plated at 20K cells per well in a 96-well plate. mAbs, diluted in PBS+2% FBS containing 30 nM huPGRN-Biotin were added to the wells (50 uL/well) and cells were incubated on ice for 1 hour. Cells were then washed twice in PBS+2% FBS and incubated for 30 minutes on ice with 50 uL per well 1:200 Steptavidin-APC (BD biosciences) in PBS+2% FBS. Cells were then washed as above and resuspended in 100 uL PBS+2% FBS. Data was acquired using the BD LSR II and analyzed using FlowJo software version 10.6 and Microsoft excel. 12 Anti-sortilin mAbs showed % blocking of huPGRN greater than 30% and were selected for further characterization. Results are depicted in FIG. 11.

Figure 12A:
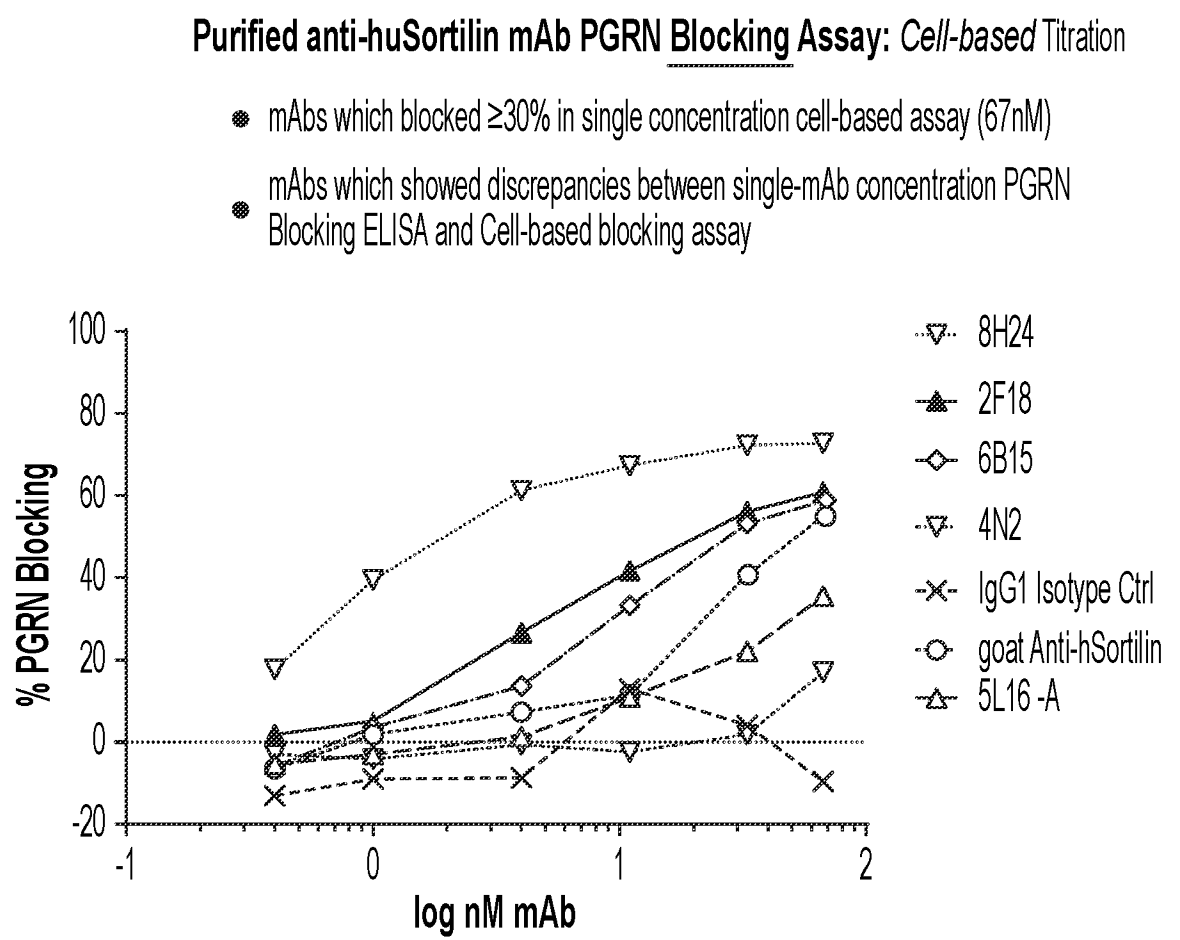

The cell-based blocking assay was repeated with the top 12 blocking mAbs using a dose titration from 67 nM to 0.4 nM. Blocking assay was carried out as above. Data was analyzed using FlowJo software version 10.6. and GraphPad Prism software. Results are depicted in FIG. 12.

The 12 mAbs fell into three tiers. Tier 1 comprised mAbs which showed high potency with regards to huPGRN blocking (8H24, 5E20, 2C14), 7 mAbs (tier2) showed medium blocking potency (2F18, 6B15,11M14,11H24, 6M23, 2P22 and 9N18). The last 2 mAbs (7A22 and 5L16) showed low huPGRN blocking potency.

Example 8: Extracellular Progranulin Levels and Surface Sortilin Levels

U251MG cells were seeded in 96-well plates and incubated overnight at 37° C.-5% $CO_2$. The next day, media was removed and fresh media containing 50 nM either anti-Sortilin mAbs, commercially available goat-anti-hSortilin (positive blocking antibody, R&D Biosystems) or Isotype control antibodies were added to the wells. Cells were then cultured for 72 hours. Supernatants were then used to determine extracellular huPGRN levels and the cells were harvested to examine cell surface sortilin levels.

Figure 13A:
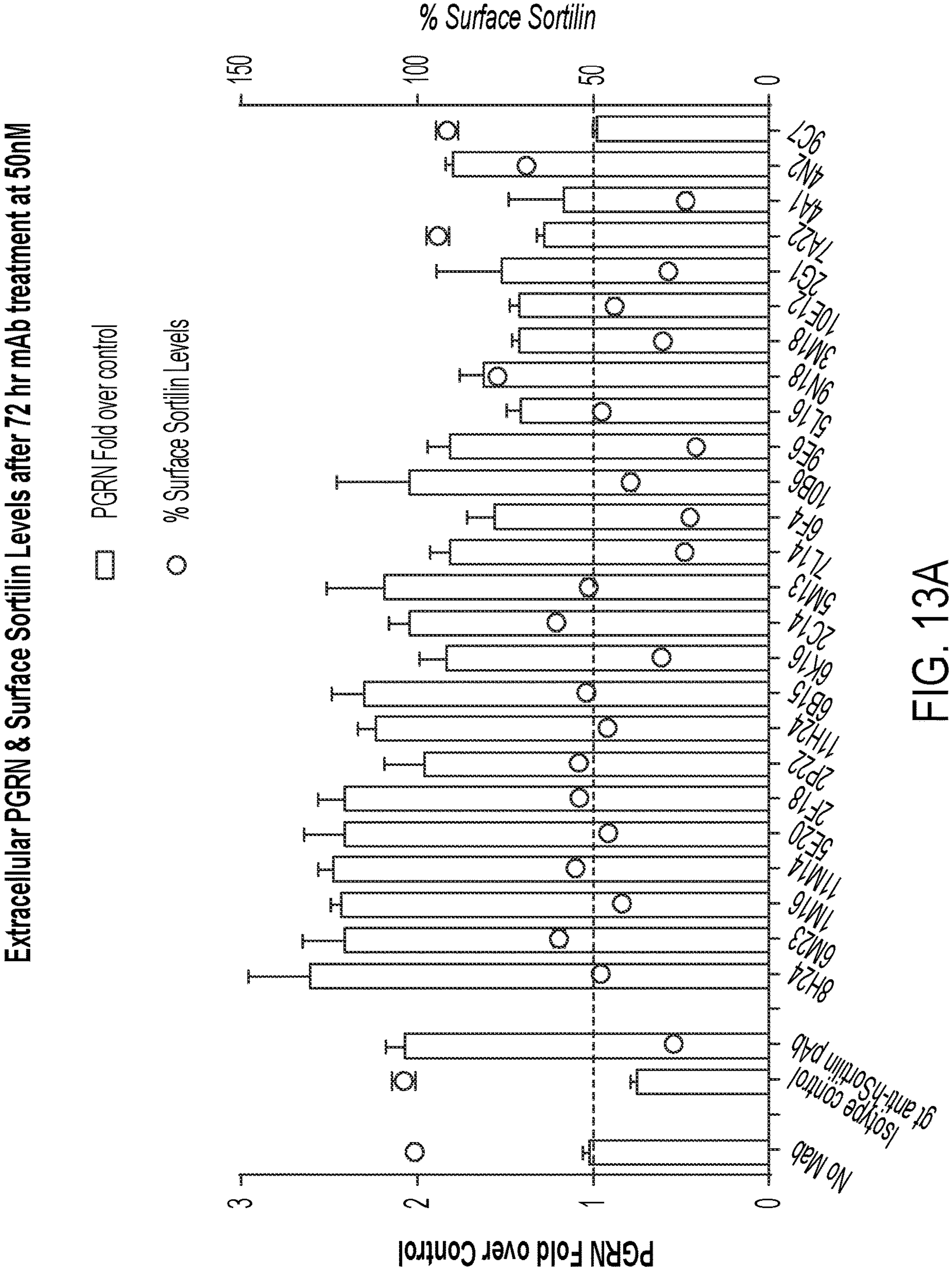
Figure 14:
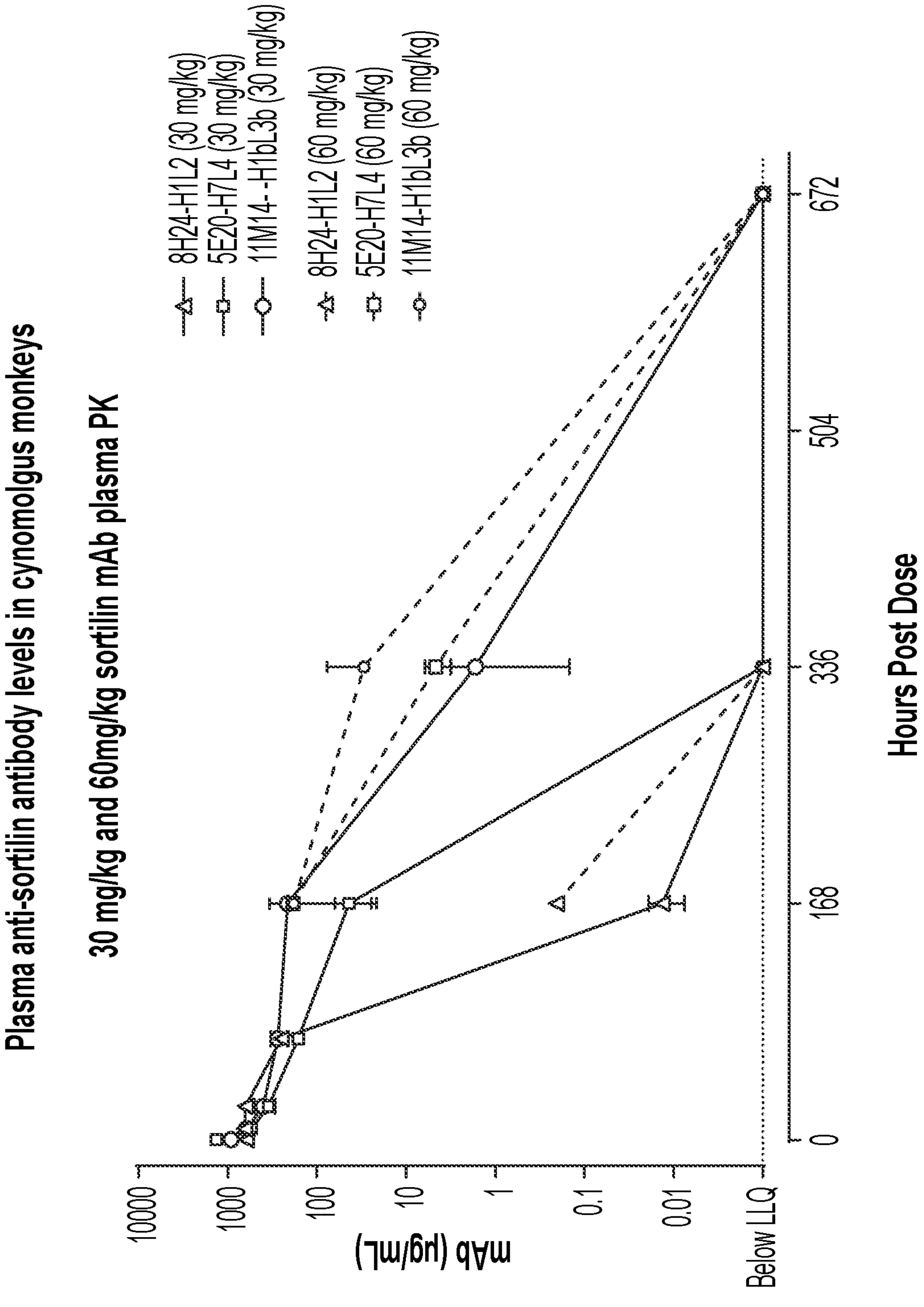
FIG. 14 depicts anti sortilin antibody hu8H24 H1L2 IgG1 LALA, hu5E20 H7L4 IgG1 LALA, or hu11M14 H1bL3b IgG1 LALA levels in plasma after 60 mg/kg dose and after 30 mg/kg dose in cynomolgus monkeys (pharmacokinetic studies). Anti-sortilin antibody levels in plasma after a 30 mg/kg or 60 mg/kg dose of Antibodies in cynomolgus monkeys. N=3 animals per Ab group. Animals received a 30 mg/kg dose followed 48 days later by a 60 mg/kg dose of anti-sortilin antibody.
Figure 15:
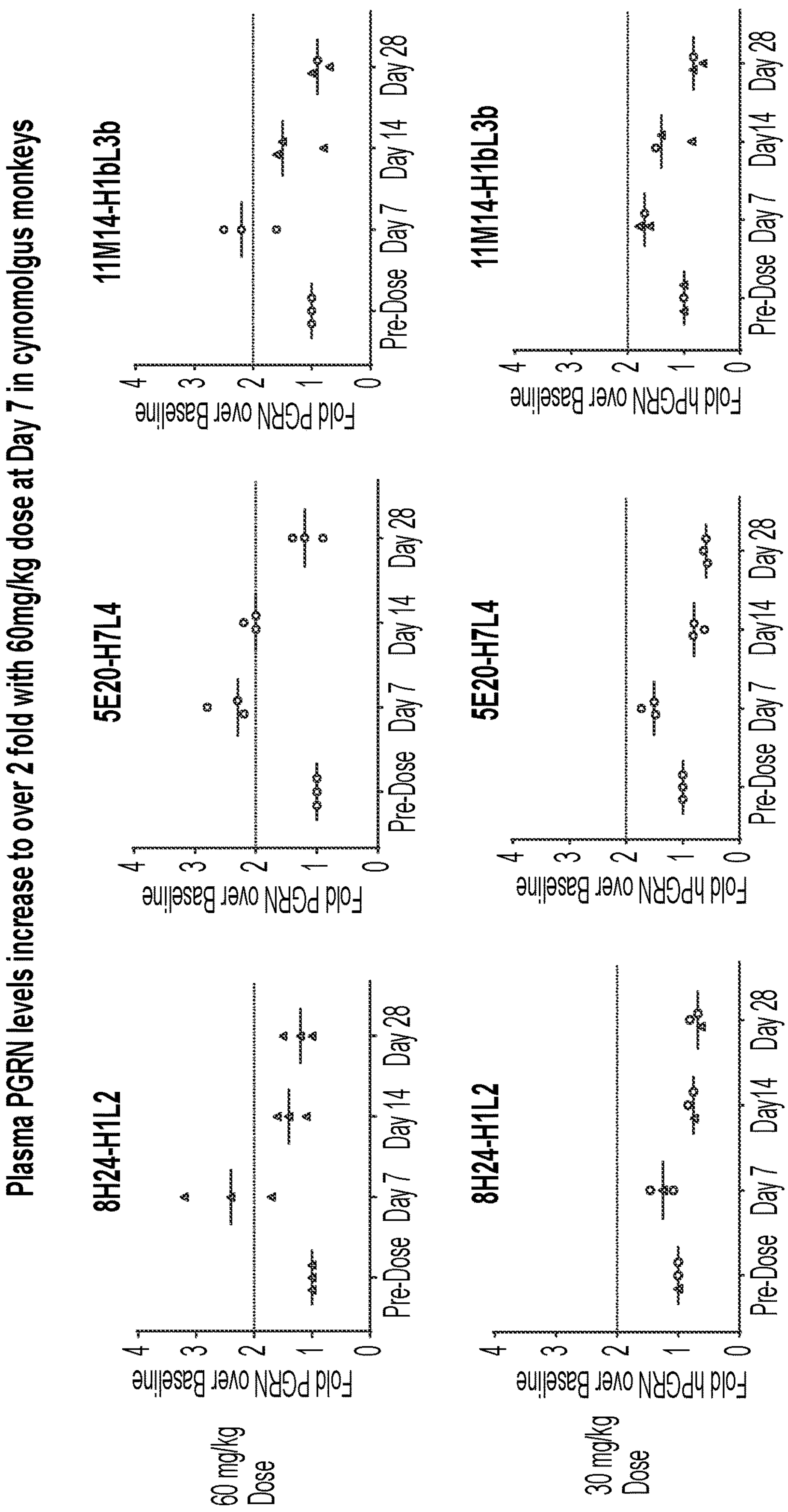
FIG. 15 depicts plasma PGRN levels after 60 mg/kg dose and after 30 mg/kg dose of hu8H24 H1L2 IgG1 LALA, hu5E20 H7L4 IgG1 LALA, or hu11M14 H1bL3b IgG1 LALA in non-human primates (pharmacodynamic studies). Fold PGRN levels in plasma after a single 30 mg/kg or 60 mg/kg dose of Antibodies in cynomolgus monkeys. N=3 animals per Ab group. Triangles denote animals which showed detectable levels of anti-drug antibodies.
Figure 16:
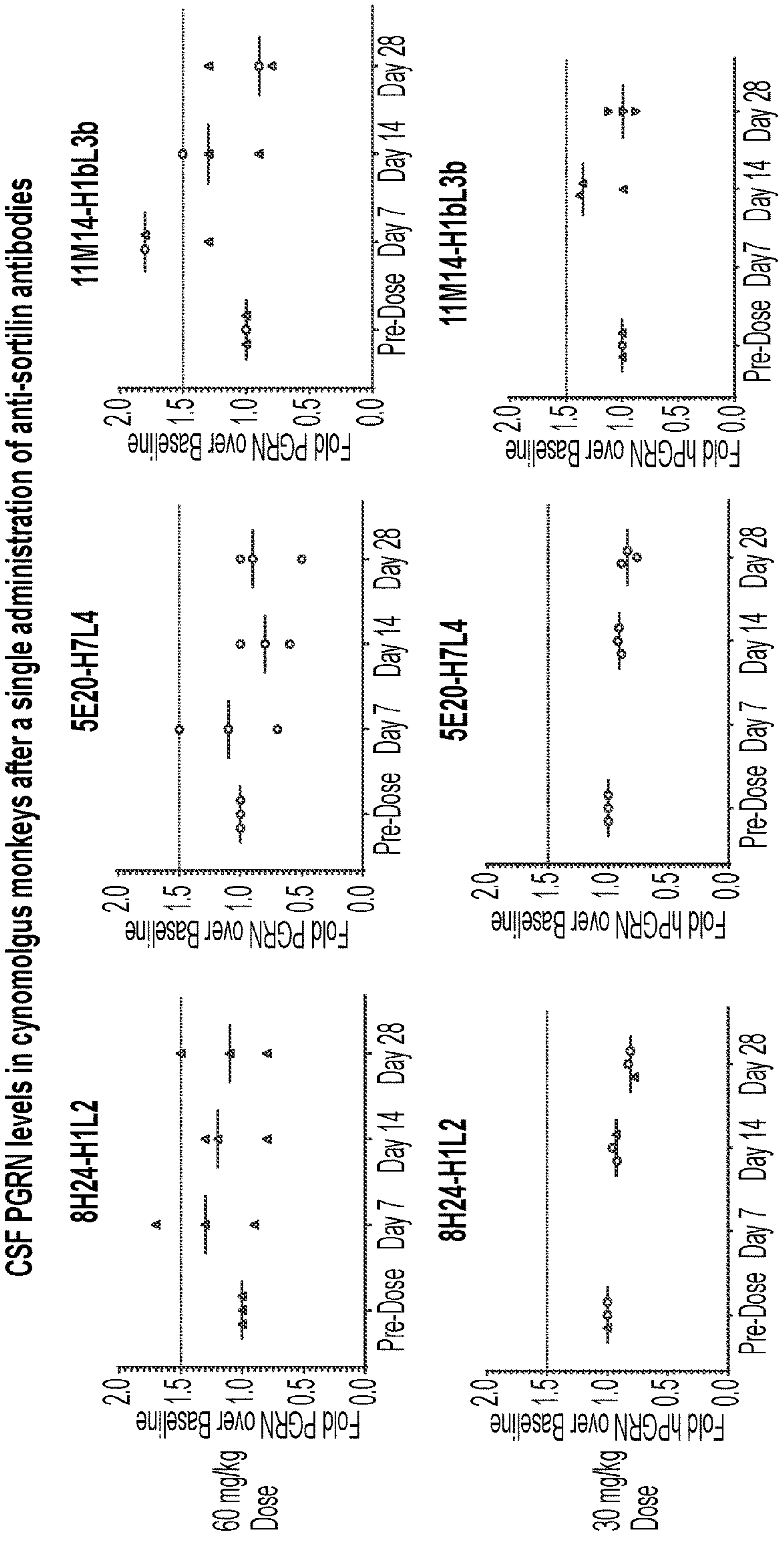
FIG. 16 depicts CSF PGRN levels after 60 mg/kg dose and after 30 mg/kg dose of hu8H24 H1L2 IgG1 LALA, hu5E20 H7L4 IgG1 LALA, or hu11M14 H1bL3b IgG1 LALA in cynomolgus monkeys (pharmacodynamic studies). Fold PGRN levels in CSF after a single 30 mg/kg or 60 mg/kg dose of Antibodies in cynomolgus monkeys. N=3 animals per Ab group. Triangles denote animals which showed the presence of anti-drug antibodies. No CSF samples were collected at Day 7 in animals treated with 30 mg/kg anti-sortilin antibodies.

The increase in PGRN levels were measured by plate-based electrochemiluminescence using Meso Scale Discovery (MSD). Standard binding 96-well MSD plates were coated with lug/mL mouse anti-huPGRN (R&D Biosystems) in PBS overnight at 4° C. plates were blocked in 3% MSD buffer A in PBS for 1 hour at room temperature. Plates were then washed 3 times in TBST. 50 uL cell supernatant was added to the wells and incubated at room temperature for 1 hour. Plates were then washed as above and 50 μL of 1 ug/mL biotinylated goat anti-huPGRN (R&D Biosystems) in 1% MSD buffer A in PBS was added to the wells and plates were incubated for 1 hour at room temperature. Plates were washed as above and 05. ug/mL SULFO-TAG-Streptavidin (MSD) in 1% MSD buffer A in PBS was added the wells and plates were incubated for 1 hour at room temperature and then washed as above. 150 uL 2×MSD read buffer T was added to the wells and the electrochemiluminescence signal was read using the Meso Sector S 600. Data was analyzed using the Discovery workbench software (MSD) and were quantitated against a standard curve using 3-fold serial dilutions starting at 100 ng/mL of recombinant huPGRN (R&D Biosystems). Fold PGRN levels over controls were calculated using Microsoft excel. Of the 25 mouse anti-huSortilin mAbs tested, 19 showed a >1.5 fold increase in huPGRN over no mAbs control or isotype control wells. Results are depicted in FIG. 13.

The percent decrease in surface sortilin levels was determined by flow cytometry. U251MG cells were harvested and plated into 96-well untreated plates. 2.5ug/mL goat anti-human sortilin antibody (R&D Biosystems) were added to the wells (50 uL/well) and cells were incubated on ice for 1 hour. Cells were then washed twice in PBS+2% FBS and incubated for 30 minutes on ice with 50 uL per well Sug/mL Alexa-fluor647-donkey anti-goat (Jackson Immunoresearch) secondary antibody in PBS+2% FBS. Cells were then washed twice as above and resuspended in 100 uL PBS+2% FBS. Data was acquired using the BD LSR II and analyzed to determine Median Fluorescent Intensity (MFI) using FlowJo software version 10.6. the Percent of cell surface huSortilin compared to no mAb control wells using MFI values was calculated using Microsoft excel. Most mAbs showed a decrease in cell surface sortilin levels in U251 cells to varying degrees. 13/25 mouse anti-huSortilin mAbs increased extracellular huPGRN levels >1.5 fold and decrease cell surface sortilin by a maximum of 60%. Results are depicted in FIG. 13.

Example 9: Characterization of Murine mAbs by BIAcore

Analysis was performed using a Biacore T200 to compare the binding affinity of murine anti-huSortilin antibodies to recombinant human Sortilin. Anti-mouse antibody was immobilized on sensor chip CM5 (GE Healthcare Life Sciences) via amine coupling, and mouse antibodies (ligand) were captured to a level to ensure a maximum binding of analyte of 50 RU (approximately 100RU of ligand binding). Various concentrations of Sortilin (ranging from 0.1 nM to 300 nM) were passed over the captured ligand at 50 L/min in running buffer (HBS+0.05% P-20, 1 mg/mL BSA) for 180-300s association time and 300-900s dissociation time. Regeneration of the chip surface was accomplished by 2 short injections of 10 mM Glycine-HCl at pH 1.7. Data was blank subtracted to both a sensor not containing ligand and 0 nM analyte concentration. Analysis was performed using a global 1:1 fit with Biacore Insight Evaluation software (v2.0) with bulk refractive index set to zero RU. Binding data are shown in Table 6.

TABLE 6

Binding data of mAbs toward human Sortilin.

| mAb | ka 1/Ms | kd 1/s | $K_D$ nM |
|---|---|---|---|
| 5E20 | 8.77e+4 | 1.39e−4 | 1.59 |
| 8H24 | 9.66e+4 | 4.40e−4 | 4.56 |
| 11M14 | 9.11e+4 | 5.69e−4 | 6.24 |
| 5M13 | 1.79e+5 | 4.11e−4 | 2.29 |
| 2C14 | 2.08e+5 | 2.45e−3 | 11.8 |
| 2F18 | 5.76e+4 | 1.62e−4 | 2.81 |

TABLE 6-continued

Binding data of mAbs toward human Sortilin.

| mAb | ka 1/Ms | kd 1/s | $K_D$ nM |
|---|---|---|---|
| 2P22 | 1.08e+5 | 2.37e−4 | 2.21 |
| 6B15 | 1.27e+5 | 1.30e−4 | 1.02 |
| 9N18 | 1.91e+5 | 1.50e−4 | 11.7 |
| 4N2 | 1.68e+5 | 5.56e−4 | 3.2 |

Example 10: Epitope Mapping of Murine 5E20

PEPperMAP linear epitope mapping was carried out by PEPperPrint GmbH. Epitope analysis of 5E20 was performed by peptide microarray analysis. The sequence of the extracellular domain of human sortilin (756 amino acids, SEQ ID NO: 1) was elongated with neutral GSGSGSG (SEQ ID NO:207) linkers at the C- and N-terminus to avoid truncated peptides. The linked and elongated antigen sequence was translated into linear 15 amino acid peptides with a peptide-peptide overlap of 14 amino acids. The resulting human sortilin peptide microarrays contained 756 different peptides printed in duplicate (1,512 spots) and were framed by additional HA (YPYDVPDYAG, SEQ ID NO:200, 46 spots) and c-Myc (EQKLISEEDL, SEQ ID NO:201, 46 spots) control peptides.

After synthesis, the microarray was blocked to prevent nonspecific binding (Rockland catalog #MB-070). Murine 5E20 was then applied to the microarray at a concentration of 1 g/mL along with positive control mouse monoclonal anti-HA (12CA5) DyLight800 (0.5 μg/ml) for 16 h at 4° C. with shaking at 140 rpm. The microarray was washed, and secondary antibody (Goat anti-mouse IgG (H+L) DyLight680 (0.2 μg/ml) was applied for 45 minutes at room temperature. After further washing, the microarray was imaged using a Licor Odyssey Imaging System.

Quantification of spot intensities and peptide annotation were based on the 16-bit gray scale tiff files at scanning intensities of 7/7 that exhibit a higher dynamic range than the 24-bit colorized tiff files; microarray image analysis was done with PepSlide® Analyzer. A software algorithm separates fluorescence intensities of each spot into raw, foreground and background signal, and calculates averaged median foreground intensities and spot-to-spot deviations of spot duplicates (see "Raw Data" tabs). Based on averaged median foreground intensities, an intensity map was generated and interactions in the peptide map highlighted by an intensity color code with red for high and white for low spot intensities. A maximum spot-to-spot deviation of 40% was tolerated, otherwise the corresponding intensity value was zeroed.

A very strong monoclonal antibody response was observed for mouse 5E20 against an epitope-like spot pattern formed by adjacent peptides with the consensus motif FTESFLT (SEQ ID NO:202); we also observed two very weak additional responses against peptides with the consensus motifs DGCILGYKEQFL (SEQ ID NO:204) and PSICLCSLEDFL (SEQ ID NO:205) presumably due to a cross-reaction based on minor sequence similarities (see underlined amino acid positions).

Example 11: Characterization of Humanized mAbs: HuSortilin Binding ELISA 384-well ELISA plates were coated with 1 ug/mL recombinant ECD-huSortilin-HIS (20 uL/well) and incubated overnight at 4° C. all plates were blocked with 3% BSA in PBS for 1 hour at room temperature. Plates were then washed with Tris buffered saline containing 0.1% Tween20 (TBST) three times. 20 μL of humanized anti-Sortilin mAbs diluted 3-fold from 20ug/mL to 0.3 ng/mL in 1% BSA in TBST were added to the wells, incubated for 1 hour at room temperature and then washed as above. Goat anti-human IgG specific-HRP (Jackson Immunoresearch) diluted 1:7000 in 1% BSA in TBST was then added at 20 uL per well to react with the bound antibodies and plates were incubated for 1 hour before being washed as above. Super signal Pico chemiluminescent ELISA substrate (ThermoFisher) was used for detection. 20 uL of substrate was added to each well and Relative Light Units (RLU) were measured immediately using the SpectraMax Paradigm (Molecular Devices). Data was analyzed and $EC_{50}$ was calculated using graphed Prism. Results for selected combinations of humanized 5E20 variants are in Table 7. Results for selected combinations of humanized 8H24 variants are in Table 8. Results for selected combinations of humanized 11M14 variants are in Table 9.

TABLE 7

| Humanized 5E20 $EC_{50}$ | |
|---|---|
| mAb | $EC_{50}$ (ug/mL) |
| 5E20H1L1 | 0.12 |
| 5E20H1L2 | 0.12 |
| 5E20H1L3 | 0.09 |
| 5E20H2L1 | 0.12 |
| 5E20H2L2 | 0.08 |
| 5E20H2L3 | 0.10 |
| 5E20H3L3 | 0.09 |
| 5E20H3L4 | 0.07 |
| 5E20H4L3 | 0.07 |
| 5E20H4L4 | 0.04 |
| 5E20H5L3 | 0.07 |
| 5E20H5L4 | 0.05 |
| 5E20H7L3 | 0.06 |
| 5E20H7L4 | 0.04 |
| chimeric 5E20 | 0.07 |

TABLE 8

| Humanized 8H24 $EC_{50}$ | |
|---|---|
| mAb | $EC_{50}$ (ug/mL) |
| 8H24H1L1 | 0.14 |
| 8H24H1L2 | 0.10 |
| 8H24H2L1 | 0.06 |
| 8H24H2L2 | 0.07 |

TABLE 9

| Humanized 11M14 $EC_{50}$ | |
|---|---|
| mAb | $EC_{50}$ (ug/mL) |
| 11M14H1bL2b | 0.08 |
| 11M14H1bL3b | 0.07 |
| 11M14H1bL4b | 0.08 |
| 11M14H2bL2b | 0.07 |
| 11M14H2bL3b | 0.13 |
| 11M14H2bL4b | 0.10 |
| 11M14H3bL2b | 0.19 |
| 11M14H3bL3b | 0.23 |
| 11M14H3bL4b | 0.10 |
| Chimeric 11M14 | 0.06 |

Example 12: Characterization of Humanized mAbs: Functional Assays

U251MG cells were seeded in 96-well plates and incubated overnight at 37° C.-5% $CO_2$. The next day, media was removed and fresh media containing 10-fold dilution from 50 nM to 0.5 nM (5E20 round 2 and 11M14 round 2) or 3-fold dilution from 50 nM to 5.6 nM (5E20 round 1 and 8H24) humanized, murine and chimeric variants of anti-Sortilin mAbs or Isotype control antibodies were added to the wells. Cells were cultured for 72 hours. Supernatants were then used to determine extracellular huPGRN levels and the cells were harvested to examine cell surface sortilin levels.

The increase in PGRN levels were measured by plate-based electrochemiluminescence using Meso Scale Discovery (MSD). Standard binding 96-well MSD plates were coated with lug/mL mouse anti-huPGRN (R&D Biosystems) in PBS overnight at 4° C. plates were then blocked in 3% MSD buffer A in PBS for 1 hour at room temperature. Plates were then washed 3 times in TBST. 50 uL supernatant was added to the wells and incubated at room temperature for 1 hour. Plates were then washed as above and 50 uL of 1 ug/mL biotinylated goat anti-huPGRN (R&D Biosystems) in 1% MSD buffer A in PBS was added to the wells and plates were incubated for 1 hour at room temperature. Plates were washed as above and 05. ug/mL SULFO-TAG-Streptavidin (MSD) in 1% MSD buffer A in PBS was added the wells and plates were incubated for 1 hour at room temperature and then washed as above. 150 uL of 2×MSD read buffer T was added to the wells and the electrochemiluminescence signal was read using the Meso Sector S 600. Data was analyzed using the Discovery workbench software (MSD) and were quantitated against a standard curve using 3-fold serial dilutions starting at 100 ng/mL of recombinant huPGRN (R&D Biosystems). Fold PGRN levels over controls were calculated using Microsoft excel. Results for selected combinations of humanized 5E20 variants are in Table 10. Results for selected combinations of humanized 8H24 variants are in Table 11. Results for selected combinations of humanized 11M14 variants are in Table 12.

The percent decrease in surface sortilin levels was determined by flow cytometry. U251MG cells were harvested and plated untreated 96-well plate. 2.5ug/mL goat anti-human sortilin antibody (R&D Biosystems) were added to the wells (50 uL/well) and cells were incubated on ice for 1 hour. Cells were then washed twice in PBS+2% FBS and incubated for 30 minutes on ice with 50 uL per well Sug/mL Alexa-fluor647-donkey anti-goat (Jackson Immunoresearch) secondary antibody in PBS+2% FBS. Cells were then washed twice as above and resuspended in 100 uL PBS+2% FBS. Data was acquired using the BD LSR II and analyzed to determine Median Fluorescent Intensity (MFI) using FlowJo software version 10.6. the Percent of cell surface huSortilin compared to no mAb control wells using MFI values was calculated using Microsoft excel. Results for selected combinations of humanized 5E20 variants are in Table 10. Results for selected combinations of humanized 8H24 variants are in Table 11. Results for selected combinations of humanized 11M14 variants are in Table 12.

TABLE 10

Humanized 5E20 variants: Increase in PGRN levels and Decrease in surface sortilin levels 5E20 Round1

| | 5E20H1L1 | 5E20H1L2 | 5E20H1L3 | 5E20H2L1 | 5E20H2L2 | 5E20H2L3 | ms5E20 | chimeric 5E20 | msIgG1 ctrl | huIgG1 ctrl |
|---|---|---|---|---|---|---|---|---|---|---|
| % Cell Surface huSortilin by median MFI | | | | | | | | | | |
| 50 nM (7.5 ug/mL) | 83 | 83 | 94 | 88 | 86 | 82 | 81 | 94 | 116 | 110 |
| 16.7 nM (2.5 ug/mL) | 83 | 82 | 94 | 92 | 89 | 84 | 82 | 94 | 114 | 105 |
| 5.6 nM (0.8 ug/mL) | 85 | 88 | 98 | 98 | 94 | 87 | 84 | 95 | 112 | 104 |
| huPGRN fold over Control | | | | | | | | | | |
| 50 nM (7.5 ug/mL) | 1.4 | 1.3 | 1.2 | 1.1 | 1.4 | 1.3 | 2.0 | 1.8 | 1.1 | 1.0 |
| 16.7 nM (2.5 ug/mL) | 1.5 | 1.5 | 1.4 | 1.6 | 1.4 | 1.4 | 2.0 | 1.8 | 1.0 | 1.0 |
| 5.6 nM (0.8 ug/mL) | 1.5 | 1.6 | 1.2 | 1.3 | 1.3 | 1.3 | 1.9 | 1.9 | 1.1 | 1.0 |

5E20 Round2

| | 5E20H3L3 | 5E20H3L4 | 5E20H4L3 | 5E20H4L4 | 5E20H5L3 | 5E20H5L4 | 5E20H7L4 | chimeric 5E20 | ms5E20new | huIgG1 ctrl |
|---|---|---|---|---|---|---|---|---|---|---|
| huPGRN fold over Control | | | | | | | | | | |
| 50 nM (7.5 ug/mL) | 0.9 | 1.2 | 1.4 | 1.6 | 1.6 | 1.6 | 1.8 | 2.1 | 1.9 | 1.2 |
| 5 nM (0.75 ug/mL) | 0.9 | 1.3 | 1.2 | 1.4 | 1.3 | 1.5 | 1.7 | 1.8 | 1.8 | 1.1 |
| 0.5 nM (0.08 ug/mL) | 0.9 | 0.9 | 1.1 | 1.4 | 1.3 | 1.1 | 1.4 | 1.9 | 1.6 | 1.1 |
| % Cell Surface huSortilin by median APC | 5E20H3L3 | 5E20H3L4 | 5E20H4L3 | 5E20H4L4 | 5E20H5L3 | 5E20H5L4 | 5E20H7L4 | chimeric 5E20 | ms5E20 | huIgG1 ctrl |
| 50 nM (7.5 ug/mL) | 61 | 60 | 63 | 57 | 59 | 60 | 65 | 63 | 50 | 104 |
| 5 nM (0.75 ug/mL) | 67 | 68 | 62 | 64 | 66 | 65 | 67 | 63 | 51 | 105 |
| 0.5 nM (0.08 ug/mL) | 90 | 90 | 87 | 87 | 89 | 85 | 85 | 77 | 70 | 106 |

TABLE 11

Humanized 8H24 variants: Increase in PGRN levels and Decrease in surface sortilin levels
8H24

| | 8H24H1L1 | 8H24H1L2 | 8H24H2L1 | 8H24H2L2 | mu8H24 | Chimeric 8H24 | msIgG2 ctrl | huIgG1 ctrl |
|---|---|---|---|---|---|---|---|---|
| huPGRN fold over Control | | | | | | | | |
| 50 nM (7.5 ug/mL) | 1.4 | 1.5 | 1.4 | 1.3 | 1.4 | 1.4 | 0.9 | 1.0 |
| 16.7 nM (2.5 ug/mL) | 1.4 | 1.5 | 1.4 | 1.4 | 1.6 | 1.5 | 1.1 | 1.0 |

TABLE 11-continued

Humanized 8H24 variants: Increase in PGRN levels and Decrease in surface sortilin levels
8H24

| | 8H24H1L1 | 8H24H1L2 | 8H24H2L1 | 8H24H2L2 | mu8H24 | Chimeric 8H24 | msIgG2 ctrl | huIgG1 ctrl |
|---|---|---|---|---|---|---|---|---|
| 5.6 nM (0.8 ug/mL) | 1.2 | 1.2 | 1.1 | 1.0 | 1.2 | 1.1 | 0.9 | 0.9 |
| % Cell Surface huSortilin by median MFI | | | | | | | | |
| 50 nM (7.5 ug/mL) | 49 | 49 | 49 | 50 | 43 | 51 | 105 | 94 |
| 16.7 nM (2.5 ug/mL) | 49 | 49 | 49 | 50 | 43 | 51 | 105 | 94 |
| 5.6 nM (0.8 ug/mL) | 86 | 81 | 82 | 84 | 77 | 76 | 102 | 101 |

TABLE 12

Humanized 11M14 variants: Increase in PGRN levels and Decrease in surface sortilin levels
11M14 Round 2

| | 11M14 H1bL2b | 11M14 H1bL3b | 11M14 H1bL4b | 11M14 H2bL2b | 11M14 H2bL3b | 11M14 H2bL4b | 11M14 H3bL2b | 11M14 H3bL3b | 11M14 H3bL4b | Chimeric 11M14 | ms11M14 | huIgG1 ctrl |
|---|---|---|---|---|---|---|---|---|---|---|---|---|
| huPGRN fold over Control | | | | | | | | | | | | |
| 50 nM (7.5 ug/mL) | 1.9 | 1.9 | 1.7 | 1.6 | 1.8 | 1.8 | 1.7 | 1.6 | 1.7 | 1.5 | 1.5 | 1.2 |
| 5 nM (0.75 ug/mL) | 1.6 | 1.7 | 1.6 | 1.7 | 1.7 | 1.6 | 1.5 | 1.5 | 1.4 | 1.5 | 1.3 | 1.1 |
| 0.5 nM (0.08 ug/mL) | 1.3 | 1.3 | 1.2 | 1.0 | 1.2 | 1.2 | 1.2 | 1.2 | 1.2 | 1.2 | 1.1 | 1.1 |
| % Cell Surface huSortilin by median MFI | | | | | | | | | | | | |
| 50 nM (7.5 ug/mL) | 65 | 67 | 69 | 71 | 72 | 75 | 77 | 78 | 74 | 75 | 58 | 104 |
| 5 nM (0.75 ug/mL) | 68 | 70 | 72 | 76 | 73 | 75 | 79 | 79 | 83 | 76 | 63 | 105 |
| 0.5 nM (0.08 ug/mL) | 77 | 76 | 81 | 80 | 82 | 80 | 87 | 90 | 92 | 85 | 75 | 106 |

Example 13: Characterization of Humanized mAbs by BIAcore

Analysis was performed using a Biacore T200 to compare the binding affinity of chimeric and humanized antibodies to recombinant human Sortilin. Anti-Human antibody was immobilized on sensor chip CM5 (GE Healthcare Life Sciences) via amine coupling, and humanized antibodies (ligand) were captured to a level to ensure a maximum binding of analyte of 50 RU (approximately 100 RU of ligand binding). Various concentrations of Sortilin (ranging from 0.1 nM to 300 nM) were passed over the captured ligand at 50 L/min in running buffer (HBS+0.05% P-20, 1 mg/mL BSA) for 300s association time and 1200s dissociation time. Regeneration of the chip surface was accomplished by 2 short injections of 3M MgCl. Data was blank subtracted to both a sensor not containing ligand and 0 nM analyte concentration. Analysis was performed using a global 1:1 fit with Biacore Insight Evaluation software (v2.0) with bulk refractive index set to zero RU. Binding data for selected combinations of 8H24 humanized variants, 5E20 humanized variants, chimeric 5E20, 11M14 humanized variants, and chimeric 11M14 are shown in Table 13.

TABLE 13

Binding data of 8H24, 5E20, and 11M14 humanized variants toward human Sortilin.

| mAb | ka 1/Ms | kd 1/s | $K_D$ nM |
|---|---|---|---|
| 8H24H1L1 | 6.37e+5 | 1.41e−3 | 2.22 |
| 8H24H1L2 | 4.50e+5 | 1.34e−3 | 2.98 |
| 8H24H2L1 | 6.84e+5 | 2.57e−3 | 2.29 |
| 8H24H2L2 | 4.66e+5 | 2.50e−3 | 3.22 |
| Chimeric 5E20 | 5.97e+5 | 3.96e−4 | 0.66 |
| 5E20H3L3 | 1.83e+5 | 2.80e−3 | 15.3 |
| 5E20H3L4 | 1.74e+5 | 2.57e−3 | 14.8 |
| 5E20H4L3 | 2.28e+5 | 1.45e−3 | 6.36 |
| 5E20H4L4 | 2.09e+5 | 1.17e−3 | 5.57 |
| 5E20H5L3 | 2.33e+5 | 1.40e−3 | 6.01 |
| 5E20H5L4 | 2.11e+5 | 1.15e−3 | 5.46 |
| 5E20H7L3 | 2.59e+5 | 1.08e−3 | 4.18 |
| 5E20H7L4 | 2.18e+5 | 1.10e−3 | 5.02 |
| Chimeric 11M14 | 3.84e+05 | 9.69e−04 | 2.52 |
| HM14H1bL2b | 3.60e+05 | 1.93e−03 | 5.37 |
| HM14H1bL3b | 3.77e+05 | 2.00e−03 | 5.30 |
| HM14H1bL4b | 3.57e+05 | 1.90e−03 | 5.32 |
| HM14H2bL2b | 4.21e+05 | 1.20e−03 | 2.86 |
| HM14H2bL3b | 3.98e+05 | 1.19e−03 | 2.99 |

TABLE 13-continued

Binding data of 8H24, 5E20, and 11M14 humanized variants toward human Sortilin.

| mAb | ka 1/Ms | kd 1/s | $K_D$ nM |
|---|---|---|---|
| HM14H2bL4b | 4.13e+05 | 1.17e−03 | 2.84 |
| HM14H3bL2b | 3.19e+05 | 2.25e−03 | 7.07 |
| HM14H3bL3b | 3.74e+05 | 3.43e−03 | 9.17 |
| HM14H3bL4b | 4.35e+05 | 3.44e−03 | 7.91 |

Example 14. Design of Humanized 5E20 Antibodies

The starting point or donor antibody for humanization was the mouse antibody 5E20. The heavy chain variable amino acid sequence of mature m5E20 is provided as SEQ ID NO:4. The light chain variable amino acid sequence of mature m5E20 is provided as SEQ ID NO:10. The heavy chain Kabat/Chothia Composite CDR1, CDR2, and CDR3 amino acid sequences are provided as SEQ ID NOS:5-7, respectively. The light chain Kabat CDR1, CDR2, and CDR3 amino acid sequences are provided as SEQ ID NOS:11-13, respectively. Kabat numbering is used throughout.

The variable kappa (Vk) of 5E20 belongs to mouse Vk subgroup 1b which corresponds to human Vk subgroup 1 and the variable heavy (Vh) to mouse Vh subgroup 3d which corresponds to human Vh subgroup 1 [Kabat E. A., et al., (1991), Sequences of Proteins of Immunological Interest, Fifth Edition. NIH Publication No. 91-3242]. 11 residue Chothia CDR-L1 is similar to Chothia canonical class 2, 7 residue Chothia CDR-L2 is of Chothia canonical class 1, 9 residue Chothia CDR-L3 is similar to Chothia canonical class 1 [Martin A C R. (2010) Protein sequence and structure analysis of antibody variable domains. In: Kontermann R and Dübel S (eds). *Antibody Engineering*. Heidelberg, Germany: Springer International Publishing AG. [Martin, 2010]. 10 residue Chothia CDR-H1 is similar to Chothia canonical class 1, 17 residue Chothia CDR-H2 is similar to Chothia canonical class 3 [Martin, 2010]. 5 residue CDR-H3 has no canonical classes. A search was made over the protein sequences in the PDB database [Deshpande N, et al., (2005) Nucleic Acids Res. 33: D233-7] to find structures, which would provide a rough structural model of 5E20. The crystal structure of an antibody fab PDB code 3V6F [Dimattia, M. A. et al., Structure 21: 133-142., 2013] for both Vh and Vk structure since it had good resolution (2.52A°) and overall sequence similarity to 5E20 Vh and Vk, retaining the same canonical structures for the loops.

The frameworks of 5E20 VH share a high degree of sequence similarity with the corresponding regions of human antibody AEX29086 VH, cloned by Bowers, E. et al. (PLoS ONE 9 (1), E81913 (2014)) The variable heavy domains of 5E20 and AEX29086 also share identical lengths for the CDR-H1, H2 loops. Similarly, the frameworks of 5E20 VL share a high degree of sequence similarity with the corresponding regions of human antibody BAH04687 VL cloned by Kurosawa, Y. et al (Direct submission 2016). The variable light domain of 5E20 and BAH04687 antibody also share identical lengths for the CDR-L1, L2 and L3 loops. Accordingly, the framework regions of AEX29086 VH and BAH04687 VL were chosen as the acceptor sequences for the CDRs of 5E20. A model of the 5E20 CDRs grafted onto the respective human frameworks for VH and VL was built and used as a guidance for further backmutations.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN: International nonproprietary names (INN) for biological and biotechnological substances (a review) (Internet) 2014. Available from: http://www. who.int/medicines/services/inn/BioRev2014.pdf) Residues were changed to align with corresponding human germ line sequence, where possible, to enhance humanness and to reduce potential immunogenicity. For humanized VLv2, VLv3, VLv4, and VLv5 variants, mutations were introduced to render the sequences more similar to human germ line gene IGKV1-12*01 (SEQ ID NO:172) For humanized VHv2, VHv3, VHv4, VHv5, VHv6, and VHv7 variants, mutations were introduced to render the sequences more similar to human germ line gene IGHV3-21*01 (SEQ ID NO:162).

Additional versions of hu5E20-VH and hu5E20-VL were designed to enable assessment of various framework residues for their contributions to antigen binding, thermostability, developability (deamination, oxidation, N-glycosylation, proteolysis and aggregation) and immunogenicity. The positions considered for mutation include those that . . .

- define the canonical CDR conformations (summarized in Martin),
- are within the Vernier zone (Foote and Winter),
- localize to the VH/VL domain interface (summarized in Leger and Saldanha),
- are susceptible to post-translational modifications, such as glycosylation or pyroglutamination,
- are occupied by residues that are predicted to clash with CDRs, according to the model of 5E20 CDRs grafted onto VH and VL frameworks, or
- are occupied by residues that are rare among sequenced human antibodies, where either the parental mouse 5E20 residue or some other residue is much more prevalent within human antibody repertoire.

Alignments of the murine 5E20 and various humanized antibodies are shown for the light chain variable regions (Table 15 and FIG. 2), and heavy chain variable regions (Table 14 and FIG. 1)

7 humanized heavy chain variable region variants and 4 humanized light chain variable region variants were constructed containing different permutations of substitutions: hu5E20VHv1, hu5E20VHv2, hu5E20VHv3, hu5E20VHv4, hu5E20VHv5, hu5E20VHv6, or hu5E20VHv7 (SEQ ID NOS:163-169, respectively); and hu5E20VLv1, hu5E20VLv2, hu5E20VLv3, or hu5E20VLv4 (SEQ ID NOS:173-176, respectively) (Tables 14 and 15). The exemplary humanized Vk and Vh designs, with backmutations and other mutations based on selected human frameworks, are shown in Tables 14 and 15, respectively. The bolded areas in Tables 14 and 15 indicate the CDRs as defined by Kabat/Chothia Composite. A "-" in the columns in Tables 14 and 15 indicates no residue at the indicated position. SEQ ID NOS:163-169, and SEQ ID NOS:173-176 contain backmutations and other mutations as shown in Table 16. The amino acids at positions in hu5E20VHv1, hu5E20VHv2, hu5E20VHv3, hu5E20VHv4, hu5E20VHv5, hu5E20VHv6, and hu5E20VHv7 are listed in Table 17. The amino acids at positions in hu5E20VLv1, hu5E20VLv2, hu5E20VLv3, and hu5E20VLv4 are listed in Table 18.

The percentage humanness for humanized VH chains hu5E20VHv1, hu5E20VHv2, hu5E20VHv3, hu5E20VHv4, hu5E20VHv5, hu5E20VHv6, and hu5E20VHv7 (SEQ ID NOS:163-169, respectively) with respect to the most similar human germline gene IGHV3-21*01 (SEQ ID NO:162), and for humanized VL chains hu5E20VLv1, hu5E20VLv2, hu5E20VLv3, and hu5E20VLv4 (SEQ ID NOS:173-176, respectively) with respect to the most similar human germline gene IGKV1-12*01 (SEQ ID NO:172) is shown in Table 19.

TABLE 14

| VH sequences | | | | | | | | | | | | |
|---|---|---|---|---|---|---|---|---|---|---|---|---|
| Kabat residue # | Linear residue # | FR or CDR | Mouse 5E20 VH (SEQ ID NO: 4) | AEX29086-VH_huFrwk (SEQ ID NO: 161) | IMGT# IGHV3-21*01 (SEQ ID NO: 162) | Hu5E20-VHv1 (SEQ ID NO: 163) | Hu5E20-VHv2 (SEQ ID NO: 164) | Hu5E20-VHv3 (SEQ ID NO: 165) | Hu5E20-VHv4 (SEQ ID NO: 166) | Hu5E20-VHv5 (SEQ ID NO: 167) | Hu5E20-VHv6 (SEQ ID NO: 168) | Hu5E20-VHv7 (SEQ ID NO: 169) |
| 1 | 1 | Fr1 | E | E | E | E | E | E | E | E | E | E |
| 2 | 2 | Fr1 | V | V | V | V | V | V | V | V | V | V |
| 3 | 3 | Fr1 | Q | Q | Q | Q | Q | Q | Q | Q | Q | Q |
| 4 | 4 | Fr1 | L | L | L | L | L | L | L | L | L | L |
| 5 | 5 | Fr1 | V | L | V | L | V | V | V | V | V | V |
| 6 | 6 | Fr1 | E | E | E | E | E | E | E | E | E | E |
| 7 | 7 | Fr1 | S | S | S | S | S | S | S | S | S | S |
| 8 | 8 | Fr1 | G | G | G | G | G | G | G | G | G | G |
| 9 | 9 | Fr1 | G | G | G | G | G | G | G | G | G | G |
| 10 | 10 | Fr1 | D | G | G | G | G | G | G | G | G | G |
| 11 | 11 | Fr1 | L | L | L | L | L | L | L | L | L | L |
| 12 | 12 | Fr1 | V | V | V | V | V | V | V | V | V | V |
| 13 | 13 | Fr1 | K | Q | K | Q | Q | Q | Q | Q | Q | Q |
| 14 | 14 | Fr1 | P | P | P | P | P | P | P | P | P | P |
| 15 | 15 | Fr1 | G | G | G | G | G | G | G | G | G | G |
| 16 | 16 | Fr1 | G | G | G | G | G | G | G | G | G | G |
| 17 | 17 | Fr1 | S | S | S | S | S | S | S | S | S | S |
| 18 | 18 | Fr1 | L | L | L | L | L | L | L | L | L | L |
| 19 | 19 | Fr1 | K | R | R | R | R | R | R | R | R | R |
| 20 | 20 | Fr1 | L | L | L | L | L | L | L | L | L | L |
| 21 | 21 | Fr1 | S | S | S | S | S | S | S | S | S | S |
| 22 | 22 | Fr1 | C | C | C | C | C | C | C | C | C | C |
| 23 | 23 | Fr1 | A | A | A | A | A | A | A | A | A | A |
| 24 | 24 | Fr1 | A | A | A | A | A | A | A | A | A | A |
| 25 | 25 | Fr1 | P | S | S | S | S | S | S | S | S | S |
| **26** | **26** | **CDR-H1** | **G** | **G** | **G** | **G** | **G** | **G** | **G** | **G** | **G** | **G** |
| **27** | **27** | **CDR-H1** | **F** | **F** | **F** | **F** | **F** | **F** | **F** | **F** | **F** | **F** |
| **28** | **28** | **CDR-H1** | **T** | **T** | **T** | **T** | **T** | **T** | **T** | **T** | **T** | **T** |
| **29** | **29** | **CDR-H1** | **F** | **F** | **F** | **F** | **F** | **F** | **F** | **F** | **F** | **F** |
| **30** | **30** | **CDR-H1** | **S** | **S** | **S** | **S** | **S** | **S** | **S** | **S** | **S** | **S** |
| **31** | **31** | **CDR-H1** | **T** | **S** | **S** | **T** | **T** | **T** | **T** | **T** | **T** | **T** |
| **32** | **32** | **CDR-H1** | **Y** | **Y** | **Y** | **Y** | **Y** | **Y** | **Y** | **Y** | **Y** | **Y** |
| **33** | **33** | **CDR-H1** | **G** | **A** | **S** | **G** | **G** | **G** | **G** | **G** | **G** | **G** |
| **34** | **34** | **CDR-H1** | **M** | **M** | **M** | **M** | **M** | **M** | **M** | **M** | **M** | **M** |
| **35** | **35** | **CDR-H1** | **S** | **S** | **N** | **S** | **S** | **S** | **S** | **S** | **S** | **S** |
| **35A** | | **CDR-H1** | — | — | — | — | — | — | — | — | — | — |
| **35B** | | **CDR-H1** | — | — | — | — | — | — | — | — | — | — |
| 36 | 36 | Fr2 | W | W | W | W | W | W | W | W | W | W |
| 37 | 37 | Fr2 | V | V | V | V | V | V | V | V | V | V |
| 38 | 38 | Fr2 | R | R | R | R | R | R | R | R | R | R |
| 39 | 39 | Fr2 | Q | Q | Q | Q | Q | Q | Q | Q | Q | Q |
| 40 | 40 | Fr2 | T | A | A | A | A | A | A | A | T | T |
| 41 | 41 | Fr2 | P | P | P | P | P | P | P | P | P | P |
| 42 | 42 | Fr2 | D | G | G | G | G | G | D | D | G | D |
| 43 | 43 | Fr2 | K | K | K | K | K | K | K | K | K | K |
| 44 | 44 | Fr2 | R | G | G | G | G | R | R | R | R | R |
| 45 | 45 | Fr2 | L | L | L | L | L | L | L | L | L | L |
| 46 | 46 | Fr2 | E | E | E | E | E | E | E | E | E | E |
| 47 | 47 | Fr2 | W | W | W | W | W | W | W | W | W | W |
| 48 | 48 | Fr2 | V | V | V | V | V | V | V | V | V | V |
| 49 | 49 | Fr2 | A | S | S | A | A | A | A | A | A | A |
| **50** | **50** | **CDR-H2** | **I** | **A** | **S** | **I** | **I** | **I** | **I** | **I** | **I** | **I** |
| **51** | **51** | **CDR-H2** | **I** | **I** | **I** | **I** | **I** | **I** | **I** | **I** | **I** | **I** |
| **52** | **52** | **CDR-H2** | **S** | **S** | **S** | **S** | **S** | **S** | **S** | **S** | **S** | **S** |
| **52A** | **53** | **CDR-H2** | **S** | **G** | **S** | **S** | **S** | **S** | **S** | **S** | **S** | **S** |
| **52B** | | **CDR-H2** | — | — | — | — | — | — | — | — | — | — |
| **52C** | | **CDR-H2** | — | — | — | — | — | — | — | — | — | — |
| **53** | **54** | **CDR-H2** | **G** | **S** | **S** | **G** | **G** | **G** | **G** | **G** | **G** | **G** |
| **54** | **55** | **CDR-H2** | **G** | **G** | **S** | **G** | **G** | **G** | **G** | **G** | **G** | **G** |
| **55** | **56** | **CDR-H2** | **S** | **G** | **S** | **S** | **S** | **S** | **S** | **S** | **S** | **S** |
| **56** | **57** | **CDR-H2** | **Y** | **S** | **Y** | **Y** | **Y** | **Y** | **Y** | **Y** | **Y** | **Y** |
| **57** | **58** | **CDR-H2** | **T** | **T** | **I** | **T** | **T** | **T** | **T** | **T** | **T** | **T** |
| **58** | **59** | **CDR-H2** | **Y** | **Y** | **Y** | **Y** | **Y** | **Y** | **Y** | **Y** | **Y** | **Y** |
| **59** | **60** | **CDR-H2** | **Y** | **Y** | **Y** | **Y** | **Y** | **Y** | **Y** | **Y** | **Y** | **Y** |
| **60** | **61** | **CDR-H2** | **S** | **A** | **A** | **S** | **S** | **S** | **S** | **S** | **S** | **S** |
| **61** | **62** | **CDR-H2** | **D** | **D** | **D** | **D** | **D** | **D** | **D** | **D** | **D** | **D** |

TABLE 14-continued

| VH sequences | | | | | | | | | | | | |
|---|---|---|---|---|---|---|---|---|---|---|---|---|
| Kabat residue # | Linear residue # | FR or CDR | Mouse 5E20 VH (SEQ ID NO: 4) | AEX29086-VH_huFrwk (SEQ ID NO: 161) | IMGT# IGHV3-21*01 (SEQ ID NO: 162) | Hu5E20-VHv1 (SEQ ID NO: 163) | Hu5E20-VHv2 (SEQ ID NO: 164) | Hu5E20-VHv3 (SEQ ID NO: 165) | Hu5E20-VHv4 (SEQ ID NO: 166) | Hu5E20-VHv5 (SEQ ID NO: 167) | Hu5E20-VHv6 (SEQ ID NO: 168) | Hu5E20-VHv7 (SEQ ID NO: 169) |
| 62 | 63 | CDR-H2 | T | S | S | T | T | T | T | T | T | T |
| 63 | 64 | CDR-H2 | V | V | V | V | V | V | V | V | V | V |
| 64 | 65 | CDR-H2 | K | R | K | K | K | K | K | K | K | K |
| 65 | 66 | CDR-H2 | G | G | G | G | G | G | G | G | G | G |
| 66 | 67 | Fr3 | R | R | R | R | R | R | R | R | R | R |
| 67 | 68 | Fr3 | F | F | F | F | F | F | F | F | F | F |
| 68 | 69 | Fr3 | T | T | T | T | T | T | T | T | T | T |
| 69 | 70 | Fr3 | I | I | I | I | I | I | I | I | I | I |
| 70 | 71 | Fr3 | S | S | S | S | S | S | S | S | S | S |
| 71 | 72 | Fr3 | R | R | R | R | R | R | R | R | R | R |
| 72 | 73 | Fr3 | D | D | D | D | D | D | D | D | D | D |
| 73 | 74 | Fr3 | N | N | N | N | N | N | N | N | N | N |
| 74 | 75 | Fr3 | A | S | A | S | S | S | S | S | S | S |
| 75 | 76 | Fr3 | K | K | K | K | K | K | K | K | K | K |
| 76 | 77 | Fr3 | N | N | N | N | N | N | N | N | N | N |
| 77 | 78 | Fr3 | T | T | S | T | S | S | S | S | S | S |
| 78 | 79 | Fr3 | L | L | L | L | L | L | L | L | L | L |
| 79 | 80 | Fr3 | Y | Y | Y | Y | Y | Y | Y | Y | Y | Y |
| 80 | 81 | Fr3 | L | L | L | L | L | L | L | L | L | L |
| 81 | 82 | Fr3 | Q | Q | Q | Q | Q | Q | Q | Q | Q | Q |
| 82 | 83 | Fr3 | M | M | M | M | M | M | M | M | M | M |
| 82A | 84 | Fr3 | S | N | N | N | N | N | N | N | N | N |
| 82B | 85 | Fr3 | S | S | S | S | S | S | S | S | S | S |
| 82C | 86 | Fr3 | L | L | L | L | L | L | L | L | L | L |
| 83 | 87 | Fr3 | K | R | R | R | R | R | R | K | R | R |
| 84 | 88 | Fr3 | S | A | A | A | A | A | A | A | A | A |
| 85 | 89 | Fr3 | E | E | E | E | E | E | E | E | E | E |
| 86 | 90 | Fr3 | D | D | D | D | D | D | D | D | D | D |
| 87 | 91 | Fr3 | T | T | T | T | T | T | T | T | T | T |
| 88 | 92 | Fr3 | A | A | A | A | A | A | A | A | A | A |
| 89 | 93 | Fr3 | M | V | V | V | V | V | V | V | V | V |
| 90 | 94 | Fr3 | Y | Y | Y | Y | Y | Y | Y | Y | Y | Y |
| 91 | 95 | Fr3 | Y | Y | Y | Y | Y | Y | Y | Y | Y | Y |
| 92 | 96 | Fr3 | C | C | C | C | C | C | C | C | C | C |
| 93 | 97 | Fr3 | S | A | A | S | S | S | S | S | S | S |
| 94 | 98 | Fr3 | R | K | R | R | R | R | R | R | R | R |
| 95 | 99 | CDR-H3 | S | S | D | S | S | S | S | S | S | S |
| 96 | | CDR-H3 | S | G | A | S | S | S | S | S | S | S |
| 97 | | CDR-H3 | S | T | F | S | S | S | S | S | S | S |
| 98 | | CDR-H3 | H | P | — | H | H | H | H | H | H | H |
| 99 | | CDR-H3 | W | W | — | W | W | W | W | W | W | W |
| 100 | | CDR-H3 | Y | Y | — | Y | Y | Y | Y | Y | Y | Y |
| 100A | | CDR-H3 | F | F | — | F | F | F | F | F | F | F |
| 100B | | CDR-H3 | — | — | — | — | — | — | — | — | — | — |
| 100C | | CDR-H3 | — | — | — | — | — | — | — | — | — | — |
| 100D | | CDR-H3 | — | — | — | — | — | — | — | — | — | — |
| 100E | | CDR-H3 | — | — | — | — | — | — | — | — | — | — |
| 100F | | CDR-H3 | — | — | — | — | — | — | — | — | — | — |
| 100G | | CDR-H3 | — | — | — | — | — | — | — | — | — | — |
| 100H | | CDR-H3 | — | — | — | — | — | — | — | — | — | — |
| 100I | | CDR-H3 | — | — | — | — | — | — | — | — | — | — |
| 100J | | CDR-H3 | — | — | — | — | — | — | — | — | — | — |
| 100K | | CDR-H3 | — | — | — | — | — | — | — | — | — | — |
| 101 | 100 | CDR-H3 | D | D | D | D | D | D | D | D | D | D |
| 102 | 101 | CDR-H3 | V | Y | V | V | V | V | V | V | V | V |
| 103 | 102 | Fr4 | W | W | W | W | W | W | W | W | W | W |
| 104 | 103 | Fr4 | G | G | G | G | G | G | G | G | G | G |
| 105 | 104 | Fr4 | T | Q | Q | Q | Q | Q | Q | Q | Q | Q |
| 106 | 105 | Fr4 | G | G | G | G | G | G | G | G | G | G |
| 107 | 106 | Fr4 | T | T | T | T | T | T | T | T | T | T |
| 108 | 107 | Fr4 | T | L | M | L | L | L | L | L | L | L |
| 109 | 108 | Fr4 | V | V | V | V | V | V | V | V | V | V |
| 110 | 109 | Fr4 | T | T | T | T | T | T | T | T | T | T |
| 111 | 110 | Fr4 | V | V | V | V | V | V | V | V | V | V |
| 112 | 111 | Fr4 | S | S | S | S | S | S | S | S | S | S |
| 113 | 112 | Fr4 | S | S | S | S | S | S | S | S | S | S |

TABLE 15

5E20 VL sequences

| Kabat residue # | Linear residue # | FR or CDR | Mouse 5E20 VL (SEQ ID NO: 10) | BAH04687-VL_huFrwk (SEQ ID NO: 171) | IGKV1-12*01 (SEQ ID NO: 172) | Hu5E20VLv1 (SEQ ID NO: 173) | Hu5E20VLv2 (SEQ ID NO: 174) | Hu5E20VLv3 (SEQ ID NO: 175) | Hu5E20VLv4 (SEQ ID NO: 176) |
|---|---|---|---|---|---|---|---|---|---|
| 1 | 1 | Fr1 | D | D | D | D | D | D | D |
| 2 | 2 | Fr1 | I | I | I | I | I | I | I |
| 3 | 3 | Fr1 | L | Q | Q | Q | Q | Q | Q |
| 4 | 4 | Fr1 | M | M | M | M | M | M | M |
| 5 | 5 | Fr1 | T | T | T | T | T | T | T |
| 6 | 6 | Fr1 | Q | Q | Q | Q | Q | Q | Q |
| 7 | 7 | Fr1 | S | S | S | S | S | S | S |
| 8 | 8 | Fr1 | P | P | P | P | P | P | P |
| 9 | 9 | Fr1 | S | S | S | S | S | S | S |
| 10 | 10 | Fr1 | S | S | S | S | S | S | S |
| 11 | 11 | Fr1 | M | L | V | L | V | V | V |
| 12 | 12 | Fr1 | S | S | S | S | S | S | S |
| 13 | 13 | Fr1 | V | A | A | A | A | A | A |
| 14 | 14 | Fr1 | S | S | S | S | S | S | S |
| 15 | 15 | Fr1 | L | V | V | V | V | V | V |
| 16 | 16 | Fr1 | G | G | G | G | G | G | G |
| 17 | 17 | Fr1 | D | D | D | D | D | D | D |
| 18 | 18 | Fr1 | T | R | R | R | R | R | R |
| 19 | 19 | Fr1 | V | V | V | V | V | V | V |
| 20 | 20 | Fr1 | S | T | T | T | T | T | T |
| 21 | 21 | Fr1 | I | I | I | I | I | I | I |
| 22 | 22 | Fr1 | T | T | T | T | T | T | T |
| 23 | 23 | Fr1 | C | C | C | C | C | C | C |
| **24** | **24** | **CDR-L1** | **H** | **R** | **R** | **H** | **H** | **H** | **H** |
| **25** | **25** | **CDR-L1** | **A** | **A** | **A** | **A** | **A** | **A** | **A** |
| **26** | **26** | **CDR-L1** | **S** | **S** | **S** | **S** | **S** | **S** | **S** |
| **27** | **27** | **CDR-L1** | **Q** | **Q** | **Q** | **Q** | **Q** | **Q** | **Q** |
| **27A** | **28** | **CDR-L1** | — | — | — | — | — | — | — |
| **27B** | **29** | **CDR-L1** | — | — | — | — | — | — | — |
| **27C** | **30** | **CDR-L1** | — | — | — | — | — | — | — |
| **27D** | **31** | **CDR-L1** | — | — | — | — | — | — | — |
| **27E** | **32** | **CDR-L1** | — | — | — | — | — | — | — |
| **27F** | | **CDR-L1** | — | — | — | — | — | — | — |
| **28** | **33** | **CDR-L1** | **G** | **S** | **G** | **G** | **G** | **G** | **G** |
| **29** | **34** | **CDR-L1** | **I** | **I** | **I** | **I** | **I** | **I** | **I** |
| **30** | **35** | **CDR-L1** | **S** | **S** | **S** | **S** | **S** | **S** | **S** |
| **31** | **36** | **CDR-L1** | **S** | **S** | **S** | **S** | **S** | **S** | **S** |
| **32** | **37** | **CDR-L1** | **N** | **Y** | **W** | **N** | **N** | **N** | **N** |
| **33** | **38** | **CDR-L1** | **I** | **L** | **L** | **I** | **I** | **I** | **I** |
| **34** | **39** | **CDR-L1** | **G** | **N** | **A** | **G** | **G** | **G** | **G** |
| 35 | 40 | Fr2 | W | W | W | W | W | W | W |
| 36 | 41 | Fr2 | L | Y | Y | L | L | L | L |
| 37 | 42 | Fr2 | Q | Q | Q | Q | Q | Q | Q |
| 38 | 43 | Fr2 | Q | Q | Q | Q | Q | Q | Q |
| 39 | 44 | Fr2 | K | K | K | K | K | K | K |
| 40 | 45 | Fr2 | P | P | P | P | P | P | P |
| 41 | 46 | Fr2 | G | G | G | G | G | G | G |
| 42 | 47 | Fr2 | K | K | K | K | K | K | K |
| 43 | 48 | Fr2 | S | A | A | A | A | A | A |
| 44 | 49 | Fr2 | F | P | P | F | F | F | F |
| 45 | 50 | Fr2 | K | K | K | K | K | K | K |
| 46 | 51 | Fr2 | G | L | L | G | G | G | G |
| 47 | 52 | Fr2 | L | L | L | L | L | L | L |
| 48 | 53 | Fr2 | I | I | I | I | I | I | I |
| 49 | 54 | Fr2 | Y | Y | Y | Y | Y | Y | Y |
| **50** | **55** | **CDR-L2** | **H** | **A** | **A** | **H** | **H** | **H** | **H** |
| **51** | **56** | **CDR-L2** | **G** | **A** | **A** | **G** | **G** | **G** | **G** |
| **52** | **57** | **CDR-L2** | **T** | **S** | **S** | **T** | **T** | **T** | **T** |
| **53** | **58** | **CDR-L2** | **N** | **S** | **S** | **N** | **N** | **N** | **N** |
| **54** | **59** | **CDR-L2** | **L** | **L** | **L** | **L** | **L** | **L** | **L** |
| **55** | **60** | **CDR-L2** | **K** | **Q** | **Q** | **K** | **K** | **K** | **K** |
| **56** | **61** | **CDR-L2** | **D** | **S** | **S** | **D** | **D** | **D** | **D** |
| 57 | 62 | Fr3 | G | G | G | G | G | G | G |
| 58 | 63 | Fr3 | V | V | V | V | V | V | V |
| 59 | 64 | Fr3 | P | P | P | P | P | P | P |
| 60 | 65 | Fr3 | S | S | S | S | S | S | S |
| 61 | 66 | Fr3 | R | R | R | R | R | R | R |
| 62 | 67 | Fr3 | F | F | F | F | F | F | F |
| 63 | 68 | Fr3 | S | S | S | S | S | S | S |
| 64 | 69 | Fr3 | G | G | G | G | G | G | G |
| 65 | 70 | Fr3 | S | S | S | S | S | S | S |
| 66 | 71 | Fr3 | G | G | G | G | G | G | G |
| 67 | 72 | Fr3 | S | S | S | S | S | S | S |

TABLE 15-continued

5E20 VL sequences

| Kabat residue # | Linear residue # | FR or CDR | Mouse 5E20 VL (SEQ ID NO: 10) | BAH04687-VL_huFrwk (SEQ ID NO: 171) | IGKV1-12*01 (SEQ ID NO: 172) | Hu5E20VLv1 (SEQ ID NO: 173) | Hu5E20VLv2 (SEQ ID NO: 174) | Hu5E20VLv3 (SEQ ID NO: 175) | Hu5E20VLv4 (SEQ ID NO: 176) |
|---|---|---|---|---|---|---|---|---|---|
| 68 | 73 | Fr3 | G | G | G | G | G | G | G |
| 69 | 74 | Fr3 | A | T | T | A | A | A | A |
| 70 | 75 | Fr3 | D | D | D | D | D | D | D |
| 71 | 76 | Fr3 | F | F | F | F | F | F | F |
| 72 | 77 | Fr3 | S | T | T | T | T | T | T |
| 73 | 78 | Fr3 | L | L | L | L | L | L | L |
| 74 | 79 | Fr3 | T | T | T | T | T | T | T |
| 75 | 80 | Fr3 | I | I | I | I | I | I | I |
| 76 | 81 | Fr3 | S | S | S | S | S | S | S |
| 77 | 82 | Fr3 | S | S | S | S | S | S | S |
| 78 | 83 | Fr3 | L | L | L | L | L | L | L |
| 79 | 84 | Fr3 | E | Q | Q | Q | Q | Q | Q |
| 80 | 85 | Fr3 | S | P | P | P | P | P | P |
| 81 | 86 | Fr3 | E | E | E | E | E | E | E |
| 82 | 87 | Fr3 | D | D | D | D | D | D | D |
| 83 | 88 | Fr3 | F | F | F | F | F | F | F |
| 84 | 89 | Fr3 | A | A | A | A | A | A | A |
| 85 | 90 | Fr3 | D | T | T | T | T | T | D |
| 86 | 91 | Fr3 | Y | Y | Y | Y | Y | Y | Y |
| 87 | 92 | Fr3 | F | Y | Y | F | F | F | F |
| 88 | 93 | Fr3 | C | C | C | C | C | C | C |
| **89** | **94** | **CDR-L3** | **V** | **Q** | **Q** | **V** | **V** | **V** | **V** |
| **90** | **95** | **CDR-L3** | **Q** | **Q** | **Q** | **Q** | **Q** | **Q** | **Q** |
| **91** | **96** | **CDR-L3** | **Y** | **S** | **A** | **Y** | **Y** | **Y** | **Y** |
| **92** | **97** | **CDR-L3** | **A** | **Y** | **N** | **A** | **A** | **A** | **A** |
| **93** | **98** | **CDR-L3** | **Q** | **S** | **S** | **Q** | **Q** | **Q** | **Q** |
| **94** | **99** | **CDR-L3** | **F** | **T** | **F** | **F** | **F** | **F** | **F** |
| **95** | **100** | **CDR-L3** | **P** | **P** | **P** | **P** | **P** | **P** | **P** |
| **95A** | | **CDR-L3** | — | — | — | — | — | — | — |
| **95B** | | **CDR-L3** | — | — | — | — | — | — | — |
| **95C** | | **CDR-L3** | — | — | — | — | — | — | — |
| **95D** | | **CDR-L3** | — | — | — | — | — | — | — |
| **95E** | | **CDR-L3** | — | — | — | — | — | — | — |
| **95F** | | **CDR-L3** | — | — | — | — | — | — | — |
| **96** | **101** | **CDR-L3** | **Y** | **L** | **Y** | **Y** | **Y** | **Y** | **Y** |
| **97** | **102** | **CDR-L3** | **T** | **T** | **T** | **T** | **T** | **T** | **T** |
| 98 | 103 | Fr4 | F | F | F | F | F | F | F |
| 99 | 104 | Fr4 | G | G | G | G | G | G | G |
| 100 | 105 | Fr4 | G | G | Q | G | G | Q | Q |
| 101 | 106 | Fr4 | G | G | G | G | G | G | G |
| 102 | 107 | Fr4 | T | T | T | T | T | T | T |
| 103 | 108 | Fr4 | K | K | K | K | K | K | K |
| 104 | 109 | Fr4 | L | V | L | V | V | V | V |
| 105 | 110 | Fr4 | E | E | E | E | E | E | E |
| 106 | 111 | Fr4 | K | I | K | I | I | K | K |
| 106A | | Fr4 | — | — | — | — | — | — | — |
| 107 | 112 | Fr4 | R | R | K | R | R | R | R |

TABLE 16

$V_H$, $V_L$ Backmutations and Other Mutations for Humanized 5E20

| $V_H$ or $V_L$ Variant | $V_H$ or $V_L$ Exon Acceptor Sequence | Changes from Acceptor Framework (or CDR) Residues (based on Kabat/Chothia Composite CDRs) |
|---|---|---|
| Hu5E20VHv1 (SEQ ID NO: 163) | GenBank Acc. # AEX29086-VH_huFrwk (SEQ ID NO: 161) IMGT# IGHV3-21*01 (SEQ ID NO: 162) | H49, H93, H94 |
| Hu5E20VHv2 (SEQ ID NO: 164) | GenBank Acc. # AEX29086-VH_huFrwk (SEQ ID NO: 161) IMGT# IGHV3-21*01 (SEQ ID NO: 162) | H5, H49, H77, H93, H94 |
| Hu5E20VHv3 (SEQ ID NO: 165) | GenBank Acc. # AEX29086-VH_huFrwk (SEQ ID NO: 161) IMGT# IGHV3-21*01 (SEQ ID NO: 162) | H5, H44, H49, H77, H93, H94 |
| Hu5E20VHv4 (SEQ ID NO: 166) | GenBank Acc. # AEX29086-VH_huFrwk (SEQ ID NO: 161) IMGT# IGHV3-21*01 (SEQ ID NO: 162) | H5, H42, H44, H49, H77, H93, H94 |

TABLE 16-continued

| $V_H$, $V_L$ Backmutations and Other Mutations for Humanized 5E20 | | |
|---|---|---|
| $V_H$ or $V_L$ Variant | $V_H$ or $V_L$ Exon Acceptor Sequence | Changes from Acceptor Framework (or CDR) Residues (based on Kabat/Chothia Composite CDRs) |
| Hu5E20VHv5 (SEQ ID NO: 167) | GenBank Acc. # AEX29086-VH_huFrwk (SEQ ID NO: 161) IMGT# IGHV3-21*01 (SEQ ID NO: 162) | H5, H42, H44, H49, H77, H83, H93, H94 |
| Hu5E20VHv6 (SEQ ID NO: 168) | GenBank Acc. # AEX29086-VH_huFrwk (SEQ ID NO: 161) IMGT# IGHV3-21*01 (SEQ ID NO: 162) | H5, H40, H44, H49, H77, H93, H94 |
| Hu5E20VHv7 (SEQ ID NO: 169) | GenBank Acc. # AEX29086-VH_huFrwk (SEQ ID NO: 161) IMGT# IGHV3-21*01 (SEQ ID NO: 162) | H5, H40, H42, H44, H49, H77, H93, H94 |
| Hu5E20VLv1 (SEQ ID NO: 173) | GenBank Acc. # BAH04687-VL_huFrwk (SEQ ID NO: 171) IMGT# IGKV1-12*01 (SEQ ID NO: 172) | L36, L44, L46, L69, L87 |
| Hu5E20VLv2 (SEQ ID NO: 174) | GenBank Acc. # BAH04687-VL_huFrwk (SEQ ID NO: 171) IMGT# IGKV1-12*01 (SEQ ID NO: 172) | L11, L36, L44, L46, L69, L87, L100 |
| Hu5E20VLv3 (SEQ ID NO: 175) | GenBank Acc. # BAH04687-VL_huFrwk (SEQ ID NO: 171) IMGT# IGKV1-12*01 (SEQ ID NO: 172) | L11, L36, L44, L46, L69, L87, L100, L106 |
| Hu5E20VLv4 (SEQ ID NO: 176) | GenBank Acc. # BAH04687-VL_huFrwk (SEQ ID NO: 171) IMGT# IGKV1-12*01 (SEQ ID NO: 172) | L11, L36, L44, L46, L69, L85, L87, L100, L106 |

TABLE 17

Kabat Numbering of Framework (or CDR) Residues (based on Kabat/Chothia Composite CDRs) for Backmutations and Other Mutations in Heavy Chains of Humanized 5E20 Antibodies

| Residue | AEX29086-VH_huFrwk (SEQ ID NO: 161) | IMGT# IGHV3-21*01 (SEQ ID NO:162) | Mouse 5E20 VH (SEQ ID NO: 4) | Hu5E20VHv1 (SEQ ID NO: 163) | Hu5E20VHv2 (SEQ ID NO: 164) |
|---|---|---|---|---|---|
| H5 | L | V | V | L | V |
| H40 | A | A | T | A | A |
| H42 | G | G | D | G | G |
| H44 | G | G | R | G | G |
| H49 | S | S | A | A | A |
| H77 | T | S | T | T | S |
| H83 | R | R | K | R | R |
| H93 | A | A | S | S | S |
| H94 | K | R | R | R | R |

| Residue | Hu5E20VHv3 (SEQ ID NO: 165) | Hu5E20VHv4 (SEQ ID NO: 166) | Hu5E20VHv5 (SEQ ID NO: 167) | Hu5E20VHv6 (SEQ ID NO: 168) | Hu5E20VHv7 (SEQ ID NO: 169) |
|---|---|---|---|---|---|
| H5 | V | V | V | V | V |
| H40 | A | A | A | T | T |
| H42 | G | D | D | G | D |
| H44 | R | R | R | R | R |
| H49 | A | A | A | A | A |
| H77 | S | S | S | S | S |
| H83 | R | R | K | R | R |
| H93 | S | S | S | S | S |
| H94 | R | R | R | R | R |

TABLE 18

Kabat Numbering of Framework Residues (based on Kabat/Chothia Composite CDRs) for Backmutations and Other Mutations in Light Chains of Humanized 5E20 Antibodies

| Residue | BAH04687-VL_huFrwk (SEQ ID NO: 171) | IGKV1-12*01 (SEQ ID NO: 172) | Mouse 5E20 VL (SEQ ID NO: 10) | Hu5E20VLv1 (SEQ ID NO: 173) | Hu5E20VLv2 (SEQ ID NO: 174) | Hu5E20VLv3 (SEQ ID NO: 175) | Hu5E20VLv4 (SEQ ID NO: 176) |
|---|---|---|---|---|---|---|---|
| L11 | L | V | M | L | V | V | V |
| L36 | Y | Y | L | L | L | L | L |
| L44 | P | P | F | F | F | F | F |
| L46 | L | L | G | G | G | G | G |
| L69 | T | T | A | A | A | A | A |
| L85 | T | T | D | T | T | T | D |
| L87 | Y | Y | F | F | F | F | F |
| L100 | G | Q | G | G | G | Q | Q |
| L106 | I | K | K | I | I | K | K |

TABLE 19

Percentage Humanness of Heavy and Light Chains of Humanized 5E20 Antibodies

| $V_H$ or $V_L$ Variant | % Humanness |
|---|---|
| Hu5E20VHv1 (SEQ ID NO: 163) | 87.8% |
| Hu5E20VHv2 (SEQ ID NO: 164) | 89.8% |
| Hu5E20VHv3 (SEQ ID NO: 165) | 86.7% |
| Hu5E20VHv4 (SEQ ID NO: 166) | 85.7% |
| Hu5E20VHv5 (SEQ ID NO: 167) | 84.7% |
| Hu5E20VHv6 (SEQ ID NO: 168) | 85.7% |
| Hu5E20VHv7 (SEQ ID NO: 169) | 84.7% |
| Hu5E20VLv1 (SEQ ID NO: 173) | 78.9% |
| Hu5E20VLv2 (SEQ ID NO: 174) | 80.0% |
| Hu5E20VLv3 (SEQ ID NO: 175) | 80.0% |
| Hu5E20VLv4 (SEQ ID NO: 176) | 78.9% |

Positions at which canonical, vernier, or interface residues differ between mouse and human acceptor sequences are candidates for substitution. Examples of canonical/CDR interacting residues include Kabat residue H94 in Table 14. Examples of vernier residues include Kabat residues H49, H93, and H94 in Table 14 and L36, L46, and L69 in Table 15. Examples of interface/packing (VH+VL) residues include Kabat residues L36, L44, L46, and L87 in Table 15.

The rationales for selection of the positions indicated in Table 14 in the heavy chain variable region as candidates for substitution are as follows.

Heavy Chain Variable Regions hu5E20-VH_v1 consists of the CDR-H1, H2, and H3 loops of 5E20-VH grafted onto the framework of AEX29086, and reverts all framework substitutions at positions that are key for defining the Chothia canonical classes, are part of the Vernier zone, or localize to the VH/VL domain interface Hu5E20-VH_v2 through Hu5E20-VH_v7 revert all framework substitutions at positions that are key for defining the Chothia canonical classes, are part of the Vernier zone, or localize to the VH/VL domain interface or contribute to structural stability, also incorporate backmutations or substitution with most frequent residue at a given position.

L5V: is a frequency-based and germline-aligning mutation. Leu is rare at this position whereas, Val is most frequent. Germline gene IGHV3-21*01 (SEQ ID NO:162) has Val at this position.

A40T: is a backmutation. Thr at this position makes a bond with K43 heavy chain to stabilize the loop which in turn maintains the conformation of CDR-H2.

G42D: Asp stabilizes the loop by bonding with K43 and T40 both in the heavy chain. This tetraloop bridging maintains conformation of the loop. Gly at this position distorts the conformation which does not allow bonding between R44 heavy chain and F98 light chain. This back mutation is made to conserve conformation.

G44R: Arg 44 makes an interchain bond with light chain Phe 98. Gly at this position would not make an interchain bond with light chain Phe98, and may make antibody unstable. Stabilization with Arg at position 44 may preserve CDR conformation. Back-mutation is made to preserve conformation and stability.

S49A: backmutation of a vernier zone residue.

T77S: is a germline-aligning mutation. Germline gene IGHV3-21*01 (SEQ ID NO:162) has Ser at this position.

R83K: As Arg and Lys are very similar residues, mutation to Lys is made to enhance stability.

A93S: backmutation of a vernier zone and VH/VL domain interface residue

K94R: backmutation of a canonical and vernier zone residue

The rationales for selection of the positions indicated in Table 15 in the light chain variable region as candidates for substitution are as follows.

Kappa Light Chain Variable Regions hu5E20-VL_v1 consists of the CDR-L1, L2, and L3 loops of 5E20-VL grafted onto the framework of BAH04687 VL along with reverting all framework substitutions at positions that are key for defining the Chothia canonical classes, are part of the Vernier zone, or locate to the VH/VL domain interface.

Hu5E20-VL_v2, hu5E20-VL_v3 and hu5E20-VL_v4 consists of the CDR-L1, L2, and L3 loops of 5E20-VL grafted onto the framework of BAH04687 VL along with reverting all framework substitutions at positions that are key for defining the Chothia canonical classes, are part of the Vernier zone, or locate to the VH/VL domain interface.

also include substitutions that contribute to structural stability or increases the humanness of the antibody.

L11V: is a germline-aligning mutation. Germline gene sequence IGKV1-12*01 (SEQ ID NO:172) has Val at this position.

Y36L: backmutation of a vernier zone and VH/VL domain interface residue

P44F: backmutation of a VH/VL domain interface residue

L46G: backmutation of a vernier zone and VH/VL domain interface residue

T69A: backmutation of a vernier zone residue

T85D: is a mutation to enhance interchain bonding,

Y87F: backmutation of a VH/VL domain interface residue

G100Q: is a germline-aligning and frequency-based mutation. Germline gene sequence IGKV1-12*01 (SEQ ID NO:172) has Gln at this position. Gln is most frequent at this position.

I106K: is a germline-aligning and frequency-based mutation. Germline gene sequence IGKV1-12*01 (SEQ ID NO:172) has Lys at this position. Lys at this position is more frequent.

Sequences of Heavy Chain Variable Regions

```
>h5E20VH version1 (87.8.% human)
                                    SEQ ID NO: 163
EVQLLESGGGLVQPGGSLRLSCAASGFTFSTYGMSWVRQAPGKGLEWVA

IISSGGSYTYYSDTVKGRFTISRDNSKNTLYLQMNSLRAEDTAVYYCSR

SSSHWYFDVWGQGTLVTVSS

>h5E20VH version2 (89.8% human)
                                    SEQ ID NO: 164
EVQLVESGGGLVQPGGSLRLSCAASGFTFSTYGMSWVRQAPGKGLEWVA

IISSGGSYTYYSDTVKGRFTISRDNSKNSLYLQMNSLRAEDTAVYYCSR

SSSHWYFDVWGQGTLVTVSS

>h5E20VH version3 (86.7% human)
                                    SEQ ID NO: 165
EVQLVESGGGLVQPGGSLRLSCAASGFTFSTYGMSWVRQAPGKRLEWVA

IISSGGSYTYYSDTVKGRFTISRDNSKNSLYLQMNSLRAEDTAVYYCSR

SSSHWYFDVWGQGTLVTVSS

>h5E20VH version4 (85.7% human)
                                    SEQ ID NO: 166
EVQLVESGGGLVQPGGSLRLSCAASGFTFSTYGMSWVRQAPDKRLEWVA

IISSGGSYTYYSDTVKGRFTISRDNSKNSLYLQMNSLRAEDTAVYYCSR

SSSHWYFDVWGQGTLVTVSS

>h5E20VH version5 (84.7% human)
                                    SEQ ID NO: 167
EVQLVESGGGLVQPGGSLRLSCAASGFTFSTYGMSWVRQAPDKRLEWVA

IISSGGSYTYYSDTVKGRFTISRDNSKNSLYLQMNSLKAEDTAVYYCSR

SSSHWYFDVWGQGTLVTVSS

>h5E20VH version6 (85.7% human)
                                    SEQ ID NO: 168
EVQLVESGGGLVQPGGSLRLSCAASGFTFSTYGMSWVRQTPGKRLEWVA

IISSGGSYTYYSDTVKGRFTISRDNSKNSLYLQMNSLRAEDTAVYYCSR

SSSHWYFDVWGQGTLVTVSS

>h5E20VH version7 (84.7% human)
                                    SEQ ID NO: 169
EVQLVESGGGLVQPGGSLRLSCAASGFTFSTYGMSWVRQTPDKRLEWVA

IISSGGSYTYYSDTVKGRFTISRDNSKNSLYLQMNSLRAEDTAVYYCSR

SSSHWYFDVWGQGTLVTVSS
```

Sequences of Kappa Light Chain Variable Regions

```
>h5E20VL version1 (78.9% human )
                                    SEQ ID NO: 173
DIQMTQSPSSLSASVGDRVTITCHASQGISSNIGWLQQKPGKAFKGLIY

HGTNLKDGVPSRFSGSGSGADFTLTISSLQPEDFATYFCVQYAQFPYTF

GGGTKVEIR
```

-continued

```
>h5E20VL version2 (80.0% human)
                                    SEQ ID NO: 174
DIQMTQSPSSVSASVGDRVTITCHASQGISSNIGWLQQKPGKAFKGLIY

HGTNLKDGVPSRFSGSGSGADFTLTISSLQPEDFATYFCVQYAQFPYTF

GQGTKVEIR

>h5E20VL version3 (80.0% human)
                                    SEQ ID NO: 175
DIQMTQSPSSVSASVGDRVTITCHASQGISSNIGWLQQKPGKAFKGLIY

HGTNLKDGVPSRFSGSGSGADFTLTISSLQPEDFATYFCVQYAQFPYTF

GQGTKVEKR

>h5E20VL version4 (78.9% human)
                                    SEQ ID NO: 176
DIQMTQSPSSVSASVGDRVTITCHASQGISSNIGWLQQKPGKAFKGLIY

HGTNLKDGVPSRFSGSGSGADFTLTISSLQPEDFADYFCVQYAQFPYTF

GQGTKVEKR
```

Example 15. Design of Humanized 8H24 Antibodies

The starting point or donor antibody for humanization was the mouse antibody 8H24. The heavy chain variable amino acid sequence of mature m8H24 is provided as SEQ ID NO:28. The light chain variable amino acid sequence of mature m8H24 is provided as SEQ ID NO:34. The heavy chain Kabat/Chothia Composite CDR1, CDR2, and CDR3 amino acid sequences are provided as SEQ ID NOS:29-31, respectively. The light chain Kabat CDR1, CDR2, and CDR3 amino acid sequences are provided as SEQ ID NOS:35-37, respectively. Kabat numbering is used throughout.

The variable kappa (Vk) of 8H24 belongs to mouse Vk subgroup 1b which corresponds to human Vk subgroup 1 and the variable heavy (Vh) to mouse Vh subgroup 3d which corresponds to human Vh subgroup 1 [Kabat E. A., et al., (1991), Sequences of Proteins of Immunological Interest, Fifth Edition. NIH Publication No. 91-3242]. 16 residue Chothia CDR-L1 is similar to Chothia canonical class 4, 7 residue Chothia CDR-L2 is of Chothia canonical class 1, 9 residue Chothia CDR-L3 is similar to Chothia canonical class 1 [Martin A C R. (2010) Protein sequence and structure analysis of antibody variable domains. In: Kontermann R and Dübel S (eds). *Antibody Engineering*. Heidelberg, Germany: Springer International Publishing AG. [Martin, 2010]. 10 residue Chothia CDR-H1 is similar to Chothia canonical class 1, 17 residue Chothia CDR-H2 is similar to Chothia canonical class 2 [Martin, 2010]. 3 residue CDR-H3 has no canonical classes. A search was made over the protein sequences in the PDB database [Deshpande N, et al., (2005) Nucleic Acids Res. 33: D233-7] to find structures which would provide a rough structural model of 8H24. The crystal structure of an antibody fab PDB code 1MRC [Pokkuluri, P. R., et al. (1994) J Mol Biol 243: 283-297] for both Vh and Vk structure since it had good resolution (2.4 Å) and overall sequence similarity to 8H24 Vh and Vk, retaining the same canonical structures for the loops.

The frameworks of 8H24 VH share a high degree of sequence similarity with the corresponding regions of human antibody AAC51714 VH, cloned by Johnson, T. A., et al. (J. Immunol. 158 (1), 235-246, 1997). The variable heavy domains of 8H24 and AAC51714 also share identical lengths for the CDR-H1, H2 loops. Similarly, the frameworks of 8H24 VL share a high degree of sequence similarity with the corresponding regions of human antibody ABC66914 VL cloned by Shriner A. K., et al (Vaccine 24 (49-50), 7159-7166 (2006)). The variable light domain of 8H24 and ABC66914 antibody also share identical lengths for the CDR-L1, L2 and L3 loops. Accordingly, the framework regions of AAC51714 VH and ABC66914 VL were chosen as the acceptor sequences for the CDRs of 8H24. A model of the 8H24 CDRs grafted onto the respective human frameworks for VH and VL was built and used as a guidance for further backmutations.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN: International nonproprietary names (INN) for biological and biotechnological substances (a review) (Internet) 2014. Available from: http://www. who.int/medicines/services/inn/BioRev2014.pdf) Residues were changed to align with corresponding human germ line sequence, where possible, to enhance humanness and to reduce potential immunogenicity.

The amino acid sequences consisting of AAC51714VH human frameworks and 8H24 CDRs are designated hu8H24VHv1 and the amino acid sequences consisting of ABC66914 VL human framework and 8H24 CDRs are designated hu8H24VLv1. Additional versions of hu8H24-VH and hu8H24-VL were designed to enable assessment of various framework residues for their contributions to antigen binding, thermostability, developability (deamination, oxidation, N-glycosylation, proteolysis and aggregation) and immunogenicity. The positions considered for mutation include those that:

- define the canonical CDR conformations (summarized in Martin),
- are within the Vernier zone (Foote and Winter),
- localize to the VH/VL domain interface (summarized in Leger and Saldanha),
- are susceptible to post-translational modifications, such as glycosylation or pyroglutamination,
- are occupied by residues that are predicted to clash with CDRs, according to the model of 8H24 CDRs grafted onto VH and VL frameworks, or
- are occupied by residues that are rare among sequenced human antibodies, where either the parental mouse 8H24 residue or some other residue is much more prevalent within human antibody repertoire.

Alignments of the murine 8H24 and various humanized antibodies are shown for the light chain variable regions (Table 21 and FIG. 4), and heavy chain variable regions (Table 20 and FIG. 3).

2 humanized heavy chain variable region variants and 2 humanized light chain variable region variants were constructed containing different permutations of substitutions: hu8H24VHv1 or hu8H24VHv2, (SEQ ID NOS:180-181, respectively); and hu8H24VLv1 or hu8H24VLv2 (SEQ ID NOS:185-186, respectively) (Tables 20 and 21). The exemplary humanized Vk and Vh designs, with backmutations and other mutations based on selected human frameworks, are shown in Tables 21 and 20, respectively. The bolded areas in Tables 20 and 21 indicate the CDRs as defined by Kabat/Chothia Composite. A "-" in the columns in Tables 20 and 21 indicates no residue at the indicated position. SEQ ID NOS:180-181, and SEQ ID NOS:185-186 contain backmutations and other mutations as shown in Table 22. The amino acids at positions in hu8H24VHv1 and hu8H24VHv2 are listed in Table 23. The amino acids at positions in hu8H24VLv1 and hu8H24VLv2 are listed in Table 24.

The percentage humanness for humanized VH chains hu8H24VHv1 and hu8H24VHv2 (SEQ ID NOS:180-181, respectively) with respect to the most similar human germline gene IMGT #IGHV1-69*08_IGHJ1*01 (SEQ ID NO:179), and for humanized VL chains hu8H24VLv1 and hu8H24VLv2 (SEQ ID NOS:185-186 respectively) with respect to the most similar human germline gene IMGT #IGKV2-40*01 (SEQ ID NO:184) is shown in Table 25.

TABLE 20

8H24 VH sequences

| Kabat residue # | Linear residue # | FR or CDR | Mouse 8H24 VH (SEQ ID NO: 28) | GenBank Acc. # AAC51714-VH_huFrwk (SEQ ID NO: 178) | IMGT# IGHV1-69*08_IGHJ1*01 (SEQ ID NO: 179) | Hu8H24VHv1 (SEQ ID NO: 180) | Hu8H24VHv2 (SEQ ID NO: 181) |
|---|---|---|---|---|---|---|---|
| 1 | 1 | Fr1 | Q | Q | Q | Q | Q |
| 2 | 2 | Fr1 | A | V | V | A | A |
| 3 | 3 | Fr1 | Y | Q | Q | Q | Q |
| 4 | 4 | Fr1 | L | L | L | L | L |
| 5 | 5 | Fr1 | Q | V | V | V | V |
| 6 | 6 | Fr1 | Q | Q | Q | Q | Q |
| 7 | 7 | Fr1 | S | S | S | S | S |
| 8 | 8 | Fr1 | G | G | G | G | G |
| 9 | 9 | Fr1 | T | A | A | A | A |
| 10 | 10 | Fr1 | E | E | E | E | E |
| 11 | 11 | Fr1 | L | V | V | V | V |
| 12 | 12 | Fr1 | V | K | K | K | V |
| 13 | 13 | Fr1 | R | K | K | K | K |
| 14 | 14 | Fr1 | P | P | P | P | P |
| 15 | 15 | Fr1 | G | G | G | G | G |
| 16 | 16 | Fr1 | A | S | S | S | S |
| 17 | 17 | Fr1 | S | S | S | S | S |
| 18 | 18 | Fr1 | V | V | V | V | V |
| 19 | 19 | Fr1 | K | K | K | K | K |
| 20 | 20 | Fr1 | M | V | V | V | V |
| 21 | 21 | Fr1 | S | S | S | S | S |
| 22 | 22 | Fr1 | C | C | C | C | C |
| 23 | 23 | Fr1 | K | K | K | K | K |

TABLE 20-continued

| 8H24 VH sequences | | | | | | | |
|---|---|---|---|---|---|---|---|
| Kabat residue # | Linear residue # | FR or CDR | Mouse 8H24 VH (SEQ ID NO: 28) | GenBank Acc. # AAC51714-VH_huFrwk (SEQ ID NO: 178) | IMGT# IGHV1-69*08_IGHJ1*01 (SEQ ID NO: 179) | Hu8H24VHv1 (SEQ ID NO: 180) | Hu8H24VHv2 (SEQ ID NO: 181) |
| 24 | 24 | Fr1 | A | A | A | A | A |
| 25 | 25 | Fr1 | S | S | S | S | S |
| **26** | **26** | **CDR-H1** | **G** | **G** | **G** | **G** | **G** |
| **27** | **27** | **CDR-H1** | **Y** | **G** | **G** | **Y** | **Y** |
| **28** | **28** | **CDR-H1** | **T** | **T** | **T** | **T** | **T** |
| **29** | **29** | **CDR-H1** | **F** | **F** | **F** | **F** | **F** |
| **30** | **30** | **CDR-H1** | **T** | **S** | **S** | **T** | **T** |
| **31** | **31** | **CDR-H1** | **S** | **S** | **S** | **S** | **S** |
| **32** | **32** | **CDR-H1** | **Y** | **Y** | **Y** | **Y** | **Y** |
| **33** | **33** | **CDR-H1** | **S** | **A** | **T** | **S** | **S** |
| **34** | **34** | **CDR-H1** | **M** | **I** | **I** | **M** | **M** |
| **35** | **35** | **CDR-H1** | **H** | **S** | **S** | **H** | **H** |
| **35A** | | **CDR-H1** | — | — | — | — | — |
| **35B** | | **CDR-H1** | — | — | — | — | — |
| 36 | 36 | Fr2 | W | W | W | W | W |
| 37 | 37 | Fr2 | V | V | V | V | V |
| 38 | 38 | Fr2 | K | R | R | R | R |
| 39 | 39 | Fr2 | Q | Q | Q | Q | Q |
| 40 | 40 | Fr2 | T | A | A | A | A |
| 41 | 41 | Fr2 | P | P | P | P | P |
| 42 | 42 | Fr2 | R | G | G | G | G |
| 43 | 43 | Fr2 | Q | Q | Q | Q | Q |
| 44 | 44 | Fr2 | G | G | G | G | G |
| 45 | 45 | Fr2 | L | L | L | L | L |
| 46 | 46 | Fr2 | E | E | E | E | E |
| 47 | 47 | Fr2 | W | W | W | W | W |
| 48 | 48 | Fr2 | I | M | M | I | I |
| 49 | 49 | Fr2 | G | G | G | G | G |
| **50** | **50** | **CDR-H2** | **A** | **G** | **R** | **A** | **A** |
| **51** | **51** | **CDR-H2** | **I** | **I** | **I** | **I** | **I** |
| **52** | **52** | **CDR-H2** | **Y** | **I** | **I** | **Y** | **Y** |
| **52A** | **53** | **CDR-H2** | **P** | **P** | **P** | **P** | **P** |
| **52B** | | **CDR-H2** | — | — | — | — | — |
| **52C** | | **CDR-H2** | — | — | — | — | — |
| **53** | **54** | **CDR-H2** | **G** | **I** | **I** | **G** | **G** |
| **54** | **55** | **CDR-H2** | **N** | **F** | **L** | **N** | **N** |
| **55** | **56** | **CDR-H2** | **D** | **G** | **G** | **D** | **D** |
| **56** | **57** | **CDR-H2** | **A** | **T** | **T** | **A** | **A** |
| **57** | **58** | **CDR-H2** | **T** | **A** | **A** | **T** | **T** |
| **58** | **59** | **CDR-H2** | **S** | **N** | **N** | **S** | **S** |
| **59** | **60** | **CDR-H2** | **Y** | **Y** | **Y** | **Y** | **Y** |
| **60** | **61** | **CDR-H2** | **N** | **A** | **A** | **N** | **N** |
| **61** | **62** | **CDR-H2** | **Q** | **Q** | **Q** | **Q** | **Q** |
| **62** | **63** | **CDR-H2** | **K** | **K** | **K** | **K** | **K** |
| **63** | **64** | **CDR-H2** | **F** | **F** | **F** | **F** | **F** |
| **64** | **65** | **CDR-H2** | **K** | **Q** | **Q** | **K** | **K** |
| **65** | **66** | **CDR-H2** | **G** | **G** | **G** | **G** | **G** |
| 66 | 67 | Fr3 | K | R | R | R | R |
| 67 | 68 | Fr3 | A | V | V | A | A |
| 68 | 69 | Fr3 | T | T | T | T | T |
| 69 | 70 | Fr3 | L | I | I | L | L |
| 70 | 71 | Fr3 | T | T | T | T | T |
| 71 | 72 | Fr3 | V | A | A | V | V |
| 72 | 73 | Fr3 | D | D | D | D | D |
| 73 | 74 | Fr3 | K | K | K | K | K |
| 74 | 75 | Fr3 | S | S | S | S | S |
| 75 | 76 | Fr3 | S | T | T | T | T |
| 76 | 77 | Fr3 | S | S | S | S | S |
| 77 | 78 | Fr3 | T | T | T | T | T |
| 78 | 79 | Fr3 | A | A | A | A | A |
| 79 | 80 | Fr3 | Y | Y | Y | Y | Y |
| 80 | 81 | Fr3 | M | M | M | M | M |
| 81 | 82 | Fr3 | Q | E | E | E | E |
| 82 | 83 | Fr3 | L | L | L | L | L |
| 82A | 84 | Fr3 | S | S | S | S | S |
| 82B | 85 | Fr3 | S | S | S | S | S |
| 82C | 86 | Fr3 | L | L | L | L | L |
| 83 | 87 | Fr3 | T | R | R | R | R |
| 84 | 88 | Fr3 | S | S | S | S | S |
| 85 | 89 | Fr3 | E | E | E | E | E |
| 86 | 90 | Fr3 | D | D | D | D | D |

TABLE 20-continued

| 8H24 VH sequences | | | | | | | |
|---|---|---|---|---|---|---|---|
| Kabat residue # | Linear residue # | FR or CDR | Mouse 8H24 VH (SEQ ID NO: 28) | GenBank Acc. # AAC51714-VH_huFrwk (SEQ ID NO: 178) | IMGT# IGHV1-69*08_IGHJ1*01 (SEQ ID NO: 179) | Hu8H24VHv1 (SEQ ID NO: 180) | Hu8H24VHv2 (SEQ ID NO: 181) |
| 87 | 91 | Fr3 | S | T | T | T | T |
| 88 | 92 | Fr3 | A | A | A | A | A |
| 89 | 93 | Fr3 | V | V | V | V | V |
| 90 | 94 | Fr3 | Y | Y | Y | Y | Y |
| 91 | 95 | Fr3 | F | Y | Y | F | F |
| 92 | 96 | Fr3 | C | C | C | C | C |
| 93 | 97 | Fr3 | A | A | A | A | A |
| 94 | 98 | Fr3 | R | R | R | R | R |
| **95** | **99** | **CDR-H3** | **E** | **A** | **A** | **E** | **E** |
| **96** | | **CDR-H3** | **G** | **Y** | **E** | **G** | **G** |
| **97** | | **CDR-H3** | **Y** | **C** | **Y** | **Y** | **Y** |
| **98** | | **CDR-H3** | **Y** | **S** | **F** | **Y** | **Y** |
| **99** | | **CDR-H3** | **G** | **S** | — | **G** | **G** |
| **100** | | **CDR-H3** | **S** | **T** | — | **S** | **S** |
| **100A** | | **CDR-H3** | **S** | **S** | — | **S** | **S** |
| **100B** | | **CDR-H3** | **F** | **C** | — | **F** | **F** |
| **100C** | | **CDR-H3** | **E** | **Y** | — | **E** | **E** |
| **100D** | | **CDR-H3** | **A** | **K** | — | **A** | **A** |
| **100E** | | **CDR-H3** | **W** | **T** | — | **W** | **W** |
| **100F** | | **CDR-H3** | **F** | **G** | — | **F** | **F** |
| **100G** | | **CDR-H3** | — | — | — | — | — |
| **100H** | | **CDR-H3** | — | — | — | — | — |
| **100I** | | **CDR-H3** | — | — | — | — | — |
| **100J** | | **CDR-H3** | — | — | — | — | — |
| **100K** | | **CDR-H3** | — | — | — | — | — |
| **101** | **100** | **CDR-H3** | **A** | **F** | **Q** | **A** | **A** |
| **102** | **101** | **CDR-H3** | **S** | **V** | **H** | **S** | **S** |
| 103 | 102 | Fr4 | W | W | W | W | W |
| 104 | 103 | Fr4 | G | G | G | G | G |
| 105 | 104 | Fr4 | Q | Q | Q | Q | Q |
| 106 | 105 | Fr4 | G | G | G | G | G |
| 107 | 106 | Fr4 | T | T | T | T | T |
| 108 | 107 | Fr4 | L | L | L | T | T |
| 109 | 108 | Fr4 | V | V | V | V | V |
| 110 | 109 | Fr4 | T | T | T | T | T |
| 111 | 110 | Fr4 | V | V | V | V | V |
| 112 | 111 | Fr4 | S | S | S | S | S |
| 113 | 112 | Fr4 | A | S | S | S | S |

TABLE 21

| 8H24 VL sequences | | | | | | | |
|---|---|---|---|---|---|---|---|
| Kabat residue # | Linear residue # | FR or CDR | Mouse 8H24 VL (SEQ ID NO:34) | GenBank Acc. # ABC66914-VL huFrwk (SEQ ID NO: 183) | IMGT# IGKV2-40*01 (SEQ ID NO: 184) | Hu8H24VLv1 (SEQ ID NO: 185) | Hu8H24VLv2 (SEQ ID NO: 186) |
| 1 | 1 | Fr1 | D | D | D | D | D |
| 2 | 2 | Fr1 | V | I | I | V | V |
| 3 | 3 | Fr1 | L | V | V | V | V |
| 4 | 4 | Fr1 | M | M | M | M | M |
| 5 | 5 | Fr1 | T | T | T | T | T |
| 6 | 6 | Fr1 | Q | Q | Q | Q | Q |
| 7 | 7 | Fr1 | T | T | T | T | T |
| 8 | 8 | Fr1 | P | P | P | P | P |
| 9 | 9 | Fr1 | L | L | L | L | S |
| 10 | 10 | Fr1 | S | S | S | S | S |
| 11 | 11 | Fr1 | L | L | L | L | L |
| 12 | 12 | Fr1 | P | P | P | P | P |
| 13 | 13 | Fr1 | V | V | V | V | V |
| 14 | 14 | Fr1 | S | T | T | T | T |
| 15 | 15 | Fr1 | L | P | P | P | P |
| 16 | 16 | Fr1 | G | G | G | G | G |
| 17 | 17 | Fr1 | D | E | E | E | E |
| 18 | 18 | Fr1 | Q | P | P | P | P |

TABLE 21-continued

| Kabat residue # | Linear residue # | FR or CDR | Mouse 8H24 VL (SEQ ID NO:34) | GenBank Acc. # ABC66914-VL huFrwk (SEQ ID NO: 183) | IMGT# IGKV2-40*01 (SEQ ID NO: 184) | Hu8H24VLv1 (SEQ ID NO: 185) | Hu8H24VLv2 (SEQ ID NO: 186) |
|---|---|---|---|---|---|---|---|
| 8H24 VL sequences | | | | | | | |
| 19 | 19 | Fr1 | A | A | A | A | A |
| 20 | 20 | Fr1 | S | S | S | S | S |
| 21 | 21 | Fr1 | I | I | I | I | I |
| 22 | 22 | Fr1 | S | S | S | S | S |
| 23 | 23 | Fr1 | C | C | C | C | C |
| **24** | **24** | **CDR-L1** | **R** | **R** | **R** | **R** | **R** |
| **25** | **25** | **CDR-L1** | **S** | **S** | **S** | **S** | **S** |
| **26** | **26** | **CDR-L1** | **S** | **S** | **S** | **S** | **S** |
| **27** | **27** | **CDR-L1** | **Q** | **Q** | **Q** | **Q** | **Q** |
| **27A** | **28** | **CDR-L1** | **S** | **S** | **S** | **S** | **S** |
| **27B** | **29** | **CDR-L1** | **I** | **L** | **L** | **I** | **I** |
| **27C** | **30** | **CDR-L1** | **V** | **L** | **L** | **V** | **V** |
| **27D** | **31** | **CDR-L1** | **H** | **H** | **D** | **H** | **H** |
| **27E** | **32** | **CDR-L1** | **S** | **S** | **S** | **S** | **S** |
| **27F** | | **CDR-L1** | — | — | **D** | — | — |
| **28** | **33** | **CDR-L1** | **N** | **N** | **D** | **N** | **N** |
| **29** | **34** | **CDR-L1** | **G** | **G** | **G** | **G** | **G** |
| **30** | **35** | **CDR-L1** | **N** | **Y** | **N** | **N** | **N** |
| **31** | **36** | **CDR-L1** | **T** | **N** | **T** | **T** | **T** |
| **32** | **37** | **CDR-L1** | **Y** | **Y** | **Y** | **Y** | **Y** |
| **33** | **38** | **CDR-L1** | **L** | **L** | **L** | **L** | **L** |
| **34** | **39** | **CDR-L1** | **E** | **D** | **D** | **E** | **E** |
| 35 | 40 | Fr2 | W | W | W | W | W |
| 36 | 41 | Fr2 | Y | Y | Y | Y | Y |
| 37 | 42 | Fr2 | L | L | L | L | L |
| 38 | 43 | Fr2 | Q | Q | Q | Q | Q |
| 39 | 44 | Fr2 | K | K | K | K | K |
| 40 | 45 | Fr2 | P | P | P | P | P |
| 41 | 46 | Fr2 | G | G | G | G | G |
| 42 | 47 | Fr2 | Q | Q | Q | Q | Q |
| 43 | 48 | Fr2 | S | S | S | S | S |
| 44 | 49 | Fr2 | P | P | P | P | P |
| 45 | 50 | Fr2 | K | Q | Q | Q | Q |
| 46 | 51 | Fr2 | L | L | L | L | L |
| 47 | 52 | Fr2 | L | L | L | L | L |
| 48 | 53 | Fr2 | I | I | I | I | I |
| 49 | 54 | Fr2 | Y | Y | Y | Y | Y |
| **50** | **55** | **CDR-L2** | **K** | **L** | **T** | **K** | **K** |
| **51** | **56** | **CDR-L2** | **V** | **G** | **L** | **V** | **V** |
| **52** | **57** | **CDR-L2** | **S** | **S** | **S** | **S** | **S** |
| **53** | **58** | **CDR-L2** | **N** | **N** | **Y** | **N** | **N** |
| **54** | **59** | **CDR-L2** | **R** | **R** | **R** | **R** | **R** |
| **55** | **60** | **CDR-L2** | **F** | **A** | **A** | **F** | **F** |
| **56** | **61** | **CDR-L2** | **S** | **S** | **S** | **S** | **S** |
| 57 | 62 | Fr3 | G | G | G | G | G |
| 58 | 63 | Fr3 | V | V | V | V | V |
| 59 | 64 | Fr3 | P | P | P | P | P |
| 60 | 65 | Fr3 | D | D | D | D | D |
| 61 | 66 | Fr3 | R | R | R | R | R |
| 62 | 67 | Fr3 | F | F | F | F | F |
| 63 | 68 | Fr3 | S | S | S | S | S |
| 64 | 69 | Fr3 | G | G | G | G | G |
| 65 | 70 | Fr3 | S | S | S | S | S |
| 66 | 71 | Fr3 | G | G | G | G | G |
| 67 | 72 | Fr3 | S | S | S | S | S |
| 68 | 73 | Fr3 | G | G | G | G | G |
| 69 | 74 | Fr3 | T | T | T | T | T |
| 70 | 75 | Fr3 | D | D | D | D | D |
| 71 | 76 | Fr3 | F | F | F | F | F |
| 72 | 77 | Fr3 | T | T | T | T | T |
| 73 | 78 | Fr3 | L | L | L | L | L |
| 74 | 79 | Fr3 | K | K | K | K | T |
| 75 | 80 | Fr3 | I | I | I | I | I |
| 76 | 81 | Fr3 | S | S | S | S | S |
| 77 | 82 | Fr3 | R | R | R | R | R |
| 78 | 83 | Fr3 | V | V | V | V | V |
| 79 | 84 | Fr3 | E | E | E | E | E |
| 80 | 85 | Fr3 | A | A | A | A | A |
| 81 | 86 | Fr3 | E | E | E | E | E |
| 82 | 87 | Fr3 | D | D | D | D | D |
| 83 | 88 | Fr3 | L | V | V | V | V |

TABLE 21-continued

| 8H24 VL sequences | | | | | | | |
|---|---|---|---|---|---|---|---|
| Kabat residue # | Linear residue # | FR or CDR | Mouse 8H24 VL (SEQ ID NO:34) | GenBank Acc. # ABC66914-VL huFrwk (SEQ ID NO: 183) | IMGT# IGKV2-40*01 (SEQ ID NO: 184) | Hu8H24VLv1 (SEQ ID NO: 185) | Hu8H24VLv2 (SEQ ID NO: 186) |
| 84 | 89 | Fr3 | G | G | G | G | G |
| 85 | 90 | Fr3 | V | V | V | V | V |
| 86 | 91 | Fr3 | Y | Y | Y | Y | Y |
| 87 | 92 | Fr3 | Y | Y | Y | Y | Y |
| 88 | 93 | Fr3 | C | C | C | C | C |
| **89** | **94** | **CDR-L3** | **F** | **M** | **M** | **F** | **F** |
| **90** | **95** | **CDR-L3** | **Q** | **Q** | **Q** | **Q** | **Q** |
| **91** | **96** | **CDR-L3** | **G** | **A** | **R** | **G** | **G** |
| **92** | **97** | **CDR-L3** | **S** | **L** | **I** | **S** | **S** |
| **93** | **98** | **CDR-L3** | **H** | **Q** | **E** | **H** | **H** |
| **94** | **99** | **CDR-L3** | **V** | **T** | **F** | **V** | **V** |
| **95** | **100** | **CDR-L3** | **L** | **P** | **P** | **L** | **L** |
| **95A** | | **CDR-L3** | — | — | — | — | — |
| **95B** | | **CDR-L3** | — | — | — | — | — |
| **95C** | | **CDR-L3** | — | — | — | — | — |
| **95D** | | **CDR-L3** | — | — | — | — | — |
| **95E** | | **CDR-L3** | — | — | — | — | — |
| **95F** | | **CDR-L3** | — | — | — | — | — |
| **96** | **101** | **CDR-L3** | **P** | **L** | **L** | **P** | **P** |
| **97** | **102** | **CDR-L3** | **T** | **T** | **T** | **T** | **T** |
| 98 | 103 | Fr4 | F | F | F | F | F |
| 99 | 104 | Fr4 | G | G | G | G | G |
| 100 | 105 | Fr4 | G | G | G | G | G |
| 101 | 106 | Fr4 | G | G | G | G | G |
| 102 | 107 | Fr4 | T | T | T | T | T |
| 103 | 108 | Fr4 | K | K | K | K | K |
| 104 | 109 | Fr4 | L | V | V | V | V |
| 105 | 110 | Fr4 | E | E | E | E | E |
| 106 | 111 | Fr4 | I | I | I | I | I |
| 106A | | Fr4 | — | — | — | — | — |
| 107 | 112 | Fr4 | R | K | K | K | K |

TABLE 22

| $V_H$, $V_L$ Backmutations and Other Mutations for Humanized 8H24 | | |
|---|---|---|
| $V_H$ or $V_L$ Variant | $V_H$ or $V_L$ Exon Acceptor Sequence | Changes from Acceptor Framework (or CDR) Residues (based on Kabat/Chothia Composite CDRs) |
| Hu8H24VHv1 (SEQ ID NO: 180) | GenBank Acc. # AAC51714-VH_huFrwk (SEQ ID NO: 178)<br>IMGT# IGHV1-69*08_IGHJ1*01 (SEQ ID NO: 179) | H2, H48, H67, H71, H91, H108 |
| Hu8H24VHv2 (SEQ ID NO:181) | GenBank Acc. # AAC51714-VH_huFrwk (SEQ ID NO: 178)<br>IMGT# IGHV1-69*08_IGHJ1*01 (SEQ ID NO: 179) | H2, H12, H48, H67, H71, H91, H108 |
| Hu8H24VLv1 (SEQ ID NO: 185) | GenBank Acc. # ABC66914-VL_huFrwk (SEQ ID NO: 183)<br>IMGT# IGKV2-40*01 (SEQ ID NO: 184) | L2 |
| Hu8H24VLv2 (SEQ ID NO: 186) | GenBank Acc. # ABC66914-VL_huFrwk (SEQ ID NO: 183)<br>IMGT# IGKV2-40*01 (SEQ ID NO: 184) | L2, L9, L74 |

TABLE 23

Kabat Numbering of Framework (or CDR) Residues (based on Kabat/Chothia Composite CDRs) for Backmutations and Other Mutations in Heavy Chains of Humanized 8H24 Antibodies

| Residue | GenBank Acc. # AAC51714-VH_huFrwk (SEQ ID NO: 178) | IMGT# IGHV1-69*08_IGHJ1*01 (SEQ ID NO: 179) | Mouse 8H24 VH (SEQ ID NO: 28) | Hu8H24VHv1 (SEQ ID NO: 180) | Hu8H24VHv2 (SEQ ID NO: 181) |
|---|---|---|---|---|---|
| H2 | V | V | A | A | A |
| H12 | K | K | V | K | V |
| H48 | M | M | I | I | I |
| H67 | V | V | A | A | A |
| H71 | A | A | V | V | V |
| H91 | Y | Y | F | F | F |
| H108 | L | L | L | T | T |

TABLE 24

Kabat Numbering of Framework Residues (based on Kabat/Chothia Composite CDRs) for Backmutations and Other Mutations in Light Chains of Humanized 8H24 Antibodies

| Residue | GenBank Acc. # ABC66914-VL_huFrwk (SEQ ID NO: 183) | IMGT# IGKV2-40*01 (SEQ ID NO: 184) | Mouse 8H24 VL (SEQ ID NO: 34) | Hu8H24VLv1 (SEQ ID NO: 185) | Hu8H24VLv2 (SEQ ID NO: 186) |
|---|---|---|---|---|---|
| L2 | I | I | V | V | V |
| L9 | L | L | L | L | S |
| L74 | K | K | K | K | T |

TABLE 25

Percentage Humanness of Heavy and Light Chains of Humanized 8H24 Antibodies

| $V_H$ or $V_L$ Variant | % Humanness |
|---|---|
| Hu8H24VHv1 (SEQ ID NO: 180) | 81.6% |
| Hu8H24VHv2 (SEQ ID NO: 181) | 80.6% |
| Hu8H24VLv1 (SEQ ID NO: 185) | 88.4% |
| Hu8H24VLv2 (SEQ ID NO: 186) | 86.3% |

Positions at which canonical, vernier, or interface residues differ between mouse and human acceptor sequences are candidates for substitution. Examples of canonical/CDR interacting residues include Kabat residues H71 in Table 20 and L2 in Table 21. Examples of vernier residues include Kabat residues H2, H48, H67, and H71 in Table 20 and L2 in Table 21. Examples of interface/packing (VH+VL) residues include Kabat residue H91 in Table 20.

The rationales for selection of the positions indicated in Table 20 in the heavy chain variable region as candidates for substitution are as follows.

Heavy Chain Variable Regions hu8H24-VH_v1 consists of the CDR-H1, H2, and H3 loops of 8H24-VH grafted onto the framework of AAC51714 VH, and reverts all framework substitutions at positions that are key for defining the Chothia canonical classes, are part of the Vernier zone, or localize to the VH/VL domain interface Hu8H24-VH_v2 reverts all framework substitutions at positions that are key for defining the Chothia canonical classes, are part of the Vernier zone, or localize to the VH/VL domain interface or contribute to structural stability. H824-VH_v2 incorporates backmutations or substitution with most frequent residue at a given position.

V2A: Backmutation of a vernier zone residue

K12V: Side chain of Lys clashes with Val18, murine sequence at this position is Val, Val is most frequent residue at this position. Backmutation also increases humanness of the sequence.

M48I: Backmutation of a vernier zone residue

V67A: Backmutation of a vernier zone residue

A71V: Backmutation of a canonical and a vernier zone residue

Y91F: Backmutation of a VH/VL domain interface residue

L108T: This back mutation is made to reduce immunogenicity

The rationales for selection of the positions indicated in Table 21 in the light chain variable region as candidates for substitution are as follows.

Kappa Light Chain Variable Regions hu8H24-VL_v1 consists of the CDR-L1, L2, and L3 loops of 8H24-VL grafted onto the framework of ABC66914 VL along with reverting all framework substitutions at positions that are key for defining the Chothia canonical classes, are part of the Vernier zone, or locate to the VH/VL domain interface.

Hu8H24-VL_v2

Hu8H24-VLv2 includes substitutions that contribute to structural stability or increase the humanness of the antibody.

I2V: Backmutation of a canonical and a vernier zone residue

L9S: Corresponding germline sequence has Leu at this position, but Ser is most frequent at this position. Given that this is a surface exposed residue and Leu is hydrophobic whereas Ser is hydrophilic, having a hydrophilic residue at this position may increase developability (optimization of deamination, oxidation, N-glycosylation, proteolysis and aggregation).

K74T: murine and germline have Lys at this position but Thr is most frequent residue at this position. Being surface exposed Lys could lead to increase in surface charge patches. Thr at this position may increase developability (optimization of deamination, oxidation, N-glycosylation, proteolysis and aggregation).

Sequences of Heavy Chain Variable Regions

```
>h8H24VH version1 (81.6.% human)
QAQLVQSGAEVKKPGSSVKVSCKASGYTFTSYSMHWVRQAPGQGLEWIGA

IYPGNDATSYNQKFKGRATLTVDKSTSTAYMELSSLRSEDTAVYFCAREG

YYGSSFEAWFASWGQGTTVTVSS

>h8H24VH version2 (80.6% human)
QAQLVQSGAEVVKPGSSVKVSCKASGYTFTSYSMHWVRQAPGQGLEWIGA

IYPGNDATSYNQKFKGRATLTVDKSTSTAYMELSSLRSEDTAVYFCAREG

YYGSSFEAWFASWGQGTTVTVSS
```

Sequences of Kappa Light Chain Variable Regions

```
>h8H24VL version1 (88.4% human)
DVVMTQTPLSLPVTPGEPASISCRSSQSIVHSNGNTYLEWYLQKPGQSPQ

LLIYKVSNRFSGVPDRFSGSGSGTDFTLKISRVEAEDVGVYYCFQGSHVL

PTFGGGTKVEIK

>h8H24VL version2 (86.3% human)
DVVMTQTPSSLPVTPGEPASISCRSSQSIVHSNGNTYLEWYLQKPGQSPQ

LLIYKVSNRFSGVPDRFSGSGSGTDFTLTISRVEAEDVGVYYCFQGSHVL

PTFGGGTKVEIK
```

Example 16. Design of Humanized 11M14 Antibodies

The starting point or donor antibody for humanization was the mouse antibody 11M14. The heavy chain variable amino acid sequence of mature m11M14 is provided as SEQ ID NO:52. The light chain variable amino acid sequence of mature m11M14 is provided as SEQ ID NO:58. The heavy chain Kabat/Chothia Composite CDR1, CDR2, and CDR3 amino acid sequences are provided as SEQ ID NOS:53-55, respectively. The light chain Kabat CDR1, CDR2, and CDR3 amino acid sequences are provided as SEQ ID NOS:59-61, respectively. Kabat numbering is used throughout.

The variable kappa (Vk) of 11M14 belongs to mouse Vk subgroup 5 which corresponds to human Vk subgroup 1 and the variable heavy (Vh) to mouse Vh subgroup 3d which corresponds to human Vh subgroup 3 [Kabat E. A., et al., (1991), Sequences of Proteins of Immunological Interest, Fifth Edition. NIH Publication No. 91-3242]. 11 residue Chothia CDR-L1 is similar to Chothia canonical class 2, 7 residue Chothia CDR-L2 is of Chothia canonical class 1, 10 residue Chothia CDR-L3 is not similar to any Chothia canonical class [Martin A C R. (2010) Protein sequence and structure analysis of antibody variable domains. In: Kontermann R and Dübel S (eds). *Antibody Engineering*. Heidelberg, Germany: Springer International Publishing AG. [Martin, 2010]. 10 residue Chothia CDR-H1 is similar to Chothia canonical class 1, 17 residue Chothia CDR-H2 is similar to Chothia canonical class 3 [Martin, 2010]. 8 residue CDR-H3 has no canonical classes. A search was made over the protein sequences in the PDB database [Deshpande N, et al., (2005) Nucleic Acids Res. 33: D233-7] to find structures, which would provide a rough structural model of 11M14. The crystal structure of an antibody fab PDB code 1MQK [Essen, L. O. et al., 2003, Acta Crystallogr., Sect]) 59: 677-687] for both Vh and Vk structure since it had good resolution (1.28 Å) and overall sequence similarity to 11M14 Vh and Vk, retaining the same canonical structures for the loops.

A search of the non-redundant protein sequence database from NCBI allowed selection of suitable human frameworks into which to graft the murine 11M14 CDRs. For Vk, a human kappa light chain with NCBI accession code CBZ39892 (EMBL accession:FR820882) [Colombo, M. et al, Direct Submission 2011] was chosen. This has the same canonical classes for CDR-L1 & L2 and belongs to human germline IGKV1D-39'01 according to IMGT convention. It is a member of Kabat human kappa subgroup 1. For Vh, human Ig heavy chain ACS96198 (DBSOURCE:FJ489037) [Jimenz-Gomez, G. et al, 2010, J. Leukoc. Biol. 87 (3), 523-530] was chosen, again with the same canonical classes and belonging to human germline IGHV3-48'03. It is a member of Kabat human heavy subgroup 3. Accordingly, the framework regions of ACS96198 VH and CBZ39892 VL were chosen as the acceptor sequences for the CDRs of 11M14. A model of the 11M14 CDRs grafted onto the respective human frameworks for VH and VL was built and used as a guidance for further backmutations.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN: International nonproprietary names (INN) for biological and biotechnological substances (a review) (Internet) 2014. Available from: http://www.who.int/medicines/services/inn/BioRev2014.pdf) Residues were changed to align with corresponding human germ line sequence, where possible, to enhance humanness and to reduce potential immunogenicity. For humanized VLv2b, VL3b, and VL4b variants, mutations were introduced to render the sequences more similar to human germ line IGKV1-39*01 (SEQ ID NO:195)

Additional versions of hu11M14-VH and hu11M14-VL were designed to enable assessment of various framework residues for their contributions to antigen binding, thermostability, developability (deamination, oxidation, N-glycosylation, proteolysis and aggregation) and immunogenicity. The positions considered for mutation include those that . . .

- define the canonical CDR conformations (summarized in Martin A C R. (2010) Protein sequence and structure analysis of antibody variable domains. In: Kontermann R and Dübel S (eds). Antibody Engineering. Heidelberg, Germany: Springer International Publishing AG).
- are within the Vernier zone (Foote J and Winter G. (1992) Antibody framework residues affecting the conformation of the hypervariable loops. *J Mol Biol.* 224(2): 487-99).
- localize to the VH/VL domain interface (summarized in Leger O J P and Saldanha J. (2000) Preparation of recombinant antibodies from immune rodent spleens and the design of their humanisation by CDR grafting.

In: Shepherd P and Dean C (eds). *Monoclonal Antibodies: A Practical Approach*. Oxford, UK: Oxford University Press).

are susceptible to post-translational modifications, such as glycosylation or pyroglutamination, are occupied by residues that are predicted to clash with CDRs, according to the model of 11M14 CDRs grafted onto VH and VL frameworks, or are occupied by residues that are rare among sequenced human antibodies, where either the parental mouse 11M14 residue or some other residue is much more prevalent within human antibody repertoire.

Alignments of the murine 11M14 and various humanized antibodies are shown for the light chain variable regions (Table 27 and FIG. 6), and heavy chain variable regions (Table 26 and FIG. 5).

3 humanized heavy chain variable region variants and 4 humanized light chain variable region variants were constructed containing different permutations of substitutions: hu11M14VHv1b, hu11M14VHv2b, or hu11M14VHv3b, (SEQ ID NOS:190-192, respectively); and hu11M14VLv1b, hu11M14VLv2b, hu11M14VLv3b, or hu11M14VLv4b (SEQ ID NOS:196-199 respectively) (Tables 26 and 27).

The exemplary humanized Vk and Vh designs, with backmutations and other mutations based on selected human frameworks, are shown in Tables 27 and 26, respectively. The bolded areas in Tables 26 and 27 indicate the CDRs as defined by Kabat/Chothia Composite. A "-" in the columns in Tables 26 and 27 indicates no residue at the indicated position. SEQ ID NOS:190-192, and SEQ ID NOS:196-199 contain backmutations and other mutations as shown in Table 28. The amino acids at positions in hu11M14VHv1b, hu11M14VHv2b, and hu11M14VHv3b are listed in Table 29. The amino acids at positions in hu11M14VLv1b, hu11M14VLv2b, hu11M14VLv3b, and hu11M14VLv4b are listed in Table 30.

The percentage humanness for humanized VH chains hu11M14VHv1b, hu11M14VHv2b, and hu11M14VHv3b (SEQ ID NOS:190-192, respectively) with respect to the most similar human germline gene IGHV3-48*03 (SEQ ID NO:189), and for humanized VL chains in hu11M14VLv1b, hu11M14VLv2b, hu11M14VLv3b, and hu11M14VLv4b (SEQ ID NOS:196-199 respectively) with respect to the most similar human germline gene IGKV1-39*01 (SEQ ID NO:195) is shown in Table 31. NOS:196-199 respectively) with respect to the most similar human germline gene IGKV1-39*01 (SEQ ID NO:195) is shown in Table 31.

TABLE 26

11M14 VH sequences

| Kabat residue # | Linear residue # | FR or CDR | Mouse 11M14 VH (SEQ ID NO:) | GenBank Acc. # ACS96198-VH_huFrwk (SEQ ID NO: 188) | IMGT# IGHV3-48*03 (SEQ ID NO: 189 | Hu11M14VHv1b (SEQ ID NO: 190) | Hu11M14VHv2b (SEQ ID NO: 191) | Hu11M14VHv3b (SEQ ID NO: 192) |
|---|---|---|---|---|---|---|---|---|
| 1 | 1 | Fr1 | E | E | E | E | E | E |
| 2 | 2 | Fr1 | V | V | V | V | V | V |
| 3 | 3 | Fr1 | Q | Q | Q | Q | Q | Q |
| 4 | 4 | Fr1 | L | L | L | L | L | L |
| 5 | 5 | Fr1 | V | V | V | V | V | V |
| 6 | 6 | Fr1 | E | E | E | E | E | E |
| 7 | 7 | Fr1 | S | S | S | S | S | S |
| 8 | 8 | Fr1 | G | G | G | G | G | G |
| 9 | 9 | Fr1 | G | G | G | G | G | G |
| 10 | 10 | Fr1 | D | G | G | G | G | G |
| 11 | 11 | Fr1 | L | L | L | L | L | L |
| 12 | 12 | Fr1 | V | V | V | V | V | V |
| 13 | 13 | Fr1 | K | Q | Q | Q | Q | Q |
| 14 | 14 | Fr1 | P | P | P | P | P | P |
| 15 | 15 | Fr1 | G | G | G | G | G | G |
| 16 | 16 | Fr1 | G | G | G | G | G | G |
| 17 | 17 | Fr1 | S | S | S | S | S | S |
| 18 | 18 | Fr1 | L | L | L | L | L | L |
| 19 | 19 | Fr1 | K | R | R | R | R | R |
| 20 | 20 | Fr1 | L | L | L | L | L | L |
| 21 | 21 | Fr1 | S | S | S | S | S | S |
| 22 | 22 | Fr1 | C | C | C | C | C | C |
| 23 | 23 | Fr1 | A | A | A | A | A | A |
| 24 | 24 | Fr1 | A | A | A | A | A | A |
| 25 | 25 | Fr1 | S | S | S | S | S | S |
| **26** | **26** | **CDR-H1** | **G** | **G** | **G** | **G** | **G** | **G** |
| **27** | **27** | **CDR-H1** | **F** | **F** | **F** | **F** | **F** | **F** |
| **28** | **28** | **CDR-H1** | **T** | **T** | **T** | **T** | **T** | **T** |
| **29** | **29** | **CDR-H1** | **F** | **F** | **F** | **F** | **F** | **F** |
| **30** | **30** | **CDR-H1** | **N** | **S** | **S** | **N** | **N** | **N** |
| **31** | **31** | **CDR-H1** | **I** | **S** | **S** | **I** | **I** | **I** |
| **32** | **32** | **CDR-H1** | **Y** | **Y** | **Y** | **Y** | **Y** | **Y** |
| **33** | **33** | **CDR-H1** | **G** | **E** | **E** | **G** | **G** | **G** |
| **34** | **34** | **CDR-H1** | **M** | **M** | **M** | **M** | **M** | **M** |
| **35** | **35** | **CDR-H1** | **S** | **N** | **N** | **S** | **S** | **S** |
| **35A** | | **CDR-H1** | — | — | — | — | — | — |
| **35B** | | **CDR-H1** | — | — | — | — | — | — |
| 36 | 36 | Fr2 | W | W | W | W | W | W |
| 37 | 37 | Fr2 | V | V | V | V | V | V |
| 38 | 38 | Fr2 | R | R | R | R | R | R |

TABLE 26-continued

11M14 VH sequences

| Kabat residue # | Linear residue # | FR or CDR | Mouse 11M14 VH (SEQ ID NO:) | GenBank Acc. # ACS96198-VH_huFrwk (SEQ ID NO: 188) | IMGT# IGHV3-48*03 (SEQ ID NO: 189 | Hu11M14VHv1b (SEQ ID NO: 190) | Hu11M14VHv2b (SEQ ID NO: 191) | Hu11M14VHv3b (SEQ ID NO: 192) |
|---|---|---|---|---|---|---|---|---|
| 39 | 39 | Fr2 | Q | Q | Q | Q | Q | Q |
| 40 | 40 | Fr2 | T | A | A | A | A | A |
| 41 | 41 | Fr2 | P | P | P | P | P | P |
| 42 | 42 | Fr2 | D | G | G | G | G | G |
| 43 | 43 | Fr2 | K | K | K | K | K | K |
| 44 | 44 | Fr2 | R | G | G | G | G | G |
| 45 | 45 | Fr2 | L | L | L | L | L | L |
| 46 | 46 | Fr2 | E | E | E | E | E | E |
| 47 | 47 | Fr2 | W | W | W | W | W | W |
| 48 | 48 | Fr2 | V | V | V | V | V | V |
| 49 | 49 | Fr2 | A | S | S | A | A | A |
| **50** | **50** | **CDR-H2** | **T** | **Y** | **Y** | **T** | **T** | **T** |
| **51** | **51** | **CDR-H2** | **I** | **I** | **I** | **I** | **I** | **I** |
| **52** | **52** | **CDR-H2** | **S** | **S** | **S** | **S** | **S** | **S** |
| **52A** | **53** | **CDR-H2** | **S** | **S** | **S** | **S** | **S** | **S** |
| **52B** | | **CDR-H2** | — | — | — | — | — | — |
| **52C** | | **CDR-H2** | — | — | — | — | — | — |
| **53** | **54** | **CDR-H2** | **G** | **S** | **S** | **G** | **G** | **G** |
| **54** | **55** | **CDR-H2** | **G** | **G** | **G** | **G** | **G** | **G** |
| **55** | **56** | **CDR-H2** | **I** | **S** | **S** | **I** | **I** | **I** |
| **56** | **57** | **CDR-H2** | **Y** | **T** | **T** | **Y** | **Y** | **Y** |
| **57** | **58** | **CDR-H2** | **T** | **I** | **I** | **T** | **T** | **T** |
| **58** | **59** | **CDR-H2** | **Y** | **Y** | **Y** | **Y** | **Y** | **Y** |
| **59** | **60** | **CDR-H2** | **Y** | **Y** | **Y** | **Y** | **Y** | **Y** |
| **60** | **61** | **CDR-H2** | **P** | **A** | **A** | **P** | **P** | **P** |
| **61** | **62** | **CDR-H2** | **D** | **D** | **D** | **D** | **D** | **D** |
| **62** | **63** | **CDR-H2** | **I** | **S** | **S** | **I** | **I** | **I** |
| **63** | **64** | **CDR-H2** | **L** | **V** | **V** | **L** | **L** | **L** |
| **64** | **65** | **CDR-H2** | **K** | **K** | **K** | **K** | **K** | **K** |
| **65** | **66** | **CDR-H2** | **G** | **G** | **G** | **G** | **G** | **G** |
| 66 | 67 | Fr3 | R | R | R | R | R | R |
| 67 | 68 | Fr3 | F | F | F | F | F | F |
| 68 | 69 | Fr3 | T | T | T | T | T | T |
| 69 | 70 | Fr3 | I | I | I | I | I | I |
| 70 | 71 | Fr3 | S | S | S | S | S | S |
| 71 | 72 | Fr3 | R | R | R | R | R | R |
| 72 | 73 | Fr3 | D | D | D | D | D | D |
| 73 | 74 | Fr3 | N | N | N | N | N | N |
| 74 | 75 | Fr3 | A | A | A | A | A | A |
| 75 | 76 | Fr3 | K | K | K | K | K | K |
| 76 | 77 | Fr3 | N | N | N | N | N | N |
| 77 | 78 | Fr3 | T | S | S | S | S | S |
| 78 | 79 | Fr3 | L | L | L | L | L | L |
| 79 | 80 | Fr3 | Y | Y | Y | Y | Y | Y |
| 80 | 81 | Fr3 | L | L | L | L | L | G |
| 81 | 82 | Fr3 | Q | Q | Q | Q | Q | Q |
| 82 | 83 | Fr3 | M | M | M | M | M | M |
| 82A | 84 | Fr3 | S | N | N | N | N | N |
| 82B | 85 | Fr3 | S | S | S | S | S | S |
| 82C | 86 | Fr3 | L | L | L | L | G | L |
| 83 | 87 | Fr3 | K | R | R | R | R | R |
| 84 | 88 | Fr3 | S | A | A | A | A | A |
| 85 | 89 | Fr3 | E | E | E | E | E | E |
| 86 | 90 | Fr3 | D | D | D | D | D | D |
| 87 | 91 | Fr3 | T | T | T | T | T | T |
| 88 | 92 | Fr3 | A | A | A | A | A | A |
| 89 | 93 | Fr3 | M | V | V | V | V | V |
| 90 | 94 | Fr3 | Y | Y | Y | Y | Y | Y |
| 91 | 95 | Fr3 | Y | Y | Y | Y | Y | Y |
| 92 | 96 | Fr3 | C | C | C | C | C | C |
| 93 | 97 | Fr3 | A | A | A | A | A | A |
| 94 | 98 | Fr3 | R | R | R | R | R | R |
| **95** | **99** | **CDR-H3** | **H** | **E** | **Y** | **H** | **H** | **H** |
| **96** | | **CDR-H3** | **P** | **N** | **F** | **P** | **P** | **P** |
| **97** | | **CDR-H3** | **G** | **I** | — | **G** | **G** | **G** |
| **98** | | **CDR-H3** | **G** | **A** | — | **G** | **G** | **G** |
| **99** | | **CDR-H3** | **A** | **A** | — | **A** | **A** | **A** |
| **100** | | **CDR-H3** | **M** | **F** | — | **M** | **M** | **M** |
| **100A** | | **CDR-H3** | | — | — | — | — | — |
| **100B** | | **CDR-H3** | | — | — | — | — | — |
| **100C** | | **CDR-H3** | | — | — | — | — | — |

TABLE 26-continued

11M14 VH sequences

| Kabat residue # | Linear residue # | FR or CDR | Mouse 11M14 VH (SEQ ID NO:) | GenBank Acc. # ACS96198-VH_huFrwk (SEQ ID NO: 188) | IMGT# IGHV3-48*03 (SEQ ID NO: 189 | Hu11M14VHv1b (SEQ ID NO: 190) | Hu11M14VHv2b (SEQ ID NO: 191) | Hu11M14VHv3b (SEQ ID NO: 192) |
|---|---|---|---|---|---|---|---|---|
| **100D** | | **CDR-H3** | | — | — | — | — | — |
| **100E** | | **CDR-H3** | | — | — | — | — | — |
| **100F** | | **CDR-H3** | | — | — | — | — | — |
| **100G** | | **CDR-H3** | — | — | — | — | — | — |
| **100H** | | **CDR-H3** | — | — | — | — | — | — |
| **100I** | | **CDR-H3** | — | — | — | — | — | — |
| **100J** | | **CDR-H3** | — | — | — | — | — | — |
| **100K** | | **CDR-H3** | — | — | — | — | — | — |
| **101** | **100** | **CDR-H3** | **D** | **D** | **D** | **D** | **D** | **D** |
| **102** | **101** | **CDR-H3** | **Y** | **Y** | **Y** | **Y** | **Y** | **Y** |
| 103 | 102 | Fr4 | W | W | W | W | W | W |
| 104 | 103 | Fr4 | G | G | G | G | G | G |
| 105 | 104 | Fr4 | Q | Q | Q | Q | Q | Q |
| 106 | 105 | Fr4 | G | G | G | G | G | G |
| 107 | 106 | Fr4 | T | T | T | T | T | T |
| 108 | 107 | Fr4 | S | L | L | L | L | L |
| 109 | 108 | Fr4 | V | V | V | V | V | V |
| 110 | 109 | Fr4 | T | T | T | T | T | T |
| 111 | 110 | Fr4 | V | V | V | V | V | V |
| 112 | 111 | Fr4 | S | S | S | S | S | S |
| 113 | 112 | Fr4 | S | S | S | S | S | S |

TABLE 27

11M14 VL sequences

| Kabat residue # | Linear residue # | FR or CDR | Mouse 11M14 VL (SEQ ID NO:58) | GenBank Acc. # CBZ39892-VL huFrwk (SEQ ID NO: 194) | IMGT# IGKV1-39*01 (SEQ ID NO: 195) | Mouse 11M14 VH (SEQ ID NO:52) | Hu11M14VLv1b (SEQ ID NO: 196) | Hu11M14VLv2b (SEQ ID NO: 197) | Hu11M14VLv3b (SEQ ID NO: 198) |
|---|---|---|---|---|---|---|---|---|---|
| 1 | 1 | Fr1 | D | D | D | D | D | D | D |
| 2 | 2 | Fr1 | I | I | I | I | I | I | I |
| 3 | 3 | Fr1 | Q | Q | Q | Q | Q | Q | Q |
| 4 | 4 | Fr1 | M | M | M | M | M | M | M |
| 5 | 5 | Fr1 | T | T | T | T | T | T | T |
| 6 | 6 | Fr1 | Q | Q | Q | Q | Q | Q | Q |
| 7 | 7 | Fr1 | S | S | S | S | S | S | S |
| 8 | 8 | Fr1 | P | P | P | P | P | P | P |
| 9 | 9 | Fr1 | A | S | S | S | S | S | S |
| 10 | 10 | Fr1 | S | S | S | S | S | S | S |
| 11 | 11 | Fr1 | L | L | L | L | L | L | L |
| 12 | 12 | Fr1 | S | S | S | S | S | S | S |
| 13 | 13 | Fr1 | V | A | A | A | A | A | A |
| 14 | 14 | Fr1 | S | S | S | S | S | S | S |
| 15 | 15 | Fr1 | V | V | V | V | V | V | V |
| 16 | 16 | Fr1 | G | G | G | G | G | G | G |
| 17 | 17 | Fr1 | E | D | D | D | D | D | D |
| 18 | 18 | Fr1 | T | R | R | R | R | R | R |
| 19 | 19 | Fr1 | V | V | V | V | V | V | V |
| 20 | 20 | Fr1 | T | T | T | T | T | T | T |
| 21 | 21 | Fr1 | I | I | I | I | I | I | I |
| 22 | 22 | Fr1 | T | T | T | T | T | T | T |
| 23 | 23 | Fr1 | C | C | C | C | C | C | C |
| **24** | **24** | **CDR-L1** | **R** | **R** | **R** | **R** | **R** | **R** | **R** |
| **25** | **25** | **CDR-L1** | **V** | **A** | **A** | **V** | **V** | **V** | **V** |
| **26** | **26** | **CDR-L1** | **S** | **S** | **S** | **S** | **S** | **S** | **S** |
| **27** | **27** | **CDR-L1** | **E** | **Q** | **Q** | **E** | **E** | **E** | **E** |
| **27A** | **28** | **CDR-L1** | — | **S** | **S** | — | — | — | |
| **27B** | **29** | **CDR-L1** | — | **I** | **I** | — | — | — | |
| **27C** | **30** | **CDR-L1** | — | **S** | **S** | — | — | — | |
| **27D** | **31** | **CDR-L1** | — | **S** | **S** | — | — | — | — |
| **27E** | **32** | **CDR-L1** | — | **Y** | **Y** | — | — | — | — |
| **27F** | | **CDR-L1** | — | — | — | — | — | — | — |
| **28** | **33** | **CDR-L1** | **N** | — | — | **N** | **N** | **N** | **N** |
| **29** | **34** | **CDR-L1** | **I** | — | — | **I** | **I** | **I** | **I** |

TABLE 27-continued

11M14 VL sequences

| Kabat residue # | Linear residue # | FR or CDR | Mouse 11M14 VL (SEQ ID NO:58) | GenBank Acc. # CBZ39892-VL huFrwk (SEQ ID NO: 194) | IMGT# IGKV1-39*01 (SEQ ID NO: 195) | Mouse 11M14 VH (SEQ ID NO:52) | Hu11M14VLv1b (SEQ ID NO: 196) | Hu11M14VLv2b (SEQ ID NO: 197) | Hu11M14VLv3b (SEQ ID NO: 198) |
|---|---|---|---|---|---|---|---|---|---|
| **30** | **35** | **CDR-L1** | **Y** | — | — | **Y** | **Y** | **Y** | **Y** |
| **31** | **36** | **CDR-L1** | **S** | — | — | **S** | **S** | **S** | **S** |
| **32** | **37** | **CDR-L1** | **N** | — | — | **N** | **N** | **N** | **N** |
| **33** | **38** | **CDR-L1** | **L** | **L** | **L** | **L** | **L** | **L** | **L** |
| **34** | **39** | **CDR-L1** | **A** | **N** | **N** | **A** | **A** | **A** | **A** |
| 35 | 40 | Fr2 | W | W | W | W | W | W | W |
| 36 | 41 | Fr2 | Y | Y | Y | Y | Y | Y | Y |
| 37 | 42 | Fr2 | Q | Q | Q | Q | Q | Q | Q |
| 38 | 43 | Fr2 | Q | Q | Q | Q | Q | Q | Q |
| 39 | 44 | Fr2 | K | K | K | K | K | K | K |
| 40 | 45 | Fr2 | Q | P | P | P | P | P | P |
| 41 | 46 | Fr2 | G | G | G | G | G | G | G |
| 42 | 47 | Fr2 | K | K | K | K | K | K | K |
| 43 | 48 | Fr2 | S | A | A | A | S | S | S |
| 44 | 49 | Fr2 | P | P | P | P | P | P | P |
| 45 | 50 | Fr2 | H | K | K | K | K | K | K |
| 46 | 51 | Fr2 | L | L | L | L | L | L | L |
| 47 | 52 | Fr2 | L | L | L | L | L | L | L |
| 48 | 53 | Fr2 | V | I | I | V | V | V | V |
| 49 | 54 | Fr2 | Y | Y | Y | Y | Y | Y | Y |
| **50** | **55** | **CDR-L2** | **A** | **A** | **A** | **A** | **A** | **A** | **A** |
| **51** | **56** | **CDR-L2** | **A** | **A** | **A** | **A** | **A** | **A** | **A** |
| **52** | **57** | **CDR-L2** | **T** | **S** | **S** | **T** | **T** | **T** | **T** |
| **53** | **58** | **CDR-L2** | **N** | **S** | **S** | **N** | **N** | **N** | **N** |
| **54** | **59** | **CDR-L2** | **L** | **L** | **L** | **L** | **L** | **G** | **I** |
| **55** | **60** | **CDR-L2** | **A** | **Q** | **Q** | **A** | **A** | **A** | **A** |
| **56** | **61** | **CDR-L2** | **D** | **S** | **S** | **D** | **D** | **D** | **D** |
| 57 | 62 | Fr3 | G | G | G | G | G | G | G |
| 58 | 63 | Fr3 | V | V | V | V | V | V | V |
| 59 | 64 | Fr3 | P | P | P | P | P | P | P |
| 60 | 65 | Fr3 | S | S | S | S | S | S | S |
| 61 | 66 | Fr3 | R | R | R | R | R | R | R |
| 62 | 67 | Fr3 | F | F | F | F | F | F | F |
| 63 | 68 | Fr3 | S | S | S | S | S | S | S |
| 64 | 69 | Fr3 | G | G | G | G | G | G | G |
| 65 | 70 | Fr3 | S | S | S | S | S | S | S |
| 66 | 71 | Fr3 | G | G | G | G | G | G | G |
| 67 | 72 | Fr3 | S | S | S | S | S | S | S |
| 68 | 73 | Fr3 | G | G | G | G | G | G | G |
| 69 | 74 | Fr3 | T | T | T | T | T | T | T |
| 70 | 75 | Fr3 | Q | D | D | D | D | D | D |
| 71 | 76 | Fr3 | Y | F | F | Y | Y | Y | Y |
| 72 | 77 | Fr3 | S | T | T | T | T | T | T |
| 73 | 78 | Fr3 | L | L | L | L | L | L | L |
| 74 | 79 | Fr3 | K | T | T | T | T | T | T |
| 75 | 80 | Fr3 | I | I | I | I | I | I | I |
| 76 | 81 | Fr3 | N | N | S | N | S | S | S |
| 77 | 82 | Fr3 | S | S | S | S | S | S | S |
| 78 | 83 | Fr3 | L | L | L | L | L | L | L |
| 79 | 84 | Fr3 | Q | Q | Q | Q | Q | Q | Q |
| 80 | 85 | Fr3 | S | P | P | P | P | P | P |
| 81 | 86 | Fr3 | E | E | E | E | E | E | E |
| 82 | 87 | Fr3 | D | D | D | D | D | D | D |
| 83 | 88 | Fr3 | F | F | F | F | F | F | F |
| 84 | 89 | Fr3 | G | A | A | A | A | A | A |
| 85 | 90 | Fr3 | S | T | T | T | T | T | T |
| 86 | 91 | Fr3 | Y | Y | Y | Y | Y | Y | Y |
| 87 | 92 | Fr3 | Y | Y | Y | Y | Y | Y | Y |
| 88 | 93 | Fr3 | C | C | C | C | C | C | C |
| **89** | **94** | **CDR-L3** | **Q** | **Q** | **Q** | **Q** | **Q** | **Q** | **Q** |
| **90** | **95** | **CDR-L3** | **H** | **Q** | **Q** | **H** | **H** | **H** | **H** |
| **91** | **96** | **CDR-L3** | **F** | **S** | **S** | **F** | **F** | **F** | **F** |
| **92** | **97** | **CDR-L3** | **W** | **Y** | **Y** | **W** | **W** | **W** | **W** |
| **93** | **98** | **CDR-L3** | **G** | **S** | **S** | **G** | **G** | **G** | **G** |
| **94** | **99** | **CDR-L3** | **T** | **T** | **T** | **T** | **T** | **T** | **T** |
| **95** | **100** | **CDR-L3** | **P** | **P** | **P** | **P** | **P** | **P** | **P** |
| **95A** | | **CDR-L3** | **P** | — | — | — | — | — | — |
| **95B** | | **CDR-L3** | — | — | — | — | — | — | — |
| **95C** | | **CDR-L3** | — | — | — | — | — | — | — |
| **95D** | | **CDR-L3** | — | — | — | — | — | — | — |
| **95E** | | **CDR-L3** | — | — | — | — | — | — | — |

TABLE 27-continued

| 11M14 VL sequences | | | | | | | | | |
|---|---|---|---|---|---|---|---|---|---|
| Kabat residue # | Linear residue # | FR or CDR | Mouse 11M14 VL (SEQ ID NO:58) | GenBank Acc. # CBZ39892-VL huFrwk (SEQ ID NO: 194) | IMGT# IGKV1-39*01 (SEQ ID NO: 195) | Mouse 11M14 VH (SEQ ID NO:52) | Hu11M14VLv1b (SEQ ID NO: 196) | Hu11M14VLv2b (SEQ ID NO: 197) | Hu11M14VLv3b (SEQ ID NO: 198) |
| **95F** | | **CDR-L3** | — | — | — | — | — | — | — |
| **96** | **101** | **CDR-L3** | **W** | **Y** | **Y** | **W** | **W** | **W** | **W** |
| **97** | **102** | **CDR-L3** | **T** | **T** | **T** | **T** | **T** | **T** | **T** |
| 98 | 103 | Fr4 | F | F | F | F | F | F | F |
| 99 | 104 | Fr4 | G | G | G | G | G | G | G |
| 100 | 105 | Fr4 | G | Q | Q | Q | Q | Q | Q |
| 101 | 106 | Fr4 | G | G | G | G | G | G | G |
| 102 | 107 | Fr4 | T | T | T | T | T | T | T |
| 103 | 108 | Fr4 | K | K | K | K | K | K | K |
| 104 | 109 | Fr4 | L | L | L | L | L | L | L |
| 105 | 110 | Fr4 | E | E | E | E | E | E | E |
| 106 | 111 | Fr4 | I | I | I | I | I | I | I |
| 106A | | Fr4 | — | — | — | — | — | — | — |
| 107 | 112 | Fr4 | R | K | K | K | K | K | K |

TABLE 28

| $V_H$, $V_L$ Backmutations and Other Mutations for Humanized 11M14 | | |
|---|---|---|
| $V_H$ or $V_L$ Variant | $V_H$ or $V_L$ Exon Acceptor Sequence | Changes from Acceptor Framework (or CDR) Residues (based on Kabat/Chothia Composite CDRs) |
| Hu11M14VHv1b (SEQ ID NO: 190) | GenBank Acc. # ACS96198-VH_huFrwk (SEQ ID NO: 188) IMGT# IGHV3-48*03 (SEQ ID NO: 189) | H49 |
| Hu11M14VHv2b (SEQ ID NO: 191) | GenBank Acc. # ACS96198-VH_huFrwk (SEQ ID NO: 188) IMGT# IGHV3-48*03 (SEQ ID NO: 189 | H49, H82c |
| Hu11M14VHv3b (SEQ ID NO: 192) | GenBank Acc. # ACS96198-VH_huFrwk (SEQ ID NO: 188) IMGT# IGHV3-48*03 (SEQ ID NO: 189 | H49, H80 |
| Hu11M14VLv1b (SEQ ID NO: 196) | GenBank Acc. # CBZ39892-VL_huFrwk (SEQ ID NO: 194) IMGT# IGKV1-39*01 (SEQ ID NO: 195) | L48, L71 |
| Hu11M14VLv2b (SEQ ID NO: 197) | GenBank Acc. # CBZ39892-VL_huFrwk (SEQ ID NO: 194) IMGT# IGKV1-39*01 (SEQ ID NO: 195) | L43, L48, L71, L76 |
| Hu11M14VLv3b (SEQ ID NO: 198) | GenBank Acc. # CBZ39892-VL_huFrwk (SEQ ID NO: 194) IMGT# IGKV1-39*01 (SEQ ID NO: 195) | L43, L48, L54, L71, L76 |
| Hu11M14VLv4b (SEQ ID NO: 199) | GenBank Acc. # CBZ39892-VL_huFrwk (SEQ ID NO: 194) IMGT# IGKV1-39*01 (SEQ ID NO: 195) | L43, L48, L54, L71, L76 |

TABLE 29

| Kabat Numbering of Framework (or CDR) Residues (based on Kabat/Chothia Composite CDRs) for Backmutations and Other Mutations in Heavy Chains of Humanized 11M14 Antibodies | | | | | | |
|---|---|---|---|---|---|---|
| Residue | GenBank Acc. # ACS96198-VH_huFrwk (SEQ ID NO: 188) | IMGT# IGHV3-48*03 (SEQ ID NO: 189 | Mouse 11M14 VH (SEQ ID NO: 52) | Hu11M14VHv1b (SEQ ID NO: 190) | Hu11M14VHv2b (SEQ ID NO: 191) | Hu11M14VHv3b (SEQ ID NO: 192) |
| H49 | S | S | A | A | A | A |
| H80 | L | L | L | L | L | G |
| H82c | L | L | L | L | G | L |

TABLE 30

Kabat Numbering of Framework Residues (based on Kabat/Chothia Composite CDRs) for Backmutations and Other Mutations in Light Chains of Humanized 11M14 Antibodies

| Residue | GenBank Acc. # CBZ39892-VL huFrwk (SEQ ID NO: 194) | IMGT# IGKV1-39*01 (SEQ ID NO: 195) | Mouse 11M14 VL (SEQ ID NO:58) | Hu11M14VLv1b (SEQ ID NO: 196) | Hu11M14VLv2b (SEQ ID NO: 197) | Hu11M14VLv3b (SEQ ID NO: 198) | Hu11M14VLv4b (SEQ ID NO: 199) |
|---|---|---|---|---|---|---|---|
| L43 | A | A | S | A | S | S | S |
| L48 | I | I | V | V | V | V | V |
| L54 | L | L | L | L | L | G | I |
| L71 | F | F | Y | Y | Y | Y | Y |
| L76 | N | S | N | N | S | S | s |

TABLE 31

Percentage Humanness of Heavy and Light Chains of Humanized 11M14 Antibodies

| $V_H$ or $V_L$ Variant | % Humanness |
|---|---|
| Hu11M14VHv1b (SEQ ID NO: 190) | 86.7% |
| Hu11M14VHv2b (SEQ ID NO: 191) | 85.7% |
| Hu11M14VHv3b (SEQ ID NO: 192) | 85.7% |
| Hu11M14VLv1b (SEQ ID NO: 196) | 83.2% |
| Hu11M14VLv2b (SEQ ID NO: 197) | 83.2% |
| Hu11M14VLv3b (SEQ ID NO: 198) | 82.1% |
| Hu11M14VLv4b (SEQ ID NO: 199) | 82.1% |

Positions at which canonical, vernier, or interface residues differ between mouse and human acceptor sequences are candidates for substitution. Examples of canonical/CDR interacting residues include Kabat residue L71 in Table 27. Examples of vernier residues include Kabat residues H49 in Table 26 and L48 and L71 in Table 27.

The rationales for selection of the positions indicated in Table 26 in the heavy chain variable region as candidates for substitution are as follows.

Heavy Chain Variable Regions hu11M14-VH_v1b consists of the CDR-H1, H2, and H3 loops of 11M14-VH grafted onto the framework of ACS96198 VH. And reverts all framework substitutions at positions that are key for defining the Chothia canonical classes, are part of the Vernier zone, or localize to the VH/VL domain interface or contribute to structural stability hu11M14-VH_v2b and hu11M14-VH_v3b incorporates backmutations or substitution with most frequent residue at a given position. along with reverting all framework substitutions at positions that are key for defining the Chothia canonical classes, are part of the Vernier zone, or locate to the VH/VL domain interface, or reduce immunogenicity.

S49A: Backmutation of a vernier zone residue.

L80G: Leu at this position is immunogenic as indicated by IEDB analysis. A deimmunization analysis predicts immunogenicity reduction by Gly substitution. Gly substitution at positions 80 and 82c to mitigate immunogenicity are mutually exclusive and are tried in different VH versions.

L82cG: Leu at this position is immunogenic as indicated by IEDB analysis. A deimmunization analysis predicts immunogenicity reduction by Gly substitution.

The rationales for selection of the positions indicated in Table 27 in the light chain variable region as candidates for substitution are as follows.

Kappa Light Chain Variable Regions hu11M14-VL_v1b consists of the CDR-L1, L2, and L3 loops of 11M14-VL grafted onto the framework of CBZ39892 VL along with reverting all framework substitutions at positions that are key for defining the Chothia canonical classes, are part of the Vernier zone, or locate to the VH/VL domain interface.

hu11M14-VL_v2b, hu11M14-VL_v3b, hu11M14-VL_v4b include substitutions that contribute to structural stability or increases the humanness of the antibody or reduce immunogenicity.

A43S: Stability-enhancing mutation. Ser stabilizes the structure by making inter chain bonds with Tyr 91 and Gly 104 both in the heavy chain. This back mutation is made to maintain conformation and to keep the antibody structure stable.

I48V: Backmutation of a vernier zone residue.

L54G: Leu at this position is immunogenic as indicated by IEDB analysis; a deimmunization analysis predicts immunogenicity reduction by Gly substitution. Gly substitution at position 54 is predicted to mitigate immunogenicity.

L54I: Leu at this position is immunogenic as indicated by IEDB analysis; a deimmunization analysis predicts immunogenicity reduction by Ile substitution. Ile substitution at position 54 is predicted to mitigate immunogenicity.

F71Y: Backmutation of a canonical and vernier zone residue.

N76S: Germline-aligning mutation. Germline gene IGKV1-39*01 (SEQ ID NO:195) has Ser at this position.

The designs based on these human frameworks were:

Sequences of Heavy Chain Variable Regions

SEQ ID NO: 190

```
>h11M14VH version1b (86.7% human)
EVQLVESGGGLVQPGGSLRLSCAASGFTFNIYGMSWVRQAPGKGLEWVAT
ISSGGIYTYYPDILKGRFTISRDNAKNSLYLQMNSLRAEDTAVYYCARHP
GGAMDYWGQGTLVTVSS
```

SEQ ID NO: 191

```
>h11M14VH version2b (85.7% human)
EVQLVESGGGLVQPGGSLRLSCAASGFTFNIYGMSWVRQAPGKGLEWVAT
ISSGGIYTYYPDILKGRFTISRDNAKNSLYLQMNSGRAEDTAVYYCARHP
GGAMDYWGQGTLVTVSS
```

-continued

SEQ ID NO: 192

```
>h11M14VH version3b (85.7% human)
EVQLVESGGGLVQPGGSLRLSCAASGFTFNIYGMSWVRQAPGKGLEWVAT
ISSGGIYTYYPDILKGRFTISRDNAKNSLYGQMNSLRAEDTAVYYCARHP
GGAMDYWGQGTLVTVSS
```

Sequences of Kappa Light Chain Variable Regions

SEQ ID NO: 196

```
>h11M14VL version1b (83.2% human)
DIQMTQSPSSLSASVGDRVTITCRVSENIYSNLAWYQQKPGKAPKLLVYA
ATNLADGVPSRFSGSGSGTDYTLTINSLQPEDFATYYCQHFWGTPPWTFG
QGTKLEIK
```

SEQ ID NO: 197

```
>h11M14VL version2b (83.2% human)
DIQMTQSPSSLSASVGDRVTITCRVSENIYSNLAWYQQKPGKSPKLLVYA
ATNLADGVPSRFSGSGSGTDYTLTISSLQPEDFATYYCQHFWGTPPWTFG
QGTKLEIK
```

SEQ ID NO: 198

```
>h11M14VL version3b (82.1% human)
DIQMTQSPSSLSASVGDRVTITCRVSENIYSNLAWYQQKPGKSPKLLVYA
ATNGADGVPSRFSGSGSGTDYTLTISSLQPEDFATYYCQHFWGTPPWTFG
QGTKLEIK
```

SEQ ID NO: 199

```
>h11M14VL version4b (82.1% human)
DIQMTQSPSSLSASVGDRVTITCRVSENIYSNLAWYQQKPGKSPKLLVYA
ATNIADGVPSRFSGSGSGTDYTLTISSLQPEDFATYYCQHFWGTPPWTFG
QGTKLEIK
```

Example 17. Antibody Epitope Mapping by Peptide Microarray Analysis

PEPperMAP Conformational epitope mapping was carried out by PEPperPrint GmbH. Epitope analysis of 11M14 and 8H24 was performed by peptide microarray analysis. The sequence of the extracellular domain of human sortilin (756 amino acids; SEQ ID NO: 1) was elongated with neutral GSGSGSG (SEQ ID NO:207) linkers at the C- and N-terminus to avoid truncated peptides. The linked and elongated antigen sequence was translated into 7, 10 and 13 amino acid peptides with a peptide-peptide overlap of 6, 9 and 12 amino acids. After peptide synthesis, all peptides were cyclized via a thioether linkage between a C-terminal cysteine and an appropriately modified N-terminus. The resulting conformational peptide microarrays contained 2,283 different peptides printed in duplicate (4,566 peptide spots), and were framed by additional HA (YPYDVPDYAG, SEQ ID NO:200; 70 spots) and c-Myc (EQKLISEEDL, SEQ ID NO:201; 70 spots) control peptides linear 15 amino acid peptides with a peptide-peptide overlap of 14 amino acids. The resulting human sortilin peptide microarrays contained 756 different peptides printed in duplicate (1,512 spots) and were framed by additional HA (YPYDVPDYAG, SEQ ID NO:200; 46 spots) and c-Myc (EQKLISEEDL, SEQ ID NO:201; 46 spots) control peptides.

After synthesis, the microarray was blocked to prevent nonspecific binding (Rockland catalog #MB-070). Murine 11M14 or 8H24 was then applied to the microarray at a concentrations ranging from 10 μg/mL to 100 μg/mL along with positive control mouse monoclonal anti-HA (12CA5) DyLight800 (0.5 μg/ml) for 16 h at 4° C. with shaking at 140 rpm. The microarray was washed, and secondary antibody (Goat anti-mouse IgG (H+L) DyLight680 (0.2 μg/ml) was applied for 45 minutes at room temperature. After further washing, the microarray was imaged using a Licor Odyssey Imaging System.

Quantification of spot intensities and peptide annotation were based on the 16-bit gray scale tiff files that exhibit a higher dynamic range than the 24-bit colorized tiff files. Microarray image analysis was done with PepSlide". A software algorithm breaks down fluorescence intensities of each spot into raw, foreground and background signal, and calculates averaged median foreground intensities and spot-to-spot deviations of spot duplicates. Based on averaged median foreground intensities, intensity maps were generated and interactions in the peptide maps highlighted by an intensity color code with red for high and white for low spot intensities. We tolerated a maximum spot-to-spot deviation of 40%, otherwise the corresponding intensity value was zeroed.

Results

For 8H24, An antibody response against an epitope-like spot pattern formed by peptides with the consensus motif RTEFGMAIGP. (SEQ ID NO:213).

For 11M14, a very weak antibody response was observed against an epitope-like spot pattern formed by adjacent peptides with the consensus motif WGFTESFLTS (SEQ ID NO:214).

Example 18. Antibody Epitope Mapping Via Structural Guided Mutagenesis

Rationale:

Rough epitope of the 5E20 antibody was previously determined to be within amino acids 557-560 of SEQ ID NO:215 (ESFL; SEQ ID NO:203) using peptide arrays at PEPperPrint GmbH; see Example 10. Similarly, SORT1-Progranulin interaction experimental data indicated that Progranulin binding to Sortilin is blocked by 5E20 mAb (See Example 7). SORT1-PRGN interaction data for 8H24 and 11M24 antibodies showed that they also block binding of PGRN to sortilin (See Example 7). Therefore, it was reasoned that 8H24 and 11M14 must also bind to the SORT1 loops/domains projecting in the similar plane on 3D structure.

During the first round of mutagenesis multiple amino acid mutations in hSORT1 were made within the loops/domains that were structurally adjacent to the 5E20 epitope. Fourteen hSORT1 mutants with multiple amino acid mutations in targeted loop regions were generated during de novo DNA synthesis at Atum Bio (CRO) during the first round of mutagenesis (Table 32). Numbering of Loop Area and Mutations is based on sortilin ECD without the 33-amino acid signal peptide (SEQ ID NO:215). These mutants were subcloned into expression vector and a His×8 tag was attached to the C-terminus of all mutants. Mutant proteins were generated by transient transfection of plasmids into HTEK293 cells. Conditioned media was directly used for ELISA assay to measure antibody binding, wild type SORT1 protein was used a control.

TABLE 32

| Sortilin antibody epitope mutagenesis round 1 mutants: | | | |
|---|---|---|---|
| Mutant | SEQ ID NO: | Loop area - aa | Mutations |
| hSORT1_ECD_Emut1 | 216 | 70-76 | H70A, D74A, L75A, R76A |
| hSORT1_ECD_Emut2a | 217 | 97-104 | F97A, H98A, V102A, M104A |
| hSORT1_ECD_Emut2b | 218 | 106-112 | F106A, Q108A, K110A, L112 |
| hSORT1_ECD_Emut3 | 219 | 123-131 | D123A, D126A, N130A, T131A |
| hSORT1_ECD_Emut4 | 220 | 155-163 | V155A, S156A, S159A, R160A, R163 |
| hSORT1_ECD_Emut5 | 221 | 176-182 | Q176A, D178A, H182A |
| hSORT1_ECD_Emut6N | 222 | 203-207 & | E203A, W207A, E218A, H220A, K221A |
| | | 218-221 | |
| hSORT1_ECD_Emut8N | 223 | 238-247, | Y238A, K244A, L247A, Q247A, E248A, |
| | | 247-250 & | F250A, M285A, D288A, D289A |
| | | 285-289 | |
| hSORT1_ECD_Emut11N | 224 | 333-338, | D333A, D337A, T338A, Y362A, T364A, |
| | | 362-365 & | T365A, L386A, E388A, N390A, Q392A |
| | | 386-392 | |
| hSORT1_ECD_Emut14N | 225 | 437-440 & | Q437A, L439A, N440A, D463A, T465A, |
| | | 463-471 | V469A, D471A |
| hSORT1_ECD_Emut16 | 226 | 484-490 | K484A, K483A, H490A |
| hSORT1_ECD_Emut17 | 227 | 505-512 | E505A, S507A, R509A, N512A |
| hSORT1_ECD_Emut18 | 228 | 528-531 | T528A, R531A |
| hSORT1_ECD_Emut19 | 229 | 557-560 | E557A, S558A, F559A, L560A |

Amino Acid Sequence of the Human Sortilin Extra-Cellular Domain Mutants to Determine Anti-SORT1 Antibody Epitope—Mutagenesis Round 2:

hSORT1 ECD Loop domain mutants that showed reduced binding for any of the antibodies (5E20, 8H24 or 11M14) were considered for second round of mutagenesis to further refine the antibody epitope. Thirteen single amino acid mutants and one double mutant were generated during the epitope refinement round 2 (Table 33) Numbering of mutations is based on sortilin ECD without the 33-amino acid signal peptide (SEQ ID NO:215). Mutant binding to the antibodies was measured using ELISA assay and Biacore. Mutants that showed reduced or abolished binding were considered to be constituting respective antibody. These mutants were mapped on hSORT1 3D model.

TABLE 33

| SORT1 Epitope mutagenesis Round 2 | | |
|---|---|---|
| Mutant | SEQ ID NO: | Mutations |
| hSORT1_ECD_Emut20 | 230 | D74A |
| hSORT1_ECD_Emut21 | 231 | R76A |
| hSORT1_ECD_Emut22 | 232 | F97A |
| hSORT1_ECD_Emut23 | 233 | K110 |
| hSORT1_ECD_Emut24 | 234 | L560A |
| hSORT1_ECD_Emut25 | 235 | T561A |
| hSORT1_ECD_Emut26 | 236 | Q563 |
| hSORT1_ECD_Emut27 | 237 | P510A |
| hSORT1_ECD_Emut28 | 238 | P533A |
| hSORT1_ECD_Emut29 | 239 | Y535A |
| hSORT1_ECD_Emut30 | 240 | E557A |
| hSORT1_ECD_Emut31 | 241 | F559A |

TABLE 33-continued

| SORT1 Epitope mutagenesis Round 2 | | |
|---|---|---|
| Mutant | SEQ ID NO: | Mutations |
| hSORT1_ECD_Emut32 | 243 | E558 |
| hSORT1_ECD_Emut33 | 243 | F137 & 141 |

Results:

After two rounds of mutagenesis and structural analysis, epitopes for 8H24 and 11M14 were mapped to the amino acids listed below. Additionally, mutagenesis allowed further refinement of the epitope for 5E20, also listed below. Numbering of residues in epitopes below are based on sortilin ECD without the 33-amino acid signal peptide (SEQ ID NO:215).

8H24 epitope: D74, R76, F97, K110, Y535, L560, and E557

11M14 epitope: K110, Y535, E557, T561, Q563, D74, P510, S558, F559, and L560

5E20 epitope (refined): E557, S558, F559, L560, P510, and Y535

Example 19. Fe LALA and YTE Mutant Generation

The Fe region of human IgG antibodies (hIgGs) interacts with multiple Fcγ receptor (FcγR) and complement proteins and mediates immune effector functions, which are important for many therapeutic applications, e.g. elimination of targeted cells via antibody-dependent cellular-cytotoxicity (ADCC), -phagocytosis (ADCP) or complement-dependent cytotoxicity (CDC).

To develop antibodies with reduced immune effector functions, different Fe mutations were employed. The so-called 'LALA' double mutation (Leu234Ala together with Leu235Aia) was first described as a molecule with diminished effector functions (Lund, J., et al (1992) *Mol. Immunol.,* 29, 53-59; Tamm and Schmidt, 1997, Int Rev Immunol 16(1-2):57-85). Fe variant L234A/L235A (LALA) (numbering according to EU nomenclature) mutant has been shown to have either eliminated or reduced interaction with FcγRs (FcγRIa, FcγRIIa, FcγRIIa and FcγRIIa) and exhibit significantly reduced effector function. Additionally, Fc LALA mutants have also been shown to have diminished interaction with complement proteins resulting in reduced complement-dependent cytotoxicity (CDC).

hu11M14 H1b heavy chain (SEQ ID NO:250), hu8H24 H1 heavy chain (SEQ ID NO:251), and hu5E20 H7 heavy chain (SEQ ID NO:252) incorporate LALA mutations in the human IgG1 heavy chain constant region.

TABLE 34

Antibodies with LALA mutations

| Name | SEQ ID NO of heavy chain: | SEQ ID NO of light chain |
|---|---|---|
| hu11M14 H1bL3b_IgG1 LALA_ | 250 | 245 |
| hu8H24 H1L2_IgG1 LALA_ | 251 | 247 |
| hu5E20 H7L4_IgG1 LALA_ | 252 | 249 |

Additionally, to engineer these antibodies to have improved pharmacokinetics, YTE (M252T/S254T/T256E) (numbering according to EU nomenclature) mutations in the Fe region (W. F. Dall'Acqua et al. 2006 J. Biol. Chem. 281:23514-23) were incorporated. YTE mutant has been shown to have enhanced binding/interaction to the neonatal Fc receptor (FcRn); thereby leading to antibody half-life extension in circulation. YTE mutations were generated simultaneously along with LALA mutations during de novo DNA synthesis at Atum CRO. Modified Fc region was subcloned into an expression vector placing modified Fc region 3' to the variable heavy domain to express full length heavy chain incorporating LALA and YTE mutations.

hu11M14 H1b heavy chain (SEQ ID NO:244), hu8H24 H1 heavy chain (SEQ ID NO:246), and hu5E20 H7 heavy chain (SEQ ID NO:248) incorporate LALA and YTE mutations in the human IgG1 heavy chain constant region.

TABLE 35

Antibodies with LALA/YTE mutations

| Name | SEQ ID NO of heavy chain: | SEQ ID NO of light chain |
|---|---|---|
| hu11M14 H1bL3b_IgG1 LALA_YTE | 244 | 245 |
| hu8H24 H1L2_IgG1 LALA_YTE | 246 | 247 |
| hu5E20 H7L4_IgG1 LALA_YTE | 248 | 249 |

Example 21. Multiple Dose Pharmacokinetic and Pharmacodynamic Studies in Non-Human Primates "Multiple dose pharmacokinetic and pharmacodynamic studies were conducted in non-human Primates. Cynomolgus monkey (*Macaca fascicularis*) [Males: 36-42 months of age, weight 2.6-3.1 kg; Females: 32-47 months of age, weight 2.1-3.2 kg] were administered test compound according to the protocol below. Cynomolgus monkeys were treated with hu8H24 H1L2_IgG1_LALA, hu5E20 H7L4_IgG1_LALA, and hu11M14 H1bL3b_IgG1 LALA at doses of 30 mg/kg and 60 mg/kg.

A. Multiple Dose Studies: Dosing

TABLE 36

Dosing in Multiple dose pharmacokinetic and pharmacodynamic studies

| Group No. | Test Material | Day of Dosing | Dose Level (mg/kg) | Dose Volume (mL/kg)[a] | Dose Concentration (mg/mL) | No. of Females |
|---|---|---|---|---|---|---|
| 1 | hu8H24 H1L2_IgG1_LALA | 1 | 30 | 6 | 5 | 3 |
| | heavy chain SEQ ID NO: 252 | 50 | 60 | 10 | 6 | |
| | light chain SEQ ID NO: 247 | | | | | |
| 2 | hu5E20 H7L4_IgG1_LALA | 1 | 30 | 6 | 5 | 3 |
| | heavy chain SEQ ID NO: 252 | 50 | 60 | 10 | 6 | |
| | light chain SEQ ID NO: 249 | | | | | |
| 3 | hu11M14 H1bL3b_IgG1 LALA | 1 | 30 | 6 | 5 | 3 |
| | heavy chain SEQ ID NO: 250 | 50 | 60 | 10 | 6 | |
| | light chain SEQ ID NO: 245 | | | | | |

[a]Based on the most recent body weight measurement.

Dose Route: Intravenous (slow Bolus) injection

Frequency & Duration: Once on Day 1 and Day 50

Method: The first day of dosing was designated as Day 1. The animals were temporarily restrained for dose administration and were not sedated. The test articles were administered to the appropriate animals via a suitable peripheral vein. The dose volume for each animal was based on the most recent body weight measurement.

B. Multiple Dose Studies: Pharmacokinetic Evaluation

Blood and CSF were drawn from the animals at multiple time-points after dosing (see Tables 37-38) to obtain anti-Sortilin antibody concentrations in plasma and cerebrospinal fluid (CSF), which are measurements of anti-Sortilin antibody pharmacokinetics. Sample collection was as in Table 37 and methods, target volume, and anticoagulant as in Table 38.

TABLE 37

| Bioanalytical sample collection for Multiple Dose Studies, Pharmacokinetics Sample Collection Time Points | | |
|---|---|---|
| Group Nos. | Study Day | Time Points (Relative to Dosing) |
| 1 to 3 | Day 1 | Pre; Day 1, 0.25 and 8 hr post |
| | Day 2 | Day 1, 24 hr post |
| | Day 4 | Day 1, 72 hr post |
| | Day 8 | Day 1, 168 hr post |
| | Day 15 | Day 1, 336 hr post |
| | Day 29 | Day 1, 672 hr post |
| | Day 50 | Pre; Day 50, 0.25 and 8 hr post |
| | Day 51 | Day 50, 24 hr post |
| | Day 53 | Day 50, 72 hr post |
| | Day 57 | Day 50, 168 hr post |
| | Day 64 | Day 50, 336 hr post |
| | Day 78 | Day 50, 672 hr post |

TABLE 38

| Methods, Target Volume, Anticoagulant for Multiple Dose Studies, Pharmacokinetics | |
|---|---|
| Method/Comments: | Venipuncture |
| Target Volume (mL) | 0.5 |
| Anticoagulant: | K3EDTA |

1. Pharmacokinetic Analysis, Multiple Dose Studies

Anti-Sortilin antibody concentrations were assayed using a plate-based electrochemiluminescence using Meso Scale Discovery (MSD). Standard binding 96-well MSD plates were coated with 2ug/mL human Sortilin protein (R&D Biosystems) in PBS overnight at 4° C. plates were blocked in 300 MSD buffer A in PBS for 1 hour at room temperature. Plates were then washed 3 times in TBST. 50 μL of appropriately diluted CSF or Plasma was added to the wells and incubated at room temperature for 2 hours. Plates were then washed as above and 50 μL of 1 ug/mL goat anti-human IgG-ST (Bethyl labs) in 1% MSD buffer A in PBS was added to the wells and plates were incubated for 1 hour at room temperature and then washed as above. 140 uL 2×MSD read buffer T was added to the wells and the electrochemiluminescence signal was read using the Meso Sector S 600. Data was analyzed using the Discovery workbench software (MSD) and antibody levels were quantitated against a standard curve using 4-fold serial dilutions starting at 0.5 ug/mL of each Anti-sortilin antibody used in the study.

2. Results from Pharmacokinetic Analysis, Multiple Dose Studies

Rapid antibody clearance was observed with all three antibodies, hu11M14 H1bL3b_IgG1 LALA, hu8H24 H1L2_IgG1_LALA, and hu5E20 H7L4_IgG1_LALA, with a single dose of 30 mg/kg. 60 mg/kg only slightly increased exposure. (Table 39 and FIG. 14)

TABLE 39

Plasma Anti-Sortilin Antibody Levels in Cynomolgus Monkeys

| Time | 8H24-H1L2 (mg/ml) | | 5E20-H7L4 (mg/ml) | | 11M14-H1bL3b (mg/ml) | |
|---|---|---|---|---|---|---|
| (hr) | 30 mg/kg | 60 mg/kg | 30 mg/kg | 60 mg/kg | 30 mg/kg | 60 mg/kg |
| 0.25 | 619 ± 84 | ND | 1348 ± 156 | ND | 921 ± 69 | ND |
| 8 | 647 ± 42 | ND | 545 ± 72 | ND | 615 ± 110 | ND |
| 24 | 631 ± 120 | ND | 351 ± 23 | ND | 401 ± 107 | ND |
| 72 | 251 ± 39 | ND | 162 ± 21 | ND | 274 ± 59 | ND |
| 168 | 0.01 ± 0.01 | 19 ± 33 | 44 ± 19 | 186 ± 27 | 213 ± 33 | 182 ± 160 |
| 336 | BLQ | BLQ | BLQ | 4.7 ± 1.5 | 1.7 ± 1.5 | 30 ± 47 |
| 672 | BLQ | BLQ | BLQ | BLQ | BLQ | BLQ |

Data represents Mean ± SD,
n = 3/group
ND = No Data
BLQ = Below limit of quantification C. Multiple Dose Studies: Pharmacodynamic Evaluation Progranulin (PGRN) levels, which are a measurement of pharmacodynamics, were also determined from Plasma and cerebrospinal fluid (CSF). Sample collection was as in Table 40 and methods, target volume, and anticoagulant as in Table 41.

1. Pharmacodynamic Sample Collection for Multiple Dose Studies, Plasma

TABLE 40

| Pharmacodynamic Sample collection for Multiple Dose Studies, Plasma Sample Collection Time Points | | |
|---|---|---|
| Group Nos. | Study Day/Week | Time Points (Relative to Dosing |
| All animals | Week −1 | — |
| 1 to 3 | Day 8 | Day 1, 168 hr post |
| | Day 15 | Day 1, 336 hr post |
| | Day 29 | Day 1, 672 hr post |
| | Day 48 | — |
| | Day 57 | Day 50, 168 hr post |
| | Day 64 | Day 50, 336 hr post |
| | Day 78 | Day 50, 672 hr post |

TABLE 41

| Methods, Target Volume, Anticoagulant for Multiple Dose Studies, Pharmacodynamics, Plasma | |
|---|---|
| Method/Comments: | Venipuncture |
| Target Volume (mL): | Week −1 to Day 29: 0.5 mL<br>Day 48 to Day 78: 1.0 mL |
| Anticoagulant: | K3EDTA |

2. Pharmacodynamic Sample collection for Multiple Dose Studies, CSF

Timepoints: All animals: Week −1

Groups 1 to 3: Days 15, 29, 48, 57, 64, and 78

Target volume: Approximately 0.5 mL

Procedure The animals were given Buprenorphine SR (0.20 mg/kg) SQ SID and Meloxicam SR (0.60 mg/kg) SQ SID pre-procedure.

Animals were pre-anesthetized with Ketamine HCl (10-15 mg/kg) IM. Dexdomitor 0.06 mg/kg IM was administered for additional anesthesia.

3. Pharmacodynamic Sample Analysis Multiple Dose Studies

Progranulin levels were measured by plate-based electrochemiluminescence using Meso Scale Discovery (MSD). Standard binding 384-well MSD plates were coated with 1 ug/mL goat anti-huPGRN (R&D Biosystems) in PBS overnight at 4° C. plates were blocked in 300 MSD buffer A in PBS for 1 hour at room temperature. Plates were then washed 3 times in TBST. 20 μL of appropriately diluted CSF or Plasma was added to the wells and incubated at room temperature for 2 hours. Plates were then washed as above and 20 μL of 1 ug/mL biotinylated goat anti-huPGRN (R&D Biosystems) in 1% MSD buffer A in PBS was added to the wells and plates were incubated for 1 hour at room temperature. Plates were washed as above and 05. ug/mL SULFO-TAG-Streptavidin (MSD) in 1% MSD buffer A in PBS was added the wells and plates were incubated for 30 min to 1 hour at room temperature and then washed as above. 40 uL 2χ MSD read buffer T was added to the wells and the electrochemiluminescence signal was read using the Meso Sector S 600. Data was analyzed using the Discovery workbench software (MSD) and were quantitated against a standard curve using 3-fold serial dilutions starting at 200 ng/mL of recombinant huPGRN (R&D Biosystems). Fold PGRN levels over controls were calculated using Microsoft Excel.

4. Results from Pharmacodynamic Analysis Multiple Dose Studies

For all three antibodies, hu11M14 H1bL3b_IgG1 LALA, hu8H24 H1L2_IgG1_LALA, and hu5E20 H7L4_IgG1_LALA, the levels of PGRN in the plasma (Table 42 and FIG. 15) increased in a dose dependent manner and showed a greater than 2 fold increase in PGRN levels with the 60 mg/kg dose at Day 7 post dose. PGRN levels in the CSF (Table 43 and FIG. 16) show a ≥1.5 fold increase on day 7 with the 60 mg/kg dose.

TABLE 42

Change in Plasma Progranulin from Pre-dose Baseline in Cynomolgus Monkeys

| | 8H24-H1L2 | | 5E20-H7L4 | | 11M14-H1bL3b | |
|---|---|---|---|---|---|---|
| | 30 mg/kg | 60 mg/kg | 30 mg/kg | 60 mg/kg | 30 mg/kg | 60 mg/kg |
| Day 7 | 1.26 ± 0.19 | 2.43 ± 0.75 | 1.57 ± 0.14 | 2.43 ± 0.32 | 1.70 ± 0.10 | 2.10 ± 0.46 |
| Day 14 | 0.78 ± 0.06 | 1.37 ± 0.25 | 0.75 ± 0.11 | 2.07 ± 0.32 | 1.26 ± 0.35 | 1.30 ± 0.44 |
| Day 28 | 0.71 ± 0.10 | 1.23 ± 0.25 | 0.60 ± 0.03 | 1.17 ± 0.25 | 0.77 ± 0.10 | 0.87 ± 0.15 |

Data represents Mean ± SD fold change over pre-dose baseline levels of progranulin, n = 3/group

TABLE 43

Change in CSF Progranulin from Pre-dose Baseline in Cynomolgus Monkeys

| | 8H24-H1L2 | | 5E20-H7L4 | | 11M14-H1bL3b | |
|---|---|---|---|---|---|---|
| | 30 mg/kg | 60 mg/kg | 30 mg/kg | 60 mg/kg | 30 mg/kg | 60 mg/kg |
| Day 7 | ND | 1.30 ± 0.40 | ND | 1.10 ± 0.40 | ND | 1.63 ± 0.29 |
| Day 14 | 0.94 ± 0.02 | 1.10 ± 0.26 | 0.91 ± 0.02 | 0.80 ± 0.20 | 1.24 ± 0.22 | 1.23 ± 0.31 |
| Day 28 | 0.81 ± 0.03 | 1.13 ± 0.35 | 0.83 ± 0.07 | 0.80 ± 0.26 | 1.00 ± 0.12 | 1.00 ± 0.26 |

Data represents Mean ± SD fold change over pre-dose baseline levels of progranulin, n = 3/group ND = No Data

Example 22. Repeat Dose Pharmacokinetic and Pharmacodynamic Studies in Non-Human Primates Repeat dose pharmacokinetic and pharmacodynamic studies were conducted in non-human Primates. Cynomolgus monkey (*Macaca fascicularis*) [Males: 36-42 months of age, weight 2.6-3.1 kg; Females: 32-47 months of age, weight 2.1-3.2 kg] were administered test compound according to the protocol below. Cynomolgus monkeys were treated with hu11M14 H1bL3b_IgG1 LALA or hu11M14 H1bL3b_IgG1 LALA_YTE at 4 weekly repeat doses of 60 mg/kg.

A. Repeat Dose Studies: Dosing

TABLE 44

Repeat dose pharmacokinetic and pharmacodynamic studies

| Group No. | Test Material | Dose Level (mg/kg)[a] | Dose Volume (mL/kg) | Dose Concentration (mg/mL) | No. of Animals Males | No. of Animals Females |
|---|---|---|---|---|---|---|
| 1 | hu11M14H1bL3b IgG1 LALA heavy chain SEQ ID NO: 250 light chain SEQ ID NO: 245 | 60 | 10 | 6 | 2 | 2 |
| 2 | hu11M14H1bL3b IgG1 LALA YTE heavy chain SEQ ID NO: 244 light chain SEQ ID NO: 245 | 60 | 10 | 6 | 2 | 2 |

TBD = to be determined.
[a]Based on the most recent body weight measurement.

B. Pharmacokinetic Evaluation, Repeat Dose Studies

Blood and CSF were drawn from the animals at multiple time-points after dosing (see Tables 45-46) to obtain anti-Sortilin antibody concentrations in plasma and cerebrospinal fluid (CSF), which are measurements of anti-Sortilin antibody pharmacokinetics 1. Pharmacokinetic Sample Collection for Repeat Dose Studies, Plasma

TABLE 45

Bioanalytical sample collection for Repeat Dose Studies, Pharmacokinetics Sample Collection Time Points

| Group Nos. | Study Day/Week | Time Points (Relative to Dosing |
|---|---|---|
| All animals | Day 1 | Day 1: pre |
| 1 and 2 | Day 1 | Day 1: 0.25 and 8 hr post |
| | Day 2 | Day 1: 24 hr post |
| | Day 4 | Day 1: 72 hr post |
| | Day 6 | Day 1: 120 hr post |
| | Day 8 | Day 1: 168 hr post (prior to dosing on Day 8) |
| | Day 9 | Day 8: 24 hr post |
| | Day 11 | Day 8: 72 hr post |
| | Day 13 | Day 8: 120 hr post |
| | Day 15 | Day 8: 168 hr post (prior to dosing on Day 15) |
| | Day 16 | Day 15: 24 hr post |
| | Day 18 | Day 15: 72 hr post |
| | Day 20 | Day 15: 120 hr post |
| | Day 22 | Day 15: 168 hr post (prior to dosing on Day 22) |
| | Day 22 | Day 22: 0.25 and 8 hr post |
| | Day 23 | Day 22: 24 hr post |
| | Day 25 | Day 22: 72 hr post |
| | Day 27 | Day 22: 120 hr post |
| | Day 29 | Day 22: 168 hr post |
| | Day 32 | Day 22: 240 hr post |
| | Day 36 | Day 22: 336 hr post |

TABLE 46

Methods, Target Volume, Anticoagulant for Repeat Dose Studies, Pharmacokinetics

| | |
|---|---|
| Method/Comments: | Venipuncture |
| Target Volume (mL)a: | 0.5 |
| Anticoagulant: | K3EDTA |

X = sample to be collected;
— = not applicable;
hr = hour;
min = minute.
aUnless otherwise stated, additional collection of protocol-specified blood samples are permitted (e.g., due to unacceptable sample quality) since the total blood collected is below the Testing Facility IACUC recommended maximum blood volume limit.

2. Pharmacokinetic Analysis, Repeat Dose Studies

Anti-Sortilin antibody (hu11M14 H1bL3b_IgG1 LALA and hu11M14 H1bL3b_IgG1 LALA_YTE)concentrations were assayed using a plate-based electrochemiluminescence using Meso Scale Discovery (MSD). Standard binding 96-well MSD plates were coated with 2ug/mL human Sortilin protein (R&D Biosystems) in PBS overnight at 4° C. plates were blocked in 3% MSD buffer A in PBS for 1 hour at room temperature. Plates were then washed 3 times in TBST. 50 μL of appropriately diluted CSF or Plasma was added to the wells and incubated at room temperature for 2 hours. Plates were then washed as above and 50 μL of 1 ug/mL goat anti-human IgG-ST (Bethyl labs) in 1% MSD buffer A in PBS was added to the wells and plates were incubated for 1 hour at room temperature and then washed as above. 140 uL 2×MSD read buffer T was added to the wells and the electrochemiluminescence signal was read using the Meso Sector S 600. Data was analyzed using the Discovery workbench software (MSD) and antibody levels were quantitated against a standard curve using 4-fold serial dilutions starting at 0.5 ug/mL of each Anti-sortilin antibody used in the study.

Figure 17:
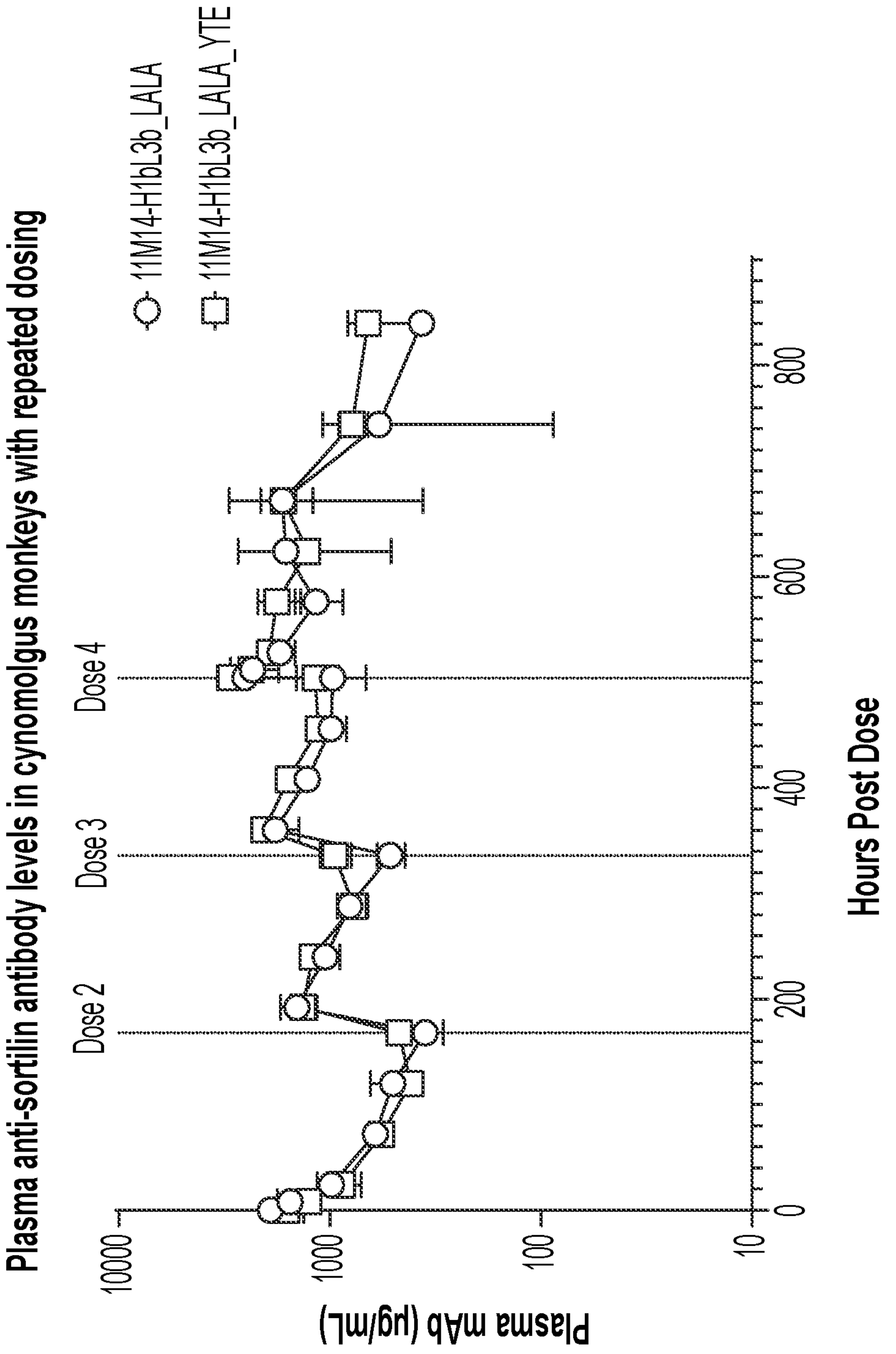
FIG. 17 depicts anti sortilin antibody levels in plasma after 4 weekly repeat 60 mg/kg doses of hu11M14 H1bL3b_IgG1_LALA or hu11M14 H1bL3b_IgG1_LALA_YTE in cynomolgus monkeys (pharmacokinetic studies). Mean±SD Anti-sortilin antibody plasma levels with 4 weekly repeat doses of 60 mg/kg of Ab. N=4.

Table 47 and FIG. 17 show hu11M14 H1bL3b_IgG1 LALA and hu11M14 H1bL3b_IgG1 LALA_YTE levels in plasma with 4 weekly repeat doses of 60 mg/kg of hu11M14 H1bL3b_IgG1 LALA and hu11M14 H1bL3b_IgG1 LALA_YTE.

TABLE 47

Plasma Anti-Sortilin Antibody Levels Following 4 Weekly Doses in Cynomolgus Monkeys

| Time (hr) | 11M14-H1bL3b_LALA Antibody [mg/ml] | 11M14-H1bL3b_LALA_YTE Antibody [mg/ml] |
|---|---|---|
| 0.25 | 1992 ± 145 | 1609 ± 277 |
| 8 | 1552 ± 233 | 1265 ± 113 |
| 24 | 989 ± 164 | 878 ± 167 |
| 72 | 611 ± 76 | 571 ± 44 |
| 120 | 506 ± 139 | 416 ± 34 |
| 168 | 354 ± 63 | 472 ± 42 |
| 192 | 1437 ± 285 | 1350 ± 152 |
| 240 | 1056 ± 152 | 1211 ± 23 |
| 288 | 807 ± 115 | 774 ± 113 |
| 336 | 519 ± 78 | 953 ± 159 |
| 360 | 1819 ± 412 | 2054 ± 146 |
| 408 | 1287 ± 75 | 1578 ± 144 |
| 456 | 990 ± 152 | 1137 ± 148 |
| 504 | 973 ± 296 | 1178 ± 267 |
| 504.25 | 2540 ± 313 | 2974 ± 448 |
| 512 | 2339 ± 187 | 2364 ± 602 |
| 528 | 1730 ± 261 | 1943 ± 113 |
| 576 | 1167 ± 294 | 1794 ± 413 |
| 624 | 1623 ± 1107 | 1277 ± 115 |
| 672 | 1687 ± 1324 | 1666 ± 461 |
| 744 | 589 ± 501 | 789 ± 125 |
| 840 | 370 ± 457 | 663 ± 68 |

Data represents Mean ± SD, n = 4/group
Animals were dosed with 60 mg/kg antibody at 0.25, 168, 336, and 504 hrs Table 48 includes the plasma mean $C_{max}$, mean $AUC^{0-168\ hr}$ after the first and fourth dose and total $AUC^{0-840\ hr}$ for each of the antibodies tested, hu11M14 H1bL3b_IgG1 LALA and hu11M14 H1bL3b_IgG1 LALA_YTE. N=4 for each Ab.

TABLE 48

| | hu11M14 H1bL3b_IgG1 LALA | hu11M14 H1bL3b_IgG1 LALA_YTE. |
|---|---|---|
| Day 1: $AUC^{0-168}$ ug * h/mL | 119,618 | 108,027 |
| Day 22: $AUC^{0-168}$ ug * h/mL | 267,353 | 289,150 |
| Total $AUC^{0-840hr}$ | 877,775 | 972,313 |
| Day 1: $C_{max}$ ug/mL | 1,922 | 1,609 |
| Day 22: $C_{max}$ ug/mL | 2,540 | 2,974 |

Figure 18:
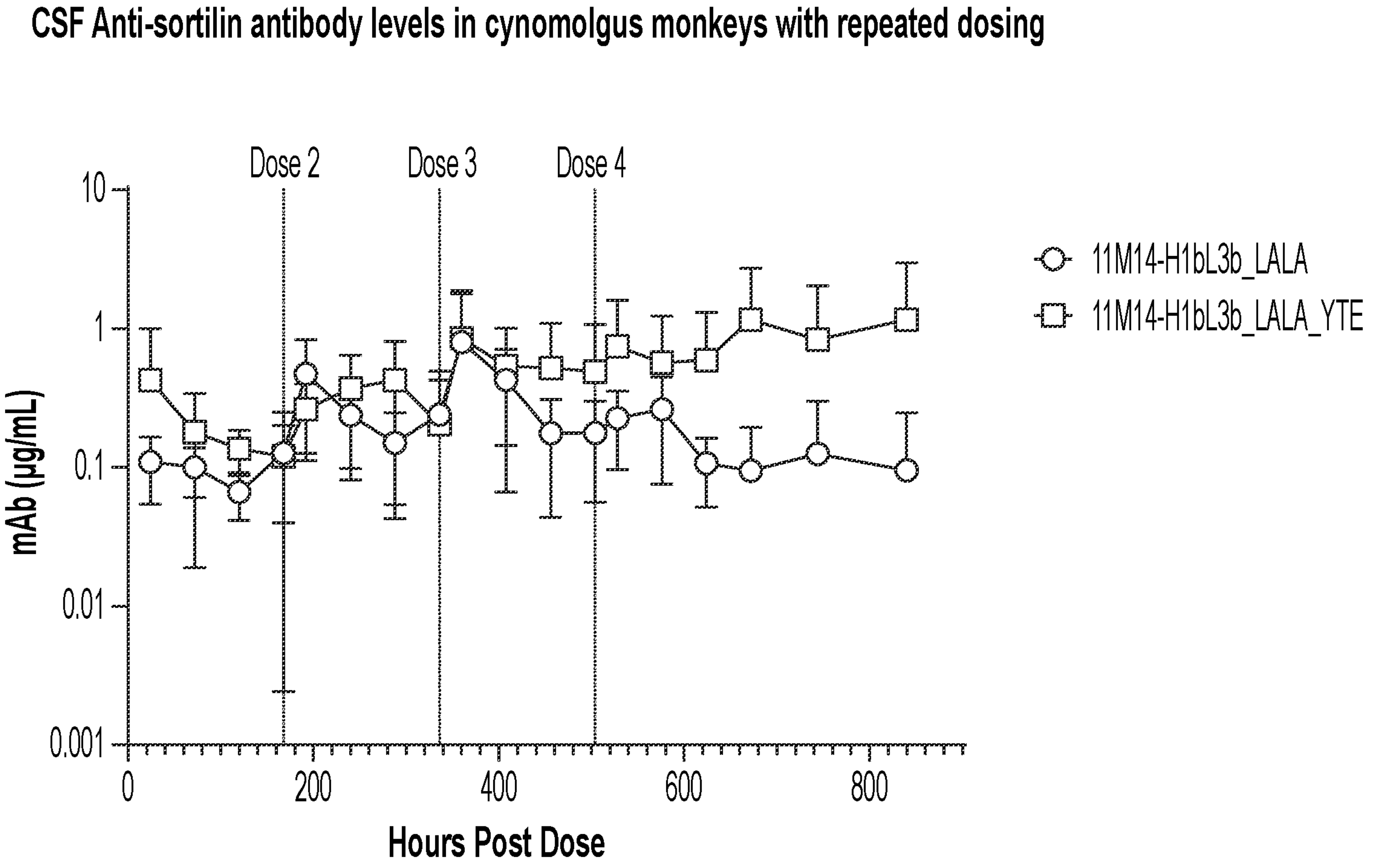
FIG. 18 depicts anti sortilin antibody levels in CSF after 4 weekly repeat 60 mg/kg doses of hu11M14 H1bL3b_IgG1_LALA or hu11M14 H1bL3b_IgG1_LALA_YTE in cynomolgus monkeys (pharmacokinetic studies). Mean±SD Anti-Sortilin Ab CSF levels with 4 weekly repeat doses of 60 mg/kg of Ab. N=4 for hu11M14 H1bL3b_IgG1_LALA and N=3 for hu11M14 H1bL3b_IgG1_LALA_YTE.
Figure 19:
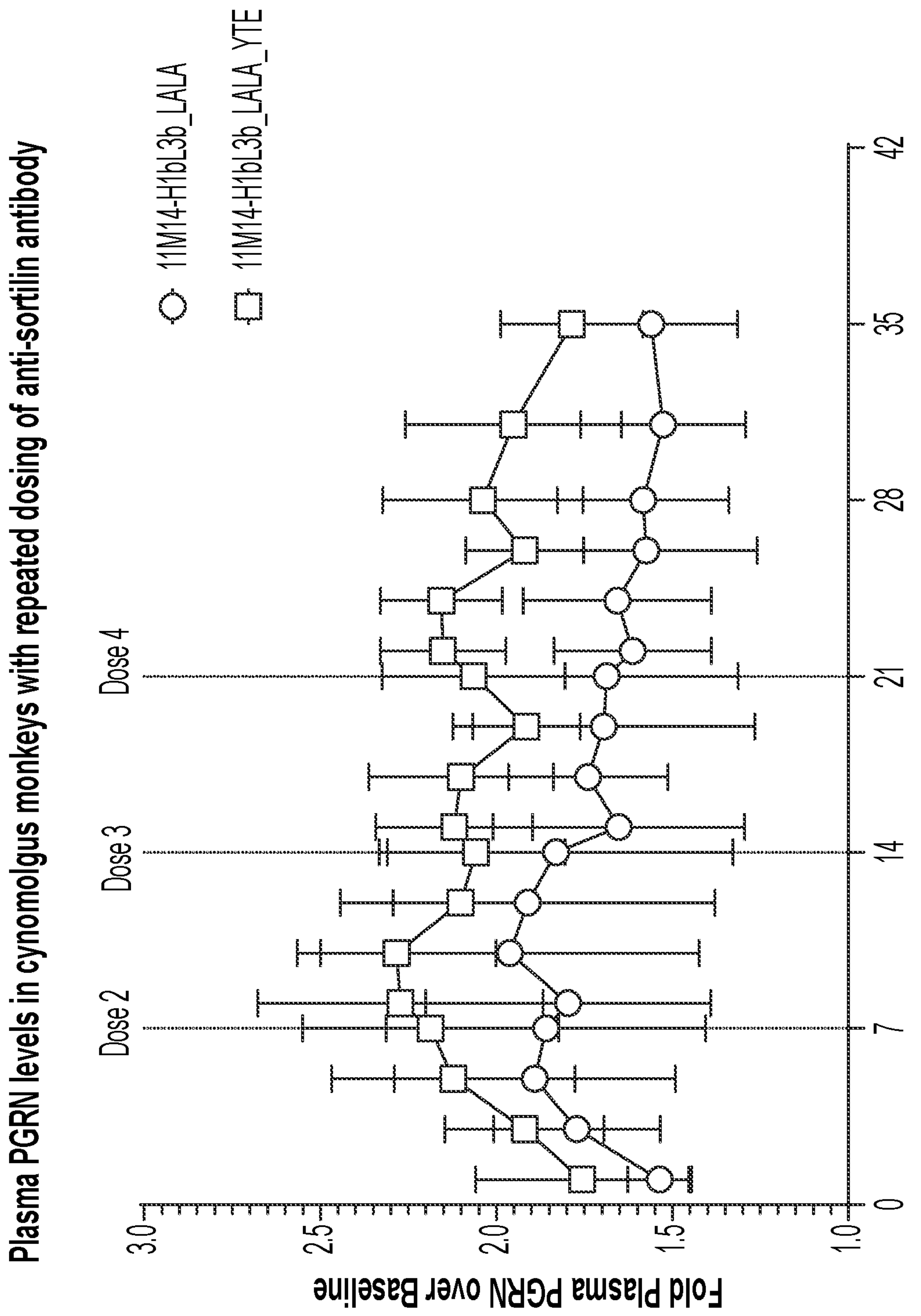
FIG. 19 depicts plasma progranulin levels in cynomolgus monkeys after after 4 weekly repeat 60 mg/kg doses of hu11M14 H1bL3b_IgG1_LALA or hu11M14 H1bL3b_IgG1_LALA_YTE (pharmacodynamic studies). Mean±SD Fold PGRN levels in plasma in cynomolgus monkeys. N=4 animals per Ab group.
Figure 20:
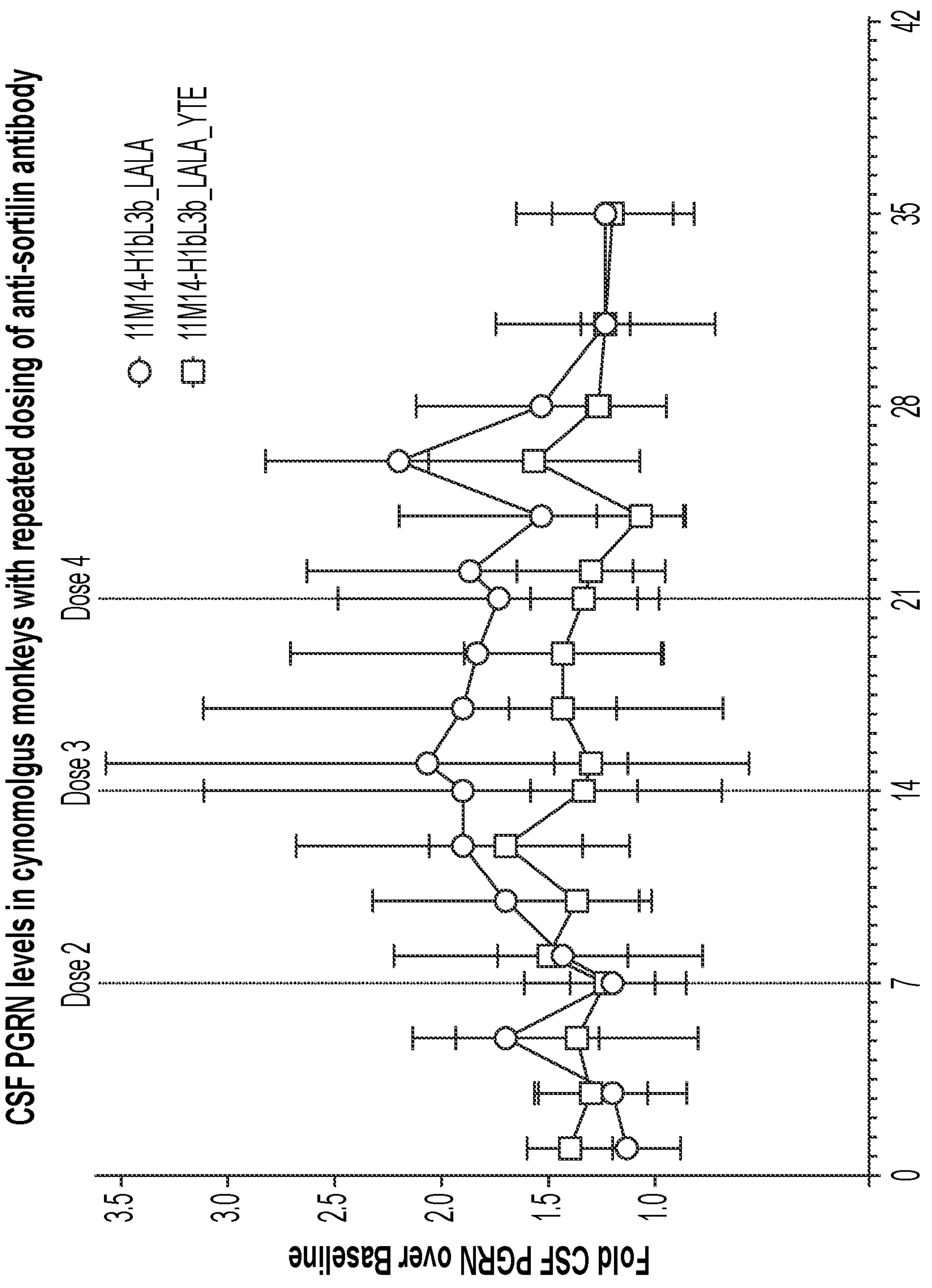
FIG. 20 depicts CSF progranulin levels in cynomolgus monkeys after 4 weekly repeat 60 mg/kg doses of hu11M14 H1bL3b_IgG1_LALA or hu11M14 H1bL3b_IgG1_LALA_YTE (pharmacodynamic studies). Mean±SD Fold PGRN levels in CSF in cynomolgus monkeys. N=4 animals in hu11M14 H1bL3b_IgG1_LALA group and N=3 in hu11M14 H1bL3b_IgG1_LALA_YTE group.

Table 49 and FIG. 18 show hu11M14 H1bL3b_IgG1 LALA and hu11M14 H1bL3b_IgG1 LALA_YTE CSF levels with 4 weekly repeat doses of 60 mg/kg of hu11M14 H1bL3b_IgG1 LALA or hu11M14 H1bL3b_IgG1 LALA_YTE.

TABLE 49

CSF Anti-Sortilin Antibody Levels Following 4 Weekly Doses in Cynomolgus Monkeys

| Time (hr) | 11M14-H1bL3b_LALA Antibody [mg/ml] | 11M14-H1bL3b_LALA_YTE Antibody [mg/ml] |
|---|---|---|
| 24 | 0.11 ± 0.06 | 0.43 ± 0.58 |
| 72 | 0.10 ± 0.04 | 0.18 ± 0.16 |
| 120 | 0.07 ± 0.03 | 0.14 ± 0.05 |
| 168 | 0.13 ± 0.12 | 0.12 ± 0.08 |
| 192 | 0.47 ± 0.36 | 0.26 ± 0.14 |
| 240 | 0.24 ± 0.16 | 0.37 ± 0.27 |
| 288 | 0.15 ± 0.10 | 0.43 ± 0.38 |
| 336 | 0.24 ± 0.25 | 0.20 ± 0.22 |
| 360 | 0.80 ± 0.99 | 0.85 ± 1.03 |
| 408 | 0.43 ± 0.28 | 0.54 ± 0.47 |
| 456 | 0.18 ± 0.13 | 0.52 ± 0.57 |
| 504 | 0.18 ± 0.12 | 0.49 ± 0.58 |
| 528 | 0.23 ± 0.13 | 0.75 ± 0.84 |
| 576 | 0.26 ± 0.19 | 0.57 ± 0.66 |
| 624 | 0.11 ± 0.06 | 0.59 ± 0.72 |
| 672 | 0.10 ± 0.10 | 1.16 ± 1.56 |
| 744 | 0.13 ± 0.17 | 0.83 ± 1.20 |
| 840 | 0.10 ± 0.15 | 1.16 ± 1.81 |

Data represents Mean ± SD, n = 3-4/group
Animals were dosed with 60 mg/kg antibody at 0.25, 168, 336, and 504 hrs 3. Results from Pharmacokinetic Analysis, Repeat Dose Studies Results: Repeat dose with either hu11M14 H1bL3b_IgG1 LALA or hu11M14 H1bL3b_IgG1 LALA_YTE showed increased antibody exposure in the plasma and CSF. hu11M14 H1bL3b_IgG1 LALA_YTE variant showed greater accumulation of antibody over time and a slightly more sustained response.

C. Repeat Dose Studies: Pharmacodynamic Evaluation

Progranulin (PGRN) levels, which is a measurement of pharmacodynamics, were also Determined from Plasma and CSF. Samples were collected as in Table 50.

1. Pharmacodynamic Sample Collection for Repeat Dose Studies, Plasma and CSF

TABLE 50

Bioanalytical sample collection for Repeat Dose Studies, Pharmacodynamics, Plasma & CSF Sample Collection Time Points

| Group Nos. | Study Day/Week | Time Points (Relative to Dosing |
|---|---|---|
| All animals | Day −4 | — |
| All animals | Day −2 | — |
| 1 and 2 | Day 2 | Day 1: 24 hr post |
| | Day 4 | Day 1: 72 hr post |
| | Day 6 | Day 1: 120 hr post |
| | Day 8 | Day 1: 168 hr post (prior to dosing on Day 8) |
| | Day 9 | Day 8: 24 hr post |
| | Day 11 | Day 8: 72 hr post |
| | Day 13 | Day 8: 120 hr post |
| | Day 15 | Day 8: 168 hr post (prior to dosing on Day 15) |
| | Day 16 | Day 15: 24 hr post |
| | Day 18 | Day 15: 72 hr post |
| | Day 20 | Day 15: 120 hr post |
| | Day 22 | Day 15: 168 hr post (prior to dosing on Day 22) |
| | Day 23 | Day 22: 24 hr post |
| | Day 25 | Day 22: 72 hr post |
| | Day 27 | Day 22: 120 hr post |
| | Day 29 | Day 22: 168 hr post |
| | Day 32 | Day 22: 240 hr post |
| | Day 36 | Day 22: 336 hr post |

2. Pharmacodynamic Sample Analysis Repeat Dose Studies, CSF & Plasma PGRN Levels Progranulin levels were measured by plate-based electro-chemiluminescence using Meso Scale Discovery (MSD). Standard binding 384-well MSD plates were coated with 1 ug/mL goat anti-huPGRN (R&D Biosystems) in PBS overnight at 4° C. plates were blocked in 3% MSD buffer A in PBS for 1 hour at room temperature. Plates were then washed 3 times in TBST. 20 μL of appropriately diluted CSF or Plasma was added to the wells and incubated at room temperature for 2 hours. Plates were then washed as above and 20 μL of 1 ug/mL biotinylated goat anti-huPGRN (R&D Biosystems) in 1% MSD buffer A in PBS was added to the wells and plates were incubated for 1 hour at room temperature. Plates were washed as above and 05. ug/mL SULFO-TAG-Streptavidin (MSD) in 1% MSD buffer A in PBS was added the wells and plates were incubated for 30 min to 1 hour at room temperature and then washed as above. 40 uL 2χ MSD read buffer T was added to the wells and the electrochemiluminescence signal was read using the Meso Sector S 600. Data was analyzed using the Discovery workbench software (MSD) and were quantitated against a standard curve using 3-fold serial dilutions starting at 200 ng/mL of recombinant huPGRN (R&D Biosystems). Fold PGRN levels over controls were calculated using Microsoft Excel.

3. Results from Pharmacodynamics Analysis for Plasma and CSF Progranulin, Repeat Dose Studies:

Plasma PGRN levels increase over 2-fold that of baseline in plasma (Table 51 and FIG. 19) in animals treated with either hu11M14 H1bL3b_IgG1 LALA or hu11M14 H1bL3b_IgG1 LALA_YTE. Both Antibody groups (hu11M14 H1bL3b_IgG1 LALA or hu11M14 H1bL3b_IgG1 LALA_YTE) show a sustained PGRN levels greater than baseline two weeks after final dose. Overall Plasma PGRN levels were higher with hu11M14 H1bL3b_IgG1 LALA_YTE. As seen in Table 52 and FIG. 20, CSF PGRN levels show a >1.5 fold increase which do not drop to baseline levels 2 weeks after the final dose.

TABLE 51

Changes in Plasma Progranulin Levels Following 4 Weekly Doses of Anti-Sortilin Antibody in Cynomolgus Monkeys

| Time (Days) | 11M14-H1bL3b_LALA Fold Change Over Pre-Dose | 11M14-H1bL3b_LALA_YTE Fold Change Over Pre-Dose |
|---|---|---|
| 1 | 1.54 ± 0.09 | 1.76 ± 0.30 |
| 3 | 1.77 ± 0.24 | 1.92 ± 0.23 |
| 5 | 1.89 ± 0.40 | 2.12 ± 0.35 |
| 7 | 1.86 ± 0.45 | 2.19 ± 0.36 |
| 8 | 1.80 ± 0.41 | 2.27 ± 0.40 |
| 10 | 1.96 ± 0.54 | 2.28 ± 0.28 |
| 12 | 1.91 ± 0.53 | 2.10 ± 0.19 |
| 14 | 1.83 ± 0.50 | 2.06 ± 0.25 |
| 15 | 1.65 ± 0.36 | 2.12 ± 0.22 |
| 17 | 1.74 ± 0.23 | 2.10 ± 0.26 |
| 19 | 1.70 ± 0.43 | 1.92 ± 0.15 |
| 21 | 1.69 ± 0.37 | 2.07 ± 0.26 |
| 22 | 1.61 ± 0.22 | 2.15 ± 0.18 |
| 24 | 1.66 ± 0.27 | 2.16 ± 0.17 |
| 26 | 1.57 ± 0.31 | 1.92 ± 0.17 |
| 28 | 1.58 ± 0.24 | 2.04 ± 0.28 |
| 31 | 1.53 ± 0.23 | 1.95 ± 0.31 |
| 35 | 1.56 ± 0.24 | 1.79 ± 0.20 |

Data represents Mean ± SD, n = 4/group

Animals were dosed with 60 mg/kg antibody on days 0, 7, 14, and 21

TABLE 52

Changes in CSF Progranulin Levels Following 4 Weekly Doses of Anti-Sortilin Antibody in Cynomolgus Monkeys

| Time (Days) | 11M14-H1bL3b_LALA Fold Change Over Pre-Dose | 11M14-H1bL3b_LALA_YTE Fold Change Over Pre-Dose |
|---|---|---|
| 1 | 1.13 ± 0.25 | 1.40 ± 0.20 |
| 3 | 1.20 ± 0.35 | 1.30 ± 0.26 |
| 5 | 1.70 ± 0.44 | 1.37 0.57 |
| 7 | 1.20 ± 0.20 | 1.23 ± 0.38 |
| 8 | 1.43 ± 0.31 | 1.50 ± 0.72 |
| 10 | 1.70 ± 0.62 | 1.37 ± 0.35 |
| 12 | 1.90 ± 0.78 | 1.70 ± 0.36 |
| 14 | 1.90 ± 1.21 | 1.33 ± 0.25 |
| 15 | 2.07 ± 1.50 | 1.30 ± 0.17 |
| 17 | 1.90 ± 1.22 | 1.43 ± 0.25 |
| 19 | 1.83 ± 0.87 | 1.43 ± 0.46 |
| 21 | 1.73 ± 0.75 | 1.33 ± 0.25 |
| 22 | 1.87 ± 0.76 | 1.30 ± 0.35 |
| 24 | 1.53 ± 0.67 | 1.07 ± 0.21 |
| 26 | 2.20 ± 0.62 | 1.57 ± 0.49 |
| 28 | 1.53 ± 0.59 | 1.27 ± 0.06 |
| 31 | 1.23 ± 0.51 | 1.23 ± 0.12 |
| 35 | 1.23 ± 0.42 | 1.20 ± 0.28 |

Data represents Mean ± SD, n = 3/group

Animals were dosed with 60 mg/kg antibody on days 0, 7, 14, and 21

4. Pharmacodynamic Sample Analysis Repeat Dose Studies, Sortilin Levels in White Blood Cells Peripheral Blood Mononuclear cells (PBMCs) isolated from whole blood were lysed in cell lysis buffer. Sortilin levels were measured by plate-based electrochemiluminescence using Meso Scale Discovery (MSD). Standard binding 384-well MSD plates were coated with 1 ug/mL goat anti-huSortilin (R&D Biosystems) in PBS overnight at 4° C. plates were blocked in 3% MSD buffer A in PBS for 1 hour at room temperature. Plates were then washed 3 times in TBST. 20 uL diluted lysates were added to the wells and incubated at room temperature for 2 hours. Plates were then washed as above and 20 μL of 1 ug/mL biotinylated goat anti-huSortilin (R&D Biosystems) in 1% MSD buffer A in PBS was added to the wells and plates were incubated for 1 hour at room temperature. Plates were washed as above and 0.5ug/mL SULFO-TAG-Streptavidin (MSD) in 1% MSD buffer A in PBS was added the wells and plates were incubated for 30 min to 1 hour at room temperature and then washed as above. 40 uL 2×MSD read buffer T was added to the wells and the electrochemiluminescence signal was read using the Meso Sector S 600. Data was analyzed using the Discovery workbench software (MSD) and were quantitated against a standard curve using 3-fold serial dilutions starting at 100 ng/mL of recombinant huSortilin.

5. Results from Pharmacodynamics Analysis for Sortilin Levels in White Blood Cells As shown in Table 53 and FIG. 21, sortilin protein levels in PBMCs decrease after treatment with both antibodies, hu11M14 H1bL3b_IgG1 LALA and hu11M14 H1bL3b_IgG1 LALA_YTE.

TABLE 53

Changes in Sortilin Levels in PBMCs from Cynomolgus Monkeys Treated with Anti-Sortilin Antibodies

| Time (Days) | 11M14-H1bL3b_LALA % Change from Pre-Dose | 11M14-H1bL3b_LALA_YTE % Change from Pre-Dose |
|---|---|---|
| 1 | 82 ± 13 | 117 ± 51 |
| 7 | 25 ± 9 | 51 ± 28 |
| 8 | 21 ± 6 | 36 ± 20 |
| 14 | 22 ± 11 | 32 ± 8 |

TABLE 53-continued

| Changes in Sortilin Levels in PBMCs from Cynomolgus Monkeys Treated with Anti-Sortilin Antibodies | | |
|---|---|---|
| Time (Days) | 11M14-H1bL3b_LALA % Change from Pre-Dose | 11M14-H1bL3b_LALA_YTE % Change from Pre-Dose |
| 15 | 22 ± 6 | 30 ± 5 |
| 21 | 23 ± 12 | 41 ± 20 |
| 22 | 26 ± 8 | 36 ± 22 |
| 28 | 13 ± 6 | 23 ± 5 |
| 31 | 28 ± 4 | 33 ± 20 |
| 35 | 22 ± 10 | 25 ± 8 |

Data represents Mean ± SD, n = 4/group
Animals were dosed with 60 mg/kg antibody on days 0, 7, 14, and 21
Sortilin levels were normalized to total protein and expressed as a percent of pre-dose baseline values 6. Overall Results from Repeat Dose Studies:

Taken together, in vivo non-human primate results show a sustained response. Weekly 60 mg·kg doses increase antibody exposure and lead to increased PGRN levels over baseline. A roughly 75% sustained decrease in Sortilin levels is observed in PMBCs beginning after the first dose. hu11M14 H1bL3b_IgG1 LALA_YTE variant shows slightly better PK and Plasma PD profile over hu11M14 H1bL3b_IgG1 LALA, potentially due to Ab half-life extension properties of hu11M14 H1bL3b_IgG1 LALA_YTE variant.

Listing of Sequences

SEQ ID NO:1> Amino acid sequence of human sortilin extracellular domain

MERPWGAADGLSRWPHGLGLLLLLQLLPP-
STLSQDRLDAPPPPAAPLPRWSGPIGVSWG
LRAAAAGGAFPRGGRWRR-
SAPGEDEECGRVRDFVAKLANNTHQHVFD-
DLRGSVSLSW VGDSTGVILVLTTFHVPLVI-
MTFGQSKLYRSEDYGKNFKDITDLINNTFIRTEF-
GMAIGPE NSGKVVLTAEVSGGSRGGRIFRSSD-
FAKNFVQTDLPFHPLTQMMYSPQNSDYLLAL-
STE NGLWVSKNFGGKWE-
EIHKAVCLAKWGSDNTIFFTTYANGSCKADL-
GALELWRTSDLG KSFKTIGVKIYSFGLGGRFL-
FASVMADKDTTRRIHVSTDQGDTWS-
MAQLPSVGQEQFYS
ILAANDDMVFMHVDEPGDTGFGTIFTSDDR-
GIVYSKSLDRHLYTTTGGETDFTNVTSLR
GVYITSVLSEDNSIQTMITFDQGGRWTTH-
LRKPENSECDATAKNKNECSLHIHASYSISQK
LNVPMAPLSEPNAVGIVIAHGSVG-
DAISVMVPDVYISDDGGYSWTKMLEGPHYY-
TILDS GGIIVAIEHSSRPINVIKFSTDE-
GQCWQTYTFTRDPIYFTGLASEPGARSMNISIW-
GFTESFL TSQWVSYTIDFKDILERNCEEKDYTIW-
LAHSTDPEDYEDGCILGYKEQFLRLRKSSVCQN
GRDYVVTKQPSICLCSLEDFLCDFGYYRPEND-
SKCVEQPELKGHDLEFCLYGREEHLTT
NGYRKIPGDKCQGGVNPVREVKDLKKKCTSN-
FLSPEKQNSKSNS

SEQ ID NO:2> Murine 5E20VH nucleotide sequence (mIgG1):

ATGAACTTCGGGCTCAGCTTGAT-
TTTCCTTGCCCTTATTT-
TAAAAGGTGTCCAGTGTG
AGGTGCAGCTGGTGGAGTCTGGGGGAGACT-
TAGTGAAGCCTGGAGGGTCCCTGAAA
CTCTCCTGTGCAGCCCCTGGATT-
CACTTTCAGTACTTATGG-
CATGTCTTGGGTTCGCC AGACTCCA-
GACAAGAGGCTGGAGTGGGTCGCAATCATTA-
GTAGTGGTGGTAGTTAC ACCTACTATTCA-
GACACTGTGAAGGGGCGATTCAC-
CATCTCCAGAGACAATGCCAA
GAACACCCTGTACCTGCAAATGAGCAGTCT-
GAAGTCTGAGGACACAGCCATGTATT ATTGTT-
CAAGGAGTAGTAGCCACTGGTATTTC-
GATGTCTGGGGCACAGGGACCACGG
TCACCGTCTCCTCA

SEQ ID NO:3> amino acid sequence for signal peptide for murine 5E20VH

MNFGLSLIFLALILKGVQC

SEQ ID NO: 4> Murine >5E20VH amino acid sequence

EVQLVESGGDLVKPGGSLKLSCAAPGFTF-
STYGMSWVRQTPDKRLEWVAIISSGGSYTY
YSDTVKGRFTISRDNAKNTLYLQMSSLKSED-
TAMYYCSRSSSHWYFDVWGTGTTVTVS S

SEQ ID NO:5> Murine 5E20_Kabat Chothia Composite CDR-H1 amino acid sequence:

GFTFSTYGMS

SEQ ID NO:6> Murine 5E20_Kabat Chothia Composite CDR-H2 amino acid sequence:

IISSGGSYTYYSDTVKG

SEQ ID NO:7> Murine 5E20_Kabat Chothia Composite CDR-H3 amino acid sequence:

SSSHWYFDV

SEQ ID NO:8> Murine 5E20VL nucleotide sequence (kappa):

ATGGTCCTTGCTCAGTTTCTTGCAT-
TCTTGTTGCTTTGGTTTCCAGGTGCAAGATGTG
ACATCCTGATGACCCAATCTCCATCCTC-
CATGTCTGTATCTCTGGGAGACACAGTCA
GCATCACTTGCCATGCAAGTCAGGGCATT-
AGCAGTAATATAGGGTGGTTGCAGCAG
AAACCAGGGAAATCATTTAAGGGCCTGATC-
TATCATGGAACCAACTTGAAAGATGG AGTTC-
CATCAAGGTTCAGTGGCAGTGGATCTG-
GAGCAGATTTTTCTCTCACCATCAG
CAGCCTGGAATCTGAAGATTTTGCAGACTAT-
TTCTGTGTTCAGTATGCTCAGTTTCCG
TACACGTTCGGAGGGGGGACCAAGCTG-
GAAAAAAGA

SEQ ID NO:9> amino acid sequence for signal peptide for murine 5E20VL

MVLAQFLAFLLLWFPGARC

SEQ ID NO:10> Murine 5E20VL Vk amino acid sequence

DILMTQSPSSMSVSLGDTVSITCHASQ-
GISSNIGWLQQKPGKSFKGLIYHGTNLKDGVPS
RFSGSGSGADFSLTISSLESED-
FADYFCVQYAQFPYTFGGGTKLEKR

SEQ ID NO: 11> Murine 5E20_Kabat Chothia Composite CDR-L1 amino acid sequence

HASQGISSNIG

SEQ ID NO: 12> Murine 5E20_Kabat Chothia Composite CDR-L2 amino acid sequence

HGTNLKD

SEQ ID NO:13> Murine 5E20_Kabat Chothia Composite CDR-L3 amino acid sequence

VQYAQFPYT

SEQ ID NO:14> Kabat CDR-H1 of mouse 5E20 antibody

TYGMS

SEQ ID NO:15> Chothia CDR-H1 of mouse 5E20 antibody

GFTSTY

SEQ ID NO:16> Chothia CDR-H2 of mouse 5E20 antibody
SSGGSY
SEQ ID NO:17> AbM CDR-H2 of mouse 5E20 antibody
IISSGGSYTY
SEQ ID NO:18> Contact CDR-H1 of mouse 5E20 antibody
STYGMS
SEQ ID NO:19> Contact CDR-H2 of mouse 5E20 antibody
WVAIISSGGSYTY
SEQ ID NO:20> Contact CDR-H3 of mouse 5E20 antibody
SRSSSHWYFD
SEQ ID NO:21> Contact CDR-L1 of mouse 5E20 antibody
SSNIGWL
SEQ ID NO:22> Contact CDR-L2 of mouse 5E20 antibody
GLIYHGTNLK
SEQ ID NO:23> Contact CDR-L3 of mouse 5E20 antibody
VQYAQFPY
SEQ ID NO:24> amino acid sequence of a chimeric 5E20 heavy chain
EVQLVESGGDLVKPGGSLKLSCAAPGFTF-
STYGMSWVRQTPDKRLEWVAIISSGG-
SYTYYSDTV KGRFTISRDNAKNTLY-
LQMSSLKSEDTAMYYCSRSSSHWYFDVWGTG-
TTVTVSSASTKGPSVFP LAPSSKSTSGGTAAL-
GCLVKDYFPEPVTVSWNSGALTSGVHTFPAV-
LQSSGLYSLSSVVTVPSS
SIGTQTYICNVNHKPSNTKVDKKVEPKSCDKTH-
TCPPCPAPEAAGGPSVFLFPPKPKDTIMISR TPE-
VTCVVVDVSHEDPE-
VKFNWYVDGVEVHNAKTKPREEQYNSTYRV-
VSVLIVLHQDWLNGKEY KCKVSNKALPA-
PIEKTISKAKGQPREPQVYTLPPSREEMT-
KNQVSLTCLVKGFYPSDIAVEWES NGQPEN-
NYKTTPPVLDSDGSFFLYSKLTVDKSRWQQGN-
VFSCSVMHEALHNHYTQKSLSLSPGK
SEQ ID NO:25> amino acid sequence of a chimeric 5E20 light chain
DILMTQSPSSMSVSLGDTVSITCHASQ-
GISSNIGWLQQKPGKSFKGLIYHGTNLKDGVPS
RFSGSGSGADFSLTISSLESED-
FADYFCVQYAQFPY-
TFGGGTKLEIKRTVAAPSVFIFPPSD EQLKSG-
TASVVCLLNNFYPREAKVQWKVDNALQSGNS-
QESVTEQDSKDSTYSLSSTLTL SKADYEKHKVY-
ACEVTHQGLSSPVTKSFNRGEC
SEQ ID NO: 26> Murine 8H24VH nucleotide sequence (IgG2c):
ATGGGATTCAGCAG-
GATCTTTCTCTTCCTCCTGTCAGTAACTA-
CAGGTGTCCACTCCC AGGCTTATCTA-
CAGCAGTCTGGGACTGAGCTGGTGAGGCCTG-
GGGCCTCAGTGAAG
ATGTCCTGCAAGGCTTCTGGCTACACATT-
TACCAGTTACAGTATGCACTGGGTAAAG
CAGACACCTAGACAGGGCCTGGAATGGATTG-
GAGCTATTTATCCAGGAAATGATGC TACTTCC-
TACAATCAGAAGTTCAAGGGCAAGGC-
CACACTGACTGTAGACAAATCCTC
CAGCACAGCCTA-
CATGCAGCTCAGCAGCCTGACATCTGAA-
GACTCTGCGGTCTATTT
CTGTGCAAGAGAGGGCTAC-
TACGGTAGTAGCTTCGAAGCCTGGTTTGCTTC-
TTGGGG CCAAGGGACTCTGGT-
CACTGTCTCTGCA
SEQ ID NO:27> Murine > amino acid sequence for murine 8H24VH signal peptide
MGFSRIFLFLLSVTTGVHS
SEQ ID NO:28> Murine 8H24Vh amino acid sequence
QAYLQQSGTELVRPGASVKMSCKASGYTFTSYS-
MHWVKQTPRQGLEWIGAIYPGNDAT SYN-
QKFKGKATLTVDKSSSTAYMQLSSLTSED-
SAVYFCAREGYYGSSFEAWFASWGQG
TLVTVSA
SEQ ID NO:29> Murine 8H24_Kabat Chothia Composite CDR-H1 amino acid sequence:
GYTFTSYSMH
SEQ ID NO:30> Murine 8H24_Kabat Chothia Composite CDR-H2 amino acid sequence:
GAIYPGNDATSYNQKFKG
SEQ ID NO:31> Murine 8H24 Kabat Chothia Composite CDR-H3 amino acid sequence:
EGYYGSSFEAWFAS
SEQ ID NO:32> Murine 8H24VL nucleotide sequence (kappa):
ATGAAGTTGCCTGTTAGGCTGTTGGTGCT-
GATGTTCTGGATTCCTGGTTCCAGCAGTG
ATGTTTTGATGACCCAAACTC-
CACTTTCCCTGCCTGTCAGTCTTGGAGAT-
CAAGCCTC CATCTCTTGCAGATCTAGTCAGAG-
CATTGTACATAGTAATGGAAACACCTATTTAGA
ATGGTACCTGCAGAAACCAGGCCAGTCTC-
CAAAGCTCCTGATCTACAAAGTTTCCAA
CCGATTTTCTGGGGTCCCA-
GACAGGTTCAGTGGCAGTGGATCAGGGACA-
GATTTCAC ACTCAAGATCAGCAGAGTG-
GAGGCTGAGGATCTGGGAGTTTATTACTGCTTT-
CAAGG
TTCACATGTTCTTCCGACGTTCGGTG-
GAGGCACCAAGCTGGAAATCAAA
SEQ ID NO:33> amino acid sequence for murine 8H24VL signal peptide
MKLPVRLLVLMFWIPGSSS
SEQ ID NO:34> Murine 8H24Vk amino acid sequence
DVLMTQTPLSLPVSLGDQASISCRSSQSIVHSNGN-
TYLEWYLQKPGQSPKLLIYKVSNRF
SGVPDRFSGSGSGTDFTLKISRVEAE-
DLGVYYCFQGSHVLPTFGGGTKLEIK
SEQ ID NO:35> Murine 8H24 Kabat Chothia Composite CDR-L1 amino acid sequence:
RSSQSIVHSNGNTYLE
SEQ ID NO:36> Murine 8H24 Kabat Chothia Composite CDR-L2 amino acid sequence:
KVSNRFS
SEQ ID NO:37> Murine 8H24_Kabat Chothia Composite CDR-L3 amino acid sequence:
FQGSHVLPT
SEQ ID NO:38> Kabat CDR-H1 of mouse 8H24 antibody
SYSMH
SEQ ID NO:39> Chothia CDR-H1 of mouse 8H24 antibody
GYTFTSY
SEQ ID NO:40> Chothia CDR-H2 of mouse 8H24 antibody
YPGNDA
SEQ ID NO:41> AbM CDR-H2 of mouse 8H24 antibody
AIYPGNDATS SEQ ID NO:42> Contact CDR-H1 of mouse 8H24 antibody

TSYSMH

SEQ ID NO:43> Contact CDR-H2 of mouse 8H24 antibody

WIGAIYPGNDATS

SEQ ID NO:44> Contact CDR-H3 of mouse 8H24 antibody

AREGYYGSSFEAWFA

SEQ ID NO:45> Contact CDR-L1 of mouse 8H24 antibody

NTYLEWY

SEQ ID NO:46> Contact CDR-L2 of mouse 8H24 antibody

LLIYKVSNRF

SEQ ID NO:47> Contact CDR-L3 of mouse 8H24 antibody

FQGSHVLP

SEQ ID NO:48> amino acid sequence of a chimeric 8H24 heavy chain

QAYLQQSGTELVRPGASVKMSCKASGYTFTSYS-MHWVKQTPRQGLEWIGATYPGNDAT SYN-QKFKGKATLTVDKSSSTAYMQLSSLTSED-SAVYFCAREGYYGSSFEAWFASWGQG TLVTVSAASTKGPSVFPLAPSSKSTSGGTAAL-GCLVKDYFPEPVTVSWNSGALTSGVHTF PAVLQSSGLYS-LSSVVTVPSSSLGTQTYICNVNHKPSNTKVDK-KVEPKSCDKTHTCPPCP APEAAGGPSVFLFPPKPKDTLMISRTPE-VTCVVVDVSHEDPEVKFNWYVDGVEVHNAK TKPREEQYN-STYRVVSVLTVLHQDWLNGKEYKCKVSNKAL-PAPIEKTISKAKGQPREPQ VYTLPPSREEMT-KNQVSLTCLVKGFYPSDIAVEWESNGQPENNY-KTTPPVLDSDGSFFL YSK-LTVDKSRWQQGNVFSCSVMHEALHN-HYTQKSLSLSPGK

SEQ ID NO:49> amino acid sequence of a chimeric 8H24 light chain

DVLMTQTPLSLPVSLGDQASISCRSSQSIVHSNGN-TYLEWYLQKPGQSPKLLIYKVSNRF SGVPDRFSGSGSGTDFTLKISRVEAE-DLGVYYCFQGSHVLPTFGGGTKLEIKRTVAAPSV FIFPPSDEQLKSGTASVVCLLNNFY-PREAKVQWKVDNALQSGNSQESVTEQDSKDS-TYS LSSTLTLSKADYEKHKVYACE-VTHQGLSSPVTKSFNRGEC

SEQ ID NO:50> Murine 11M14VH nucleotide sequence (IgG1):

ATGAACTTCGGGCTCAGCTTGAT-TTTCCTTGCCCTTATTT-TAAAAGGTGTCCAGTGTG AGGTA-CAGCTGGTGGAGTCTGGGGGAGACTTAGTGA-AGCCTGGAGGGTCCCTGAAA CTCTCCTGTGCAGCCTCTGGATTCACTTT-CAATATCTATGGCATGTCTTGGGTTCGCC AGACTCCAGACAAGAGGCTG-GAGTGGGTCGCAACCATTAGTTCTGGTGGTAT-TTATA CCTACTATCCAGACATTTTGAAGGGGC-GATTCACCATCTCCAGAGACAATGCCAAGA ACACCCTGTACCTGCAAATGAGCAGTCT-GAAGTCTGAGGACACAGCCATGTATTACT GTGCAAGACATCCGGGTGGGGCTATGGAC-TACTGGGGTCAAGGAACCTCAGTCACC GTCTCCTCA

SEQ ID NO:51> amino acid sequence for murine 11M14VH signal peptide

MNFGLSLIFLALILKGVQC

SEQ ID NO:52> Murine 11M14Vh amino acid sequence

EVOLVESGGDLVKPGGSLKLS-CAASGFTFNIYGMSWVRQTPDKRLEWVATISSG-GIYTY YPDILKGRFTISRDNAKNT-LYLQMSSLKSEDTAMYYCARHPGGAMDYWG-QGTSVTVSS

SEQ ID NO:53> Murine 11M14_Kabat Chothia Composite CDR-H1 amino acid sequence:

GFTFNIYGMS

SEQ ID NO:54> Murine 11M14_Kabat Chothia Composite CDR-H2 amino acid sequence:

TISSGGIYTYYPDILKG

SEQ ID NO:55> Murine 11M14_Kabat Chothia Composite CDR-H3 amino acid sequence:

HPGGAMDY

SEQ ID NO:56> Murine 11M14Vk nucleotide sequence (kappa)

ATGAGTGTGCC-CACTCAGGTCCTGGGGTTGCTGCTGCTGTGG CTTACAGATGCCAGA TGTGACATCCA-GATGACTCAGTCTCCAGCCTCCCTATCTGTAT-CTGTGGGAGAAACT GTCACCATCA-CATGTCGAGTAAGTGAGAATATTTACAGTAATT-TAGCATGGTATCAG CAGAAACAGG-GAAAATCTCCTCACCTCCTGGTCTATGCTGC-AACAAACTTAGCAGAT GGTGTGCCAT-CAAGGTTCAGTGGCAGTG-GATCAGGCACACAGTATTCCCTCAAGATC AACAGCCTGCAGTCTGAAGATTTTGGGAGTT-ATTACTGTCAACATTTTTGGGGTACT CCTCCGTGGACGTTCGGTGGAGGCAC-CAAGCTGGAAATCAAA

SEQ ID NO:57> amino acid sequence for murine 11M14Vk signal peptide

MSVPTQVLGLLLLWLTDARC

SEQ ID NO:58> Murine 11M14Vk amino acid sequence

DIQMTQSPASLSVSVGETVTITCRVSENIYSN-LAWYQQKQGKSPHLLVYAATNLADGVP SRFSGSGSGTQYSLKIN-SLQSEDFGSYYCQHFWGTPPWTFGGGTKLEIK

SEQ ID NO:59> Murine 11M14 Kabat Chothia Composite CDR-L1 amino acid sequence:

RVSENIYSNLA

SEQ ID NO:60> Murine 11M14 Kabat Chothia Composite CDR-L2 amino acid sequence:

AATNLAD

SEQ ID NO:61> Murine 11M14_Kabat Chothia Composite CDR-L3 amino acid sequence:

QHFWGTPPWT

SEQ ID NO:62> Kabat CDR-H1 of mouse 11M14 antibody

IYGMS

SEQ ID NO:63: Chothia CDR-H1 of mouse 11M14 antibody

GFTFNIY

SEQ ID NO:64: Chothia CDR-H2 of mouse 11M14 antibody

SSGGIY

SEQ ID NO:65 AbM CDR-H2 of mouse 11M14 antibody

TISSGGIYTY

SEQ ID NO:66: Contact CDR-H1 of mouse 11M14 antibody

NIYGMS

SEQ ID NO:67: Contact CDR-H2 of mouse 11M14 antibody

WVATISSGGIYTY

SEQ ID NO:68: Contact CDR-H3 of mouse 11M14 antibody

ARHPGGAMD

SEQ ID NO:69: Contact CDR-L1 of mouse 11M14 antibody

YSNLAWY

SEQ ID NO:70: Contact CDR-L2 of mouse 11M14 antibody

LLVYAATNLA

SEQ ID NO:71 Contact CDR-L3 of mouse 11M14 antibody

QHFWGTPPW

SEQ ID NO:72 Alternate Kabat-Chothia CDR-L2 (present in Hu11M14VLv3b, SEQ ID NO: 198)

AATNGAD

SEQ ID NO:73: Alternate Kabat-Chothia CDR-L2 (present in Hu11M14VLv4b, SEQ ID NO: 199)

AATNIAD

SEQ ID NO:74: Alternate Contact CDR-L2 (present in Hu11M14VLv3b, SEQ ID NO: 198)

LLVYAATNGA

SEQ ID NO:75: Alternate Contact CDR-L2 (present in Hu11M14VLv4b, SEQ ID NO: 199)

LLVYAATNIA

SEQ ID NO:76> Murine 5M13VH nucleotide sequence (IgG1):

GATGTGCAGCTTCAG-
GAGTCGGGACCTGGCCTGGT-
GAAACCTTCTCAGTCTCTGTCC
CTCACCTGCACTGTCACTGGCTATTCAAT-
CACCAGTGATTATGCCTGGAACTGGATC
CGGCAGTTTCCAGGAAACAAACTGGAGTG-
GATGGGCTACATAAGCTCCAGTGGTAG
CACTAGCTACAACCCATCTCT-
CAAAAGTCGAATCTCTGTCACTCGAGACA-
CATCCAA GAACCAGTTCTTCCTGCAGTTGAAT-
TTTGTGACTGCTGAGGACACAGCCACATATTA
CTGTGCATTTGTCACTACGACTATGGAC-
TACTGGGGTCAAGGAACCTCAGTCACCGT
CTCCTCA

SEQ ID NO:77> amino acid sequence for Murine 5M13VH signal peptide

MRVLILLWLFTAFPGILS

SEQ ID NO:78> Murine 5M13VH amino acid sequence

DVQLQESGPGLVKP-
SQSLSLTCTVTGYSITSDYAWNWIRQFPGN-
KLEWMGYISSSGSTS
YNPSLKSRISVTRDTSKNQFFLQLNFVTAED-
TATYYCAFVTTTMDYWGQGTSVTVSS

SEQ ID NO:79> Murine 5M13_Kabat Chothia Composite CDR-H1 amino acid sequence:

GYSITSDYAWN

SEQ ID NO:80> Murine 5M13_Kabat Chothia Composite CDR-H2 amino acid sequence:

YISSSGSTSYNPSLKS

SEQ ID NO:81> Murine 5M13_Kabat Chothia Composite CDR-H3 amino acid sequence:

VTTTMDY

SEQ ID NO: 82> Murine 5M13VL nucleotide sequence (kappa):

ATGAAGTTGCCTGTTAGGCTGTTGGTGCT-
GATGTTCTGGATTCCTGCTTCCAGCAGTG
ATGTTGTGATGACCCAAACTC-
CACTCTCCCTGCCTGTCAGTCTTGGAGAT-
CAAGCCT CCATCTCTTGCA-
GATCTAGTCAGAGCCTTGTACACAGTAATGG-
AAACACCTATTTAC
ATTGGTACCTGCAGAAGCCAGGCCAGTCTC-
CAAAGCTCCTGATCTACACAGTTTCCA ACC-
GATTTTCTGGGGTCCCA-
GACAGGTTCAGTGGCAGTGGATCAGGGACA-
GATTTCA CACTCAAGATCAGCAGAGTG-
GAGGCTGAGGATCTGGGAGTTTAT-
TTCTGCTCTCAAA GTACACATGTTCCATT-
CACGTTCGGCTCGGGGACAAAGTTGGAAATA-
AAA

SEQ ID NO:83> amino acid sequence for Murine 5M13VL signal peptide

MKLPVRLLVLMFWIPASSS

SEQ ID NO:84> Murine 5M13VL Vk amino acid sequence:

DVVMTQTPLSLPVSLGDQASISCRSSQSLVHSNGN-
TYLHWYLQKPGQSPKLLIYTVSNRF
SGVPDRFSGSGSGTDFTLKISRVEAE-
DLGVYFCSQSTHVPFTFGSGTKLEIK

SEQ ID NO:85> Murine 5M13_Kabat Chothia Composite CDR-L1 amino acid sequence:

RSSQSLVHSNGNTYLH

SEQ ID NO:86> Murine 5M13_Kabat Chothia Composite CDR-L2 amino acid sequence:

TVSNRFS

SEQ ID NO:87> Murine 5M13_Kabat Chothia Composite CDR-L3 amino acid sequence:

SQSTHVPFT

SEQ ID NO:88> Murine 2F18VH nucleotide sequence (mIgG1):

ATGAACTTCGGGCTCAGCTTGAT-
TTTCCTTGCCCTTATTTTA-
CAAGGTGTCCAGTGTG AGGTGCAGCTGGTG-
GAGTCTGGGGGAGACTTAGTGAAGCCTGGA-
GGGTCCCTGAAA CTCTCCTGTGCAGCCTCTG-
GATTCACTTTCAATATCTATGG-
CATGTCTTGGGTTCGCC AGACTCCA-
GACAAGAGGCTGGAGTGGGTCGCAACCATT-
AGTACTGGTGGTATTTAC ACCTACTATCCA-
GACAGTGTGAAGGGGCGATTCAC-
CATCTCCAGAGACAAT-
GCCAA GAACACCCTGTACCTGCAAAT-
GAGCAGTCTGAAGTCTGAGGACACAGC-
CATGTATT ATTGTGCAAGA-
CATCCGGTTGGGGCTCTGGACTACTGGGGTC-
AAGGAACCTCAGTCA CCGTCTCCTCAGC-
CAAAACGACACCCCCATCTGTCTATC-
CACTGGCCCCTGGATCTG CTGCC-
CAAACTAACTCCATGGTGACCCTGGGATGCC-
TGGTCAAGGGCTATTTCCCTG
AGCCAGTGACAGTGACCTGGAACTCTG-
GATCCCTGTCCAGCGGT

SEQ ID NO:89> amino acid sequence for murine 2F18VH signal peptide

MNFGLSLIFLALILQGVQC

SEQ ID NO:90> Murine > amino acid sequence 2F18VH

EVOLVESGGDLVKPGGSLKLS-
CAASGFTFNIYGMSWVRQTPDKRLEWVATISTG-
GIYTY YPDSVKGRFTISRDNAKNT-
LYLQMSSLKSEDTAMYYCARHPVGALDYWGQ-
GTSVTVSS

SEQ ID NO:91> Murine 2F18_Kabat Chothia Composite CDR-H1 amino acid sequence:

GFTFNIYGMS

SEQ ID NO:92> Murine 2F18_Kabat Chothia Composite CDR-H2 amino acid sequence:

TISTGGIYTYYPDSVKG

SEQ ID NO:93> Murine 2F18_Kabat Chothia Composite CDR-H3 amino acid sequence:

HPVGALDY

SEQ ID NO:94> Murine 2F18VL nucleotide sequence (kappa)

ATGAGTGTGCC-
CACTCAGGTCCTGGGGTTGCTGCTGCTGTGG-
CTTACAGATGCCAGA TGTGA-
CATCCAGGTGACTCAGTCTCCAGCCTCCCTAT-
CTGTATCTGTGGGAGAAACT GTCACCATCA-
CATGTCGAGCAAGTGAGAATATTTACAGTAAT-
TTAGCATGGTATCAG CAGAAACAGG-
GAAAATCTCCTCACCTCCTGGTCTATACTGCA-
ACAACCTTAGCAGAT GGTGTGCCAT-
CAAGGTTCAGTGGCAGTG-
GATCAGGCACACAGTATTCCCTCAAGATC
AACAGCCTGCAGTCTGAAGATTTTGGGAGTT-
ATTACTGTCAACATTTTTGGGGTACT
CCTCCGTGGACGTTCGGTGGAGGCAC-
CAAGCTGGAAATCAAACGGGCTGATGCTGC
ACCAACTGTATCCATCTTCCCACCATCCAGT-
GAGCAGTTAACATCTGGAGGTGCCTC
AGTCGTGTGCTTCTTGAACAACTTC-
TACCCCAGAGACATCAATGTCAAGTGGAAGAT
TGATGGCAGTGAACGACAAAATGGCGTCCT-
GAACAGTTGGACTGATCAG

SEQ ID NO: 95> amino acid sequence for murine 2F18VL signal peptide

MSVPTQVLGLLLLWLTDARC

SEQ ID NO:96> Murine Vk_2F18VL amino acid sequence

DIQVTQSPASLSVSVGETVTITCRASENIYSN-
LAWYQQKQGKSPHLLVYTATTLADGVPS
RFSGSGSGTQYSLKIN-
SLQSEDFGSYYCQHFWGTPPWTFGGGTKLEIK

SEQ ID NO:97> Murine 2F18_Kabat Chothia Composite CDR-L1 amino acid sequence:

RASENIYSNLA

SEQ ID NO:98> Murine 2F18_Kabat Chothia Composite CDR-L2 amino acid sequence:

TATTLAD

SEQ ID NO:99> Murine 2F18 Kabat Chothia Composite CDR-L3 amino acid sequence:

QHFWGTPPWT

SEQ ID NO: 100> Murine 2P22VH nucleotide sequence (IgG2b):

ATGAACTTCGGGCTCAGCTTGAT-
TTTCCTTGCCCTTATTT-
TAAAAGGTGTCCAGTGTG
AGGTGCAGCTGGTGGAGTCTGGGGGAGACT-
TAGTGAAGCCTGGAGGGTCCCTGAAA
CTCTCCTGTGCAGCCTCTGGATT-
CACTTTCAGTATCTATGG-
CATGTCTTGGGTTCGCC AGACTCCA-
GACAAGAAGCTGGAGTGGGTCGCAGCCATTA-
GTAGTGGTGGTATTTAT ACCTATTATCCA-
GACAGTGTGAAGGGGCGATTCAC-
CATCTCCAGAGACAACGCCAA
GAACACCCTGTACCTGCAAATGAGCAGTCT-
GAAGTCTGCGGACACAGCCATGTATTA CTGTA-
CAAGAAATGATTACGACTGGTTTGCT-
TACTGGGGCCAAGGGACTCTGGTCAC
TGTCTCTGCAGCCAAAACAACACCCC-
CATCAGTCTATCCACTGGCCCCTGGGTGTGG
AGATACAACTGGTTCCTCTGTGACTCTGG-
GATGCCTGGTCAAGGGCTACTTCCCTGA G

SEQ ID NO: 101> amino acid sequence for murine 2P22VH signal peptide

MNFGLSLIFLALILKGVQC

SEQ ID NO:102> Murine 2P22VH amino acid sequence

EVQLVESGGDLVKPGGSLKLS-
CAASGFTFSIYGMSWVRQTPDKKLEWVAAISSG-
GIYTY YPDSVKGRFTISRDNAKNT-
LYLQMSSLKSADTAMYYCTRNDYDWFAYWG-
QGTLVTVS A

SEQ ID NO: 103> Murine 2P22_Kabat Chothia Composite CDR-H1 amino acid sequence

GFTFSIYGMS

SEQ ID NO:104> Murine 2P22_Kabat Chothia Composite CDR-H2 amino acid sequence

AISSGGIYTYYPDSVKG

SEQ ID NO: 105> Murine 2P22_Kabat Chothia Composite CDR-H3 amino acid sequence

NDYDWFAY

SEQ ID NO: 106> Murine 2P22VL nucleotide sequence (kappa)

ATGAGGGCTCCTGCACAGAT-
TTTTGGCTTCTTGTTGCTCTTGTTTCCAGGTA-
CCAGAT GTGACATCCAGATGACCCAGTCTC-
CATCCTCCTTATCTGCCTCTCTGGGAGAAAGAG
TCAGTCTCACTTGTCGGGCAAGTCAGGACAT-
TGGTAGTAGCTTAAACTGGCTTCAGC
AGGAACCAGATGGAACTATTAAACGCCTGATC-
TACGCCACATCCAGTTTAGATTCTG GTGTCCC-
CAAAAGGTTCAGTGGCAGTAGGTCTGGGTCA-
GATTATTCTCTCACCATCA
GCAGCCTTGAGTCTGAAGATTTTGTAGACTAT-
TACTGTCTACAATATGCTAGTTCTCC GTA-
CACGTTCGGAGGGGGGACCAAGCTG-
GAAATAAAGCGGGCTGATGCTGCACCAA
CTGTATCCATCTTCCCACCATCCAGTGAGCAGT-
TAACATCTGGAGGTGCCTCAGTCG
TGTGCTTCTTGAACAACTTCTACCCCAGAGA-
CATCAATGTCAAGTGGAAGATTGATG GCAGT-
GAACGACAAAATGGCGTCCT-
GAACAGTTGGACTGATCAG

SEQ ID NO: 107> amino acid sequence for 2P22VL signal peptide

MRAPAQIFGFLLLLFPGTRC

SEQ ID NO: 108> Murine >Vk 2P22VL amino acid sequence

DIQMTQSPSSLSASLGERVSLTCRASQ-
DIGSSLNWLQQEPDGTIKRLIYATSSLDSGVPKR
FSGSRSGSDYSLTISSLESEDFVDYYCLQYASSPY-
TFGGGTKLEIK

SEQ ID NO:109> Murine 2P22_Kabat Chothia Composite CDR-L1 amino acid sequence:

RASQDIGSSLN

SEQ ID NO:110> Murine 2P22_Kabat Chothia Composite CDR-L2 amino acid sequence:

ATSSLDS

SEQ ID NO:111> Murine 2P22_Kabat Chothia Composite CDR-L3 amino acid sequence:

LQYASSPYT

SEQ ID NO: 112> Murine 6B15VH nucleotide sequence (IgG1):

ATGAACTTCGGGCTCAGCTTGAT-
TTTCCTTGCCCTTATTT-
TAAAAGGTGTCCAGTGTG
AGGTGCAGCTGGTGGAGTCTGGGGGAGACT-

TAGTGAAGCCTGGAGGGTCCCTGAAA CTCTCCTGTGCAGCCCCTGGATT-CACTTTCAGTACTTATGG-CATGTCTTGGGTTCGCC AGACTCCA-GACAAGAGGCTGGAGTGGGTCGCAATCATTA-GTAGTGGTGGTAGTTAC ACCTACTATTCA-GACACTGTGAAGGGGCGATTCAC-CATCTCCAGAGACAATGCCAA GAACACCCT-GAACCTGCAAATGAGCAGTCTGAAGTCTGA-GGACACAGCCATGTACT TTTGTT-CAAGGAGTAGTAGCCACTGGTATTTC-GATGTCTGGGGCACGGGGACCACGG TCACCGTCTCCTCAGCCAAAACGACACCCC-CATCTGTCTATCCACTGGCCCCTGGAT CTGCTGCCCAAACTAACTC-CATGGTGACCCTGGGATGCCTGGTCAAGGGCT-ATTTCC CTGAGCCAGTGACAGTGACCTG-GAACTCTGGATCCCTGTCCAGCGGT

SEQ ID NO: 113> amino acid sequence for 6B15VH signal peptide

MNFGLSLIFLALILKGVQC

SEQ ID NO: 114> Murine 6B15VH amino acid sequence

EVOLVESGGDLVKPGGSLKLSCAAPGFTF-STYGMSWVRQTPDKRLEWVAIISSGGSYTY YSDTVKGRFTISRDNAKNTLNLQMSSLKSED-TAMYFCSRSSSHWYFDVWGTGTTVTVS S

SEQ ID NO: 115> Murine 6B15_Kabat Chothia Composite CDR-H1 amino acid sequence:

GFTFSTYGMS

SEQ ID NO: 116> Murine 6B15_Kabat Chothia Composite CDR-H2 amino acid sequence:

IISSGGSYTYYSDTVKG

SEQ ID NO: 117> Murine 6B15_Kabat Chothia Composite CDR-H3 amino acid sequence:

SSSHWYFDV

SEQ ID NO: 118> Murine 6B15VL nucleotide sequence (kappa)

ATGGTCCTTGCTCAGTTTCTTGCAT-TCTTGTTGCTTTGGTTTCCAGGTGCAAGATGTG ACATCCTGATGACCCAATTTCCATCCTC-CATGTCTGTATCTCTGGGAGACACAGTCA GCATCACTTGCCATGCAAGTCAGGGCATT-AGCAGTAATATAGGGTGGTTGCAGCAG AAACCAGGGAAATCATTTAAGGGCCTGATC-TATCATGGAACCAACTTGAAAGATGG AGTTC-CATCAAGGTTCAGTGGCAGTGGATCTG-GAACAGATTTTCTCTCACCATCAG CAGCCTGGAATCTGAAGATTTTGCAGACTAT-TACTGTGTACAGTATGCTCAGTTTCC GTA-CACGTTCGGAGGGGGGACCAAGCTG-GAAAAAAGACGGGCTGATGCTGCACCAA CTGTATCCATCTTCCCACCATCCAGTGAGCAGT-TAACATCTGGAGGTGCCTCAGTCG TGTGCTTCTTGAACAACTTCTACCCCAGAGA-CATCAATGTCAAGTGGAAGATTGATG GCAGT-GAACGACAAAATGGCGTCCT-GAACAGTTGGACTGATCAG

SEQ ID NO: 119> amino acid sequence for 6B15VL signal peptide

MVLAQFLAFLLLWFPGARC

SEQ ID NO: 120> Murine 6B15VL Vk_6B15 amino acid sequence

DILMTQFPSSMSVSLGDTVSITCHASQ-GISSNIGWLQQKPGKSFKGLIYHGTNLKDGVPS RFSGSGSGTDFSLTISSLESED-FADYYCVQYAQFPYTFGGGTKLEKR

SEQ ID NO: 121> Murine 6B15_Kabat Chothia Composite CDR-L1 amino acid sequence:

HASQGISSNIG

SEQ ID NO: 122> Murine 6B15_Kabat Chothia Composite CDR-L2 amino acid sequence:

HGTNLKD

SEQ ID NO: 123> Murine 6B15_Kabat Chothia Composite CDR-L3 amino acid sequence:

VQYAQFPYT

SEQ ID NO: 124> Murine 2C14VH nucleotide sequence (IgG1):

ATGAACTTCGGGCTCAGCTTGAT-TTTCCTTGCCCTTATTT-TAAAAGGTGTCCAGTGTG AGGTGCAGCTGGTGGAGTCTGGGGGAGACT-TAGTGAAGCCTGGAGGGTCCCTGAAA CTCTCCTGTGCAGCCTCTGGATTCACTTT-CAATACCCATGGCATGTCTTGGGTTCGCC AGACTCCGGACAAGAGTCTG-GAGTGGGTCGCAACCATT-AGTACTGGTGGTTTTTACA CCTCCTATCCA-GACAGTGTGAAGGGGCGATTCACCATCTCCA-GAGACAATGCCAAG AACACCCTGTTCCTGCAAATGAGCAGTCT-GAAGTCTGAGGACACAGCCATGTATTAC TGTGCAAAGAGTAGTAGCCACTGGTACTTC-GATGTCTGGGGCACAGGGACCACGGT CACCGTCTCCTCAGCCAAAACGACACCCC-CATCTGTCTATCCACTGGCCCCTGGATC TGCTGCCCAAACTAACTCCATGGTGACCCTGG-GATGCCTGGTCAAGGGCTATTTCCC TGAGCCAGTGACAGTGACCTGGAACTCTG-GATCCCTGTCCAGCGGT

SEQ ID NO: 125> amino acid sequence for 2C14VH signal peptide

MNFGLSLIFLALILKGVQC

SEQ ID NO: 126> Murine 2C14VH amino acid sequence

EVOLVESGGDLVKPGGSLKLS-CAASGFTFNTHGMSWVRQTPDKSLEWVA-TISTGGFYT SYPDSVKGRFTISRD-NAKNTLFLQMSSLKSEDTAMYYCAKSSSHWY-FDVWGTGTTVTV SS

SEQ ID NO: 127> Murine 2C14_Kabat Chothia Composite CDR-H1 amino acid sequence:

GFTFNTHGMS

SEQ ID NO: 128> Murine 2C14_Kabat Chothia Composite CDR-H2 amino acid sequence:

TISTGGFYTSYPDSVKG

SEQ ID NO: 129> Murine 2C14_Kabat Chothia Composite CDR-H3 amino acid sequence:

SSSHWYFDV

SEQ ID NO: 130> Murine 2C14VL nucleotide sequence (kappa)

ATGGTCCTTGCTCAGTTTCTTGCAT-TCTTGTTGCTTTGGTTTCCAGGTGCAAGATGTG ACATCCTGATGACCCAATCTCCATCCTC-CATGTCTGTATCTCTGGGAGACACAGTCA GCATCACTTGCCATGCAAGTCAGGG-CATCAGTAGTAATATAGGGTGGTTGCAGCAG AAACCAGGGAAATCATTTAAGGGCCTGATC-TATCATGGAACCAACTTGGAAGATGG AGTTC-CATCAAGGTTCAGTGGCAGTGGATCTG-GAGCAGATTATTCTCTCACCATCAG TAGCCTGGAATATGAAGATTTTGCAGACTAT-TACTGTGTACAGTATGCTCACTTTCC GTA-CACGTTCGGAGGGGGGACCAAGCTG-GAAATAAAACGGGCTGATGCTGCACCAA

CTGTATCCATCTTCCCACCATCCAGTGAGCAGT-TAACATCTGGAGGTGCCTCAGTCG TGTGCTTCTTGAACAACTTCTACCCCAGAGA-CATCAATGTCAAGTGGAAGATTGATG GCAGT-GAACGACAAAATGGCGTCCT-GAACAGTTGGACTGATCAG

SEQ ID NO: 131> amino acid sequence for 2C14VL signal peptide

MVLAQFLAFLLLWFPGARC

SEQ ID NO: 132> Murine 2C14VL Vk 2C14 amino acid sequence

DILMTQSPSSMSVSLGDTVSITCHASQ-GISSNIGWLQQKPGKSFKGLIYHGTNLEDGVPSR FSGSGSGADYSLTISSLEYED-FADYYCVQYAHFPYTFGGGTKLEIK

SEQ ID NO: 133> Murine 2C14_Kabat Chothia Composite CDR-L1 amino acid sequence:

HASQGISSNIG

SEQ ID NO:134> Murine 2C14_Kabat Chothia Composite CDR-L2 amino acid sequence:

HGTNLED

SEQ ID NO: 135> Murine 2C14_Kabat Chothia Composite CDR-L3 amino acid sequence:

VQYAHFPYT

SEQ ID NO: 136> Murine 9N18VH nucleotide sequence (IgG2b):

ATGGGATGGAACTGGATCTTTATTT-TAATCCTGTCAGTAACTACAGGAGTCCACTCT GAGATCCAGCTGCAGCAGTCTGGACCT-GAGCTGGTGAAGCCTGGGGCTTCAGTGAA GATATCCTGCAAGGCTTCTGGTTACTCATT-CACTGGCTACTACATGAACTGGGTGAA GCAAAGTCCTGAAAAGAGCCTTGAGTGGAT-TGGAGAGATTAATCCTATCACTGGTG GTAC-TACCTACAACCAGAATTTCAAGGCCAAGGC-CACATTGACTGTAGACAAATCCT CCAGCACAGCCTACCTGCAGCTCAG-GAGCCTGACATCTGAGGACTCTGCAGTCTATT ACTGTGCATCCGAT-TACTTCGGTAGTAACTCCTGGTTTGCT-TACTGGGGCCAAGGGA CTCTGGT-CACTGTCTCTGCAGCCAAAACAACACCCCCA-TCAGTCTATCCACTGGCCC CTGGGTGTG-GAGATACAACTGGTTCCTCTGTGACTCTGG-GATGCCTGGTCAAGGGCT ACTTCCCTGAG

SEQ ID NO: 137> amino acid sequence for 9N18VH signal peptide

MGWNWIFILILSVTTGVHS

SEQ ID NO: 138> Murine 9N18VH amino acid sequence

EIQLQQSGPELVKPGASVKISCK-ASGYSFTGYYMNWVKQSPEKSLEWIGEIN-PITGGTTY NQNFKAKATLTVDKSSSTAY-LQLRSLTSEDSAVYYCASDYFGSNSWFAYWGQ-GTLVTV SA

SEQ ID NO: 139> Murine 9N18_Kabat Chothia Composite CDR-H1 amino acid sequence:

GYSFTGYYMN

SEQ ID NO:140> Murine 9N18_Kabat Chothia Composite CDR-H2 amino acid sequence:

EINPITGGTTYNQNFKA

SEQ ID NO: 141> Murine 9N18_Kabat Chothia Composite CDR-H3 amino acid sequence:

DYFGSNSWFAY

SEQ ID NO:142> Murine 9N18VL nucleotide sequence (kappa)

ATGAAGTTGCCTGTTAGGCTGTTGGTGGT-GATGTTCTGGATTCCTGCTTCCAGCAGTG ATGTTTTGATGACCCAAACTC-CACTCTCCCTGCCTGTCAGTCTTGGAGAT-CAAGCCTC CATCTCTTGCAGATCTAGTCAGAG-CATTGTACATAGAAATGGAAACACCTATTTAGA ATGGTACCTGCAGAAACCAGGCCAGTCTC-CAAAGCTCCTGATCTACAAAGTTTCCAA CCGATTTTCTGGGGTCCCA-GACAGGTTCAGTGGCAGTGGATCAGGGACA-GATTTCAC ACTCAGGATCAGCAGAGTG-GAGGCTGAGGATCTGGGAGTTTATTACTGCTTT-CAAGG TTCACATGTTCCGTACACGTTCG-GAGGGGGGACCAAGCTG-GAAATAAAACGGGCTG ATGCTGCAC-CAACTGTATCCATCTTCCCACCATCCAGTGAG-CAGTTAACATCTGGAG GTGCCTCAGTCGTGTGCTTCTTGAACAACTTC-TACCCCAGAGACATCAATGTCAAGT GGAA-GATTGATGGCAGT-GAACGACAAAATGGCGTCCTGAACAGTTGG-ACTGATCAG

SEQ ID NO: 143> amino acid sequence for 9N18VL signal peptide

MKLPVRLLVVMFWIPASSS

SEQ ID NO: 144> Murine 9N18VL Vk 9N18 amino acid sequence

DVLMTQTPLSLPVSLGDQASISCRSSQSIVHRNGN-TYLEWYLQKPGQSPKLLIYKVSNRF SGVPDRFSGSGSGTDFTLRISRVEAE-DLGVYYCFQGSHVPYTFGGGTKLEIK

SEQ ID NO: 145> Murine 9N18_Kabat Chothia Composite CDR-L1 amino acid sequence:

RSSQSIVHRNGNTYLE

SEQ ID NO: 146> Murine 9N18_Kabat Chothia Composite CDR-L2 amino acid sequence:

KVSNRFS

SEQ ID NO: 147> Murine 9N18_Kabat Chothia Composite CDR-L3 amino acid sequence:

FQGSHVPYTF

SEQ ID NO: 148> Murine 4N2VH nucleotide sequence (IgG3):

ATGAACTTCGGGCTCAGCTTGAT-TTTCCTTGTCCTAATTT-TAAAAGGTGTCCAGTGTG AAGT-GAAGCTGGTGGAGTCTGGGGGAGGCTTAGT-GAAGCCTGGAGGGTCCCTGAAA CTCTCCTGTGGAGCCTCTGGATT-CACTTTCAGTAACTATGT-CATGTCTTGGGTTCGCC AGACTCCGGAGAG-GAGGCTGGAGTGGGTCGCAACCATTAGTGGT-GGTGGTCGTTAC TCCTACTATCCAGACAGTGT-GAAGGGGCGATTCACCATCTCCAGA-GACAATGCCAA GAACAACCTGTACCTA-CAAATGAGCAGTCTGAGGTCTGAGGACACG-GCCTTATATTA CTGTGGAAGACAGGATGAT-TACGACTCTTTTCCTTACTGTGGC-CAAGGGACTCTGGT CACTGTCTCTGTAGCTA-CAACAACAGCCCCATCTGTCTATCCCTTGGTC-CCTGGCTGC GGTGACACA

SEQ ID NO: 149> amino acid sequence for murine 4N2VH signal peptide

MNFGLSLIFLVLILKGVQC

SEQ ID NO: 150> Murine 4N2VH Vh 4N2 amino acid sequence

EVKLVESGGGLVKPGGSLKLSC-GASGFTFSNYVMSWVRQTPERRLEWVATISGG-GRYS YYPDSVKGRFTISRDNAKNN-LYLQMSSLRSEDTALYYCGRQDDYDSFPYCGQ-GTLVTV SV

SEQ ID NO: 151> Murine 4N2 Kabat Chothia Composite CDR-H1 amino acid sequence:

GFTFSNYVMS

SEQ ID NO: 152> Murine 4N2_Kabat Chothia Composite CDR-H2 amino acid sequence:

TISGGGRYSYYPDSVKG

SEQ ID NO: 153> Murine 4N2_Kabat Chothia Composite CDR-H3 amino acid sequence:

QDDYDSFPY

SEQ ID NO: 154> Murine 4N2VL nucleotide sequence (kappa)

ATGGTATCCACACCTCAGTTCCTTGTAT-TTTTGCTTTTCTGGATTCCAGCCTCCAGAG GTGACATCTTGCTGACTCAGTCTCCAGC-CATCCTGTCTGTGAGTCTAGGAGAAAGAG TCAGTTTCTCCTGCAGGGCCAGTCAGAGCAT-TGGCACAAGCATACACTGGTTTCAGC TAAGAACAAATGGTTCTCCAAGGCTTCTCAT-AAAGTATGCTTCTGAGCCCATCTCTG GGATCCCTTCCAGGTTTAGTGGCAGTG-GATCAGGGACAGATTTTACTCTTAGCATCA ATAGTGTGGAATCTGAAGATATTGCAGATTAT-TTCTGTCAACAAAGTAAGAGCTGGC CAAT-CACGTTCGGTACTGGGACCAAGCTGGAGCT-GAAACGGGCTGATGCTGCACCA ACTGTATCCATCTTCCCACCATCCAGT-GAGCAGTTAACATCTGGAGGTGCCTCAGTC GTGTGCTTCTTGAACAACTTCTACCCCAGAGA-CATCAATGTCAAGTGGAAGATTGAT GGCAGT-GAACGACAAAATGGCGTCCT-GAACAGTTGGACTGATCAG

SEQ ID NO: 155> amino acid sequence for murine 4N2VL signal peptide

MVSTPQFLVFLLFWIPASRG

SEQ ID NO: 156> Murine > Murine 4N2VL Vk_4N2 amino acid sequence

DILLTQ-SPAILSVSLGERVSFSCRASQSIGTSIHWFQL-RINGSPRLLIKYASEPISGIPSRFSG SGSGTDFTLSINSVESEDI-ADYFCQQSKSWPITFGTGTKLELK

SEQ ID NO: 157> Murine 4N2_Kabat Chothia Composite CDR-L1 amino acid sequence:

RASQSIGTSIH

SEQ ID NO: 158> Murine 4N2_Kabat Chothia Composite CDR-L2 amino acid sequence:

YASEPIS

SEQ ID NO: 159> Murine 4N2_Kabat Chothia Composite CDR-L3 amino acid sequence:

QQSKSWPIT

SEQ ID NO: 160 >3V6F-VH_mSt

EVOLVESGGDLVKPGGSLKLS-CAASGFTFSSYGMSWVRQTPDKRLEWVATIS-SGGNYIYYPDTVKGRFTISRD NAKNT-LYLQMSSLKSEDTAMYYCTREGAYSGSSSYPM-DYWGQGTSVTVSS

SEQ ID NO: 161>AEX29086-VH_huFrwk

EVQLLESGGGLVQPGGSLRLSCAASGFTFSSYAM-SWVRQAPGKGLEWVSAISGSGGSTYYADSVR-GRFTISR DNSKNTLYLQMNSLRAEDTAVYY-CAKSGTPWYFDYWGQGTLVTVSS

SEQ ID NO: 162>IGHV3-21*01

EVOLVESGGGLVKPGGSLRLSCAASGFTFSSYS-MNWVRQAPGKGLEWVSSISSSSSYIYY-ADSVKGRFTISRD NAKNSLYLQMNSLRAED-TAVYYCARDAFDVWGQGTMVTVSS

SEQ ID NO: 163>h5E20VH version1 (87.8. % human)

EVQLLESGGGLVQPGGSLRLSCAASGFTF-STYGMSWVRQAPGKGLEWVAIISSGG-SYTYYSDTVKGRFTISRD NSKNTLYLQMNSL-RAEDTAVYYCSRSSSHWYFDVWGQGTLVTVSS

SEQ ID NO: 164>h5E20VH version2 (89.8% human)

EVOLVESGGGLVQPGGSLRLSCAASGFTF-STYGMSWVRQAPGKGLEWVAIISSGG-SYTYYSDTVKGRFTISR DNSKNSLYLQMNSL-RAEDTAVYYCSRSSSHWYFDVWGQGTLVTVSS

SEQ ID NO: 165>h5E20VH version3 (86.7% human)

EVOLVESGGGLVQPGGSLRLSCAASGFTF-STYGMSWVRQAPGKRLEWVAIISSGG-SYTYYSDTVKGRFTISR DNSKNSLYLQMNSL-RAEDTAVYYCSRSSSHWYFDVWGQGTLVTVSS

SEQ ID NO: 166>h5E20VH version4 (85.7% human)

EVOLVESGGGLVQPGGSLRLSCAASGFTF-STYGMSWVRQAPDKRLEWVAIISSGG-SYTYYSDTVKGRFTISRD NSKNSLYLQMNSL-RAEDTAVYYCSRSSSHWYFDVWGQGTLVTVSS

SEQ ID NO: 167>h5E20VH version5 (84.7% human)

EVOLVESGGGLVQPGGSLRLSCAASGFTF-STYGMSWVRQAPDKRLEWVAIISSGG-SYTYYSDTVKGRFTISRD NSKNSLYLQMNSL-KAEDTAVYYCSRSSSHWYFDVWGQGTLVTVSS

SEQ ID NO: 168>h5E20VH version6 (85.7% human)

EVOLVESGGGLVQPGGSLRLSCAASGFTF-STYGMSWVRQTPGKRLEWVAIISSGG-SYTYYSDTVKGRFTISRD NSKNSLYLQMNSL-RAEDTAVYYCSRSSSHWYFDVWGQGTLVTVSS

SEQ ID NO: 169>h5E20VH version7 (84.7% human)

EVOLVESGGGLVQPGGSLRLSCAASGFTF-STYGMSWVRQTPDKRLEWVAIISSGG-SYTYYSDTVKGRFTISRD NSKNSLYLQMNSL-RAEDTAVYYCSRSSSHWYFDVWGQGTLVTVSS

SEQ ID NO: 170 >3V6F-VL_mSt

NIMMTQSPSSLAVSAGEKVTMNCK-SSQSVLYSSNQKNYLAWYQQKPGQSPKLLIY-WASTRESGVPDRFTGS GSGTDFTLTISSVQTED-LAVYYCHQYLSSYMYTFGGGTKLEIK

SEQ ID NO: 171>BAH04687-VL_huFrwk

DIQMTQSPSSLSASVGDRVTITCRASQSIS-SYLNWYQQKPGKAPKLLI-YAASSLQSGVPSRFSGSGSGTDFTLTI SSLQPED-FATYYCQQSYSTPLTFGGGTKVEIR

SEQ ID NO: 172>IGKV1-12*01

DIQMTQSPSSVSASVGDRVTITCRASQGISS-WLAWYQQKPGKAPKLLI-YAASSLQSGVPSRFSGSGSGTDFTL TISSLOPED-FATYYCQQANSFPYTFGQGTKLEKR

SEQ ID NO: 173>h5E20VL version1 (78.9% human measured against IGKV2-29*02)

DIQMTQSPSSLSASVGDRVTITCHASQ-GISSNIGWLQQKPGKAFKGLIYHGTNLKDGVP-SRFSGSGSGADFTL TISSLOPEDFA-TYFCVQYAQFPYTFGGGTKVEIR

SEQ ID NO: 174>h5E20VL version2 (80.0% human)

DIQMTQSPSSVSASVGDRVTITCHASQ-GISSNIGWLQQKPGKAFKGLIYHGTNLKDGVPS-RFSGSGSGADFT LTISSLOPEDFA-TYFCVQYAQFPYTFGQGTKVEIR

SEQ ID NO: 175>h5E20VL version3 (80.0% human)
DIQMTQSPSSVSASVGDRVTITCHASQ-GISSNIGWLQQKPGKAFKGLIYHGTNLKDGVPS-RFSGSGSGADFT LTISSLOPEDFA-TYFCVQYAQFPYTFGQGTKVEKR SEQ ID NO: 176>h5E20VL version4 (78.9% human)
DIQMTQSPSSVSASVGDRVTITCHASQ-GISSNIGWLQQKPGKAFKGLIYHGTNLKDGVP-SRFSGSGSGADFT LTISSLOPED-FADYFCVQYAQFPYTFGQGTKVEKR SEQ ID NO: 177 >1MRC-VH_mSt
QVQLQQSGAELVKPGASVKLSCKASGYTFT-SYWMQWVKQRPGQGLEWIGEIDPSD-SYTNYNQKFKGKATL TVDTSSSTAYMQLSSLT-SEDSAVYYCANLRGYFDYWGQGTTLTVSS SEQ ID NO: 178>AAC51714-VH_huFrwk
QVQLVQSGAEVKKPGSSVKVSCK-ASGGTFSSYAISWVRQAPGQGLEWMGGIIP-IFGTANYAQKFQGRVTIT ADKS-TSTAYMELSSLRSEDTAVYYCARAYCSST-SCYKTGFVWGQGTLVTVSS SEQ ID NO: 179>IGHV1-69*08_IGHJ1*01
QVQLVQSGAEVKKPGSSVKVSCKASGGTFSSY-TISWVRQAPGQGLEWMGRIIPILGTAN-YAQKFQGRVTITA DKSTSTAYMELSSLRSED-TAVYYCARAEYFQHWGQGTLVTVSS SEQ ID NO:180>h8H24VH version1 (81.6. % human)
QAQLVQSGAEVKKPGSSVKVSCKASGYTFTSYS-MHWVRQAPGQGLEWIGAIYPGNDATSYN-QKFKGRATL TVDKSTSTAYMELSSLRSED-TAVYFCAREGYYGSSFEAWFASWGQGTTVTVSS SEQ ID NO: 181>h8H24VH version2 (80.6% human)
QAQLVQSGAEVVKPGSSVKVSCKASGYTFTSYS-MHWVRQAPGQGLEWIGAIYPGNDATSYN-QKFKGRATL TVDKSTSTAYMELSSLRSED-TAVYFCAREGYYGSSFEAWFASWGQGTTVTVSS SEQ ID NO: 182 >1MRC-VL_mSt
DVVMTQTPLSLPVSLGDQASISCRSSQSLVHSNGN-TYLHWYLQKPGQSPKLLIYKVSNRFSGVPDRF-SGSGSG TDFTLKISRVEAE-DLGVYFCSQSTHVPRTFGGGTKLEIK SEQ ID NO: 183>ABC66914-VL_huFrwk
DIVMTQTPLSLPVTPGEPASISCRSSQSLLHSNGY-NYLDWYLQKPGQSPQLLIYLGSN-RASGVPDRFSGSGSG TDFTLKISRVEAE-DVGVYYCMQALQTPLTFGGGTKVEIK SEQ ID NO: 184>IGKV2-40*01
DIVMTQTPLSLPVTPGEPASISCRSSQSLLDSDDGN-TYLDWYLQKPGQSPQLLIYTLSYR-ASGVPDRFSGSGSG TDFTLKISRVEAE-DVGVYYCMQRIEFPLTFGGGTKVEIK SEQ ID NO: 185>h8H24VL version1 (88.4% human)
DVVMTQTPLSLPVTPGEPASISCRSSQSIVHSNGN-TYLEWYLQKPGQSPQLLIYKVSNRFSGVPDRF-SGSGSG TDFTLKISRVEAE-DVGVYYCFQGSHVLPTFGGGTKVEIK SEQ ID NO: 186>h8H24VL version2 (86.3% human)
DVVMTQTPSSLPVTPGEPASISCRSSQSIVHSNGN-TYLEWYLQKPGQSPQLLIYKVSNRFSGVPDRF-SGSGSG TDFTLTISRVEAE-DVGVYYCFQGSHVLPTFGGGTKVEIK SEQ ID NO: 187>1MQK-VH_mSt
EVKLQESGGDLVQPGGSLKLSCAASGFTFS-SYTMSWVRQTPEKRLEWVASINNGG-GRTYYPDTVKGRFTISR DNAKNT-LYLQMSSLKSEDTAMYYCVRHEYYYAMDYW-GQGTTVTVSS SEQ ID NO: 188>ACS96198-VH_huFrwk
EVOLVESGGGLVQPGGSLRLS-CAASGFTFSSYEMNWVRQAPGKGLEWVSYIS-SSGSTIYYADSVKGRFTISRD NAKNS-LYLQMNSLRAEDTAVYYCARENIAAFDYWGQ-GTLVTVSSGS SEQ ID NO: 189>IGHV3-48*03
EVOLVESGGGLVQPGGSLRLS-CAASGFTFSSYEMNWVRQAPGKGLEWVSYIS-SSGSTIYYADSVKGRFTISRD NAKNS-LYLQMNSLRAEDTAVYYCARYFDYWGQGTLV-TVSS SEQ ID NO: 190>h11M14VH version1b (86.7% human)
EVOLVESGGGLVQPGGSLRLS-CAASGFTFNIYGMSWVRQAPGKGLEWVATIS-SGGIYTYYPDILKGRFTISRD NAKNS-LYLQMNSLRAEDTAVYYCARHPGGAMDYWG-QGTLVTVSS SEQ ID NO: 191>h11M14VH version2b (85.7% human)
EVOLVESGGGLVQPGGSLRLS-CAASGFTFNIYGMSWVRQAPGKGLEWVATIS-SGGIYTYYPDILKGRFTISRD NAKNSLYLQMNS-GRAEDTAVYYCARHPGGAMDYWGQGTLVTVSS SEQ ID NO:192>h11M14VH version3b (85.7% human)
EVOLVESGGGLVQPGGSLRLS-CAASGFTFNIYGMSWVRQAPGKGLEWVATIS-SGGIYTYYPDILKGRFTISRD NAKNS-LYGQMNSLRAEDTAVYYCARHPGGAMDYWG-QGTLVTVSS SEQ ID NO: 193>1MQK-VL_mSt
DIELTQTPVSLSASVGETVTITCRASENIYSY-LAWYQQKQGK-SPQFLVYNAKTLGEGVPSRFSGSGSGTQFSLKI NSLLPEDFGSYYCQHHYGTPPLTFGGGTKLEIK SEQ ID NO: 194>CBZ39892-VL_huFrwk
DIQMTQSPSSLSASVGDRVTITCRASQSIS-SYLNWYQQKPGKAPKLLI-YAASSLQSGVPSRFSGSGSGTDFTLTI NSLOPED-FATYYCQQSYSTPPYTFGQGTKLEIK SEQ ID NO: 195>IGKV1-39*01
DIQMTQSPSSLSASVGDRVTITCRASQSIS-SYLNWYQQKPGKAPKLLI-YAASSLQSGVPSRFSGSGSGTDFTLTI SSLQPED-FATYYCQQSYSTPYTFGQGTKLEIK SEQ ID NO: 196>h11M14VL version1b (83.2% human)
DIQMTQSPSSLSASVGDRVTITCRVSENIYSN-LAWYQQKPGKAPKLLVYAATN-LADGVPSRFSGSGSGTDYTL TINSLOPEDFA-TYYCQHFWGTPPWTFGQGTKLEIK SEQ ID NO: 197>h11M14VL version2b (83.2% human)
DIQMTQSPSSLSASVGDRVTITCRVSENIYSN-LAWYQQKPGKSPKLLVYAATN-LADGVPSRFSGSGSGTDYTL TISSLOPEDFA-TYYCQHFWGTPPWTFGQGTKLEIK SEQ ID NO: 198>h11M14VL version3b (82.1% human)
DIQMTQSPSSLSASVGDRVTITCRVSENIYSN-LAWYQQKPGKSPKLLVYAATNGAD-GVPSRFSGSGSGTDYTL TISSLQPEDFA-TYYCQHFWGTPPWTFGQGTKLEIK SEQ ID NO: 199>h11M14VL version4b (82.1% human)
DIQMTQSPSSLSASVGDRVTITCRVSENIYSN-LAWYQQKPGKSPKLLVYAAT-NIADGVPSRFSGSGSGTDYTL TISSLOPEDFA-TYYCQHFWGTPPWTFGQGTKLEIK SEQ ID NO:200 HA peptide
YPYDVPDYAG SEQ ID NO:201 c-Myc peptide
EQKLISEEDL
SEQ ID NO:202 consensus motif of a peptide bound by antibody 5E20
FTESFLT
SEQ ID NO:203: consensus motif of a peptide bound by antibody 5E20
ESFL
SEQ ID NO:204 peptide bound by antibody 5E20
DGCILGYKEQFL
SEQ ID NO:205 peptide bound by antibody 5E20
PSICLCSLEDFL
SEQ ID NO:206 sequence motif bound by antibody 5E20
E(S/Q/D)FL
SEQ ID NO:207 Linker sequence
GSGSGSG
SEQ ID NO:208 amino acid sequence of chimeric 11M14 heavy chain
EVOLVESGGDLVKPGGSLKLS-
CAASGFTFNIYGMSWVRQTPDKRLEWVATISSG-
GIYTY YPDILKGRFTISRDNAKNT-
LYLQMSSLKSEDTAMYYCARHPGGAMDYWG-
QGTSVTVSS ASTKGPSVFPLAPSSKST-
SGGTAALGCLVKDYFPEPVTVSWNSGALT-
SGVHTFPAVLQSS GLYS-
LSSVVTVPSSSLGTQTYICNVNHKPSNTKVDK-
KVEPKSCDKTHTCPPCPAPEAAG
GPSVFLFPPKPKDTLMISRTPE-
VTCVVVDVSHEDPE-
VKFNWYVDGVEVHNAKTKPREEQ
YNSTYRVVSVLTVLHQDWLNGKEYKCKVSNKA-
LPAPIEKTISKAKGQPREPQVYTLPPS REEMT-
KNQVSLTCLVKGFYPSDIAVEWESNGQPEN-
NYKTTPPVLDSDGSFFLYSKLTVD
KSRWQQGNVFSCSVMHEALHNHYTQKSLSL-
SPGK
SEQ ID NO:209 amino acid sequence of chimeric 11M14 light chain
DIQMTQSPASLSVSVGETVTITCRVSENIYSN-
LAWYQQKQGKSPHLLVYAATNLADGVP
SRFSGSGSGTQYSLKIN-
SLQSEDFGSYYCQHFWGTPPWTFGGGTKLEIK-
RTVAAPSVFIFP PSDEQLKSGTASVVCLLNNFY-
PREAKVQWKVDNALQSGNSQESVTEQDSKDS-
TYSLSST LTLSKADYEKHKVYACE-
VTHQGLSSPVTKSFNRGEC
SEQ ID NO:210 amino acid sequence of residues 523-610 of sortilin
HYYTILDSGGIIVAIEHSSRPINVIKFSTDE-
GQCWQTYTFTRDPIYFTGLASEPGARSMNISI
WGFTESFLTSQWVSYTIDFKDILER
SEQ ID NO:211 amino acid sequence of a sortilin peptide
FTESFLTSQW
SEQ ID NO:212 amino acid sequence of a sortilin peptide
LTSQW
SEQ ID NO:213 amino acid sequence of a peptide bound by antibody 8H24
RTEFGMAIGP
SEQ ID NO:214 amino acid sequence of a peptide bound by antibody 11M14
WGFTESFLTS
SEQ ID NO:215; Amino acid sequence of human sortilin extracellular domain without signal peptide
QDRLDAPPPPAAPLPRWSGPIGVSWGL-
RAAAAGGAFPRGGRWRRSAPGEDEECGRVRD
FVAKLANNTHQHVFDDLRGSVSLSWVGD-
STGVILVLTTFHVPLVIMTFGQSKLYRSEDY
GKNFKDITDLINNTFIRTEFGMAIGPENSGKVVL-
TAEVSGGSRGGRIFRSSDFAKNFVQTD
LPFHPLTQMMYSPQNSDYLLALSTENGLWV-
SKNFGGKWEEIHKAVCLAKWGSDNTIFF TTY-
ANGSCKADLGALELWRTSDLGKSFKTIGV-
KIYSFGLGGRFLFASVMADKDTTRRIH
VSTDQGDTWSMAQLPSVGQEQFYSI-
LAANDDMVFMHVDEPGDTGFGTIFTSDDRGIVY
SKSLDRHLYTTTGGETDFTNVT-
SLRGVYITSVLSEDNSIQTMITFDQGGRWTH-
LRKPENS ECDATAKNKNECSLHIHASYS-
ISQKLNVPMAPLSEPNAVGIVIAHGSVGDAISV-
MVPDV YISDDGGYSWTKMLEGPHYYTILDSG-
GIIVAIEHSSRPINVIKFSTDEGQCWQTYTFTRDP
IYFTGLASEPGARSMNISIWGFTESFLTSQWV-
SYTIDFKDILERNCEEKDYTIWLAHSTDP
EDYEDGCILGYKEQFLRLRKSSVCQN-
GRDYVVTKQPSICLCSLEDFLCDFGYYRPENDS
KCVEQPELKGHDLEFCLYGREEHLTTNGYRKIP-
GDKCQGGVNPVREVKDLKKKCTSNF
LSPEKQNSKSNS
SEQ ID NO:216 amino acid sequence of hSORT1_ECD_Emut1:
MERPWGAADGLSRWPHGLGLLLLLQLLPP-
STLSQDRLDAPPPPAAPLPRWSGPIGVSWGLRA
AAAGGAFPRGGRWRRSAPGEDEECGRVRDF-
VAKLANNTHQAVFDAAAGSVSLSWVGDSTG
VILVLTTFHVPLVIMTFGQSK-
LYRSEDYGKNFKDITDLINNTFIRTEFGMAIG-
PENSGKVVLTAEV SGGSRGGRIFRSSD-
FAKNFVQTDLPFHPLTQMMYSPQNSDYLLALS-
TENGLWVSKNFGGKWE EIHKAVCLAKWGSDN-
TIFFTTYANGSCKADL-
GALELWRTSDLGKSFKTIGVKIYSFGLGGRFLFA
SVMADKDTTRRIHVSTDQGDTWS-
MAQLPSVGQEQFYSI-
LAANDDMVFMHVDEPGDTGFGTIF TSDDR-
GIVYSKSLDRHLYTTTGGETDFTNVTSLRGVYI-
TSVLSEDNSIQTMITFDQGGRWTHLR KPENSEC-
DATAKNKNECSLHIHASYSISQKLNVPMA-
PLSEPNAVGIVIAHGSVGDAISVMVPDVY
ISDDGGYSWTKMLEGPHYYTILDSG-
GIIVAIEHSSRPINVIKFSTDE-
GQCWQTYTFTRDPIYFTGL ASEPGARSM-
NISIWGFTESFLTSQWVSYTIDFKDILERNCEEK-
DYTIWLAHSTDPEDYEDGCILG
YKEQFLRLRKSSVCQNGRDYVVTKQPSI-
CLCSLEDFLCDFGYYRPEND-
SKCVEQPELKGHDLE
FCLYGREEHLTTNGYRKIPGDKCQGGVNPVRE-
VKDLKKKCTSNFLSPEKQNSKSNSGGSGGS
GGSHHHHHHHH
SEQ ID NO:217 amino acid sequence of hSORT1_ECD_Emut2a:
MERPWGAADGLSRWPHGLGLLLLLQLLPP-
STLSQDRLDAPPPPAAPLPRWSGPIGVSWGLRA
AAAGGAFPRGGRWRRSAPGEDEECGRVRDF-
VAKLANNTHQHVFDDLRGSVSLSWVGDSTG
VILVLTTAAVPLAIATFGQSK-
LYRSEDYGKNFKDITDLINNTFIRTEFGMAIG-
PENSGKVVLTAEVS GGSRGGRIFRSSD-
FAKNFVQTDLPFHPLTQMMYSPQNSDYLLALS-
TENGLWVSKNFGGKWEE IHKAVCLAKWGSDN-
TIFFTTYANGSCKADL-
GALELWRTSDLGKSFKTIGVKIYSFGLGGRFL-
FAS
VMADKDTTRRIHVSTDQGDTWS- MAQLPSVGQEQFYSI-LAANDDMVFMHVDEPGDTGFGTIFT SDDR-GIVYSKSLDRHLYTTTGGETDFTNVTSLRGVYI-TSVLSEDNSIQTMITFDQGGRWTHLRK PENSEC-DATAKNKNECSLHIHASYSISQKLNVPMA-PLSEPNAVGIVIAHGSVGDAISVMVPDVYI SDDGGYSWTKMLEGPHYYTILDSG-GIIVAIEHSSRPINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH SEQ ID NO:218 amino acid sequence of hSORT1_ECD_Emut2b:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTAGASALAR-SEDYGKNFKDITDLINNTFIRTEFGMAIG-PENSGKVVLTAEVS GGSRGGRIFRSSD-FAKNFVQTDLPFHPLTQMMYSPQNSDYLLALS-TENGLWVSKNFGGKWEE IHKAVCLAKWGSDN-TIFFTTYANGSCKADL-GALELWRTSDLGKSFKTIGVKIYSFGLGGRFL-FAS VMADKDTTRRIHVSTDQGDTWS-MAQLPSVGQEQFYSI-LAANDDMVFMHVDEPGDTGFGTIFT SDDR-GIVYSKSLDRHLYTTTGGETDFTNVTSLRGVYI-TSVLSEDNSIQTMITFDQGGRWTHLRK PENSEC-DATAKNKNECSLHIHASYSISQKLNVPMA-PLSEPNAVGIVIAHGSVGDAISVMVPDVYI SDDGGYSWTKMLEGPHYYTILDSG-GIIVAIEHSSRPINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:219 amino acid sequence of hSORT1_ECD_Emut3:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKAITALINAAFIRTEFGMAIG-PENSGKVVLTAEVS GGSRGGRIFRSSD-FAKNFVQTDLPFHPLTQMMYSPQNSDYLLALS-TENGLWVSKNFGGKWEE IHKAVCLAKWGSDN-TIFFTTYANGSCKADL-GALELWRTSDLGKSFKTIGVKIYSFGLGGRFL-FAS VMADKDTTRRIHVSTDQGDTWS-MAQLPSVGQEQFYSI-LAANDDMVFMHVDEPGDTGFGTIFT SDDR-GIVYSKSLDRHLYTTTGGETDFTNVTSLRGVYI-TSVLSEDNSIQTMITFDQGGRWTHLRK PENSEC-DATAKNKNECSLHIHASYSISQKLNVPMA-PLSEPNAVGIVIAHGSVGDAISVMVPDVYI SDDGGYSWTKMLEGPHYYTILDSG-GIIVAIEHSSRPINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:220 amino acid sequence of hSORT1_ECD_Emut4:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEA AGGAAGGAIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:221 amino acid sequence of hSORT1_ECD_Emut5:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSDFAKNF-VATALPFAPLTQMMYSPQNSDYLLALSTENGLWV-SKNFGGKWE EIHKAVCLAKWGSDNTIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-

GQCWQTYTFTRDPIYFTGL ASEPGARSMNISIWGFTESFLTSQWVSYTIDFKDILERNCEEKDYTIWLAHSTDPEDYEDGCILG YKEQFLRLRKSSVCQNGRDYVVTKQPSICLCSLEDFLCDFGYYRPENDSKCVEQPELKGHDLE FCLYGREEHLTTNGYRKIPGDKCQGGVNPVREVKDLKKKCTSNFLSPEKQNSKSNSGGSGGS GGSHHHHHHHH

SEQ ID NO:222 amino acid sequence of hSORT1_ECD_Emut6N:

MERPWGAADGLSRWPHGLGLLLLLQLLPPSTLSQDRLDAPPPPAAPLPRWSGPIGVSWGLRA AAAGGAFPRGGRWRRSAPGEDEECGRVRDFVAKLANNTHQHVFDDLRGSVSLSWVGDSTG VILVLTTFHVPLVIMTFGQSKLYRSEDYGKNFKDITDLINNTFIRTEFGMAIGPENSGKVVLTAEV SGGSRGGRIFRSSDFAKNFVQTDLPFHPLTQMMYSPQNSDYLLALSTANGLAVSKNFGGKWE AIAAAVCLAKWGSDNTIFFTTYANGSCKADLGALELWRTSDLGKSFKTIGVKIYSFGLGGRFLFA SVMADKDTTRRIHVSTDQGDTWSMAQLPSVGQEQFYSILAANDDMVFMHVDEPGDTGFGTIF TSDDRGIVYSKSLDRHLYTTTGGETDFTNVTSLRGVYITSVLSEDNSIQTMITFDQGGRWTHLR KPENSECDATAKNKNECSLHIHASYSISQKLNVPMAPLSEPNAVGIVIAHGSVGDAISVMVPDVY ISDDGGYSWTKMLEGPHYYTILDSGGIIVAIEHSSRPINVIKFSTDEGQCWQTYTFTRDPIYFTGL ASEPGARSMNISIWGFTESFLTSQWVSYTIDFKDILERNCEEKDYTIWLAHSTDPEDYEDGCILG YKEQFLRLRKSSVCQNGRDYVVTKQPSICLCSLEDFLCDFGYYRPENDSKCVEQPELKGHDLE FCLYGREEHLTTNGYRKIPGDKCQGGVNPVREVKDLKKKCTSNFLSPEKQNSKSNSGGSGGS GGSHHHHHHHH

SEQ ID NO:223 amino acid sequence of hSORT1_ECD_Emut8N:

MERPWGAADGLSRWPHGLGLLLLLQLLPPSTLSQDRLDAPPPPAAPLPRWSGPIGVSWGLRA AAAGGAFPRGGRWRRSAPGEDEECGRVRDFVAKLANNTHQHVFDDLRGSVSLSWVGDSTG VILVLTTFHVPLVIMTFGQSKLYRSEDYGKNFKDITDLINNTFIRTEFGMAIGPENSGKVVLTAEV SGGSRGGRIFRSSDFAKNFVQTDLPFHPLTQMMYSPQNSDYLLALSTENGLWVSKNFGGKWE EIHKAVCLAKWGSDNTIFFTTAANGSCAADAGALELWRTSDLGKSFKTIGVKIYSFGLGGRFLFA SVAAAAATTRRIHVSTDQGDTWSMAQLPSVGAAQAYSILAANDDMVFMHVDEPGDTGFGTIFT SDDRGIVYSKSLDRHLYTTTGGETDFTNVTSLRGVYITSVLSEDNSIQTMITFDQGGRWTHLRK PENSECDATAKNKNECSLHIHASYSISQKLNVPMAPLSEPNAVGIVIAHGSVGDAISVMVPDVYI SDDGGYSWTKMLEGPHYYTILDSGGIIVAIEHSSRPINVIKFSTDEGQCWQTYTFTRDPIYFTGL ASEPGARSMNISIWGFTESFLTSQWVSYTIDFKDILERNCEEKDYTIWLAHSTDPEDYEDGCILG YKEQFLRLRKSSVCQNGRDYVVTKQPSICLCSLEDFLCDFGYYRPENDSKCVEQPELKGHDLE FCLYGREEHLTTNGYRKIPGDKCQGGVNPVREVKDLKKKCTSNFLSPEKQNSKSNSGGSGGS GGSHHHHHHHH

SEQ ID NO:224 amino acid sequence of hSORT1_ECD_Emut11N:

MERPWGAADGLSRWPHGLGLLLLLQLLPPSTLSQDRLDAPPPPAAPLPRWSGPIGVSWGLRA AAAGGAFPRGGRWRRSAPGEDEECGRVRDFVAKLANNTHQHVFDDLRGSVSLSWVGDSTG VILVLTTFHVPLVIMTFGQSKLYRSEDYGKNFKDITDLINNTFIRTEFGMAIGPENSGKVVLTAEV SGGSRGGRIFRSSDFAKNFVQTDLPFHPLTQMMYSPQNSDYLLALSTENGLWVSKNFGGKWE EIHKAVCLAKWGSDNTIFFTTYANGSCKADLGALELWRTSDLGKSFKTIGVKIYSFGLGGRFLFA SVMADKDTTRRIHVSTDQGDTWSMAQLPSVGQEQFYSILAANDDMVFMHVAEPGAAGFGTIF TSDDRGIVYSKSLDRHLATAAGGETDFTNVTSLRGVYITSVASADASAQTMITFDQGGRWTHL RKPENSECDATAKNKNECSLHIHASYSISQKLNVPMAPLSEPNAVGIVIAHGSVGDAISVMVPD VYISDDGGYSWTKMLEGPHYYTILDSGGIIVAIEHSSRPINVIKFSTDEGQCWQTYTFTRDPIYFT GLASEPGARSMNISIWGFTESFLTSQWVSYTIDFKDILERNCEEKDYTIWLAHSTDPEDYEDGCI LGYKEQFLRLRKSSVCQNGRDYVVTKQPSICLCSLEDFLCDFGYYRPENDSKCVEQPELKGHD LEFCLYGREEHLTTNGYRKIPGDKCQGGVNPVREVKDLKKKCTSNFLSPEKQNSKSNSGGSG GSGGSHHHHHHHH

SEQ ID NO:225 amino acid sequence of hSORT1_ECD_Emut14N:

MERPWGAADGLSRWPHGLGLLLLLQLLPPSTLSQDRLDAPPPPAAPLPRWSGPIGVSWGLRA AAAGGAFPRGGRWRRSAPGEDEECGRVRDFVAKLANNTHQHVFDDLRGSVSLSWVGDSTG VILVLTTFHVPLVIMTFGQSKLYRSEDYGKNFKDITDLINNTFIRTEFGMAIGPENSGKVVLTAEV SGGSRGGRIFRSSDFAKNFVQTDLPFHPLTQMMYSPQNSDYLLALSTENGLWVSKNFGGKWE EIHKAVCLAKWGSDNTIFFTTYANGSCKADLGALELWRTSDLGKSFKTIGVKIYSFGLGGRFLFA SVMADKDTTRRIHVSTDQGDTWSMAQLPSVGQEQFYSILAANDDMVFMHVDEPGDTGFGTIF TSDDRGIVYSKSLDRHLYTTTGGETDFTNVTSLRGVYITSVLSEDNSIQTMITFDQGGRWTHLR KPENSECDATAKNKNECSLHIHASYSISAKAAVPMAPLSEPNAVGIVIAHGSVGAAASVMAPAV YISDDGGYSWTKMLEGPHYYTILDSGGIIVAIEHSSRPINVIKFSTDEGQCWQTYTFTRDPIYFTG LASEPGARSMNISIWGFTESFLTSQWVSYTIDFKDILERNCEEKDYTIWLAHSTDPEDYEDGCIL GYKEQFLRLRKSSVCQNGRDYVVTKQPSICLCSLEDFLCDFGYYRPENDSKCVEQPELKGHDL EFCLYGREEHLTTNGYRKIPGDKCQGGVNPVREVKDLKKKCTSNFLSPEKQNSKSNSGGSGG SGGSHHHHHHHH

SEQ ID NO:226 amino acid sequence of hSORT1_ECD_Emut16:

MERPWGAADGLSRWPHGLGLLLLLQLLPPSTLSQDRLDAPPPPAAPLPRWSGPIGVSWGLRA AAAGGAFPRGGRWRRSAPGEDEECGRVRDFVAKLANNTHQHVFDDLRGSVSLSWVGDSTG

VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTAMLAGPAYYTILDSG-GIIVAIEHSSRPINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:227 amino acid sequence of hSORT1_ECD_Emut17:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSGGIIVAIA-HASAPIAVIKFSTDEGQCWQTYTFTRDPIYFTGL ASEPGARSMNISIWGFTESFLTSQWV-SYTIDFKDILERNCEEKDYTIWLAH-STDPEDYEDGCILG YKEQFLRLRKSSVCQN-GRDYVVTKQPSICLCSLEDFLCDFGYYRPENDS-KCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:228 amino acid sequence of hSORT1_ECD_Emut18:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYAFTADPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:229 amino acid sequence of hSORT1_ECD_Emut19:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTAAAATSQWVSYTIDFKDILERNCEE-KDYTIWLAHSTDPEDYEDGCIL GYKEQFLRLRKSSVCQNGRDYVVTKQPSI-CLCSLEDFLCDFGYYRPEND-SKCVEQPELKGHDL EFCLYGREEHLTTNGYRKIPGDKCQGGVNPVR-EVKDLKKKCTSNFLSPEKQNSKSNSGGSGG SGGSHHHHHHHH

SEQ ID NO:230 amino acid sequence of hSORT1_ECD_Emut20:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDALRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-

TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:231 amino acid sequence of hSORT1_ECD_Emut21:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLAGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:232 amino acid sequence of hSORT1_ECD_Emut22:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTAHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO: 233 amino acid sequence of hSORT1_ECD_Emut23:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVI-MTFGQSALYRSEDYGKNFKDITDLINNTFIR-TEFGMAIGPENSGKVVLTAEV SGGSRGGRI-FRSSDFAKNFVQTDLPFHPLTQMMYSPQNSDY-LLALSTENGLWVSKNFGGKWE EIHKAVCLAKWGSDNTIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:234 amino acid sequence of hSORT1_ECD_Emut24:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTESFATSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-

SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO: 235 amino acid sequence of hSORT1_ECD_Emut25:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTESFLASQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO: 236 amino acid sequence of hSORT1_ECD_Emut26:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTESFLTSAWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:237 amino acid sequence of hSORT1_ECD_Emut27:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRAINVIKFSTDE-GQCWQTYTFTRDPIYFTGL ASEPGARSM-NISIWGFTESFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:238 amino acid sequence of hSORT1_ECD_Emut28:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDEGQCWQTYTFTR-DAIYFTGL ASEPGARSMNISIWGFTESFLTSQWV-SYTIDFKDILERNCEEKDYTIWLAHSTDPEDYE-DGCILG YKEQFLRLRKSSVCQN-GRDYVVTKQPSICLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:239 amino acid sequence of hSORT1_ECD_Emut29:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG

VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDEGQCWQTYTFTRD-PIAFTGL ASEPGARSMNISIWGFTESFLTSQWV-SYTIDFKDILERNCEEKDYTIWLAHSTDPEDYE-DGCILG YKEQFLRLRKSSVCQN-GRDYVVTKQPSICLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:240 amino acid sequence of hSORT1_ECD_Emut30:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTASFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:241 amino acid sequence of hSORT1_ECD_Emut31:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTESALTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO:242 amino acid sequence of hSORT1_ECD_Emut32:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEFGMAIG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-TSVLSEDNSIQTMITFDQGGRWTHLR KPENSEC-DATAKNKNECSLHIHASYSISQKLNVPMA-PLSEPNAVGIVIAHGSVGDAISVMVPDVY ISDDGGYSWTKMLEGPHYYTILDSG-GIIVAIEHSSRPINVIKFSTDE-GQCWQTYTFTRDPIYFTGL ASEPGARSM-NISIWGFTEAFLTSQWVSYTIDFKDILERNCEEK-DYTIWLAHSTDPEDYEDGCILG YKEQFLRLRKSSVCQNGRDYVVTKQPSI-CLCSLEDFLCDFGYYRPEND-SKCVEQPELKGHDLE FCLYGREEHLTTNGYRKIPGDKCQGGVNPVRE-VKDLKKKCTSNFLSPEKQNSKSNSGGSGGS GGSHHHHHHHH

SEQ ID NO: 243 amino acid sequence of hSORT1_ECD_Emut33:

MERPWGAADGLSRWPHGLGLLLLLQLLPP-STLSQDRLDAPPPPAAPLPRWSGPIGVSWGLRA AAAGGAFPRGGRWRRSAPGEDEECGRVRDF-VAKLANNTHQHVFDDLRGSVSLSWVGDSTG VILVLTTFHVPLVIMTFGQSK-LYRSEDYGKNFKDITDLINNTFIRTEAGMAAG-PENSGKVVLTAEV SGGSRGGRIFRSSD-FAKNFVQTDLPFHPLTQMMYSPQNSDYLLALS-TENGLWVSKNFGGKWE EIHKAVCLAKWGSDN-TIFFTTYANGSCKADL-GALELWRTSDLGKSFKTIGVKIYSFGLGGRFLFA SVMADKDTTRRIHVSTDQGDTWS-MAQLPSVGQEQFYSI-LAANDDMVFMHVDEPGDTGFGTIF TSDDR-GIVYSKSLDRHLYTTTGGETDFTNVTSLRGVYI-

TSVLSEDNSIQTMITFDQGGRWTHLR KPENSEC-
DATAKNKNECSLHIHASYSISQKLNVPMA-
PLSEPNAVGIVIAHGSVGDAISVMVPDVY
ISDDGGYSWTKMLEGPHYYTILDSG-
GIIVAIEHSSRPINVIKFSTDE-
GQCWQTYTFTRDPIYFTGL ASEPGARSM-
NISIWGFTESFLTSQWVSYTIDFKDILERNCEEK-
DYTIWLAHSTDPEDYEDGCILG
YKEQFLRLRKSSVCQNGRDYVVTKQPSI-
CLCSLEDFLCDFGYYRPEND-
SKCVEQPELKGHDLE
FCLYGREEHLTTNGYRKIPGDKCQGGVNPVRE-
VKDLKKKCTSNFLSPEKQNSKSNSGGSGGS
GGSHHHHHHHH

SEQ ID NO:244 hu11M14_H1b_IgG1 LALA_YTE—Heavy chain amino acid sequence:

EVQLVESGGGLVQPGGSLRLS-
CAASGFTFNIYGMSWVRQAPGKGLEWVATIS-
SGGIYTY YPDILKGRFTISRDNAKNS-
LYLQMNSLRAEDTAVYYCARHPGGAMDYWG
QGTL VTVSS ASTKGPSVFPLAPSSKST-
SGGTAALGCLVKDYFPEPVTVSWNSGALT-
SGVHTFPAVLQSS GLYS-
LSSVVTVPSSSLGTQTYICNVNHKPSNTKVDKKVE-
PKSCDKTHTCPPCPAPEAAG
GPSVFLFPPKPKDTLYITREPE-
VTCVVVDVSHEDPE-
VKFNWYVDGVEVHNAKTKPREEQ
YNSTYRVVSVLTVLHQDWLNGKEYKCKVSNKA-
LPAPIEKTISKAKGQPREPQVYTLPPS REEMT-
KNQVSLTCLVKGFYPSDIAVEWESNGQPEN-
NYKTTPPVLDSDGSFFLYSKLTVD
KSRWQQGNVFSCSVMHEALHNHYTQKSLSL-
SPGK

SEQ ID NO:245 hu11M14_L3b—Light chain amino acid sequence:

DIQMTQSPSSLSASVGDRVTITCRVSENIYSN-
LAWYQQKPGKSPKLLVYAATNGADGVP
SRFSGSGSGTDYTLTISSLQPEDFA-
TYYCQHFWGTPPWTFGQGTKLEIKRTVAAPSV-
FIFP PSDEQLKSGTASVVCLLNNFY-
PREAKVQWKVDNALQSGNSQESVTEQDSKDS-
TYSLSST LTLSKADYEKHKVYACE-
VTHQGLSSPVTKSFNRGEC

SEQ ID NO:246 hu 8H24_H1 IgG1 LALA_YTE—Heavy chain amino acid sequence:

QAQLVQSGAEVKKPGSSVKVSCKASGYTFTSYS-
MHWVRQAPGQGLEWIGAIYPGNDA TSYN-
QKFKGRATLTVDKSTSTAYMELSSLRSED-
TAVYFCAREGYYGSSFEAWFASWGQ
GTTVTVSSASTKGPSVFPLAPSSKSTSGGTAAL-
GCLVKDYFPEPVTVSWNSGALTSGVHT
FPAVLQSSGLYS-
LSSVVTVPSSSLGTQTYICNVNHKPSNTKVDK-
KVEPKSCDKTHTCPPC
PAPEAAGGPSVFLFPPKPKDTLYITREPE-
VTCVVVDVSHEDPEVKFNWYVDGVEVHNAK
TKPREEQYN-
STYRVVSVLTVLHQDWLNGKEYKCKVSNKAL-
PAPIEKTISKAKGQPREPQ VYTLPPSREEMT-
KNQVSLTCLVKGFYPSDIAVEWESNGQPENNY-
KTTPPVLDSDGSFFL YSK-
LTVDKSRWQQGNVFSCSVMHEALHN-
HYTQKSLSLSPGK

SEQ ID NO:247 hu8H24_L2—Light chain amino acid sequence:

DVVMTQTPSSLPVTPGEPASISCRSSQSIVHSNGN-
TYLEWYLQKPGQSPQLLIYKVSNRFS
GVPDRFSGSGSGTDFTLTISRVEAE-
DVGVYYCFQGSHVLPTFGGGTKVEIKRTVAAP-
SVF IFPPSDEQLKSGTASVVCLLNNFY-
PREAKVQWKVDNALQSGNSQESVTEQDSKDS-
TYSL SSTLTLSKADYEKHKVYACE-
VTHQGLSSPVTKSFNRGEC

SEQ ID NO:248 hu5E20_H7_IgG1 LALA_YTE—Heavy chain amino acid sequence:

EVQLVESGGGLVQPGGSLRLSCAASGFTF-
STYGMSWVRQTPDKRLEWVAIISSGGSYTY
YSDTVKGRFTISRDNSKNSLYLQMNSLRAED-
TAVYYCSRSSSHWYFDVWGQGTLVTVS SAS-
TKGPSVFPLAPSSKSTSGGTAALGCLVKDYF-
PEPVTVSWNSGALTSGVHTFPAVLQS
SGLYS-
LSSVVTVPSSSLGTQTYICNVNHKPSNTKVDK-
KVEPKSCDKTHTCPPCPAPEAAG
GPSVFLFPPKPKDTLYITREPE-
VTCVVVDVSHEDPE-
VKFNWYVDGVEVHNAKTKPREEQ
YNSTYRVVSVLTVLHQDWLNGKEYKCKVSNKA-
LPAPIEKTISKAKGQPREPQVYTLPPS REEMT-
KNQVSLTCLVKGFYPSDIAVEWESNGQPEN-
NYKTTPPVLDSDGSFFLYSKLTVD
KSRWQQGNVFSCSVMHEALHNHYTQKSLSL-
SPGK

SEQ ID NO:249 hu5E20 L4-Light chain amino acid sequence:

DIQMTQSPSSVSASVGDRVTITCHASQ-
GISSNIGWLQQKPGKAFKGLIYHGTNLKDGVPS
RFSGSGSGADFTLTISSLQPED-
FADYFCVQYAQFPY-
TFGQGTKVEKRRTVAAPSVFIFPPS DEQLKSG-
TASVVCLLNNFYPREAKVQWKVDNALQSGNS-
QESVTEQDSKDSTYSLSSTL TLSKADYEKHKVY-
ACEVTHQGLSSPVTKSFNRGEC

SEQ ID NO:250 hu11M14VHv1b_IgG1_LALA heavy chain amino acid sequence

EVQLVESGGGLVQPGGSLRLS-
CAASGFTFNIYGMSWVRQAPGKGLEWVATIS-
SGGIYTY YPDILKGRFTISRDNAKNS-
LYLQMNSLRAEDTAVYYCARHPGGAMDYWG-
QGTLVTVSS ASTKGPSVFPLAPSSKSTSGGTAAL-
GCLVKDYFPEPVTVSWNSGALT-
SGVHTFPAVLQSS GLYS-
LSSVVTVPSSSLGTQTYICNVNHKPSNTKVDKK-
VEPKSCDKTHTCPPCPAPEAAG
GPSVFLFPPKPKDTLMISRTPE-
VTCVVVDVSHEDPE-
VKFNWYVDGVEVHNAKTKPREEQ
YNSTYRVVSVLTVLHQDWLNGKEYKCKVSNKA-
LPAPIEKTISKAKGQPREPQVYTLPPS REEMT-
KNQVSLTCLVKGFYPSDIAVEWESNGQPEN-
NYKTTPPVLDSDGSFFLYSKLTVD
KSRWQQGNVFSCSVMHEALHNHYTQKSLSL-
SPGK

SEQ ID NO:251 hu8H24_H1_IgG1_LALA heavy chain amino acid sequence

QAQLVQSGAEVKKPGSSVKVSCKASGYTFTSYS-MHWVRQAPGQGLEWIGAIYPGNDA TSYN-QKFKGRATLTVDKSTSTAYMELSSLRSED-TAVYFCAREGYYGSSFEAWFASWGQ GTTVTVSSASTKGPSVFPLAPSSKSTSGGTAAL-GCLVKDYFPEPVTVSWNSGALTSGVHT FPAVLQSSGLYS-LSSVVTVPSSSLGTQTYICNVNHKPSNTKVDK-KVEPKSCDKTHTCPPC PAPEAAGGPSVFLFPPKPKDTLMISRTPE-VTCVVVDVSHEDPEVKFNWYVDGVEVHNA KTKPREEQYN-STYRVVSVLTVLHQDWLNGKEYKCKVSNKAL-PAPIEKTISKAKGQPREP QVYTLPPSREEMT-KNQVSLTCLVKGFYPSDIAVEWESNGQPENNY-KTTPPVLDSDGSFF LYSK-LTVDKSRWQQGNVFSCSVMHEALHN-HYTQKSLSLSPGK

SEQ ID NO:252 hu5E20 H7_IgG1_LALA heavy chain amino acid sequence

EVOLVESGGGLVQPGGSLRLSCAASGFTF-STYGMSWVRQTPDKRLEWVAIISSGG-SYTYYSDTV KGRFTISRDNSKNSLYLOMNSL-RAEDTAVYYCSRSSSHWYFDVWGQGTLVTVS-SASTKGPSVFP LAPSSKSTSGGTAAL-GCLVKDYFPEPVTVSWNSGALT-SGVHTFPAVLQSSGLYSLSSVVTVPSS SLGTQTYICNVNHKPSNTKVDKKVE-PKSCDKTHTCPPCPA-PEAAGGPSVFLFPPKPKDTLMISR TPE-VTCVVVDVSHEDPEVKFNWYVDGVEVHNAK-TKPREEQYNSTYRVVSVLTVLHQDWLNGKEY KCKVSNKALPA-PIEKTISKAKGQPREPQVYTLPPSREEMT-KNQVSLTCLVKGFYPSDIAVEWES NGQPEN-NYKTTPPVLDSDGSFFLYSKLTVDKSRWQQGN-VFSCSVMHEALHNHYTQKSLSLSPGK

---

What is claimed is:

1. A humanized antibody specifically binding to sortilin, comprising three light chain CDRs and three heavy chain CDRs of a mouse antibody characterized by a heavy chain variable region having an amino acid sequence comprising SEQ ID NO: 52 and a light chain variable region having an amino acid sequence comprising SEQ ID NO: 58, except that Kabat position L54 can be L, G, or I.

2. The humanized antibody of claim 1, wherein the humanized antibody comprises a humanized mature heavy chain variable region comprising the three Kabat/Chothia Composite heavy chain CDRs of SEQ ID NOs: 53-55 and a humanized mature light chain variable region comprising the three Kabat/Chothia Composite light chain CDRs of SEQ ID NOs: 59-61, except that Kabat position L54 can be L, G, or I.

3. The humanized antibody of claim 1, comprising a humanized mature heavy chain variable region having an amino acid sequence at least 90% identical to any one of SEQ ID NOs: 190-192, and a humanized mature light chain variable region having an amino acid sequence at least 90% identical to any one of SEQ ID NOs: 196-199.

4. The humanized antibody of claim 3, wherein at least one of the following positions is occupied by the amino acid as specified: Kabat position H49 is occupied by A, Kabat position H80 is occupied by L or G, and Kabat position H82c is occupied by L or G.

5. The humanized antibody of claim 4, provided Kabat position H49 is occupied by A.

6. The humanized antibody of claim 4, provided Kabat positions H49 and H82c are occupied by A and G, respectively.

7. The humanized antibody of claim 4, provided Kabat positions H49 and H80 are occupied by A and G, respectively.

8. The humanized antibody of claim 3, wherein at least one of the following positions is occupied by the amino acid as specified: Kabat position L43 is A or S, Kabat position L48 is V, Kabat position L54 is L, G, or I, Kabat position L71 is Y, and Kabat position L76 is N or S.

9. The humanized antibody of claim 8, provided Kabat positions L48 and L71 are occupied by V and Y respectively.

10. The humanized antibody of claim 8, provided Kabat positions L43, L48, L71, and L76 are occupied by S, V, Y, and S, respectively.

11. The humanized antibody of claim 8, provided Kabat positions L43, L48, L54, L71, and L76 are occupied by S, V, G, Y, and S, respectively.

12. The humanized antibody of claim 8, provided Kabat positions L43, L48, L54, L71, and L76 are occupied by S, V, I, Y, and S, respectively.

13. The humanized antibody of claim 3, comprising a humanized mature heavy chain variable region having an amino acid sequence at least 95% identical to at least one of SEQ ID NOs: 190-192 and a humanized mature light chain variable region having an amino acid sequence at least 95% identical to at least one of SEQ ID NOs: 196-199.

14. The humanized antibody of claim 13, wherein the humanized mature heavy chain variable region has an amino acid sequence of any one of SEQ ID NOs: 190-192, and the humanized mature light chain variable region has an amino acid sequence of any one of SEQ ID NOs: 196-199.

15. The humanized antibody of claim 14, wherein:

the humanized mature heavy chain variable region has an amino acid sequence of SEQ ID NO: 190 and the humanized mature light chain variable region has an amino acid sequence of SEQ ID NO: 196;

the humanized mature heavy chain variable region has an amino acid sequence of SEQ ID NO:190 and the humanized mature light chain variable region has an amino acid sequence of SEQ ID NO:197;

the humanized mature heavy chain variable region has an amino acid sequence of SEQ ID NO:190 and the humanized mature light chain variable region has an amino acid sequence of SEQ ID NO:198;

the humanized mature heavy chain variable region has an amino acid sequence of SEQ ID NO:190 and the humanized mature light chain variable region has an amino acid sequence of SEQ ID NO:199;

the humanized mature heavy chain variable region has an amino acid sequence of SEQ ID NO:191 and the humanized mature light chain variable region has an amino acid sequence of SEQ ID NO:196;

the humanized mature heavy chain variable region has an amino acid sequence of SEQ ID NO:191 and the humanized mature light chain variable region has an amino acid sequence of SEQ ID NO:197;

the humanized mature heavy chain variable region has an amino acid sequence of SEQ ID NO: 191 and the humanized mature light chain variable region has an amino acid sequence of SEQ ID NO: 198;

the humanized mature heavy chain variable region has an amino acid sequence of SEQ ID NO:191 and the humanized mature light chain variable region has an amino acid sequence of SEQ ID NO:199;

the humanized mature heavy chain variable region has an amino acid sequence of SEQ ID NO:192 and the humanized mature light chain variable region has an amino acid sequence of SEQ ID NO:196;

the humanized mature heavy chain variable region has an amino acid sequence of SEQ ID NO:192 and the humanized mature light chain variable region has an amino acid sequence of SEQ ID NO:197;

the humanized mature heavy chain variable region has an amino acid sequence of SEQ ID NO:192 and the humanized mature light chain variable region has an amino acid sequence of SEQ ID NO:198; or the humanized mature heavy chain variable region has an amino acid sequence of SEQ ID NO:192 and the humanized mature light chain variable region has an amino acid sequence of SEQ ID NO:199.

16. The humanized antibody of claim 1 that is an intact antibody.

17. The humanized antibody of claim 1 that is an antigen-binding antibody fragment.

18. The humanized antibody of claim 1, wherein the humanized antibody has an isotype of human IgG1.

19. The humanized antibody of claim 2, wherein the humanized mature light chain variable region is fused to a light chain constant region and the humanized mature heavy chain variable region is fused to a heavy chain constant region.

20. The humanized antibody of claim 19, wherein the heavy chain constant region is a mutant form of a natural human heavy chain constant region which has reduced binding to a Fcγ receptor relative to the natural human heavy chain constant region.

21. The humanized antibody of claim 19, wherein the heavy chain constant region is a mutant form of a natural human heavy chain constant region which has enhanced binding to a neonatal Fcγ receptor relative to the natural human heavy chain constant region.

22. The humanized antibody of claim 19, comprising:

a heavy chain of SEQ ID NO: 244 and a light chain of SEQ ID NO: 245;

a heavy chain of SEQ ID NO: 246 and a light chain of SEQ ID NO: 247;

a heavy chain of SEQ ID NO: 248 and a light chain of SEQ ID NO: 249;

a heavy chain of SEQ ID NO: 250 and a light chain of SEQ ID NO: 245;

a heavy chain of SEQ ID NO:251 and a light chain of SEQ ID NO:247; or a heavy chain of SEQ ID NO: 252 and a light chain of SEQ ID NO: 249.

23. The humanized antibody of claim 1, wherein the humanized antibody has a human IgG2 or IgG4 isotype.

24. A nucleic acid encoding a heavy chain and/or light chain of the humanized antibody of claim 1.

25. A pharmaceutical composition comprising the humanized antibody of claim 1 and a pharmaceutically-acceptable carrier.

26. A method of detecting sortilin in a subject having or at risk of a disease associated with a disease or disorder associated with changes in progranulin levels, comprising administering to a subject the humanized antibody of claim 1, and detecting the antibody bound to sortilin in the subject.

27. A method of increasing progranulin levels in a subject having or at risk of developing a disease or disorder associated with changes in progranulin levels, comprising administering to the subject an effective dose of the humanized antibody of claim 1, thereby increasing progranulin levels in the subject.

* * * * *

SEQUENCE LISTING

```
<160> NUMBER OF SEQ ID NOS: 252

<210> SEQ ID NO 1
<211> LENGTH: 756
<212> TYPE: PRT
<213> ORGANISM: Homo sapiens

<400> SEQUENCE: 1

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220
```

-continued

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

Ala Asn Gly Ser Cys Lys Ala Asp Leu Gly Ala Leu Glu Leu Trp Arg
275 280 285

Thr Ser Asp Leu Gly Lys Ser Phe Lys Thr Ile Gly Val Lys Ile Tyr
290 295 300

Ser Phe Gly Leu Gly Gly Arg Phe Leu Phe Ala Ser Val Met Ala Asp
305 310 315 320

Lys Asp Thr Thr Arg Arg Ile His Val Ser Thr Asp Gln Gly Asp Thr
325 330 335

Trp Ser Met Ala Gln Leu Pro Ser Val Gly Gln Glu Gln Phe Tyr Ser
340 345 350

Ile Leu Ala Ala Asn Asp Asp Met Val Phe Met His Val Asp Glu Pro
355 360 365

Gly Asp Thr Gly Phe Gly Thr Ile Phe Thr Ser Asp Asp Arg Gly Ile
370 375 380

Val Tyr Ser Lys Ser Leu Asp Arg His Leu Tyr Thr Thr Thr Gly Gly
385 390 395 400

Glu Thr Asp Phe Thr Asn Val Thr Ser Leu Arg Gly Val Tyr Ile Thr
405 410 415

Ser Val Leu Ser Glu Asp Asn Ser Ile Gln Thr Met Ile Thr Phe Asp
420 425 430

Gln Gly Gly Arg Trp Thr His Leu Arg Lys Pro Glu Asn Ser Glu Cys
435 440 445

Asp Ala Thr Ala Lys Asn Lys Asn Glu Cys Ser Leu His Ile His Ala
450 455 460

Ser Tyr Ser Ile Ser Gln Lys Leu Asn Val Pro Met Ala Pro Leu Ser
465 470 475 480

Glu Pro Asn Ala Val Gly Ile Val Ile Ala His Gly Ser Val Gly Asp
485 490 495

Ala Ile Ser Val Met Val Pro Asp Val Tyr Ile Ser Asp Asp Gly Gly
500 505 510

Tyr Ser Trp Thr Lys Met Leu Glu Gly Pro His Tyr Tyr Thr Ile Leu
515 520 525

Asp Ser Gly Gly Ile Ile Val Ala Ile Glu His Ser Ser Arg Pro Ile
530 535 540

Asn Val Ile Lys Phe Ser Thr Asp Glu Gly Gln Cys Trp Gln Thr Tyr
545 550 555 560

Thr Phe Thr Arg Asp Pro Ile Tyr Phe Thr Gly Leu Ala Ser Glu Pro
565 570 575

Gly Ala Arg Ser Met Asn Ile Ser Ile Trp Gly Phe Thr Glu Ser Phe
580 585 590

Leu Thr Ser Gln Trp Val Ser Tyr Thr Ile Asp Phe Lys Asp Ile Leu
595 600 605

Glu Arg Asn Cys Glu Glu Lys Asp Tyr Thr Ile Trp Leu Ala His Ser
610 615 620

Thr Asp Pro Glu Asp Tyr Glu Asp Gly Cys Ile Leu Gly Tyr Lys Glu
625 630 635 640

```
Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser
        755


<210> SEQ ID NO 2
<211> LENGTH: 411
<212> TYPE: DNA
<213> ORGANISM: Artificial sequence
<220> FEATURE:
<223> OTHER INFORMATION: Synthesized

<400> SEQUENCE: 2

atgaacttcg ggctcagctt gattttcctt gcccttattt taaaaggtgt ccagtgtgag      60

gtgcagctgg tggagtctgg gggagactta gtgaagcctg gagggtccct gaaactctcc     120

tgtgcagccc ctggattcac tttcagtact tatggcatgt cttgggttcg ccagactcca     180

gacaagaggc tggagtgggt cgcaatcatt agtagtggtg gtagttacac ctactattca     240

gacactgtga aggggcgatt caccatctcc agagacaatg ccaagaacac cctgtacctg     300

caaatgagca gtctgaagtc tgaggacaca gccatgtatt attgttcaag gagtagtagc     360

cactggtatt tcgatgtctg gggcacaggg accacggtca ccgtctcctc a              411


<210> SEQ ID NO 3
<211> LENGTH: 19
<212> TYPE: PRT
<213> ORGANISM: Artificial sequence
<220> FEATURE:
<223> OTHER INFORMATION: Synthesized

<400> SEQUENCE: 3

Met Asn Phe Gly Leu Ser Leu Ile Phe Leu Ala Leu Ile Leu Lys Gly
1               5                   10                  15

Val Gln Cys


<210> SEQ ID NO 4
<211> LENGTH: 118
<212> TYPE: PRT
<213> ORGANISM: Artificial sequence
<220> FEATURE:
<223> OTHER INFORMATION: Synthesized

<400> SEQUENCE: 4

Glu Val Gln Leu Val Glu Ser Gly Gly Asp Leu Val Lys Pro Gly Gly
1               5                   10                  15

Ser Leu Lys Leu Ser Cys Ala Ala Pro Gly Phe Thr Phe Ser Thr Tyr
            20                  25                  30
```

```
Gly Met Ser Trp Val Arg Gln Thr Pro Asp Lys Arg Leu Glu Trp Val
        35                  40                  45

Ala Ile Ile Ser Ser Gly Gly Ser Tyr Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Arg Ser Ser Ser His Trp Tyr Phe Asp Val Trp Gly Thr Gly Thr
            100                 105                 110

Thr Val Thr Val Ser Ser
        115
```

<210> SEQ ID NO 5
<211> LENGTH: 10
<212> TYPE: PRT
<213> ORGANISM: Artificial sequence
<220> FEATURE:
<223> OTHER INFORMATION: Synthesized

<400> SEQUENCE: 5

```
Gly Phe Thr Phe Ser Thr Tyr Gly Met Ser
1               5                   10
```

<210> SEQ ID NO 6
<211> LENGTH: 17
<212> TYPE: PRT
<213> ORGANISM: Artificial sequence
<220> FEATURE:
<223> OTHER INFORMATION: Synthesized

<400> SEQUENCE: 6

```
Ile Ile Ser Ser Gly Gly Ser Tyr Thr Tyr Tyr Ser Asp Thr Val Lys
1               5                   10                  15

Gly
```

<210> SEQ ID NO 7
<211> LENGTH: 9
<212> TYPE: PRT
<213> ORGANISM: Artificial sequence
<220> FEATURE:
<223> OTHER INFORMATION: Synthesized

<400> SEQUENCE: 7

```
Ser Ser Ser His Trp Tyr Phe Asp Val
1               5
```

<210> SEQ ID NO 8
<211> LENGTH: 378
<212> TYPE: DNA
<213> ORGANISM: Artificial sequence
<220> FEATURE:
<223> OTHER INFORMATION: Synthesized

<400> SEQUENCE: 8

```
atggtccttg ctcagtttct tgcattcttg ttgctttggt ttccaggtgc aagatgtgac     60

atcctgatga cccaatctcc atcctccatg tctgtatctc tgggagacac agtcagcatc    120

acttgccatg caagtcaggg cattagcagt aatatagggt ggttgcagca gaaaccaggg    180

aaatcattta agggcctgat ctatcatgga accaacttga aagatggagt tccatcaagg    240

ttcagtggca gtggatctgg agcagatttt tctctcacca tcagcagcct ggaatctgaa    300
```

```
gattttgcag actatttctg tgttcagtat gctcagtttc cgtacacgtt cggagggggg    360

accaagctgg aaaaaaga                                                  378


<210> SEQ ID NO 9
<211> LENGTH: 19
<212> TYPE: PRT
<213> ORGANISM: Artificial sequence
<220> FEATURE:
<223> OTHER INFORMATION: Synthesized

<400> SEQUENCE: 9

Met Val Leu Ala Gln Phe Leu Ala Phe Leu Leu Leu Trp Phe Pro Gly
1               5                   10                  15

Ala Arg Cys


<210> SEQ ID NO 10
<211> LENGTH: 107
<212> TYPE: PRT
<213> ORGANISM: Artificial sequence
<220> FEATURE:
<223> OTHER INFORMATION: Synthesized

<400> SEQUENCE: 10

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Lys Asp Gly Val Pro Ser Arg Phe Ser Gly
    50                  55                  60

Ser Gly Ser Gly Ala Asp Phe Ser Leu Thr Ile Ser Ser Leu Glu Ser
65                  70                  75                  80

Glu Asp Phe Ala Asp Tyr Phe Cys Val Gln Tyr Ala Gln Phe Pro Tyr
                85                  90                  95

Thr Phe Gly Gly Gly Thr Lys Leu Glu Lys Arg
            100                 105


<210> SEQ ID NO 11
<211> LENGTH: 11
<212> TYPE: PRT
<213> ORGANISM: Artificial sequence
<220> FEATURE:
<223> OTHER INFORMATION: Synthesized

<400> SEQUENCE: 11

His Ala Ser Gln Gly Ile Ser Ser Asn Ile Gly
1               5                   10


<210> SEQ ID NO 12
<211> LENGTH: 7
<212> TYPE: PRT
<213> ORGANISM: Artificial sequence
<220> FEATURE:
<223> OTHER INFORMATION: Synthesized

<400> SEQUENCE: 12

His Gly Thr Asn Leu Lys Asp
1               5


<210> SEQ ID NO 13
<211> LENGTH: 9
```

<212> TYPE: PRT
<213> ORGANISM: Artificial sequence
<220> FEATURE:
<223> OTHER INFORMATION: Synthesized

<400> SEQUENCE: 13

Val Gln Tyr Ala Gln Phe Pro Tyr Thr
1 5

<210> SEQ ID NO 14
<211> LENGTH: 5
<212> TYPE: PRT
<213> ORGANISM: Artificial sequence
<220> FEATURE:
<223> OTHER INFORMATION: Synthesized

<400> SEQUENCE: 14

Thr Tyr Gly Met Ser
1 5

<210> SEQ ID NO 15
<211> LENGTH: 7
<212> TYPE: PRT
<213> ORGANISM: Artificial sequence
<220> FEATURE:
<223> OTHER INFORMATION: Synthesized

<400> SEQUENCE: 15

Gly Phe Thr Phe Ser Thr Tyr
1 5

<210> SEQ ID NO 16
<211> LENGTH: 6
<212> TYPE: PRT
<213> ORGANISM: Artificial sequence
<220> FEATURE:
<223> OTHER INFORMATION: Synthesized

<400> SEQUENCE: 16

Ser Ser Gly Gly Ser Tyr
1 5

<210> SEQ ID NO 17
<211> LENGTH: 10
<212> TYPE: PRT
<213> ORGANISM: Artificial sequence
<220> FEATURE:
<223> OTHER INFORMATION: Synthesized

<400> SEQUENCE: 17

Ile Ile Ser Ser Gly Gly Ser Tyr Thr Tyr
1 5 10

<210> SEQ ID NO 18
<211> LENGTH: 6
<212> TYPE: PRT
<213> ORGANISM: Artificial sequence
<220> FEATURE:
<223> OTHER INFORMATION: Synthesized

<400> SEQUENCE: 18

Ser Thr Tyr Gly Met Ser
1 5

<210> SEQ ID NO 19
<211> LENGTH: 13
<212> TYPE: PRT

<213> ORGANISM: Artificial sequence
<220> FEATURE:
<223> OTHER INFORMATION: Synthesized

<400> SEQUENCE: 19

Trp Val Ala Ile Ile Ser Ser Gly Gly Ser Tyr Thr Tyr
1 5 10

<210> SEQ ID NO 20
<211> LENGTH: 10
<212> TYPE: PRT
<213> ORGANISM: Artificial sequence
<220> FEATURE:
<223> OTHER INFORMATION: Synthesized

<400> SEQUENCE: 20

Ser Arg Ser Ser Ser His Trp Tyr Phe Asp
1 5 10

<210> SEQ ID NO 21
<211> LENGTH: 7
<212> TYPE: PRT
<213> ORGANISM: Artificial sequence
<220> FEATURE:
<223> OTHER INFORMATION: Synthesized

<400> SEQUENCE: 21

Ser Ser Asn Ile Gly Trp Leu
1 5

<210> SEQ ID NO 22
<211> LENGTH: 10
<212> TYPE: PRT
<213> ORGANISM: Artificial sequence
<220> FEATURE:
<223> OTHER INFORMATION: Synthesized

<400> SEQUENCE: 22

Gly Leu Ile Tyr His Gly Thr Asn Leu Lys
1 5 10

<210> SEQ ID NO 23
<211> LENGTH: 8
<212> TYPE: PRT
<213> ORGANISM: Artificial sequence
<220> FEATURE:
<223> OTHER INFORMATION: Synthesized

<400> SEQUENCE: 23

Val Gln Tyr Ala Gln Phe Pro Tyr
1 5

<210> SEQ ID NO 24
<211> LENGTH: 448
<212> TYPE: PRT
<213> ORGANISM: Artificial sequence
<220> FEATURE:
<223> OTHER INFORMATION: Synthesized

<400> SEQUENCE: 24

Glu Val Gln Leu Val Glu Ser Gly Gly Asp Leu Val Lys Pro Gly Gly
1 5 10 15

Ser Leu Lys Leu Ser Cys Ala Ala Pro Gly Phe Thr Phe Ser Thr Tyr
20 25 30

Gly Met Ser Trp Val Arg Gln Thr Pro Asp Lys Arg Leu Glu Trp Val
35 40 45

```
Ala Ile Ile Ser Ser Gly Gly Ser Tyr Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Arg Ser Ser Ser His Trp Tyr Phe Asp Val Trp Gly Thr Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 25
<211> LENGTH: 214

<212> TYPE: PRT
<213> ORGANISM: Artificial sequence
<220> FEATURE:
<223> OTHER INFORMATION: Synthesized

<400> SEQUENCE: 25

```
Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Lys Asp Gly Val Pro Ser Arg Phe Ser Gly
    50                  55                  60

Ser Gly Ser Gly Ala Asp Phe Ser Leu Thr Ile Ser Ser Leu Glu Ser
65                  70                  75                  80

Glu Asp Phe Ala Asp Tyr Phe Cys Val Gln Tyr Ala Gln Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26
<211> LENGTH: 426
<212> TYPE: DNA
<213> ORGANISM: Artificial sequence
<220> FEATURE:
<223> OTHER INFORMATION: Synthesized

<400> SEQUENCE: 26

```
atgggattca gcaggatctt tctcttcctc ctgtcagtaa ctacaggtgt ccactcccag      60

gcttatctac agcagtctgg gactgagctg gtgaggcctg gggcctcagt gaagatgtcc     120

tgcaaggctt ctggctacac atttaccagt tacagtatgc actgggtaaa gcagacacct     180

agacagggcc tggaatggat tggagctatt tatccaggaa atgatgctac ttcctacaat     240

cagaagttca agggcaaggc cacactgact gtagacaaat cctccagcac agcctacatg     300

cagctcagca gcctgacatc tgaagactct gcggtctatt tctgtgcaag agagggctac     360

tacggtagta gcttcgaagc ctggtttgct tcttggggcc aagggactct ggtcactgtc     420

tctgca                                                                426
```

<210> SEQ ID NO 27
<211> LENGTH: 19
<212> TYPE: PRT

<213> ORGANISM: Artificial sequence
<220> FEATURE:
<223> OTHER INFORMATION: Synthesized

<400> SEQUENCE: 27

Met Gly Phe Ser Arg Ile Phe Leu Phe Leu Leu Ser Val Thr Thr Gly
1 5 10 15

Val His Ser

<210> SEQ ID NO 28
<211> LENGTH: 123
<212> TYPE: PRT
<213> ORGANISM: Artificial sequence
<220> FEATURE:
<223> OTHER INFORMATION: Synthesized

<400> SEQUENCE: 28

Gln Ala Tyr Leu Gln Gln Ser Gly Thr Glu Leu Val Arg Pro Gly Ala
1 5 10 15

Ser Val Lys Met Ser Cys Lys Ala Ser Gly Tyr Thr Phe Thr Ser Tyr
20 25 30

Ser Met His Trp Val Lys Gln Thr Pro Arg Gln Gly Leu Glu Trp Ile
35 40 45

Gly Ala Ile Tyr Pro Gly Asn Asp Ala Thr Ser Tyr Asn Gln Lys Phe
50 55 60

Lys Gly Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg Glu Gly Tyr Tyr Gly Ser Ser Phe Glu Ala Trp Phe Ala Ser
100 105 110

Trp Gly Gln Gly Thr Leu Val Thr Val Ser Ala
115 120

<210> SEQ ID NO 29
<211> LENGTH: 10
<212> TYPE: PRT
<213> ORGANISM: Artificial sequence
<220> FEATURE:
<223> OTHER INFORMATION: Synthesized

<400> SEQUENCE: 29

Gly Tyr Thr Phe Thr Ser Tyr Ser Met His
1 5 10

<210> SEQ ID NO 30
<211> LENGTH: 18
<212> TYPE: PRT
<213> ORGANISM: Artificial sequence
<220> FEATURE:
<223> OTHER INFORMATION: Synthesized

<400> SEQUENCE: 30

Gly Ala Ile Tyr Pro Gly Asn Asp Ala Thr Ser Tyr Asn Gln Lys Phe
1 5 10 15

Lys Gly

<210> SEQ ID NO 31
<211> LENGTH: 14
<212> TYPE: PRT
<213> ORGANISM: Artificial sequence
<220> FEATURE:

<223> OTHER INFORMATION: Synthesized

<400> SEQUENCE: 31

```
Glu Gly Tyr Tyr Gly Ser Ser Phe Glu Ala Trp Phe Ala Ser
1               5                   10
```

<210> SEQ ID NO 32
<211> LENGTH: 393
<212> TYPE: DNA
<213> ORGANISM: Artificial sequence
<220> FEATURE:
<223> OTHER INFORMATION: Synthesized

<400> SEQUENCE: 32

```
atgaagttgc ctgttaggct gttggtgctg atgttctgga ttcctggttc cagcagtgat     60

gttttgatga cccaaactcc actttccctg cctgtcagtc ttggagatca agcctccatc    120

tcttgcagat ctagtcagag cattgtacat agtaatggaa acacctattt agaatggtac    180

ctgcagaaac caggccagtc tccaaagctc ctgatctaca aagtttccaa ccgattttct    240

ggggtcccag acaggttcag tggcagtgga tcagggacag atttcacact caagatcagc    300

agagtggagg ctgaggatct gggagtttat tactgctttc aaggttcaca tgttcttccg    360

acgttcggtg gaggcaccaa gctggaaatc aaa                                 393
```

<210> SEQ ID NO 33
<211> LENGTH: 19
<212> TYPE: PRT
<213> ORGANISM: Artificial sequence
<220> FEATURE:
<223> OTHER INFORMATION: Synthesized

<400> SEQUENCE: 33

```
Met Lys Leu Pro Val Arg Leu Leu Val Leu Met Phe Trp Ile Pro Gly
1               5                   10                  15

Ser Ser Ser
```

<210> SEQ ID NO 34
<211> LENGTH: 112
<212> TYPE: PRT
<213> ORGANISM: Artificial sequence
<220> FEATURE:
<223> OTHER INFORMATION: Synthesized

<400> SEQUENCE: 34

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Leu Pro Thr Phe Gly Gly Gly Thr Lys Leu Glu Ile Lys
            100                 105                 110
```

<210> SEQ ID NO 35

<211> LENGTH: 16
<212> TYPE: PRT
<213> ORGANISM: Artificial sequence
<220> FEATURE:
<223> OTHER INFORMATION: Synthesized

<400> SEQUENCE: 35

Arg Ser Ser Gln Ser Ile Val His Ser Asn Gly Asn Thr Tyr Leu Glu
1 5 10 15

<210> SEQ ID NO 36
<211> LENGTH: 7
<212> TYPE: PRT
<213> ORGANISM: Artificial sequence
<220> FEATURE:
<223> OTHER INFORMATION: Synthesized

<400> SEQUENCE: 36

Lys Val Ser Asn Arg Phe Ser
1 5

<210> SEQ ID NO 37
<211> LENGTH: 9
<212> TYPE: PRT
<213> ORGANISM: Artificial sequence
<220> FEATURE:
<223> OTHER INFORMATION: Synthesized

<400> SEQUENCE: 37

Phe Gln Gly Ser His Val Leu Pro Thr
1 5

<210> SEQ ID NO 38
<211> LENGTH: 5
<212> TYPE: PRT
<213> ORGANISM: Artificial sequence
<220> FEATURE:
<223> OTHER INFORMATION: Synthesized

<400> SEQUENCE: 38

Ser Tyr Ser Met His
1 5

<210> SEQ ID NO 39
<211> LENGTH: 7
<212> TYPE: PRT
<213> ORGANISM: Artificial sequence
<220> FEATURE:
<223> OTHER INFORMATION: Synthesized

<400> SEQUENCE: 39

Gly Tyr Thr Phe Thr Ser Tyr
1 5

<210> SEQ ID NO 40
<211> LENGTH: 6
<212> TYPE: PRT
<213> ORGANISM: Artificial sequence
<220> FEATURE:
<223> OTHER INFORMATION: Synthesized

<400> SEQUENCE: 40

Tyr Pro Gly Asn Asp Ala
1 5

<210> SEQ ID NO 41
<211> LENGTH: 10

<212> TYPE: PRT
<213> ORGANISM: Artificial sequence
<220> FEATURE:
<223> OTHER INFORMATION: Synthesized

<400> SEQUENCE: 41

Ala Ile Tyr Pro Gly Asn Asp Ala Thr Ser
1 5 10

<210> SEQ ID NO 42
<211> LENGTH: 6
<212> TYPE: PRT
<213> ORGANISM: Artificial sequence
<220> FEATURE:
<223> OTHER INFORMATION: Synthesized

<400> SEQUENCE: 42

Thr Ser Tyr Ser Met His
1 5

<210> SEQ ID NO 43
<211> LENGTH: 13
<212> TYPE: PRT
<213> ORGANISM: Artificial sequence
<220> FEATURE:
<223> OTHER INFORMATION: Synthesized

<400> SEQUENCE: 43

Trp Ile Gly Ala Ile Tyr Pro Gly Asn Asp Ala Thr Ser
1 5 10

<210> SEQ ID NO 44
<211> LENGTH: 15
<212> TYPE: PRT
<213> ORGANISM: Artificial sequence
<220> FEATURE:
<223> OTHER INFORMATION: Synthesized

<400> SEQUENCE: 44

Ala Arg Glu Gly Tyr Tyr Gly Ser Ser Phe Glu Ala Trp Phe Ala
1 5 10 15

<210> SEQ ID NO 45
<211> LENGTH: 7
<212> TYPE: PRT
<213> ORGANISM: Artificial sequence
<220> FEATURE:
<223> OTHER INFORMATION: Synthesized

<400> SEQUENCE: 45

Asn Thr Tyr Leu Glu Trp Tyr
1 5

<210> SEQ ID NO 46
<211> LENGTH: 10
<212> TYPE: PRT
<213> ORGANISM: Artificial sequence
<220> FEATURE:
<223> OTHER INFORMATION: Synthesized

<400> SEQUENCE: 46

Leu Leu Ile Tyr Lys Val Ser Asn Arg Phe
1 5 10

<210> SEQ ID NO 47
<211> LENGTH: 8
<212> TYPE: PRT

<213> ORGANISM: Artificial sequence
<220> FEATURE:
<223> OTHER INFORMATION: Synthesized

<400> SEQUENCE: 47

Phe Gln Gly Ser His Val Leu Pro
1 5

<210> SEQ ID NO 48
<211> LENGTH: 453
<212> TYPE: PRT
<213> ORGANISM: Artificial sequence
<220> FEATURE:
<223> OTHER INFORMATION: Synthesized

<400> SEQUENCE: 48

Gln Ala Tyr Leu Gln Gln Ser Gly Thr Glu Leu Val Arg Pro Gly Ala
1 5 10 15

Ser Val Lys Met Ser Cys Lys Ala Ser Gly Tyr Thr Phe Thr Ser Tyr
20 25 30

Ser Met His Trp Val Lys Gln Thr Pro Arg Gln Gly Leu Glu Trp Ile
35 40 45

Gly Ala Ile Tyr Pro Gly Asn Asp Ala Thr Ser Tyr Asn Gln Lys Phe
50 55 60

Lys Gly Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg Glu Gly Tyr Tyr Gly Ser Ser Phe Glu Ala Trp Phe Ala Ser
100 105 110

Trp Gly Gln Gly Thr Leu Val Thr Val Ser Ala Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Ala
225 230 235 240

Ala Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 49
<211> LENGTH: 219
<212> TYPE: PRT
<213> ORGANISM: Artificial sequence
<220> FEATURE:
<223> OTHER INFORMATION: Synthesized

<400> SEQUENCE: 49

Asp Val Leu Met Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Leu Pro Thr Phe Gly Gly Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 50
<211> LENGTH: 408
<212> TYPE: DNA
<213> ORGANISM: Artificial sequence
<220> FEATURE:
<223> OTHER INFORMATION: Synthesized

<400> SEQUENCE: 50
atgaacttcg ggctcagctt gattttcctt gcccttattt taaaaggtgt ccagtgtgag 60
gtacagctgg tggagtctgg gggagactta gtgaagcctg gagggtccct gaaactctcc 120
tgtgcagcct ctggattcac tttcaatatc tatggcatgt cttgggttcg ccagactcca 180
gacaagaggc tggagtgggt cgcaaccatt agttctggtg gtatttatac ctactatcca 240
gacattttga aggggcgatt caccatctcc agagacaatg ccaagaacac cctgtacctg 300
caaatgagca gtctgaagtc tgaggacaca gccatgtatt actgtgcaag acatccgggt 360
ggggctatgg actactgggg tcaaggaacc tcagtcaccg tctcctca 408

<210> SEQ ID NO 51
<211> LENGTH: 19
<212> TYPE: PRT
<213> ORGANISM: Artificial sequence
<220> FEATURE:
<223> OTHER INFORMATION: Synthesized

<400> SEQUENCE: 51

Met Asn Phe Gly Leu Ser Leu Ile Phe Leu Ala Leu Ile Leu Lys Gly
1 5 10 15

Val Gln Cys

<210> SEQ ID NO 52
<211> LENGTH: 117
<212> TYPE: PRT
<213> ORGANISM: Artificial sequence
<220> FEATURE:
<223> OTHER INFORMATION: Synthesized

<400> SEQUENCE: 52

Glu Val Gln Leu Val Glu Ser Gly Gly Asp Leu Val Lys Pro Gly Gly
1 5 10 15

Ser Leu Lys Leu Ser Cys Ala Ala Ser Gly Phe Thr Phe Asn Ile Tyr
20 25 30

Gly Met Ser Trp Val Arg Gln Thr Pro Asp Lys Arg Leu Glu Trp Val
35 40 45

Ala Thr Ile Ser Ser Gly Gly Ile Tyr Thr Tyr Tyr Pro Asp Ile Leu
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr Tyr Cys
85 90 95

Ala Arg His Pro Gly Gly Ala Met Asp Tyr Trp Gly Gln Gly Thr Ser
100 105 110

Val Thr Val Ser Ser
115

<210> SEQ ID NO 53
<211> LENGTH: 10
<212> TYPE: PRT
<213> ORGANISM: Artificial sequence
<220> FEATURE:

<223> OTHER INFORMATION: Synthesized

<400> SEQUENCE: 53

Gly Phe Thr Phe Asn Ile Tyr Gly Met Ser
1 5 10

<210> SEQ ID NO 54
<211> LENGTH: 17
<212> TYPE: PRT
<213> ORGANISM: Artificial sequence
<220> FEATURE:
<223> OTHER INFORMATION: Synthesized

<400> SEQUENCE: 54

Thr Ile Ser Ser Gly Gly Ile Tyr Thr Tyr Tyr Pro Asp Ile Leu Lys
1 5 10 15

Gly

<210> SEQ ID NO 55
<211> LENGTH: 8
<212> TYPE: PRT
<213> ORGANISM: Artificial sequence
<220> FEATURE:
<223> OTHER INFORMATION: Synthesized

<400> SEQUENCE: 55

His Pro Gly Gly Ala Met Asp Tyr
1 5

<210> SEQ ID NO 56
<211> LENGTH: 384
<212> TYPE: DNA
<213> ORGANISM: Artificial sequence
<220> FEATURE:
<223> OTHER INFORMATION: Synthesized

<400> SEQUENCE: 56
atgagtgtgc ccactcaggt cctggggttg ctgctgctgt ggcttacaga tgccagatgt 60
gacatccaga tgactcagtc tccagcctcc ctatctgtat ctgtgggaga aactgtcacc 120
atcacatgtc gagtaagtga gaatatttac agtaatttag catggtatca gcagaaacag 180
ggaaaatctc ctcacctcct ggtctatgct gcaacaaact tagcagatgg tgtgccatca 240
aggttcagtg gcagtggatc aggcacacag tattccctca agatcaacag cctgcagtct 300
gaagattttg ggagttatta ctgtcaacat ttttggggta ctcctccgtg gacgttcggt 360
ggaggcacca agctggaaat caaa 384

<210> SEQ ID NO 57
<211> LENGTH: 20
<212> TYPE: PRT
<213> ORGANISM: Artificial sequence
<220> FEATURE:
<223> OTHER INFORMATION: Synthesized

<400> SEQUENCE: 57

Met Ser Val Pro Thr Gln Val Leu Gly Leu Leu Leu Leu Trp Leu Thr
1 5 10 15

Asp Ala Arg Cys
20

<210> SEQ ID NO 58
<211> LENGTH: 108
<212> TYPE: PRT

```
<213> ORGANISM: Artificial sequence
<220> FEATURE:
<223> OTHER INFORMATION: Synthesized

<400> SEQUENCE: 58

Asp Ile Gln Met Thr Gln Ser Pro Ala Ser Leu Ser Val Ser Val Gly
1               5                   10                  15

Glu Thr Val Thr Ile Thr Cys Arg Val Ser Glu Asn Ile Tyr Ser Asn
            20                  25                  30

Leu Ala Trp Tyr Gln Gln Lys Gln Gly Lys Ser Pro His Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Pro
                85                  90                  95

Trp Thr Phe Gly Gly Gly Thr Lys Leu Glu Ile Lys
            100                 105


<210> SEQ ID NO 59
<211> LENGTH: 11
<212> TYPE: PRT
<213> ORGANISM: Artificial sequence
<220> FEATURE:
<223> OTHER INFORMATION: Synthesized

<400> SEQUENCE: 59

Arg Val Ser Glu Asn Ile Tyr Ser Asn Leu Ala
1               5                   10


<210> SEQ ID NO 60
<211> LENGTH: 7
<212> TYPE: PRT
<213> ORGANISM: Artificial sequence
<220> FEATURE:
<223> OTHER INFORMATION: Synthesized

<400> SEQUENCE: 60

Ala Ala Thr Asn Leu Ala Asp
1               5


<210> SEQ ID NO 61
<211> LENGTH: 10
<212> TYPE: PRT
<213> ORGANISM: Artificial sequence
<220> FEATURE:
<223> OTHER INFORMATION: Synthesized

<400> SEQUENCE: 61

Gln His Phe Trp Gly Thr Pro Pro Trp Thr
1               5                   10


<210> SEQ ID NO 62
<211> LENGTH: 5
<212> TYPE: PRT
<213> ORGANISM: Artificial sequence
<220> FEATURE:
<223> OTHER INFORMATION: Synthesized

<400> SEQUENCE: 62

Ile Tyr Gly Met Ser
1               5
```

<210> SEQ ID NO 63
<211> LENGTH: 7
<212> TYPE: PRT
<213> ORGANISM: Artificial sequence
<220> FEATURE:
<223> OTHER INFORMATION: Synthesized

<400> SEQUENCE: 63

Gly Phe Thr Phe Asn Ile Tyr
1 5

<210> SEQ ID NO 64
<211> LENGTH: 6
<212> TYPE: PRT
<213> ORGANISM: Artificial sequence
<220> FEATURE:
<223> OTHER INFORMATION: Synthesized

<400> SEQUENCE: 64

Ser Ser Gly Gly Ile Tyr
1 5

<210> SEQ ID NO 65
<211> LENGTH: 10
<212> TYPE: PRT
<213> ORGANISM: Artificial sequence
<220> FEATURE:
<223> OTHER INFORMATION: Synthesized

<400> SEQUENCE: 65

Thr Ile Ser Ser Gly Gly Ile Tyr Thr Tyr
1 5 10

<210> SEQ ID NO 66
<211> LENGTH: 6
<212> TYPE: PRT
<213> ORGANISM: Artificial sequence
<220> FEATURE:
<223> OTHER INFORMATION: Synthesized

<400> SEQUENCE: 66

Asn Ile Tyr Gly Met Ser
1 5

<210> SEQ ID NO 67
<211> LENGTH: 13
<212> TYPE: PRT
<213> ORGANISM: Artificial sequence
<220> FEATURE:
<223> OTHER INFORMATION: Synthesized

<400> SEQUENCE: 67

Trp Val Ala Thr Ile Ser Ser Gly Gly Ile Tyr Thr Tyr
1 5 10

<210> SEQ ID NO 68
<211> LENGTH: 9
<212> TYPE: PRT
<213> ORGANISM: Artificial sequence
<220> FEATURE:
<223> OTHER INFORMATION: Synthesized

<400> SEQUENCE: 68

Ala Arg His Pro Gly Gly Ala Met Asp
1 5

<210> SEQ ID NO 69
<211> LENGTH: 7
<212> TYPE: PRT
<213> ORGANISM: Artificial sequence
<220> FEATURE:
<223> OTHER INFORMATION: Synthesized

<400> SEQUENCE: 69

Tyr Ser Asn Leu Ala Trp Tyr
1               5

<210> SEQ ID NO 70
<211> LENGTH: 10
<212> TYPE: PRT
<213> ORGANISM: Artificial sequence
<220> FEATURE:
<223> OTHER INFORMATION: Synthesized

<400> SEQUENCE: 70

Leu Leu Val Tyr Ala Ala Thr Asn Leu Ala
1               5                   10

<210> SEQ ID NO 71
<211> LENGTH: 9
<212> TYPE: PRT
<213> ORGANISM: Artificial sequence
<220> FEATURE:
<223> OTHER INFORMATION: Synthesized

<400> SEQUENCE: 71

Gln His Phe Trp Gly Thr Pro Pro Trp
1               5

<210> SEQ ID NO 72
<211> LENGTH: 7
<212> TYPE: PRT
<213> ORGANISM: Artificial sequence
<220> FEATURE:
<223> OTHER INFORMATION: Synthesized

<400> SEQUENCE: 72

Ala Ala Thr Asn Gly Ala Asp
1               5

<210> SEQ ID NO 73
<211> LENGTH: 7
<212> TYPE: PRT
<213> ORGANISM: Artificial sequence
<220> FEATURE:
<223> OTHER INFORMATION: Synthesized

<400> SEQUENCE: 73

Ala Ala Thr Asn Ile Ala Asp
1               5

<210> SEQ ID NO 74
<211> LENGTH: 10
<212> TYPE: PRT
<213> ORGANISM: Artificial sequence
<220> FEATURE:
<223> OTHER INFORMATION: Synthesized

<400> SEQUENCE: 74

Leu Leu Val Tyr Ala Ala Thr Asn Gly Ala
1               5                   10

<210> SEQ ID NO 75

<211> LENGTH: 10
<212> TYPE: PRT
<213> ORGANISM: Artificial sequence
<220> FEATURE:
<223> OTHER INFORMATION: Synthesized

<400> SEQUENCE: 75

Leu Leu Val Tyr Ala Ala Thr Asn Ile Ala
1 5 10

<210> SEQ ID NO 76
<211> LENGTH: 348
<212> TYPE: DNA
<213> ORGANISM: Artificial sequence
<220> FEATURE:
<223> OTHER INFORMATION: Synthesized

<400> SEQUENCE: 76
gatgtgcagc ttcaggagtc gggacctggc ctggtgaaac cttctcagtc tctgtccctc 60
acctgcactg tcactggcta ttcaatcacc agtgattatg cctggaactg gatccggcag 120
tttccaggaa acaaactgga gtggatgggc tacataagct ccagtggtag cactagctac 180
aacccatctc tcaaaagtcg aatctctgtc actcgagaca catccaagaa ccagttcttc 240
ctgcagttga attttgtgac tgctgaggac acagccacat attactgtgc atttgtcact 300
acgactatgg actactgggg tcaaggaacc tcagtcaccg tctcctca 348

<210> SEQ ID NO 77
<211> LENGTH: 18
<212> TYPE: PRT
<213> ORGANISM: Artificial sequence
<220> FEATURE:
<223> OTHER INFORMATION: Synthesized

<400> SEQUENCE: 77

Met Arg Val Leu Ile Leu Leu Trp Leu Phe Thr Ala Phe Pro Gly Ile
1 5 10 15

Leu Ser

<210> SEQ ID NO 78
<211> LENGTH: 116
<212> TYPE: PRT
<213> ORGANISM: Artificial sequence
<220> FEATURE:
<223> OTHER INFORMATION: Synthesized

<400> SEQUENCE: 78

Asp Val Gln Leu Gln Glu Ser Gly Pro Gly Leu Val Lys Pro Ser Gln
1 5 10 15

Ser Leu Ser Leu Thr Cys Thr Val Thr Gly Tyr Ser Ile Thr Ser Asp
20 25 30

Tyr Ala Trp Asn Trp Ile Arg Gln Phe Pro Gly Asn Lys Leu Glu Trp
35 40 45

Met Gly Tyr Ile Ser Ser Ser Gly Ser Thr Ser Tyr Asn Pro Ser Leu
50 55 60

Lys Ser Arg Ile Ser Val Thr Arg Asp Thr Ser Lys Asn Gln Phe Phe
65 70 75 80

Leu Gln Leu Asn Phe Val Thr Ala Glu Asp Thr Ala Thr Tyr Tyr Cys
85 90 95

Ala Phe Val Thr Thr Thr Met Asp Tyr Trp Gly Gln Gly Thr Ser Val
100 105 110

Thr Val Ser Ser
115

<210> SEQ ID NO 79
<211> LENGTH: 11
<212> TYPE: PRT
<213> ORGANISM: Artificial sequence
<220> FEATURE:
<223> OTHER INFORMATION: Synthesized

<400> SEQUENCE: 79

Gly Tyr Ser Ile Thr Ser Asp Tyr Ala Trp Asn
1 5 10

<210> SEQ ID NO 80
<211> LENGTH: 16
<212> TYPE: PRT
<213> ORGANISM: Artificial sequence
<220> FEATURE:
<223> OTHER INFORMATION: Synthesized

<400> SEQUENCE: 80

Tyr Ile Ser Ser Ser Gly Ser Thr Ser Tyr Asn Pro Ser Leu Lys Ser
1 5 10 15

<210> SEQ ID NO 81
<211> LENGTH: 7
<212> TYPE: PRT
<213> ORGANISM: Artificial sequence
<220> FEATURE:
<223> OTHER INFORMATION: Synthesized

<400> SEQUENCE: 81

Val Thr Thr Thr Met Asp Tyr
1 5

<210> SEQ ID NO 82
<211> LENGTH: 393
<212> TYPE: DNA
<213> ORGANISM: Artificial sequence
<220> FEATURE:
<223> OTHER INFORMATION: Synthesized

<400> SEQUENCE: 82
atgaagttgc ctgttaggct gttggtgctg atgttctgga ttcctgcttc cagcagtgat 60
gttgtgatga cccaaactcc actctccctg cctgtcagtc ttggagatca agcctccatc 120
tcttgcagat ctagtcagag ccttgtacac agtaatggaa acacctattt acattggtac 180
ctgcagaagc caggccagtc tccaaagctc ctgatctaca cagtttccaa ccgattttct 240
ggggtcccag acaggttcag tggcagtgga tcagggacag atttcacact caagatcagc 300
agagtggagg ctgaggatct gggagtttat ttctgctctc aaagtacaca tgttccattc 360
acgttcggct cggggacaaa gttggaaata aaa 393

<210> SEQ ID NO 83
<211> LENGTH: 19
<212> TYPE: PRT
<213> ORGANISM: Artificial sequence
<220> FEATURE:
<223> OTHER INFORMATION: Synthesized

<400> SEQUENCE: 83

Met Lys Leu Pro Val Arg Leu Leu Val Leu Met Phe Trp Ile Pro Ala
1 5 10 15

Ser Ser Ser

<210> SEQ ID NO 84
<211> LENGTH: 112
<212> TYPE: PRT
<213> ORGANISM: Artificial sequence
<220> FEATURE:
<223> OTHER INFORMATION: Synthesized

<400> SEQUENCE: 84

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Thr Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Phe Thr Phe Gly Ser Gly Thr Lys Leu Glu Ile Lys
100 105 110

<210> SEQ ID NO 85
<211> LENGTH: 16
<212> TYPE: PRT
<213> ORGANISM: Artificial sequence
<220> FEATURE:
<223> OTHER INFORMATION: Synthesized

<400> SEQUENCE: 85

Arg Ser Ser Gln Ser Leu Val His Ser Asn Gly Asn Thr Tyr Leu His
1 5 10 15

<210> SEQ ID NO 86
<211> LENGTH: 7
<212> TYPE: PRT
<213> ORGANISM: Artificial sequence
<220> FEATURE:
<223> OTHER INFORMATION: Synthesized

<400> SEQUENCE: 86

Thr Val Ser Asn Arg Phe Ser
1 5

<210> SEQ ID NO 87
<211> LENGTH: 9
<212> TYPE: PRT
<213> ORGANISM: Artificial sequence
<220> FEATURE:
<223> OTHER INFORMATION: Synthesized

<400> SEQUENCE: 87

Ser Gln Ser Thr His Val Pro Phe Thr
1 5

<210> SEQ ID NO 88
<211> LENGTH: 555
<212> TYPE: DNA
<213> ORGANISM: Artificial sequence
<220> FEATURE:
<223> OTHER INFORMATION: Synthesized

<400> SEQUENCE: 88
atgaacttcg ggctcagctt gattttcctt gcccttattt tacaaggtgt ccagtgtgag 60
gtgcagctgg tggagtctgg gggagactta gtgaagcctg gagggtccct gaaactctcc 120
tgtgcagcct ctggattcac tttcaatatc tatggcatgt cttgggttcg ccagactcca 180
gacaagaggc tggagtgggt cgcaaccatt agtactggtg gtatttacac ctactatcca 240
gacagtgtga aggggcgatt caccatctcc agagacaatg ccaagaacac cctgtacctg 300
caaatgagca gtctgaagtc tgaggacaca gccatgtatt attgtgcaag acatccggtt 360
ggggctctgg actactgggg tcaaggaacc tcagtcaccg tctcctcagc caaaacgaca 420
cccccatctg tctatccact ggcccctgga tctgctgccc aaactaactc catggtgacc 480
ctgggatgcc tggtcaaggg ctatttccct gagccagtga cagtgacctg gaactctgga 540
tccctgtcca gcggt 555

<210> SEQ ID NO 89
<211> LENGTH: 19
<212> TYPE: PRT
<213> ORGANISM: Artificial sequence
<220> FEATURE:
<223> OTHER INFORMATION: Synthesized

<400> SEQUENCE: 89

Met Asn Phe Gly Leu Ser Leu Ile Phe Leu Ala Leu Ile Leu Gln Gly
1 5 10 15

Val Gln Cys

<210> SEQ ID NO 90
<211> LENGTH: 117
<212> TYPE: PRT
<213> ORGANISM: Artificial sequence
<220> FEATURE:
<223> OTHER INFORMATION: Synthesized

<400> SEQUENCE: 90

Glu Val Gln Leu Val Glu Ser Gly Gly Asp Leu Val Lys Pro Gly Gly
1 5 10 15

Ser Leu Lys Leu Ser Cys Ala Ala Ser Gly Phe Thr Phe Asn Ile Tyr
20 25 30

Gly Met Ser Trp Val Arg Gln Thr Pro Asp Lys Arg Leu Glu Trp Val
35 40 45

Ala Thr Ile Ser Thr Gly Gly Ile Tyr Thr Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr Tyr Cys
85 90 95

Ala Arg His Pro Val Gly Ala Leu Asp Tyr Trp Gly Gln Gly Thr Ser
100 105 110

Val Thr Val Ser Ser
115

<210> SEQ ID NO 91
<211> LENGTH: 10
<212> TYPE: PRT
<213> ORGANISM: Artificial sequence
<220> FEATURE:
<223> OTHER INFORMATION: Synthesized

<400> SEQUENCE: 91

Gly Phe Thr Phe Asn Ile Tyr Gly Met Ser
1               5                   10

<210> SEQ ID NO 92
<211> LENGTH: 17
<212> TYPE: PRT
<213> ORGANISM: Artificial sequence
<220> FEATURE:
<223> OTHER INFORMATION: Synthesized

<400> SEQUENCE: 92

Thr Ile Ser Thr Gly Gly Ile Tyr Thr Tyr Tyr Pro Asp Ser Val Lys
1               5                   10                  15

Gly

<210> SEQ ID NO 93
<211> LENGTH: 8
<212> TYPE: PRT
<213> ORGANISM: Artificial sequence
<220> FEATURE:
<223> OTHER INFORMATION: Synthesized

<400> SEQUENCE: 93

His Pro Val Gly Ala Leu Asp Tyr
1               5

<210> SEQ ID NO 94
<211> LENGTH: 561
<212> TYPE: DNA
<213> ORGANISM: Artificial sequence
<220> FEATURE:
<223> OTHER INFORMATION: Synthesized

<400> SEQUENCE: 94
atgagtgtgc ccactcaggt cctggggttg ctgctgctgt ggcttacaga tgccagatgt     60
gacatccagg tgactcagtc tccagcctcc ctatctgtat ctgtgggaga aactgtcacc    120
atcacatgtc gagcaagtga gaatatttac agtaatttag catggtatca gcagaaacag    180
ggaaaatctc ctcacctcct ggtctatact gcaacaacct tagcagatgg tgtgccatca    240
aggttcagtg gcagtggatc aggcacacag tattccctca agatcaacag cctgcagtct    300
gaagattttg ggagttatta ctgtcaacat ttttggggta ctcctccgtg gacgttcggt    360
ggaggcacca agctggaaat caaacgggct gatgctgcac caactgtatc catcttccca    420
ccatccagtg agcagttaac atctggaggt gcctcagtcg tgtgcttctt gaacaacttc    480
taccccagag acatcaatgt caagtggaag attgatggca gtgaacgaca aaatggcgtc    540
ctgaacagtt ggactgatca g                                               561

<210> SEQ ID NO 95
<211> LENGTH: 20
<212> TYPE: PRT
<213> ORGANISM: Artificial sequence
<220> FEATURE:
<223> OTHER INFORMATION: Synthesized

<400> SEQUENCE: 95

Met Ser Val Pro Thr Gln Val Leu Gly Leu Leu Leu Leu Trp Leu Thr
1               5                   10                  15

Asp Ala Arg Cys
            20

<210> SEQ ID NO 96
<211> LENGTH: 108
<212> TYPE: PRT
<213> ORGANISM: Artificial sequence
<220> FEATURE:
<223> OTHER INFORMATION: Synthesized

<400> SEQUENCE: 96

Asp Ile Gln Val Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro His Leu Leu Val
        35                  40                  45

Tyr Thr Ala Thr Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Pro
                85                  90                  95

Trp Thr Phe Gly Gly Gly Thr Lys Leu Glu Ile Lys
            100                 105

<210> SEQ ID NO 97
<211> LENGTH: 11
<212> TYPE: PRT
<213> ORGANISM: Artificial sequence
<220> FEATURE:
<223> OTHER INFORMATION: Synthesized

<400> SEQUENCE: 97

Arg Ala Ser Glu Asn Ile Tyr Ser Asn Leu Ala
1               5                   10

<210> SEQ ID NO 98
<211> LENGTH: 7
<212> TYPE: PRT
<213> ORGANISM: Artificial sequence
<220> FEATURE:
<223> OTHER INFORMATION: Synthesized

<400> SEQUENCE: 98

Thr Ala Thr Thr Leu Ala Asp
1               5

<210> SEQ ID NO 99
<211> LENGTH: 10
<212> TYPE: PRT
<213> ORGANISM: Artificial sequence
<220> FEATURE:
<223> OTHER INFORMATION: Synthesized

<400> SEQUENCE: 99

Gln His Phe Trp Gly Thr Pro Pro Trp Thr
1               5                   10

<210> SEQ ID NO 100
<211> LENGTH: 513
<212> TYPE: DNA
<213> ORGANISM: Artificial sequence
<220> FEATURE:
<223> OTHER INFORMATION: Synthesized

<400> SEQUENCE: 100
atgaacttcg ggctcagctt gattttcctt gcccttattt taaaaggtgt ccagtgtgag 60
gtgcagctgg tggagtctgg gggagactta gtgaagcctg gagggtccct gaaactctcc 120
tgtgcagcct ctggattcac tttcagtatc tatggcatgt cttgggttcg ccagactcca 180
gacaagaagc tggagtgggt cgcagccatt agtagtggtg gtatttatac ctattatcca 240
gacagtgtga aggggcgatt caccatctcc agagacaacg ccaagaacac cctgtacctg 300
caaatgagca gtctgaagtc tgcggacaca gccatgtatt actgtacaag aaatgattac 360
gactggtttg cttactgggg ccaagggact ctggtcactg tctctgcagc caaaacaaca 420
cccccatcag tctatccact ggcccctggg tgtggagata caactggttc ctctgtgact 480
ctgggatgcc tggtcaaggg ctacttccct gag 513

<210> SEQ ID NO 101
<211> LENGTH: 19
<212> TYPE: PRT
<213> ORGANISM: Artificial sequence
<220> FEATURE:
<223> OTHER INFORMATION: Synthesized

<400> SEQUENCE: 101

Met Asn Phe Gly Leu Ser Leu Ile Phe Leu Ala Leu Ile Leu Lys Gly
1 5 10 15

Val Gln Cys

<210> SEQ ID NO 102
<211> LENGTH: 117
<212> TYPE: PRT
<213> ORGANISM: Artificial sequence
<220> FEATURE:
<223> OTHER INFORMATION: Synthesized

<400> SEQUENCE: 102

Glu Val Gln Leu Val Glu Ser Gly Gly Asp Leu Val Lys Pro Gly Gly
1 5 10 15

Ser Leu Lys Leu Ser Cys Ala Ala Ser Gly Phe Thr Phe Ser Ile Tyr
20 25 30

Gly Met Ser Trp Val Arg Gln Thr Pro Asp Lys Lys Leu Glu Trp Val
35 40 45

Ala Ala Ile Ser Ser Gly Gly Ile Tyr Thr Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Ala Asp Thr Ala Met Tyr Tyr Cys
85 90 95

Thr Arg Asn Asp Tyr Asp Trp Phe Ala Tyr Trp Gly Gln Gly Thr Leu
100 105 110

Val Thr Val Ser Ala
115

<210> SEQ ID NO 103

<211> LENGTH: 10
<212> TYPE: PRT
<213> ORGANISM: Artificial sequence
<220> FEATURE:
<223> OTHER INFORMATION: Synthesized

<400> SEQUENCE: 103

Gly Phe Thr Phe Ser Ile Tyr Gly Met Ser
1 5 10

<210> SEQ ID NO 104
<211> LENGTH: 17
<212> TYPE: PRT
<213> ORGANISM: Artificial sequence
<220> FEATURE:
<223> OTHER INFORMATION: Synthesized

<400> SEQUENCE: 104

Ala Ile Ser Ser Gly Gly Ile Tyr Thr Tyr Tyr Pro Asp Ser Val Lys
1 5 10 15

Gly

<210> SEQ ID NO 105
<211> LENGTH: 8
<212> TYPE: PRT
<213> ORGANISM: Artificial sequence
<220> FEATURE:
<223> OTHER INFORMATION: Synthesized

<400> SEQUENCE: 105

Asn Asp Tyr Asp Trp Phe Ala Tyr
1 5

<210> SEQ ID NO 106
<211> LENGTH: 558
<212> TYPE: DNA
<213> ORGANISM: Artificial sequence
<220> FEATURE:
<223> OTHER INFORMATION: Synthesized

<400> SEQUENCE: 106
atgagggctc ctgcacagat ttttggcttc ttgttgctct tgtttccagg taccagatgt 60
gacatccaga tgacccagtc tccatcctcc ttatctgcct ctctgggaga aagagtcagt 120
ctcacttgtc gggcaagtca ggacattggt agtagcttaa actggcttca gcaggaacca 180
gatggaacta ttaaacgcct gatctacgcc acatccagtt tagattctgg tgtccccaaa 240
aggttcagtg gcagtaggtc tgggtcagat tattctctca ccatcagcag ccttgagtct 300
gaagattttg tagactatta ctgtctacaa tatgctagtt ctccgtacac gttcggaggg 360
gggaccaagc tggaaataaa gcgggctgat gctgcaccaa ctgtatccat cttcccacca 420
tccagtgagc agttaacatc tggaggtgcc tcagtcgtgt gcttcttgaa caacttctac 480
cccagagaca tcaatgtcaa gtggaagatt gatggcagtg aacgacaaaa tggcgtcctg 540
aacagttgga ctgatcag 558

<210> SEQ ID NO 107
<211> LENGTH: 20
<212> TYPE: PRT
<213> ORGANISM: Artificial sequence
<220> FEATURE:
<223> OTHER INFORMATION: Synthesized

<400> SEQUENCE: 107

Met Arg Ala Pro Ala Gln Ile Phe Gly Phe Leu Leu Leu Leu Phe Pro
1               5                   10                  15

Gly Thr Arg Cys
            20

<210> SEQ ID NO 108
<211> LENGTH: 107
<212> TYPE: PRT
<213> ORGANISM: Artificial sequence
<220> FEATURE:
<223> OTHER INFORMATION: Synthesized

<400> SEQUENCE: 108

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Tyr
                85                  90                  95

Thr Phe Gly Gly Gly Thr Lys Leu Glu Ile Lys
            100                 105

<210> SEQ ID NO 109
<211> LENGTH: 11
<212> TYPE: PRT
<213> ORGANISM: Artificial sequence
<220> FEATURE:
<223> OTHER INFORMATION: Synthesized

<400> SEQUENCE: 109

Arg Ala Ser Gln Asp Ile Gly Ser Ser Leu Asn
1               5                   10

<210> SEQ ID NO 110
<211> LENGTH: 7
<212> TYPE: PRT
<213> ORGANISM: Artificial sequence
<220> FEATURE:
<223> OTHER INFORMATION: Synthesized

<400> SEQUENCE: 110

Ala Thr Ser Ser Leu Asp Ser
1               5

<210> SEQ ID NO 111
<211> LENGTH: 9
<212> TYPE: PRT
<213> ORGANISM: Artificial sequence
<220> FEATURE:
<223> OTHER INFORMATION: Synthesized

<400> SEQUENCE: 111

Leu Gln Tyr Ala Ser Ser Pro Tyr Thr
1               5

<210> SEQ ID NO 112
<211> LENGTH: 558
<212> TYPE: DNA
<213> ORGANISM: Artificial sequence
<220> FEATURE:
<223> OTHER INFORMATION: Synthesized

<400> SEQUENCE: 112
atgaacttcg ggctcagctt gattttcctt gcccttattt taaaaggtgt ccagtgtgag 60
gtgcagctgg tggagtctgg gggagactta gtgaagcctg gagggtccct gaaactctcc 120
tgtgcagccc ctggattcac tttcagtact tatggcatgt cttgggttcg ccagactcca 180
gacaagaggc tggagtgggt cgcaatcatt agtagtggtg gtagttacac ctactattca 240
gacactgtga aggggcgatt caccatctcc agagacaatg ccaagaacac cctgaacctg 300
caaatgagca gtctgaagtc tgaggacaca gccatgtact tttgttcaag gagtagtagc 360
cactggtatt tcgatgtctg gggcacgggg accacggtca ccgtctcctc agccaaaacg 420
acacccccat ctgtctatcc actggcccct ggatctgctg cccaaactaa ctccatggtg 480
accctgggat gcctggtcaa gggctatttc cctgagccag tgacagtgac ctggaactct 540
ggatccctgt ccagcggt 558

<210> SEQ ID NO 113
<211> LENGTH: 19
<212> TYPE: PRT
<213> ORGANISM: Artificial sequence
<220> FEATURE:
<223> OTHER INFORMATION: Synthesized

<400> SEQUENCE: 113

Met Asn Phe Gly Leu Ser Leu Ile Phe Leu Ala Leu Ile Leu Lys Gly
1 5 10 15

Val Gln Cys

<210> SEQ ID NO 114
<211> LENGTH: 118
<212> TYPE: PRT
<213> ORGANISM: Artificial sequence
<220> FEATURE:
<223> OTHER INFORMATION: Synthesized

<400> SEQUENCE: 114

Glu Val Gln Leu Val Glu Ser Gly Gly Asp Leu Val Lys Pro Gly Gly
1 5 10 15

Ser Leu Lys Leu Ser Cys Ala Ala Pro Gly Phe Thr Phe Ser Thr Tyr
20 25 30

Gly Met Ser Trp Val Arg Gln Thr Pro Asp Lys Arg Leu Glu Trp Val
35 40 45

Ala Ile Ile Ser Ser Gly Gly Ser Tyr Thr Tyr Tyr Ser Asp Thr Val
50 55 60

Lys Gly Arg Phe Thr Ile Ser Arg Asp Asn Ala Lys Asn Thr Leu Asn
65 70 75 80

Leu Gln Met Ser Ser Leu Lys Ser Glu Asp Thr Ala Met Tyr Phe Cys
85 90 95

Ser Arg Ser Ser Ser His Trp Tyr Phe Asp Val Trp Gly Thr Gly Thr
100 105 110

Thr Val Thr Val Ser Ser
115

<210> SEQ ID NO 115
<211> LENGTH: 10
<212> TYPE: PRT
<213> ORGANISM: Artificial sequence
<220> FEATURE:
<223> OTHER INFORMATION: Synthesized

<400> SEQUENCE: 115

Gly Phe Thr Phe Ser Thr Tyr Gly Met Ser
1               5                   10

<210> SEQ ID NO 116
<211> LENGTH: 17
<212> TYPE: PRT
<213> ORGANISM: Artificial sequence
<220> FEATURE:
<223> OTHER INFORMATION: Synthesized

<400> SEQUENCE: 116

Ile Ile Ser Ser Gly Gly Ser Tyr Thr Tyr Tyr Ser Asp Thr Val Lys
1               5                   10                  15

Gly

<210> SEQ ID NO 117
<211> LENGTH: 9
<212> TYPE: PRT
<213> ORGANISM: Artificial sequence
<220> FEATURE:
<223> OTHER INFORMATION: Synthesized

<400> SEQUENCE: 117

Ser Ser Ser His Trp Tyr Phe Asp Val
1               5

<210> SEQ ID NO 118
<211> LENGTH: 555
<212> TYPE: DNA
<213> ORGANISM: Artificial sequence
<220> FEATURE:
<223> OTHER INFORMATION: Synthesized

<400> SEQUENCE: 118
atggtccttg ctcagtttct tgcattcttg ttgctttggt ttccaggtgc aagatgtgac      60
atcctgatga cccaatttcc atcctccatg tctgtatctc tgggagacac agtcagcatc     120
acttgccatg caagtcaggg cattagcagt aatatagggt ggttgcagca gaaaccaggg     180
aaatcattta agggcctgat ctatcatgga accaacttga aagatggagt tccatcaagg     240
ttcagtggca gtggatctgg aacagatttt tctctcacca tcagcagcct ggaatctgaa     300
gattttgcag actattactg tgtacagtat gctcagtttc cgtacacgtt cggagggggg     360
accaagctgg aaaaaagacg ggctgatgct gcaccaactg tatccatctt cccaccatcc     420
agtgagcagt taacatctgg aggtgcctca gtcgtgtgct tcttgaacaa cttctacccc     480
agagacatca atgtcaagtg gaagattgat ggcagtgaac gacaaaatgg cgtcctgaac     540
agttggactg atcag                                                      555

<210> SEQ ID NO 119
<211> LENGTH: 19
<212> TYPE: PRT
<213> ORGANISM: Artificial sequence
<220> FEATURE:
<223> OTHER INFORMATION: Synthesized

<400> SEQUENCE: 119

Met Val Leu Ala Gln Phe Leu Ala Phe Leu Leu Leu Trp Phe Pro Gly
1 5 10 15

Ala Arg Cys

<210> SEQ ID NO 120
<211> LENGTH: 107
<212> TYPE: PRT
<213> ORGANISM: Artificial sequence
<220> FEATURE:
<223> OTHER INFORMATION: Synthesized

<400> SEQUENCE: 120

Asp Ile Leu Met Thr Gln Phe Pro Ser Ser Met Ser Val Ser Leu Gly
1 5 10 15

Asp Thr Val Ser Ile Thr Cys His Ala Ser Gln Gly Ile Ser Ser Asn
20 25 30

Ile Gly Trp Leu Gln Gln Lys Pro Gly Lys Ser Phe Lys Gly Leu Ile
35 40 45

Tyr His Gly Thr Asn Leu Lys Asp Gly Val Pro Ser Arg Phe Ser Gly
50 55 60

Ser Gly Ser Gly Thr Asp Phe Ser Leu Thr Ile Ser Ser Leu Glu Ser
65 70 75 80

Glu Asp Phe Ala Asp Tyr Tyr Cys Val Gln Tyr Ala Gln Phe Pro Tyr
85 90 95

Thr Phe Gly Gly Gly Thr Lys Leu Glu Lys Arg
100 105

<210> SEQ ID NO 121
<211> LENGTH: 11
<212> TYPE: PRT
<213> ORGANISM: Artificial sequence
<220> FEATURE:
<223> OTHER INFORMATION: Synthesized

<400> SEQUENCE: 121

His Ala Ser Gln Gly Ile Ser Ser Asn Ile Gly
1 5 10

<210> SEQ ID NO 122
<211> LENGTH: 7
<212> TYPE: PRT
<213> ORGANISM: Artificial sequence
<220> FEATURE:
<223> OTHER INFORMATION: Synthesized

<400> SEQUENCE: 122

His Gly Thr Asn Leu Lys Asp
1 5

<210> SEQ ID NO 123
<211> LENGTH: 9
<212> TYPE: PRT
<213> ORGANISM: Artificial sequence
<220> FEATURE:
<223> OTHER INFORMATION: Synthesized

<400> SEQUENCE: 123

Val Gln Tyr Ala Gln Phe Pro Tyr Thr
1 5

<210> SEQ ID NO 124

<211> LENGTH: 558
<212> TYPE: DNA
<213> ORGANISM: Artificial sequence
<220> FEATURE:
<223> OTHER INFORMATION: Synthesized

<400> SEQUENCE: 124
atgaacttcg ggctcagctt gattttcctt gcccttattt taaaaggtgt ccagtgtgag 60
gtgcagctgg tggagtctgg gggagactta gtgaagcctg gagggtccct gaaactctcc 120
tgtgcagcct ctggattcac tttcaatacc catggcatgt cttgggttcg ccagactccg 180
gacaagagtc tggagtgggt cgcaaccatt agtactggtg gtttttacac ctcctatcca 240
gacagtgtga aggggcgatt caccatctcc agagacaatg ccaagaacac cctgttcctg 300
caaatgagca gtctgaagtc tgaggacaca gccatgtatt actgtgcaaa gagtagtagc 360
cactggtact tcgatgtctg gggcacaggg accacggtca ccgtctcctc agccaaaacg 420
acacccccat ctgtctatcc actggcccct ggatctgctg cccaaactaa ctccatggtg 480
accctgggat gcctggtcaa gggctatttc cctgagccag tgacagtgac ctggaactct 540
ggatccctgt ccagcggt 558

<210> SEQ ID NO 125
<211> LENGTH: 19
<212> TYPE: PRT
<213> ORGANISM: Artificial sequence
<220> FEATURE:
<223> OTHER INFORMATION: Synthesized

<400> SEQUENCE: 125

Met Asn Phe Gly Leu Ser Leu Ile Phe Leu Ala Leu Ile Leu Lys Gly
1 5 10 15

Val Gln Cys

<210> SEQ ID NO 126
<211> LENGTH: 118
<212> TYPE: PRT
<213> ORGANISM: Artificial sequence
<220> FEATURE:
<223> OTHER INFORMATION: Synthesized

<400> SEQUENCE: 126

Glu Val Gln Leu Val Glu Ser Gly Gly Asp Leu Val Lys Pro Gly Gly
1 5 10 15

Ser Leu Lys Leu Ser Cys Ala Ala Ser Gly Phe Thr Phe Asn Thr His
20 25 30

Gly Met Ser Trp Val Arg Gln Thr Pro Asp Lys Ser Leu Glu Trp Val
35 40 45

Ala Thr Ile Ser Thr Gly Gly Phe Tyr Thr Ser Tyr Pro Asp Ser Val
50 55 60

Lys Gly Arg Phe Thr Ile Ser Arg Asp Asn Ala Lys Asn Thr Leu Phe
65 70 75 80

Leu Gln Met Ser Ser Leu Lys Ser Glu Asp Thr Ala Met Tyr Tyr Cys
85 90 95

Ala Lys Ser Ser Ser His Trp Tyr Phe Asp Val Trp Gly Thr Gly Thr
100 105 110

Thr Val Thr Val Ser Ser
115

<210> SEQ ID NO 127

<211> LENGTH: 10
<212> TYPE: PRT
<213> ORGANISM: Artificial sequence
<220> FEATURE:
<223> OTHER INFORMATION: Synthesized

<400> SEQUENCE: 127

Gly Phe Thr Phe Asn Thr His Gly Met Ser
1               5                   10

<210> SEQ ID NO 128
<211> LENGTH: 17
<212> TYPE: PRT
<213> ORGANISM: Artificial sequence
<220> FEATURE:
<223> OTHER INFORMATION: Synthesized

<400> SEQUENCE: 128

Thr Ile Ser Thr Gly Gly Phe Tyr Thr Ser Tyr Pro Asp Ser Val Lys
1               5                   10                  15

Gly

<210> SEQ ID NO 129
<211> LENGTH: 9
<212> TYPE: PRT
<213> ORGANISM: Artificial sequence
<220> FEATURE:
<223> OTHER INFORMATION: Synthesized

<400> SEQUENCE: 129

Ser Ser Ser His Trp Tyr Phe Asp Val
1               5

<210> SEQ ID NO 130
<211> LENGTH: 555
<212> TYPE: DNA
<213> ORGANISM: Artificial sequence
<220> FEATURE:
<223> OTHER INFORMATION: Synthesized

<400> SEQUENCE: 130
atggtccttg ctcagtttct tgcattcttg ttgctttggt ttccaggtgc aagatgtgac     60
atcctgatga cccaatctcc atcctccatg tctgtatctc tgggagacac agtcagcatc    120
acttgccatg caagtcaggg catcagtagt aatatagggt ggttgcagca gaaaccaggg    180
aaatcattta agggcctgat ctatcatgga accaacttgg aagatggagt tccatcaagg    240
ttcagtggca gtggatctgg agcagattat tctctcacca tcagtagcct ggaatatgaa    300
gattttgcag actattactg tgtacagtat gctcactttc cgtacacgtt cggagggggg    360
accaagctgg aaataaaacg ggctgatgct gcaccaactg tatccatctt cccaccatcc    420
agtgagcagt taacatctgg aggtgcctca gtcgtgtgct tcttgaacaa cttctacccc    480
agagacatca atgtcaagtg gaagattgat ggcagtgaac gacaaaatgg cgtcctgaac    540
agttggactg atcag                                                     555

<210> SEQ ID NO 131
<211> LENGTH: 19
<212> TYPE: PRT
<213> ORGANISM: Artificial sequence
<220> FEATURE:
<223> OTHER INFORMATION: Synthesized

<400> SEQUENCE: 131

Met Val Leu Ala Gln Phe Leu Ala Phe Leu Leu Leu Trp Phe Pro Gly
1 5 10 15

Ala Arg Cys

<210> SEQ ID NO 132
<211> LENGTH: 107
<212> TYPE: PRT
<213> ORGANISM: Artificial sequence
<220> FEATURE:
<223> OTHER INFORMATION: Synthesized

<400> SEQUENCE: 132

Asp Ile Leu Met Thr Gln Ser Pro Ser Ser Met Ser Val Ser Leu Gly
1 5 10 15

Asp Thr Val Ser Ile Thr Cys His Ala Ser Gln Gly Ile Ser Ser Asn
20 25 30

Ile Gly Trp Leu Gln Gln Lys Pro Gly Lys Ser Phe Lys Gly Leu Ile
35 40 45

Tyr His Gly Thr Asn Leu Glu Asp Gly Val Pro Ser Arg Phe Ser Gly
50 55 60

Ser Gly Ser Gly Ala Asp Tyr Ser Leu Thr Ile Ser Ser Leu Glu Tyr
65 70 75 80

Glu Asp Phe Ala Asp Tyr Tyr Cys Val Gln Tyr Ala His Phe Pro Tyr
85 90 95

Thr Phe Gly Gly Gly Thr Lys Leu Glu Ile Lys
100 105

<210> SEQ ID NO 133
<211> LENGTH: 11
<212> TYPE: PRT
<213> ORGANISM: Artificial sequence
<220> FEATURE:
<223> OTHER INFORMATION: Synthesized

<400> SEQUENCE: 133

His Ala Ser Gln Gly Ile Ser Ser Asn Ile Gly
1 5 10

<210> SEQ ID NO 134
<211> LENGTH: 7
<212> TYPE: PRT
<213> ORGANISM: Artificial sequence
<220> FEATURE:
<223> OTHER INFORMATION: Synthesized

<400> SEQUENCE: 134

His Gly Thr Asn Leu Glu Asp
1 5

<210> SEQ ID NO 135
<211> LENGTH: 9
<212> TYPE: PRT
<213> ORGANISM: Artificial sequence
<220> FEATURE:
<223> OTHER INFORMATION: Synthesized

<400> SEQUENCE: 135

Val Gln Tyr Ala His Phe Pro Tyr Thr
1 5

<210> SEQ ID NO 136
<211> LENGTH: 522
<212> TYPE: DNA
<213> ORGANISM: Artificial sequence
<220> FEATURE:
<223> OTHER INFORMATION: Synthesized

<400> SEQUENCE: 136
atgggatgga actggatctt tattttaatc ctgtcagtaa ctacaggagt ccactctgag 60
atccagctgc agcagtctgg acctgagctg gtgaagcctg gggcttcagt gaagatatcc 120
tgcaaggctt ctggttactc attcactggc tactacatga actgggtgaa gcaaagtcct 180
gaaaagagcc ttgagtggat tggagagatt aatcctatca ctggtggtac tacctacaac 240
cagaatttca aggccaaggc cacattgact gtagacaaat cctccagcac agcctacctg 300
cagctcagga gcctgacatc tgaggactct gcagtctatt actgtgcatc cgattacttc 360
ggtagtaact cctggtttgc ttactggggc caagggactc tggtcactgt ctctgcagcc 420
aaaacaacac ccccatcagt ctatccactg gcccctgggt gtggagatac aactggttcc 480
tctgtgactc tgggatgcct ggtcaagggc tacttccctg ag 522

<210> SEQ ID NO 137
<211> LENGTH: 19
<212> TYPE: PRT
<213> ORGANISM: Artificial sequence
<220> FEATURE:
<223> OTHER INFORMATION: Synthesized

<400> SEQUENCE: 137

Met Gly Trp Asn Trp Ile Phe Ile Leu Ile Leu Ser Val Thr Thr Gly
1 5 10 15

Val His Ser

<210> SEQ ID NO 138
<211> LENGTH: 120
<212> TYPE: PRT
<213> ORGANISM: Artificial sequence
<220> FEATURE:
<223> OTHER INFORMATION: Synthesized

<400> SEQUENCE: 138

Glu Ile Gln Leu Gln Gln Ser Gly Pro Glu Leu Val Lys Pro Gly Ala
1 5 10 15

Ser Val Lys Ile Ser Cys Lys Ala Ser Gly Tyr Ser Phe Thr Gly Tyr
20 25 30

Tyr Met Asn Trp Val Lys Gln Ser Pro Glu Lys Ser Leu Glu Trp Ile
35 40 45

Gly Glu Ile Asn Pro Ile Thr Gly Gly Thr Thr Tyr Asn Gln Asn Phe
50 55 60

Lys Ala Lys Ala Thr Leu Thr Val Asp Lys Ser Ser Ser Thr Ala Tyr
65 70 75 80

Leu Gln Leu Arg Ser Leu Thr Ser Glu Asp Ser Ala Val Tyr Tyr Cys
85 90 95

Ala Ser Asp Tyr Phe Gly Ser Asn Ser Trp Phe Ala Tyr Trp Gly Gln
100 105 110

Gly Thr Leu Val Thr Val Ser Ala
115 120

<210> SEQ ID NO 139
<211> LENGTH: 10

<212> TYPE: PRT
<213> ORGANISM: Artificial sequence
<220> FEATURE:
<223> OTHER INFORMATION: Synthesized

<400> SEQUENCE: 139

Gly Tyr Ser Phe Thr Gly Tyr Tyr Met Asn
1 5 10

<210> SEQ ID NO 140
<211> LENGTH: 17
<212> TYPE: PRT
<213> ORGANISM: Artificial sequence
<220> FEATURE:
<223> OTHER INFORMATION: Synthesized

<400> SEQUENCE: 140

Glu Ile Asn Pro Ile Thr Gly Gly Thr Thr Tyr Asn Gln Asn Phe Lys
1 5 10 15

Ala

<210> SEQ ID NO 141
<211> LENGTH: 11
<212> TYPE: PRT
<213> ORGANISM: Artificial sequence
<220> FEATURE:
<223> OTHER INFORMATION: Synthesized

<400> SEQUENCE: 141

Asp Tyr Phe Gly Ser Asn Ser Trp Phe Ala Tyr
1 5 10

<210> SEQ ID NO 142
<211> LENGTH: 570
<212> TYPE: DNA
<213> ORGANISM: Artificial sequence
<220> FEATURE:
<223> OTHER INFORMATION: Synthesized

<400> SEQUENCE: 142
atgaagttgc ctgttaggct gttggtggtg atgttctgga ttcctgcttc cagcagtgat 60
gttttgatga cccaaactcc actctccctg cctgtcagtc ttggagatca agcctccatc 120
tcttgcagat ctagtcagag cattgtacat agaaatggaa acacctattt agaatggtac 180
ctgcagaaac caggccagtc tccaaagctc ctgatctaca aagtttccaa ccgattttct 240
ggggtcccag acaggttcag tggcagtgga tcagggacag atttcacact caggatcagc 300
agagtggagg ctgaggatct gggagtttat tactgctttc aaggttcaca tgttccgtac 360
acgttcggag gggggaccaa gctggaaata aaacgggctg atgctgcacc aactgtatcc 420
atcttcccac catccagtga gcagttaaca tctggaggtg cctcagtcgt gtgcttcttg 480
aacaacttct accccagaga catcaatgtc aagtggaaga ttgatggcag tgaacgacaa 540
aatggcgtcc tgaacagttg gactgatcag 570

<210> SEQ ID NO 143
<211> LENGTH: 19
<212> TYPE: PRT
<213> ORGANISM: Artificial sequence
<220> FEATURE:
<223> OTHER INFORMATION: Synthesized

<400> SEQUENCE: 143

Met Lys Leu Pro Val Arg Leu Leu Val Val Met Phe Trp Ile Pro Ala
1               5                   10                  15

Ser Ser Ser

<210> SEQ ID NO 144
<211> LENGTH: 112
<212> TYPE: PRT
<213> ORGANISM: Artificial sequence
<220> FEATURE:
<223> OTHER INFORMATION: Synthesized

<400> SEQUENCE: 144

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Arg
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 145
<211> LENGTH: 16
<212> TYPE: PRT
<213> ORGANISM: Artificial sequence
<220> FEATURE:
<223> OTHER INFORMATION: Synthesized

<400> SEQUENCE: 145

Arg Ser Ser Gln Ser Ile Val His Arg Asn Gly Asn Thr Tyr Leu Glu
1               5                   10                  15

<210> SEQ ID NO 146
<211> LENGTH: 7
<212> TYPE: PRT
<213> ORGANISM: Artificial sequence
<220> FEATURE:
<223> OTHER INFORMATION: Synthesized

<400> SEQUENCE: 146

Lys Val Ser Asn Arg Phe Ser
1               5

<210> SEQ ID NO 147
<211> LENGTH: 10
<212> TYPE: PRT
<213> ORGANISM: Artificial sequence
<220> FEATURE:
<223> OTHER INFORMATION: Synthesized

<400> SEQUENCE: 147

Phe Gln Gly Ser His Val Pro Tyr Thr Phe
1               5                   10

<210> SEQ ID NO 148
<211> LENGTH: 465
<212> TYPE: DNA
<213> ORGANISM: Artificial sequence
<220> FEATURE:
<223> OTHER INFORMATION: Synthesized

<400> SEQUENCE: 148
atgaacttcg ggctcagctt gattttcctt gtcctaattt taaaaggtgt ccagtgtgaa 60
gtgaagctgg tggagtctgg gggaggctta gtgaagcctg gagggtccct gaaactctcc 120
tgtggagcct ctggattcac tttcagtaac tatgtcatgt cttgggttcg ccagactccg 180
gagaggaggc tggagtgggt cgcaaccatt agtggtggtg gtcgttactc ctactatcca 240
gacagtgtga aggggcgatt caccatctcc agagacaatg ccaagaacaa cctgtaccta 300
caaatgagca gtctgaggtc tgaggacacg gccttatatt actgtggaag acaggatgat 360
tacgactctt ttccttactg tggccaaggg actctggtca ctgtctctgt agctacaaca 420
acagccccat ctgtctatcc cttggtccct ggctgcggtg acaca 465

<210> SEQ ID NO 149
<211> LENGTH: 19
<212> TYPE: PRT
<213> ORGANISM: Artificial sequence
<220> FEATURE:
<223> OTHER INFORMATION: Synthesized

<400> SEQUENCE: 149

Met Asn Phe Gly Leu Ser Leu Ile Phe Leu Val Leu Ile Leu Lys Gly
1 5 10 15

Val Gln Cys

<210> SEQ ID NO 150
<211> LENGTH: 118
<212> TYPE: PRT
<213> ORGANISM: Artificial sequence
<220> FEATURE:
<223> OTHER INFORMATION: Synthesized

<400> SEQUENCE: 150

Glu Val Lys Leu Val Glu Ser Gly Gly Gly Leu Val Lys Pro Gly Gly
1 5 10 15

Ser Leu Lys Leu Ser Cys Gly Ala Ser Gly Phe Thr Phe Ser Asn Tyr
20 25 30

Val Met Ser Trp Val Arg Gln Thr Pro Glu Arg Arg Leu Glu Trp Val
35 40 45

Ala Thr Ile Ser Gly Gly Gly Arg Tyr Ser Tyr Tyr Pro Asp Ser Val
50 55 60

Lys Gly Arg Phe Thr Ile Ser Arg Asp Asn Ala Lys Asn Asn Leu Tyr
65 70 75 80

Leu Gln Met Ser Ser Leu Arg Ser Glu Asp Thr Ala Leu Tyr Tyr Cys
85 90 95

Gly Arg Gln Asp Asp Tyr Asp Ser Phe Pro Tyr Cys Gly Gln Gly Thr
100 105 110

Leu Val Thr Val Ser Val
115

<210> SEQ ID NO 151
<211> LENGTH: 10
<212> TYPE: PRT
<213> ORGANISM: Artificial sequence
<220> FEATURE:
<223> OTHER INFORMATION: Synthesized

<400> SEQUENCE: 151

Gly Phe Thr Phe Ser Asn Tyr Val Met Ser
1               5                   10

<210> SEQ ID NO 152
<211> LENGTH: 17
<212> TYPE: PRT
<213> ORGANISM: Artificial sequence
<220> FEATURE:
<223> OTHER INFORMATION: Synthesized

<400> SEQUENCE: 152

Thr Ile Ser Gly Gly Gly Arg Tyr Ser Tyr Tyr Pro Asp Ser Val Lys
1               5                   10                  15

Gly

<210> SEQ ID NO 153
<211> LENGTH: 9
<212> TYPE: PRT
<213> ORGANISM: Artificial sequence
<220> FEATURE:
<223> OTHER INFORMATION: Synthesized

<400> SEQUENCE: 153

Gln Asp Asp Tyr Asp Ser Phe Pro Tyr
1               5

<210> SEQ ID NO 154
<211> LENGTH: 558
<212> TYPE: DNA
<213> ORGANISM: Artificial sequence
<220> FEATURE:
<223> OTHER INFORMATION: Synthesized

<400> SEQUENCE: 154
atggtatcca cacctcagtt ccttgtattt ttgcttttct ggattccagc ctccagaggt 60
gacatcttgc tgactcagtc tccagccatc ctgtctgtga gtctaggaga aagagtcagt 120
ttctcctgca gggccagtca gagcattggc acaagcatac actggtttca gctaagaaca 180
aatggttctc caaggcttct cataaagtat gcttctgagc ccatctctgg gatcccttcc 240
aggtttagtg gcagtggatc agggacagat tttactctta gcatcaatag tgtggaatct 300
gaagatattg cagattattt ctgtcaacaa agtaagagct ggccaatcac gttcggtact 360
gggaccaagc tggagctgaa acgggctgat gctgcaccaa ctgtatccat cttcccacca 420
tccagtgagc agttaacatc tggaggtgcc tcagtcgtgt gcttcttgaa caacttctac 480
cccagagaca tcaatgtcaa gtggaagatt gatggcagtg aacgacaaaa tggcgtcctg 540
aacagttgga ctgatcag 558

<210> SEQ ID NO 155
<211> LENGTH: 20
<212> TYPE: PRT
<213> ORGANISM: Artificial sequence
<220> FEATURE:
<223> OTHER INFORMATION: Synthesized

<400> SEQUENCE: 155

Met Val Ser Thr Pro Gln Phe Leu Val Phe Leu Leu Phe Trp Ile Pro
1               5                   10                  15

Ala Ser Arg Gly
            20

<210> SEQ ID NO 156
<211> LENGTH: 107
<212> TYPE: PRT
<213> ORGANISM: Artificial sequence
<220> FEATURE:
<223> OTHER INFORMATION: Synthesized

<400> SEQUENCE: 156

Asp Ile Leu Leu Thr Gln Ser Pro Ala Ile Leu Ser Val Ser Leu Gly
1               5                   10                  15

Glu Arg Val Ser Phe Ser Cys Arg Ala Ser Gln Ser Ile Gly Thr Ser
            20                  25                  30

Ile His Trp Phe Gln Leu Arg Thr Asn Gly Ser Pro Arg Leu Leu Ile
        35                  40                  45

Lys Tyr Ala Ser Glu Pro Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Phe Cys Gln Gln Ser Lys Ser Trp Pro Ile
                85                  90                  95

Thr Phe Gly Thr Gly Thr Lys Leu Glu Leu Lys
            100                 105

<210> SEQ ID NO 157
<211> LENGTH: 11
<212> TYPE: PRT
<213> ORGANISM: Artificial sequence
<220> FEATURE:
<223> OTHER INFORMATION: Synthesized

<400> SEQUENCE: 157

Arg Ala Ser Gln Ser Ile Gly Thr Ser Ile His
1               5                   10

<210> SEQ ID NO 158
<211> LENGTH: 7
<212> TYPE: PRT
<213> ORGANISM: Artificial sequence
<220> FEATURE:
<223> OTHER INFORMATION: Synthesized

<400> SEQUENCE: 158

Tyr Ala Ser Glu Pro Ile Ser
1               5

<210> SEQ ID NO 159
<211> LENGTH: 9
<212> TYPE: PRT
<213> ORGANISM: Artificial sequence
<220> FEATURE:
<223> OTHER INFORMATION: Synthesized

<400> SEQUENCE: 159

Gln Gln Ser Lys Ser Trp Pro Ile Thr
1               5

<210> SEQ ID NO 160
<211> LENGTH: 123
<212> TYPE: PRT
<213> ORGANISM: Artificial sequence
<220> FEATURE:

<223> OTHER INFORMATION: Synthesized

<400> SEQUENCE: 160

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Asn Tyr Ile Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Glu Gly Ala Tyr Ser Gly Ser Ser Ser Tyr Pro Met Asp Tyr
            100                 105                 110

Trp Gly Gln Gly Thr Ser Val Thr Val Ser Ser
        115                 120

<210> SEQ ID NO 161
<211> LENGTH: 118
<212> TYPE: PRT
<213> ORGANISM: Homo sapiens

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Thr Pro Trp Tyr Phe Asp Tyr Trp Gly Gln Gly Thr
            100                 105                 110

Leu Val Thr Val Ser Ser
        115

<210> SEQ ID NO 162
<211> LENGTH: 114
<212> TYPE: PRT
<213> ORGANISM: Homo sapiens

<400> SEQUENCE: 162

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Phe Asp Val Trp Gly Gln Gly Thr Met Val Thr Val
            100                 105                 110

Ser Ser


<210> SEQ ID NO 163
<211> LENGTH: 118
<212> TYPE: PRT
<213> ORGANISM: Artificial sequence
<220> FEATURE:
<223> OTHER INFORMATION: Synthesized

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ala Ile Ile Ser Ser Gly Gly Ser Tyr Thr Tyr Tyr Ser Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Ser Ser Ser His Trp Tyr Phe Asp Val Trp Gly Gln Gly Thr
            100                 105                 110

Leu Val Thr Val Ser Ser
        115


<210> SEQ ID NO 164
<211> LENGTH: 118
<212> TYPE: PRT
<213> ORGANISM: Artificial sequence
<220> FEATURE:
<223> OTHER INFORMATION: Synthesized

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ala Ile Ile Ser Ser Gly Gly Ser Tyr Thr Tyr Tyr Ser Asp Thr Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Ser Ser Ser His Trp Tyr Phe Asp Val Trp Gly Gln Gly Thr
            100                 105                 110

Leu Val Thr Val Ser Ser
        115
```

<210> SEQ ID NO 165
<211> LENGTH: 118
<212> TYPE: PRT
<213> ORGANISM: Artificial sequence
<220> FEATURE:
<223> OTHER INFORMATION: Synthesized

<400> SEQUENCE: 165

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Arg Leu Glu Trp Val
        35                  40                  45

Ala Ile Ile Ser Ser Gly Gly Ser Tyr Thr Tyr Tyr Ser Asp Thr Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Ser Ser Ser His Trp Tyr Phe Asp Val Trp Gly Gln Gly Thr
            100                 105                 110

Leu Val Thr Val Ser Ser
        115
```

<210> SEQ ID NO 166
<211> LENGTH: 118
<212> TYPE: PRT
<213> ORGANISM: Artificial sequence
<220> FEATURE:
<223> OTHER INFORMATION: Synthesized

<400> SEQUENCE: 166

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Asp Lys Arg Leu Glu Trp Val
        35                  40                  45

Ala Ile Ile Ser Ser Gly Gly Ser Tyr Thr Tyr Tyr Ser Asp Thr Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Ser Ser Ser His Trp Tyr Phe Asp Val Trp Gly Gln Gly Thr
            100                 105                 110

Leu Val Thr Val Ser Ser
        115
```

<210> SEQ ID NO 167
<211> LENGTH: 118
<212> TYPE: PRT
<213> ORGANISM: Artificial sequence
<220> FEATURE:
<223> OTHER INFORMATION: Synthesized

<400> SEQUENCE: 167

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Gly Met Ser Trp Val Arg Gln Ala Pro Asp Lys Arg Leu Glu Trp Val
35 40 45

Ala Ile Ile Ser Ser Gly Gly Ser Tyr Thr Tyr Tyr Ser Asp Thr Val
50 55 60

Lys Gly Arg Phe Thr Ile Ser Arg Asp Asn Ser Lys Asn Ser Leu Tyr
65 70 75 80

Leu Gln Met Asn Ser Leu Lys Ala Glu Asp Thr Ala Val Tyr Tyr Cys
85 90 95

Ser Arg Ser Ser Ser His Trp Tyr Phe Asp Val Trp Gly Gln Gly Thr
100 105 110

Leu Val Thr Val Ser Ser
115

<210> SEQ ID NO 168
<211> LENGTH: 118
<212> TYPE: PRT
<213> ORGANISM: Artificial sequence
<220> FEATURE:
<223> OTHER INFORMATION: Synthesized

<400> SEQUENCE: 168

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Gly Met Ser Trp Val Arg Gln Thr Pro Gly Lys Arg Leu Glu Trp Val
35 40 45

Ala Ile Ile Ser Ser Gly Gly Ser Tyr Thr Tyr Tyr Ser Asp Thr Val
50 55 60

Lys Gly Arg Phe Thr Ile Ser Arg Asp Asn Ser Lys Asn Ser Leu Tyr
65 70 75 80

Leu Gln Met Asn Ser Leu Arg Ala Glu Asp Thr Ala Val Tyr Tyr Cys
85 90 95

Ser Arg Ser Ser Ser His Trp Tyr Phe Asp Val Trp Gly Gln Gly Thr
100 105 110

Leu Val Thr Val Ser Ser
115

<210> SEQ ID NO 169
<211> LENGTH: 118
<212> TYPE: PRT
<213> ORGANISM: Artificial sequence
<220> FEATURE:
<223> OTHER INFORMATION: Synthesized

<400> SEQUENCE: 169

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Gly Met Ser Trp Val Arg Gln Thr Pro Asp Lys Arg Leu Glu Trp Val
35 40 45

Ala Ile Ile Ser Ser Gly Gly Ser Tyr Thr Tyr Tyr Ser Asp Thr Val
50 55 60

Lys Gly Arg Phe Thr Ile Ser Arg Asp Asn Ser Lys Asn Ser Leu Tyr
65 70 75 80

Leu Gln Met Asn Ser Leu Arg Ala Glu Asp Thr Ala Val Tyr Tyr Cys
85 90 95

Ser Arg Ser Ser Ser His Trp Tyr Phe Asp Val Trp Gly Gln Gly Thr
100 105 110

Leu Val Thr Val Ser Ser
115

<210> SEQ ID NO 170
<211> LENGTH: 114
<212> TYPE: PRT
<213> ORGANISM: Artificial sequence
<220> FEATURE:
<223> OTHER INFORMATION: Synthesized

<400> SEQUENCE: 170

Asn Ile Met Met Thr Gln Ser Pro Ser Ser Leu Ala Val Ser Ala Gly
1 5 10 15

Glu Lys Val Thr Met Asn Cys Lys Ser Ser Gln Ser Val Leu Tyr Ser
20 25 30

Ser Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Thr Glu Asp Leu Ala Val Tyr Tyr Cys His Gln
85 90 95

Tyr Leu Ser Ser Tyr Met Tyr Thr Phe Gly Gly Gly Thr Lys Leu Glu
100 105 110

Ile Lys

<210> SEQ ID NO 171
<211> LENGTH: 107
<212> TYPE: PRT
<213> ORGANISM: Homo sapiens

<400> SEQUENCE: 171

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Leu
85 90 95

Thr Phe Gly Gly Gly Thr Lys Val Glu Ile Arg
100 105

<210> SEQ ID NO 172
<211> LENGTH: 107
<212> TYPE: PRT
<213> ORGANISM: Homo sapiens

<400> SEQUENCE: 172

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Lys Arg
            100                 105
```

<210> SEQ ID NO 173
<211> LENGTH: 107
<212> TYPE: PRT
<213> ORGANISM: Artificial sequence
<220> FEATURE:
<223> OTHER INFORMATION: Synthesized

<400> SEQUENCE: 173

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Ser Asn
            20                  25                  30

Ile Gly Trp Leu Gln Gln Lys Pro Gly Lys Ala Phe Lys Gly Leu Ile
        35                  40                  45

Tyr His Gly Thr Asn Leu Lys Asp Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Phe Cys Val Gln Tyr Ala Gln Phe Pro Tyr
                85                  90                  95

Thr Phe Gly Gly Gly Thr Lys Val Glu Ile Arg
            100                 105
```

<210> SEQ ID NO 174
<211> LENGTH: 107
<212> TYPE: PRT
<213> ORGANISM: Artificial sequence
<220> FEATURE:
<223> OTHER INFORMATION: Synthesized

<400> SEQUENCE: 174

```
Asp Ile Gln Met Thr Gln Ser Pro Ser Ser Val Ser Ala Ser Val Gly
1               5                   10                  15

Asp Arg Val Thr Ile Thr Cys His Ala Ser Gln Gly Ile Ser Ser Asn
            20                  25                  30

Ile Gly Trp Leu Gln Gln Lys Pro Gly Lys Ala Phe Lys Gly Leu Ile
        35                  40                  45
```

Tyr His Gly Thr Asn Leu Lys Asp Gly Val Pro Ser Arg Phe Ser Gly
50 55 60

Ser Gly Ser Gly Ala Asp Phe Thr Leu Thr Ile Ser Ser Leu Gln Pro
65 70 75 80

Glu Asp Phe Ala Thr Tyr Phe Cys Val Gln Tyr Ala Gln Phe Pro Tyr
85 90 95

Thr Phe Gly Gln Gly Thr Lys Val Glu Ile Arg
100 105

<210> SEQ ID NO 175
<211> LENGTH: 107
<212> TYPE: PRT
<213> ORGANISM: Artificial sequence
<220> FEATURE:
<223> OTHER INFORMATION: Synthesized

<400> SEQUENCE: 175

Asp Ile Gln Met Thr Gln Ser Pro Ser Ser Val Ser Ala Ser Val Gly
1 5 10 15

Asp Arg Val Thr Ile Thr Cys His Ala Ser Gln Gly Ile Ser Ser Asn
20 25 30

Ile Gly Trp Leu Gln Gln Lys Pro Gly Lys Ala Phe Lys Gly Leu Ile
35 40 45

Tyr His Gly Thr Asn Leu Lys Asp Gly Val Pro Ser Arg Phe Ser Gly
50 55 60

Ser Gly Ser Gly Ala Asp Phe Thr Leu Thr Ile Ser Ser Leu Gln Pro
65 70 75 80

Glu Asp Phe Ala Thr Tyr Phe Cys Val Gln Tyr Ala Gln Phe Pro Tyr
85 90 95

Thr Phe Gly Gln Gly Thr Lys Val Glu Lys Arg
100 105

<210> SEQ ID NO 176
<211> LENGTH: 107
<212> TYPE: PRT
<213> ORGANISM: Artificial sequence
<220> FEATURE:
<223> OTHER INFORMATION: Synthesized

<400> SEQUENCE: 176

Asp Ile Gln Met Thr Gln Ser Pro Ser Ser Val Ser Ala Ser Val Gly
1 5 10 15

Asp Arg Val Thr Ile Thr Cys His Ala Ser Gln Gly Ile Ser Ser Asn
20 25 30

Ile Gly Trp Leu Gln Gln Lys Pro Gly Lys Ala Phe Lys Gly Leu Ile
35 40 45

Tyr His Gly Thr Asn Leu Lys Asp Gly Val Pro Ser Arg Phe Ser Gly
50 55 60

Ser Gly Ser Gly Ala Asp Phe Thr Leu Thr Ile Ser Ser Leu Gln Pro
65 70 75 80

Glu Asp Phe Ala Asp Tyr Phe Cys Val Gln Tyr Ala Gln Phe Pro Tyr
85 90 95

Thr Phe Gly Gln Gly Thr Lys Val Glu Lys Arg
100 105

<210> SEQ ID NO 177
<211> LENGTH: 116
<212> TYPE: PRT

<213> ORGANISM: Artificial sequence
<220> FEATURE:
<223> OTHER INFORMATION: Synthesized

<400> SEQUENCE: 177

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Asn Leu Arg Gly Tyr Phe Asp Tyr Trp Gly Gln Gly Thr Thr Leu
            100                 105                 110

Thr Val Ser Ser
        115

<210> SEQ ID NO 178
<211> LENGTH: 123
<212> TYPE: PRT
<213> ORGANISM: Homo sapiens

<400> SEQUENCE: 178

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Tyr Cys Ser Ser Thr Ser Cys Tyr Lys Thr Gly Phe Val
            100                 105                 110

Trp Gly Gln Gly Thr Leu Val Thr Val Ser Ser
        115                 120

<210> SEQ ID NO 179
<211> LENGTH: 115
<212> TYPE: PRT
<213> ORGANISM: Homo sapiens

<400> SEQUENCE: 179

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

```
Gly Arg Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu Tyr Phe Gln His Trp Gly Gln Gly Thr Leu Val Thr
            100                 105                 110

Val Ser Ser
        115


<210> SEQ ID NO 180
<211> LENGTH: 123
<212> TYPE: PRT
<213> ORGANISM: Artificial sequence
<220> FEATURE:
<223> OTHER INFORMATION: Synthesized

<400> SEQUENCE: 180

Gln Ala Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Ile
        35                  40                  45

Gly Ala Ile Tyr Pro Gly Asn Asp Ala Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Gly Tyr Tyr Gly Ser Ser Phe Glu Ala Trp Phe Ala Ser
            100                 105                 110

Trp Gly Gln Gly Thr Thr Val Thr Val Ser Ser
        115                 120


<210> SEQ ID NO 181
<211> LENGTH: 123
<212> TYPE: PRT
<213> ORGANISM: Artificial sequence
<220> FEATURE:
<223> OTHER INFORMATION: Synthesized

<400> SEQUENCE: 181

Gln Ala Gln Leu Val Gln Ser Gly Ala Glu Val Val Lys Pro Gly Ser
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Ile
        35                  40                  45

Gly Ala Ile Tyr Pro Gly Asn Asp Ala Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Gly Tyr Tyr Gly Ser Ser Phe Glu Ala Trp Phe Ala Ser
            100                 105                 110
```

```
Trp Gly Gln Gly Thr Thr Val Thr Val Ser Ser
        115                 120


<210> SEQ ID NO 182
<211> LENGTH: 112
<212> TYPE: PRT
<213> ORGANISM: Artificial sequence
<220> FEATURE:
<223> OTHER INFORMATION: Synthesized

<400> SEQUENCE: 182

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Arg Thr Phe Gly Gly Gly Thr Lys Leu Glu Ile Lys
            100                 105                 110


<210> SEQ ID NO 183
<211> LENGTH: 112
<212> TYPE: PRT
<213> ORGANISM: Homo sapiens

<400> SEQUENCE: 183

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 184
<211> LENGTH: 113
<212> TYPE: PRT
<213> ORGANISM: Homo sapiens

<400> SEQUENCE: 184

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30
```

Asp Asp Gly Asn Thr Tyr Leu Asp Trp Tyr Leu Gln Lys Pro Gly Gln
35 40 45

Ser Pro Gln Leu Leu Ile Tyr Thr Leu Ser Tyr Arg Ala Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Val Tyr Tyr Cys Met Gln
85 90 95

Arg Ile Glu Phe Pro Leu Thr Phe Gly Gly Gly Thr Lys Val Glu Ile
100 105 110

Lys

<210> SEQ ID NO 185
<211> LENGTH: 112
<212> TYPE: PRT
<213> ORGANISM: Artificial sequence
<220> FEATURE:
<223> OTHER INFORMATION: Synthesized

<400> SEQUENCE: 185

Asp Val Val Met Thr Gln Thr Pro Leu Ser Leu Pro Val Thr Pro Gly
1 5 10 15

Glu Pro Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Leu Pro Thr Phe Gly Gly Gly Thr Lys Val Glu Ile Lys
100 105 110

<210> SEQ ID NO 186
<211> LENGTH: 112
<212> TYPE: PRT
<213> ORGANISM: Artificial sequence
<220> FEATURE:
<223> OTHER INFORMATION: Synthesized

<400> SEQUENCE: 186

Asp Val Val Met Thr Gln Thr Pro Ser Ser Leu Pro Val Thr Pro Gly
1 5 10 15

Glu Pro Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Thr Ile
65 70 75 80

Ser Arg Val Glu Ala Glu Asp Val Gly Val Tyr Tyr Cys Phe Gln Gly
85 90 95

Ser His Val Leu Pro Thr Phe Gly Gly Gly Thr Lys Val Glu Ile Lys
100 105 110

<210> SEQ ID NO 187
<211> LENGTH: 118
<212> TYPE: PRT
<213> ORGANISM: Artificial sequence
<220> FEATURE:
<223> OTHER INFORMATION: Synthesized

<400> SEQUENCE: 187

Glu Val Lys Leu Gln Glu Ser Gly Gly Asp Leu Val Gln Pro Gly Gly
1 5 10 15

Ser Leu Lys Leu Ser Cys Ala Ala Ser Gly Phe Thr Phe Ser Ser Tyr
20 25 30

Thr Met Ser Trp Val Arg Gln Thr Pro Glu Lys Arg Leu Glu Trp Val
35 40 45

Ala Ser Ile Asn Asn Gly Gly Gly Arg Thr Tyr Tyr Pro Asp Thr Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr Tyr Cys
85 90 95

Val Arg His Glu Tyr Tyr Tyr Ala Met Asp Tyr Trp Gly Gln Gly Thr
100 105 110

Thr Val Thr Val Ser Ser
115

<210> SEQ ID NO 188
<211> LENGTH: 119
<212> TYPE: PRT
<213> ORGANISM: Homo sapiens

<400> SEQUENCE: 188

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Glu Met Asn Trp Val Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Glu Asn Ile Ala Ala Phe Asp Tyr Trp Gly Gln Gly Thr Leu
100 105 110

Val Thr Val Ser Ser Gly Ser
115

<210> SEQ ID NO 189
<211> LENGTH: 113
<212> TYPE: PRT
<213> ORGANISM: Homo sapiens

<400> SEQUENCE: 189

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Glu Met Asn Trp Val Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Tyr Phe Asp Tyr Trp Gly Gln Gly Thr Leu Val Thr Val Ser
100 105 110

Ser

<210> SEQ ID NO 190
<211> LENGTH: 117
<212> TYPE: PRT
<213> ORGANISM: Artificial sequence
<220> FEATURE:
<223> OTHER INFORMATION: Synthesized

<400> SEQUENCE: 190

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Ile Tyr
20 25 30

Gly Met Ser Trp Val Arg Gln Ala Pro Gly Lys Gly Leu Glu Trp Val
35 40 45

Ala Thr Ile Ser Ser Gly Gly Ile Tyr Thr Tyr Tyr Pro Asp Ile Leu
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Pro Gly Gly Ala Met Asp Tyr Trp Gly Gln Gly Thr Leu
100 105 110

Val Thr Val Ser Ser
115

<210> SEQ ID NO 191
<211> LENGTH: 117
<212> TYPE: PRT
<213> ORGANISM: Artificial sequence
<220> FEATURE:
<223> OTHER INFORMATION: Synthesized

<400> SEQUENCE: 191

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Ile Tyr
20 25 30

Gly Met Ser Trp Val Arg Gln Ala Pro Gly Lys Gly Leu Glu Trp Val
35 40 45

Ala Thr Ile Ser Ser Gly Gly Ile Tyr Thr Tyr Tyr Pro Asp Ile Leu
50 55 60

Lys Gly Arg Phe Thr Ile Ser Arg Asp Asn Ala Lys Asn Ser Leu Tyr
65 70 75 80

Leu Gln Met Asn Ser Gly Arg Ala Glu Asp Thr Ala Val Tyr Tyr Cys
85 90 95

Ala Arg His Pro Gly Gly Ala Met Asp Tyr Trp Gly Gln Gly Thr Leu
100 105 110

Val Thr Val Ser Ser
115

<210> SEQ ID NO 192
<211> LENGTH: 117
<212> TYPE: PRT
<213> ORGANISM: Artificial sequence
<220> FEATURE:
<223> OTHER INFORMATION: Synthesized

<400> SEQUENCE: 192

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Ile Tyr
20 25 30

Gly Met Ser Trp Val Arg Gln Ala Pro Gly Lys Gly Leu Glu Trp Val
35 40 45

Ala Thr Ile Ser Ser Gly Gly Ile Tyr Thr Tyr Tyr Pro Asp Ile Leu
50 55 60

Lys Gly Arg Phe Thr Ile Ser Arg Asp Asn Ala Lys Asn Ser Leu Tyr
65 70 75 80

Gly Gln Met Asn Ser Leu Arg Ala Glu Asp Thr Ala Val Tyr Tyr Cys
85 90 95

Ala Arg His Pro Gly Gly Ala Met Asp Tyr Trp Gly Gln Gly Thr Leu
100 105 110

Val Thr Val Ser Ser
115

<210> SEQ ID NO 193
<211> LENGTH: 108
<212> TYPE: PRT
<213> ORGANISM: Artificial sequence
<220> FEATURE:
<223> OTHER INFORMATION: Synthesized

<400> SEQUENCE: 193

Asp Ile Glu Leu Thr Gln Thr Pro Val Ser Leu Ser Ala Ser Val Gly
1 5 10 15

Glu Thr Val Thr Ile Thr Cys Arg Ala Ser Glu Asn Ile Tyr Ser Tyr
20 25 30

Leu Ala Trp Tyr Gln Gln Lys Gln Gly Lys Ser Pro Gln Phe Leu Val
35 40 45

Tyr Asn Ala Lys Thr Leu Gly Glu Gly Val Pro Ser Arg Phe Ser Gly
50 55 60

Ser Gly Ser Gly Thr Gln Phe Ser Leu Lys Ile Asn Ser Leu Leu Pro
65 70 75 80

Glu Asp Phe Gly Ser Tyr Tyr Cys Gln His His Tyr Gly Thr Pro Pro
85 90 95

Leu Thr Phe Gly Gly Gly Thr Lys Leu Glu Ile Lys
100 105

<210> SEQ ID NO 194
<211> LENGTH: 108
<212> TYPE: PRT

<213> ORGANISM: Homo sapiens

<400> SEQUENCE: 194

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Asn Ser Leu Gln Pro
65 70 75 80

Glu Asp Phe Ala Thr Tyr Tyr Cys Gln Gln Ser Tyr Ser Thr Pro Pro
85 90 95

Tyr Thr Phe Gly Gln Gly Thr Lys Leu Glu Ile Lys
100 105

<210> SEQ ID NO 195
<211> LENGTH: 107
<212> TYPE: PRT
<213> ORGANISM: Homo sapiens

<400> SEQUENCE: 195

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Tyr
85 90 95

Thr Phe Gly Gln Gly Thr Lys Leu Glu Ile Lys
100 105

<210> SEQ ID NO 196
<211> LENGTH: 108
<212> TYPE: PRT
<213> ORGANISM: Artificial sequence
<220> FEATURE:
<223> OTHER INFORMATION: Synthesized

<400> SEQUENCE: 196

Asp Ile Gln Met Thr Gln Ser Pro Ser Ser Leu Ser Ala Ser Val Gly
1 5 10 15

Asp Arg Val Thr Ile Thr Cys Arg Val Ser Glu Asn Ile Tyr Ser Asn
20 25 30

Leu Ala Trp Tyr Gln Gln Lys Pro Gly Lys Ala Pro Lys Leu Leu Val
35 40 45

Tyr Ala Ala Thr Asn Leu Ala Asp Gly Val Pro Ser Arg Phe Ser Gly
50 55 60

Ser Gly Ser Gly Thr Asp Tyr Thr Leu Thr Ile Asn Ser Leu Gln Pro
65 70 75 80

Glu Asp Phe Ala Thr Tyr Tyr Cys Gln His Phe Trp Gly Thr Pro Pro
85 90 95

Trp Thr Phe Gly Gln Gly Thr Lys Leu Glu Ile Lys
100 105

<210> SEQ ID NO 197
<211> LENGTH: 108
<212> TYPE: PRT
<213> ORGANISM: Artificial sequence
<220> FEATURE:
<223> OTHER INFORMATION: Synthesized

<400> SEQUENCE: 197

Asp Ile Gln Met Thr Gln Ser Pro Ser Ser Leu Ser Ala Ser Val Gly
1 5 10 15

Asp Arg Val Thr Ile Thr Cys Arg Val Ser Glu Asn Ile Tyr Ser Asn
20 25 30

Leu Ala Trp Tyr Gln Gln Lys Pro Gly Lys Ser Pro Lys Leu Leu Val
35 40 45

Tyr Ala Ala Thr Asn Leu Ala Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln His Phe Trp Gly Thr Pro Pro
85 90 95

Trp Thr Phe Gly Gln Gly Thr Lys Leu Glu Ile Lys
100 105

<210> SEQ ID NO 198
<211> LENGTH: 108
<212> TYPE: PRT
<213> ORGANISM: Artificial sequence
<220> FEATURE:
<223> OTHER INFORMATION: Synthesized

<400> SEQUENCE: 198

Asp Ile Gln Met Thr Gln Ser Pro Ser Ser Leu Ser Ala Ser Val Gly
1 5 10 15

Asp Arg Val Thr Ile Thr Cys Arg Val Ser Glu Asn Ile Tyr Ser Asn
20 25 30

Leu Ala Trp Tyr Gln Gln Lys Pro Gly Lys Ser Pro Lys Leu Leu Val
35 40 45

Tyr Ala Ala Thr Asn Gly Ala Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln His Phe Trp Gly Thr Pro Pro
85 90 95

Trp Thr Phe Gly Gln Gly Thr Lys Leu Glu Ile Lys
100 105

<210> SEQ ID NO 199
<211> LENGTH: 108
<212> TYPE: PRT
<213> ORGANISM: Artificial sequence
<220> FEATURE:
<223> OTHER INFORMATION: Synthesized

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Val Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Ala Ala Thr Asn Ile Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Pro
                85                  90                  95

Trp Thr Phe Gly Gln Gly Thr Lys Leu Glu Ile Lys
            100                 105

<210> SEQ ID NO 200
<211> LENGTH: 10
<212> TYPE: PRT
<213> ORGANISM: Artificial sequence
<220> FEATURE:
<223> OTHER INFORMATION: Synthesized

<400> SEQUENCE: 200

Tyr Pro Tyr Asp Val Pro Asp Tyr Ala Gly
1               5                   10

<210> SEQ ID NO 201
<211> LENGTH: 10
<212> TYPE: PRT
<213> ORGANISM: Artificial sequence
<220> FEATURE:
<223> OTHER INFORMATION: Synthesized

<400> SEQUENCE: 201

Glu Gln Lys Leu Ile Ser Glu Glu Asp Leu
1               5                   10

<210> SEQ ID NO 202
<211> LENGTH: 7
<212> TYPE: PRT
<213> ORGANISM: Artificial sequence
<220> FEATURE:
<223> OTHER INFORMATION: Synthesized

<400> SEQUENCE: 202

Phe Thr Glu Ser Phe Leu Thr
1               5

<210> SEQ ID NO 203
<211> LENGTH: 4
<212> TYPE: PRT
<213> ORGANISM: Artificial sequence
<220> FEATURE:
<223> OTHER INFORMATION: Synthesized

<400> SEQUENCE: 203

Glu Ser Phe Leu
1

<210> SEQ ID NO 204
<211> LENGTH: 12

<212> TYPE: PRT
<213> ORGANISM: Homo sapiens

<400> SEQUENCE: 204

Asp Gly Cys Ile Leu Gly Tyr Lys Glu Gln Phe Leu
1 5 10

<210> SEQ ID NO 205
<211> LENGTH: 12
<212> TYPE: PRT
<213> ORGANISM: Homo sapiens

<400> SEQUENCE: 205

Pro Ser Ile Cys Leu Cys Ser Leu Glu Asp Phe Leu
1 5 10

<210> SEQ ID NO 206
<211> LENGTH: 4
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: X = Ser, Gln, or Asp

<400> SEQUENCE: 206

Glu Xaa Phe Leu
1

<210> SEQ ID NO 207
<211> LENGTH: 7
<212> TYPE: PRT
<213> ORGANISM: Artificial sequence
<220> FEATURE:
<223> OTHER INFORMATION: Synthesized

<400> SEQUENCE: 207

Gly Ser Gly Ser Gly Ser Gly
1 5

<210> SEQ ID NO 208
<211> LENGTH: 447
<212> TYPE: PRT
<213> ORGANISM: Artificial sequence
<220> FEATURE:
<223> OTHER INFORMATION: Synthesized

<400> SEQUENCE: 208

Glu Val Gln Leu Val Glu Ser Gly Gly Asp Leu Val Lys Pro Gly Gly
1 5 10 15

Ser Leu Lys Leu Ser Cys Ala Ala Ser Gly Phe Thr Phe Asn Ile Tyr
20 25 30

Gly Met Ser Trp Val Arg Gln Thr Pro Asp Lys Arg Leu Glu Trp Val
35 40 45

Ala Thr Ile Ser Ser Gly Gly Ile Tyr Thr Tyr Tyr Pro Asp Ile Leu
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr Tyr Cys
85 90 95

Ala Arg His Pro Gly Gly Ala Met Asp Tyr Trp Gly Gln Gly Thr Ser
100 105 110

```
Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 209
<211> LENGTH: 215
<212> TYPE: PRT
<213> ORGANISM: Artificial sequence
<220> FEATURE:
<223> OTHER INFORMATION: Synthesized

<400> SEQUENCE: 209

```
Asp Ile Gln Met Thr Gln Ser Pro Ala Ser Leu Ser Val Ser Val Gly
1               5                   10                  15

Glu Thr Val Thr Ile Thr Cys Arg Val Ser Glu Asn Ile Tyr Ser Asn
            20                  25                  30
```

```
Leu Ala Trp Tyr Gln Gln Lys Gln Gly Lys Ser Pro His Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Pro
                85                  90                  95

Trp Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 210
<211> LENGTH: 88
<212> TYPE: PRT
<213> ORGANISM: Homo sapiens

<400> SEQUENCE: 210

His Tyr Tyr Thr Ile Leu Asp Ser Gly Gly Ile Ile Val Ala Ile Glu
1               5                   10                  15

His Ser Ser Arg Pro Ile Asn Val Ile Lys Phe Ser Thr Asp Glu Gly
            20                  25                  30

Gln Cys Trp Gln Thr Tyr Thr Phe Thr Arg Asp Pro Ile Tyr Phe Thr
        35                  40                  45

Gly Leu Ala Ser Glu Pro Gly Ala Arg Ser Met Asn Ile Ser Ile Trp
    50                  55                  60

Gly Phe Thr Glu Ser Phe Leu Thr Ser Gln Trp Val Ser Tyr Thr Ile
65                  70                  75                  80

Asp Phe Lys Asp Ile Leu Glu Arg
                85


<210> SEQ ID NO 211
<211> LENGTH: 10
<212> TYPE: PRT
<213> ORGANISM: Homo sapiens

<400> SEQUENCE: 211

Phe Thr Glu Ser Phe Leu Thr Ser Gln Trp
1               5                   10


<210> SEQ ID NO 212
<211> LENGTH: 5
<212> TYPE: PRT
<213> ORGANISM: Homo sapiens
```

<400> SEQUENCE: 212

Leu Thr Ser Gln Trp
1               5

<210> SEQ ID NO 213
<211> LENGTH: 10
<212> TYPE: PRT
<213> ORGANISM: Homo sapiens

<400> SEQUENCE: 213

Arg Thr Glu Phe Gly Met Ala Ile Gly Pro
1               5                   10

<210> SEQ ID NO 214
<211> LENGTH: 10
<212> TYPE: PRT
<213> ORGANISM: Homo sapiens

<400> SEQUENCE: 214

Trp Gly Phe Thr Glu Ser Phe Leu Thr Ser
1               5                   10

<210> SEQ ID NO 215
<211> LENGTH: 723
<212> TYPE: PRT
<213> ORGANISM: Homo sapiens

<400> SEQUENCE: 215

Gln Asp Arg Leu Asp Ala Pro Pro Pro Pro Ala Ala Pro Leu Pro Arg
1               5                   10                  15

Trp Ser Gly Pro Ile Gly Val Ser Trp Gly Leu Arg Ala Ala Ala Ala
            20                  25                  30

Gly Gly Ala Phe Pro Arg Gly Gly Arg Trp Arg Arg Ser Ala Pro Gly
        35                  40                  45

Glu Asp Glu Glu Cys Gly Arg Val Arg Asp Phe Val Ala Lys Leu Ala
    50                  55                  60

Asn Asn Thr His Gln His Val Phe Asp Asp Leu Arg Gly Ser Val Ser
65                  70                  75                  80

Leu Ser Trp Val Gly Asp Ser Thr Gly Val Ile Leu Val Leu Thr Thr
                85                  90                  95

Phe His Val Pro Leu Val Ile Met Thr Phe Gly Gln Ser Lys Leu Tyr
            100                 105                 110

Arg Ser Glu Asp Tyr Gly Lys Asn Phe Lys Asp Ile Thr Asp Leu Ile
        115                 120                 125

Asn Asn Thr Phe Ile Arg Thr Glu Phe Gly Met Ala Ile Gly Pro Glu
    130                 135                 140

Asn Ser Gly Lys Val Val Leu Thr Ala Glu Val Ser Gly Gly Ser Arg
145                 150                 155                 160

Gly Gly Arg Ile Phe Arg Ser Ser Asp Phe Ala Lys Asn Phe Val Gln
                165                 170                 175

Thr Asp Leu Pro Phe His Pro Leu Thr Gln Met Met Tyr Ser Pro Gln
            180                 185                 190

Asn Ser Asp Tyr Leu Leu Ala Leu Ser Thr Glu Asn Gly Leu Trp Val
        195                 200                 205

Ser Lys Asn Phe Gly Gly Lys Trp Glu Glu Ile His Lys Ala Val Cys
    210                 215                 220

```
Leu Ala Lys Trp Gly Ser Asp Asn Thr Ile Phe Phe Thr Thr Tyr Ala
225                 230                 235                 240

Asn Gly Ser Cys Lys Ala Asp Leu Gly Ala Leu Glu Leu Trp Arg Thr
                245                 250                 255

Ser Asp Leu Gly Lys Ser Phe Lys Thr Ile Gly Val Lys Ile Tyr Ser
            260                 265                 270

Phe Gly Leu Gly Gly Arg Phe Leu Phe Ala Ser Val Met Ala Asp Lys
        275                 280                 285

Asp Thr Thr Arg Arg Ile His Val Ser Thr Asp Gln Gly Asp Thr Trp
    290                 295                 300

Ser Met Ala Gln Leu Pro Ser Val Gly Gln Glu Gln Phe Tyr Ser Ile
305                 310                 315                 320

Leu Ala Ala Asn Asp Asp Met Val Phe Met His Val Asp Glu Pro Gly
                325                 330                 335

Asp Thr Gly Phe Gly Thr Ile Phe Thr Ser Asp Asp Arg Gly Ile Val
            340                 345                 350

Tyr Ser Lys Ser Leu Asp Arg His Leu Tyr Thr Thr Thr Gly Gly Glu
        355                 360                 365

Thr Asp Phe Thr Asn Val Thr Ser Leu Arg Gly Val Tyr Ile Thr Ser
    370                 375                 380

Val Leu Ser Glu Asp Asn Ser Ile Gln Thr Met Ile Thr Phe Asp Gln
385                 390                 395                 400

Gly Gly Arg Trp Thr His Leu Arg Lys Pro Glu Asn Ser Glu Cys Asp
                405                 410                 415

Ala Thr Ala Lys Asn Lys Asn Glu Cys Ser Leu His Ile His Ala Ser
            420                 425                 430

Tyr Ser Ile Ser Gln Lys Leu Asn Val Pro Met Ala Pro Leu Ser Glu
        435                 440                 445

Pro Asn Ala Val Gly Ile Val Ile Ala His Gly Ser Val Gly Asp Ala
    450                 455                 460

Ile Ser Val Met Val Pro Asp Val Tyr Ile Ser Asp Asp Gly Gly Tyr
465                 470                 475                 480

Ser Trp Thr Lys Met Leu Glu Gly Pro His Tyr Tyr Thr Ile Leu Asp
                485                 490                 495

Ser Gly Gly Ile Ile Val Ala Ile Glu His Ser Ser Arg Pro Ile Asn
            500                 505                 510

Val Ile Lys Phe Ser Thr Asp Glu Gly Gln Cys Trp Gln Thr Tyr Thr
        515                 520                 525

Phe Thr Arg Asp Pro Ile Tyr Phe Thr Gly Leu Ala Ser Glu Pro Gly
    530                 535                 540

Ala Arg Ser Met Asn Ile Ser Ile Trp Gly Phe Thr Glu Ser Phe Leu
545                 550                 555                 560

Thr Ser Gln Trp Val Ser Tyr Thr Ile Asp Phe Lys Asp Ile Leu Glu
                565                 570                 575

Arg Asn Cys Glu Glu Lys Asp Tyr Thr Ile Trp Leu Ala His Ser Thr
            580                 585                 590

Asp Pro Glu Asp Tyr Glu Asp Gly Cys Ile Leu Gly Tyr Lys Glu Gln
        595                 600                 605

Phe Leu Arg Leu Arg Lys Ser Ser Val Cys Gln Asn Gly Arg Asp Tyr
    610                 615                 620

Val Val Thr Lys Gln Pro Ser Ile Cys Leu Cys Ser Leu Glu Asp Phe
625                 630                 635                 640
```

```
Leu Cys Asp Phe Gly Tyr Tyr Arg Pro Glu Asn Asp Ser Lys Cys Val
                645                 650                 655

Glu Gln Pro Glu Leu Lys Gly His Asp Leu Glu Phe Cys Leu Tyr Gly
            660                 665                 670

Arg Glu Glu His Leu Thr Thr Asn Gly Tyr Arg Lys Ile Pro Gly Asp
        675                 680                 685

Lys Cys Gln Gly Gly Val Asn Pro Val Arg Glu Val Lys Asp Leu Lys
    690                 695                 700

Lys Lys Cys Thr Ser Asn Phe Leu Ser Pro Glu Lys Gln Asn Ser Lys
705                 710                 715                 720

Ser Asn Ser


<210> SEQ ID NO 216
<211> LENGTH: 773
<212> TYPE: PRT
<213> ORGANISM: Artificial sequence
<220> FEATURE:
<223> OTHER INFORMATION: Synthesized

<400> SEQUENCE: 216

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln Ala Val Phe Asp Ala Ala Ala Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 217
<211> LENGTH: 773
<212> TYPE: PRT
<213> ORGANISM: Artificial sequence
<220> FEATURE:
<223> OTHER INFORMATION: Synthesized

<400> SEQUENCE: 217

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Ala Ala Val Pro Leu Ala Ile Ala Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770

<210> SEQ ID NO 218
<211> LENGTH: 773
<212> TYPE: PRT
<213> ORGANISM: Artificial sequence
<220> FEATURE:
<223> OTHER INFORMATION: Synthesized

<400> SEQUENCE: 218

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Ala Gly Ala Ser Ala Leu
    130                 135                 140

Ala Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 219
<211> LENGTH: 773
<212> TYPE: PRT
<213> ORGANISM: Artificial sequence
<220> FEATURE:
<223> OTHER INFORMATION: Synthesized

<400> SEQUENCE: 219

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Ala Ile Thr Ala Leu
145 150 155 160

Ile Asn Ala Ala Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 220
<211> LENGTH: 773
<212> TYPE: PRT
<213> ORGANISM: Artificial sequence
<220> FEATURE:
<223> OTHER INFORMATION: Synthesized

<400> SEQUENCE: 220

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Ala Ala Gly Gly Ala
180 185 190

Ala Gly Gly Ala Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770


<210> SEQ ID NO 221
<211> LENGTH: 773
<212> TYPE: PRT
<213> ORGANISM: Artificial sequence
<220> FEATURE:
<223> OTHER INFORMATION: Synthesized

<400> SEQUENCE: 221

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Ala Thr Ala Leu Pro Phe Ala Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770


<210> SEQ ID NO 222
<211> LENGTH: 773
<212> TYPE: PRT
<213> ORGANISM: Artificial sequence
<220> FEATURE:
<223> OTHER INFORMATION: Synthesized

<400> SEQUENCE: 222

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Ala Asn Gly Leu Ala
225                 230                 235                 240

Val Ser Lys Asn Phe Gly Gly Lys Trp Glu Ala Ile Ala Ala Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770


<210> SEQ ID NO 223
<211> LENGTH: 773
<212> TYPE: PRT
<213> ORGANISM: Artificial sequence
<220> FEATURE:
<223> OTHER INFORMATION: Synthesized

<400> SEQUENCE: 223

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Ala
            260                 265                 270
```

-continued

Ala Asn Gly Ser Cys Ala Ala Asp Ala Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Ala Ala Ala
305                 310                 315                 320

Ala Ala Thr Thr Arg Arg Ile His Val Ser Thr Asp Gln Gly Asp Thr
                325                 330                 335

Trp Ser Met Ala Gln Leu Pro Ser Val Gly Ala Ala Gln Ala Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770


<210> SEQ ID NO 224
<211> LENGTH: 773
<212> TYPE: PRT
<213> ORGANISM: Artificial sequence
<220> FEATURE:
<223> OTHER INFORMATION: Synthesized

<400> SEQUENCE: 224

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Ala Glu Pro
        355                 360                 365

Gly Ala Ala Gly Phe Gly Thr Ile Phe Thr Ser Asp Asp Arg Gly Ile
    370                 375                 380

Val Tyr Ser Lys Ser Leu Asp Arg His Leu Ala Thr Ala Ala Gly Gly
385                 390                 395                 400

Glu Thr Asp Phe Thr Asn Val Thr Ser Leu Arg Gly Val Tyr Ile Thr
                405                 410                 415

Ser Val Ala Ser Ala Asp Ala Ser Ala Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 225
<211> LENGTH: 773
<212> TYPE: PRT
<213> ORGANISM: Artificial sequence
<220> FEATURE:
<223> OTHER INFORMATION: Synthesized

<400> SEQUENCE: 225

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Ala Lys Ala Ala Val Pro Met Ala Pro Leu Ser
465                 470                 475                 480

Glu Pro Asn Ala Val Gly Ile Val Ile Ala His Gly Ser Val Gly Ala
                485                 490                 495

Ala Ala Ser Val Met Ala Pro Ala Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 226
<211> LENGTH: 773
<212> TYPE: PRT
<213> ORGANISM: Artificial sequence
<220> FEATURE:
<223> OTHER INFORMATION: Synthesized

<400> SEQUENCE: 226

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Ala Met Leu Ala Gly Pro Ala Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770
```

<210> SEQ ID NO 227
<211> LENGTH: 773
<212> TYPE: PRT
<213> ORGANISM: Artificial sequence
<220> FEATURE:
<223> OTHER INFORMATION: Synthesized

<400> SEQUENCE: 227

```
Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Ala His Ala Ser Ala Pro Ile
    530                 535                 540

Ala Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 228
<211> LENGTH: 773
<212> TYPE: PRT
<213> ORGANISM: Artificial sequence
<220> FEATURE:
<223> OTHER INFORMATION: Synthesized

<400> SEQUENCE: 228

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Ala Phe Thr Ala Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770

<210> SEQ ID NO 229
<211> LENGTH: 773
<212> TYPE: PRT
<213> ORGANISM: Artificial sequence
<220> FEATURE:
<223> OTHER INFORMATION: Synthesized

<400> SEQUENCE: 229

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

-continued

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Ala Ala Ala
            580                 585                 590

Ala Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 230
<211> LENGTH: 773
<212> TYPE: PRT
<213> ORGANISM: Artificial sequence
<220> FEATURE:
<223> OTHER INFORMATION: Synthesized

<400> SEQUENCE: 230

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Ala Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 231
<211> LENGTH: 773
<212> TYPE: PRT
<213> ORGANISM: Artificial sequence
<220> FEATURE:
<223> OTHER INFORMATION: Synthesized

<400> SEQUENCE: 231

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Ala Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770

<210> SEQ ID NO 232
<211> LENGTH: 773
<212> TYPE: PRT
<213> ORGANISM: Artificial sequence
<220> FEATURE:
<223> OTHER INFORMATION: Synthesized

<400> SEQUENCE: 232

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Ala His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 233
<211> LENGTH: 773
<212> TYPE: PRT
<213> ORGANISM: Artificial sequence
<220> FEATURE:
<223> OTHER INFORMATION: Synthesized

<400> SEQUENCE: 233

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Ala Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 234
<211> LENGTH: 773
<212> TYPE: PRT
<213> ORGANISM: Artificial sequence
<220> FEATURE:
<223> OTHER INFORMATION: Synthesized

<400> SEQUENCE: 234

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Ala Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770


<210> SEQ ID NO 235
<211> LENGTH: 773
<212> TYPE: PRT
<213> ORGANISM: Artificial sequence
<220> FEATURE:
<223> OTHER INFORMATION: Synthesized

<400> SEQUENCE: 235

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Ala Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 236
<211> LENGTH: 773
<212> TYPE: PRT
<213> ORGANISM: Artificial sequence
<220> FEATURE:
<223> OTHER INFORMATION: Synthesized

<400> SEQUENCE: 236

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Ala Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770

<210> SEQ ID NO 237
<211> LENGTH: 773
<212> TYPE: PRT
<213> ORGANISM: Artificial sequence
<220> FEATURE:
<223> OTHER INFORMATION: Synthesized

<400> SEQUENCE: 237

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Ala Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770


<210> SEQ ID NO 238
<211> LENGTH: 773
<212> TYPE: PRT
<213> ORGANISM: Artificial sequence
<220> FEATURE:
<223> OTHER INFORMATION: Synthesized

<400> SEQUENCE: 238

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Ala Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770


<210> SEQ ID NO 239
<211> LENGTH: 773
<212> TYPE: PRT
<213> ORGANISM: Artificial sequence
<220> FEATURE:
<223> OTHER INFORMATION: Synthesized

<400> SEQUENCE: 239

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Ala Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770
```

```
<210> SEQ ID NO 240
<211> LENGTH: 773
<212> TYPE: PRT
<213> ORGANISM: Artificial sequence
<220> FEATURE:
<223> OTHER INFORMATION: Synthesized

<400> SEQUENCE: 240

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Ala Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
690 695 700

Gly Arg Glu Glu His Leu Thr Thr Asn Gly Tyr Arg Lys Ile Pro Gly
705 710 715 720

Asp Lys Cys Gln Gly Gly Val Asn Pro Val Arg Glu Val Lys Asp Leu
725 730 735

Lys Lys Lys Cys Thr Ser Asn Phe Leu Ser Pro Glu Lys Gln Asn Ser
740 745 750

Lys Ser Asn Ser Gly Gly Ser Gly Gly Ser Gly Gly Ser His His His
755 760 765

His His His His His
770

<210> SEQ ID NO 241
<211> LENGTH: 773
<212> TYPE: PRT
<213> ORGANISM: Artificial sequence
<220> FEATURE:
<223> OTHER INFORMATION: Synthesized

<400> SEQUENCE: 241

Met Glu Arg Pro Trp Gly Ala Ala Asp Gly Leu Ser Arg Trp Pro His
1 5 10 15

Gly Leu Gly Leu Leu Leu Leu Leu Gln Leu Leu Pro Pro Ser Thr Leu
20 25 30

Ser Gln Asp Arg Leu Asp Ala Pro Pro Pro Pro Ala Ala Pro Leu Pro
35 40 45

Arg Trp Ser Gly Pro Ile Gly Val Ser Trp Gly Leu Arg Ala Ala Ala
50 55 60

Ala Gly Gly Ala Phe Pro Arg Gly Gly Arg Trp Arg Arg Ser Ala Pro
65 70 75 80

Gly Glu Asp Glu Glu Cys Gly Arg Val Arg Asp Phe Val Ala Lys Leu
85 90 95

Ala Asn Asn Thr His Gln His Val Phe Asp Asp Leu Arg Gly Ser Val
100 105 110

Ser Leu Ser Trp Val Gly Asp Ser Thr Gly Val Ile Leu Val Leu Thr
115 120 125

Thr Phe His Val Pro Leu Val Ile Met Thr Phe Gly Gln Ser Lys Leu
130 135 140

Tyr Arg Ser Glu Asp Tyr Gly Lys Asn Phe Lys Asp Ile Thr Asp Leu
145 150 155 160

Ile Asn Asn Thr Phe Ile Arg Thr Glu Phe Gly Met Ala Ile Gly Pro
165 170 175

Glu Asn Ser Gly Lys Val Val Leu Thr Ala Glu Val Ser Gly Gly Ser
180 185 190

Arg Gly Gly Arg Ile Phe Arg Ser Ser Asp Phe Ala Lys Asn Phe Val
195 200 205

Gln Thr Asp Leu Pro Phe His Pro Leu Thr Gln Met Met Tyr Ser Pro
210 215 220

Gln Asn Ser Asp Tyr Leu Leu Ala Leu Ser Thr Glu Asn Gly Leu Trp
225 230 235 240

Val Ser Lys Asn Phe Gly Gly Lys Trp Glu Glu Ile His Lys Ala Val
245 250 255

Cys Leu Ala Lys Trp Gly Ser Asp Asn Thr Ile Phe Phe Thr Thr Tyr
260 265 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Ala
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770


<210> SEQ ID NO 242
<211> LENGTH: 773
<212> TYPE: PRT
<213> ORGANISM: Artificial sequence
<220> FEATURE:
<223> OTHER INFORMATION: Synthesized

<400> SEQUENCE: 242

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270
```

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ala Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770

<210> SEQ ID NO 243
<211> LENGTH: 773
<212> TYPE: PRT
<213> ORGANISM: Artificial sequence
<220> FEATURE:
<223> OTHER INFORMATION: Synthesized

<400> SEQUENCE: 243

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Ala Gly Met Ala Ala Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

```
Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685
```

```
Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Gly Gly Ser Gly Gly Ser Gly Gly Ser His His His
        755                 760                 765

His His His His His
    770


<210> SEQ ID NO 244
<211> LENGTH: 447
<212> TYPE: PRT
<213> ORGANISM: Artificial sequence
<220> FEATURE:
<223> OTHER INFORMATION: Synthesized

<400> SEQUENCE: 244

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ile Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Ile Tyr Thr Tyr Tyr Pro Asp Ile Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Pro Gly Gly Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Tyr Ile Thr Arg Glu
                245                 250                 255

Pro Glu Val Thr Cys Val Val Val Asp Val Ser His Glu Asp Pro Glu
            260                 265                 270
```

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 245
<211> LENGTH: 215
<212> TYPE: PRT
<213> ORGANISM: Artificial sequence
<220> FEATURE:
<223> OTHER INFORMATION: Synthesized

<400> SEQUENCE: 245

Asp Ile Gln Met Thr Gln Ser Pro Ser Ser Leu Ser Ala Ser Val Gly
1 5 10 15

Asp Arg Val Thr Ile Thr Cys Arg Val Ser Glu Asn Ile Tyr Ser Asn
20 25 30

Leu Ala Trp Tyr Gln Gln Lys Pro Gly Lys Ser Pro Lys Leu Leu Val
35 40 45

Tyr Ala Ala Thr Asn Gly Ala Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln His Phe Trp Gly Thr Pro Pro
85 90 95

Trp Thr Phe Gly Gln Gly Thr Lys Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

```
Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 246
<211> LENGTH: 453
<212> TYPE: PRT
<213> ORGANISM: Artificial sequence
<220> FEATURE:
<223> OTHER INFORMATION: Synthesized

<400> SEQUENCE: 246

Gln Ala Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Ile
        35                  40                  45

Gly Ala Ile Tyr Pro Gly Asn Asp Ala Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Gly Tyr Tyr Gly Ser Ser Phe Glu Ala Trp Phe Ala Ser
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Tyr Ile Thr Arg Glu Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 247
<211> LENGTH: 219
<212> TYPE: PRT
<213> ORGANISM: Artificial sequence
<220> FEATURE:
<223> OTHER INFORMATION: Synthesized

<400> SEQUENCE: 247

Asp Val Val Met Thr Gln Thr Pro Ser Ser Leu Pro Val Thr Pro Gly
1 5 10 15

Glu Pro Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Thr Ile
65 70 75 80

Ser Arg Val Glu Ala Glu Asp Val Gly Val Tyr Tyr Cys Phe Gln Gly
85 90 95

Ser His Val Leu Pro Thr Phe Gly Gly Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 248

<211> LENGTH: 448
<212> TYPE: PRT
<213> ORGANISM: Artificial sequence
<220> FEATURE:
<223> OTHER INFORMATION: Synthesized

<400> SEQUENCE: 248

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Gly Met Ser Trp Val Arg Gln Thr Pro Asp Lys Arg Leu Glu Trp Val
35 40 45

Ala Ile Ile Ser Ser Gly Gly Ser Tyr Thr Tyr Tyr Ser Asp Thr Val
50 55 60

Lys Gly Arg Phe Thr Ile Ser Arg Asp Asn Ser Lys Asn Ser Leu Tyr
65 70 75 80

Leu Gln Met Asn Ser Leu Arg Ala Glu Asp Thr Ala Val Tyr Tyr Cys
85 90 95

Ser Arg Ser Ser Ser His Trp Tyr Phe Asp Val Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Tyr Ile Thr Arg
245 250 255

Glu Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 249
<211> LENGTH: 214
<212> TYPE: PRT
<213> ORGANISM: Artificial sequence
<220> FEATURE:
<223> OTHER INFORMATION: Synthesized

<400> SEQUENCE: 249

Asp Ile Gln Met Thr Gln Ser Pro Ser Ser Val Ser Ala Ser Val Gly
1               5                   10                  15

Asp Arg Val Thr Ile Thr Cys His Ala Ser Gln Gly Ile Ser Ser Asn
            20                  25                  30

Ile Gly Trp Leu Gln Gln Lys Pro Gly Lys Ala Phe Lys Gly Leu Ile
        35                  40                  45

Tyr His Gly Thr Asn Leu Lys Asp Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Asp Tyr Phe Cys Val Gln Tyr Ala Gln Phe Pro Tyr
                85                  90                  95

Thr Phe Gly Gln Gly Thr Lys Val Glu Lys Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 250
<211> LENGTH: 447
<212> TYPE: PRT
<213> ORGANISM: Artificial sequence
<220> FEATURE:
<223> OTHER INFORMATION: Synthesized

<400> SEQUENCE: 250

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Ile Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Ile Tyr Thr Tyr Tyr Pro Asp Ile Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Pro Gly Gly Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly Lys
435 440 445

<210> SEQ ID NO 251
<211> LENGTH: 453
<212> TYPE: PRT
<213> ORGANISM: Artificial sequence
<220> FEATURE:
<223> OTHER INFORMATION: Synthesized

<400> SEQUENCE: 251

Gln Ala Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Ser Met His Trp Val Arg Gln Ala Pro Gly Gln Gly Leu Glu Trp Ile
35 40 45

Gly Ala Ile Tyr Pro Gly Asn Asp Ala Thr Ser Tyr Asn Gln Lys Phe
50 55 60

Lys Gly Arg Ala Thr Leu Thr Val Asp Lys Ser Thr Ser Thr Ala Tyr
65 70 75 80

Met Glu Leu Ser Ser Leu Arg Ser Glu Asp Thr Ala Val Tyr Phe Cys
85 90 95

Ala Arg Glu Gly Tyr Tyr Gly Ser Ser Phe Glu Ala Trp Phe Ala Ser
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Ala
225 230 235 240

Ala Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 252
<211> LENGTH: 448
<212> TYPE: PRT
<213> ORGANISM: Artificial sequence
<220> FEATURE:
<223> OTHER INFORMATION: Synthesized

<400> SEQUENCE: 252

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Gly Met Ser Trp Val Arg Gln Thr Pro Asp Lys Arg Leu Glu Trp Val
35 40 45

Ala Ile Ile Ser Ser Gly Gly Ser Tyr Thr Tyr Tyr Ser Asp Thr Val
50 55 60

Lys Gly Arg Phe Thr Ile Ser Arg Asp Asn Ser Lys Asn Ser Leu Tyr
65 70 75 80

Leu Gln Met Asn Ser Leu Arg Ala Glu Asp Thr Ala Val Tyr Tyr Cys
85 90 95

Ser Arg Ser Ser Ser His Trp Tyr Phe Asp Val Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

-continued

```
Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```